(12) United States Patent
Boese et al.

(10) Patent No.: US 11,174,245 B2
(45) Date of Patent: Nov. 16, 2021

(54) BENZIMIDAZOLE COMPOUNDS AND DERIVATIVES AS EGFR INHIBITORS

(71) Applicant: Boehringer Ingelheim International GmbH, Ingelheim am Rhein (DE)

(72) Inventors: Dietrich Boese, Erzhausen (DE); Georg Dahmann, Biberach an der Riss (DE); Harald Engelhardt, Ebreichsdorf (AT); Mark Petronczki, Vienna (AT); Dirk Scharn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/970,705

(22) PCT Filed: Feb. 20, 2019

(86) PCT No.: PCT/EP2019/054208
§ 371 (c)(1),
(2) Date: Aug. 18, 2020

(87) PCT Pub. No.: WO2019/162323
PCT Pub. Date: Aug. 29, 2019

(65) Prior Publication Data
US 2020/0377476 A1 Dec. 3, 2020

(30) Foreign Application Priority Data
Feb. 21, 2018 (EP) .................... 18157881

(51) Int. Cl.
| | | |
|---|---|---|
| C07D 401/14 | (2006.01) |
| A61K 31/4355 | (2006.01) |
| A61K 31/437 | (2006.01) |
| A61K 31/438 | (2006.01) |
| A61K 31/4439 | (2006.01) |
| A61K 31/444 | (2006.01) |
| A61K 31/4545 | (2006.01) |
| A61K 31/496 | (2006.01) |
| A61K 31/5025 | (2006.01) |
| A61K 31/519 | (2006.01) |
| A61K 31/5355 | (2006.01) |
| A61K 31/5377 | (2006.01) |
| C07D 401/12 | (2006.01) |
| C07D 405/14 | (2006.01) |
| C07D 409/14 | (2006.01) |
| C07D 413/14 | (2006.01) |
| C07D 491/048 | (2006.01) |
| C07D 491/107 | (2006.01) |
| C07D 498/04 | (2006.01) |

(52) U.S. Cl.
CPC ......... *C07D 401/14* (2013.01); *A61K 31/437* (2013.01); *A61K 31/438* (2013.01); *A61K 31/4355* (2013.01); *A61K 31/444* (2013.01); *A61K 31/4439* (2013.01); *A61K 31/4545* (2013.01); *A61K 31/496* (2013.01); *A61K 31/5025* (2013.01); *A61K 31/519* (2013.01); *A61K 31/5355* (2013.01); *A61K 31/5377* (2013.01); *C07D 401/12* (2013.01); *C07D 405/14* (2013.01); *C07D 409/14* (2013.01); *C07D 413/14* (2013.01); *C07D 491/048* (2013.01); *C07D 491/107* (2013.01); *C07D 498/04* (2013.01)

(58) Field of Classification Search
None
See application file for complete search history.

(56) References Cited

FOREIGN PATENT DOCUMENTS

| WO | 2003030902 A1 | 4/2003 |
|---|---|---|
| WO | 2003041708 A1 | 5/2003 |
| WO | 2004014369 A1 | 2/2004 |
| WO | 2004014905 A1 | 2/2004 |
| WO | 2005079791 A1 | 9/2005 |
| WO | 2007133983 A3 | 3/2008 |
| WO | 2012018668 A1 | 2/2012 |
| WO | 2013184757 | 12/2013 |
| WO | 2013184766 A1 | 12/2013 |
| WO | 2014036016 A1 | 3/2014 |
| WO | 2014081718 A1 | 5/2014 |
| WO | 2014210354 A1 | 12/2014 |

(Continued)

OTHER PUBLICATIONS

International Search Report PCT/EP2019/054208 dated Apr. 24, 2019.

(Continued)

*Primary Examiner* — Brian J Davis
(74) *Attorney, Agent, or Firm* — Edouard G. Lebel

(57) ABSTRACT

The present invention encompasses compounds of formula (I) (I), wherein the groups $R^1$ to $R^5$ have the meanings given in the claims and specification, their use as inhibitors of mutant EGFR, pharmaceutical compositions which contain compounds of this kind and their use as medicaments/medical uses, especially as agents for treatment and/or prevention of oncological diseases.

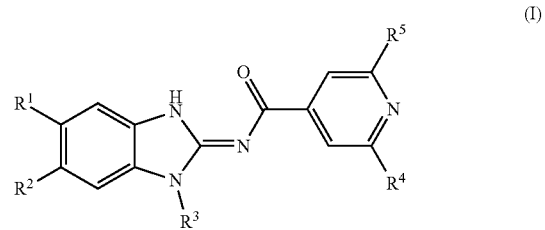

(I)

23 Claims, No Drawings

(56) References Cited

FOREIGN PATENT DOCUMENTS

| | | |
|---|---|---|
| WO | 2015143148 A1 | 9/2015 |
| WO | 2015143161 A1 | 9/2015 |
| WO | 2016176473 A1 | 11/2016 |
| WO | 2016185333 A1 | 11/2016 |
| WO | 2017004383 A1 | 1/2017 |
| WO | 2017049068 A1 | 3/2017 |
| WO | 2017049069 A1 | 3/2017 |

OTHER PUBLICATIONS

Gancia, Emanuela et al. "Discovery of LRRK2 inhibitors by using an ensemble of virtual screening methods" (2017) Bioorganic & Medicinal Chemistry Letters, vol. 27, 2520-2527.
Lelais, Gerald et al. "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers" (2016) Journal of Medicinal Chemistry, vol. 59, 6671-6689.
Bersanelli, Melissa et al. "L718Q Mutation as New Mechanism of Acquired Resistance to AZD9291 in EGFR-Mutated NSCLC" (2016) Journal of Thoracic Oncology, vol. 11, No. 10: e121-123.
Blakely, Collin M. et al. "Resiliency of lung cancers to EGFR inhibitor treatment unveiled offering opportunities to divide and conquer EGFR inhibitor resistance" (2012) Cancer Discov. 2(10), 872-875.
Bryan, Marian C. et al. "Pyridones as Highly Selective, Noncovalent Inhibitors of T790M Double Mutants of EGFR" (2016) ACS, Medicinal Chemistry Letters, 7, 100-104.
Chan, Bryan K. et al. "Discovery of Noncovalent, Mutant-Selective Epidermal Growth Factor Receptor Inhibitor" (2016) Journal of Medicinal Chemistry, 59, 9080-9093.
Chen, Kai et al. "Novel Mutations on EGFR Leu792 Potentially Correlate to Acquired Resistance to Osimertinib in Advanced NSCLC" (2016) Journal of Thoracic Oncology, vol. 12, No. 6, e65-68.
Chen, Li et al. "Novel 4-arylaminoquinazoline derivatives with (E)-propen-1-yl moiety as petent EGFR inhibitors with enhanced antiproliferative activities against tumor cells" (2017) European Journal of Medicinal Chemistry, 138, 689-697.
Cross, Darren A.E. et al. "AZD9291, an irreversible EGFR TKI, overcomes T790M-mediated resistance to EGFR inhibitors in lung cancer" (2014) Cancer Discov., 4 (9), 1046-1061.
Engel, Julian et al. "Insight into the Inhibition of Drug-Resistant Mutants of the the Receptor Tyrosine Kinase EGFR" (2016) Angew. Chem. Int. Ed. 55, 10909-10912.
Gunther, Marcel et al. "Trisubstituted Pyridinylimidazoles as Potent inhibitors of the Clinically Resistant L858R/T790M/C797S EGFR Mutant: Targeting of Both Hydrophobic Regions and the Phosphate Binding Site" (2017) Journal of Medicinal Chemistry, 60, 5613-5637.
Hanan, Emily J. et al. "Discovery of Selective and Noncovalent Diaminopyrimidine-Based Inhibitors of Epidermal Growth Factor Receptor Containing the T790M Resistance Mutation" (2014) Journal of Medicinal Chemistry, 57, 10176-10191.
Heald, Robert et al. "Noncovalent Mutant Selective Epidermal Growth Factor Receptor Inhibitors: A Lead Optimization Case Study" (2015) Journal of Medicinal Chemistry, 58, 8877-8895.
Janne, Pasi A. et al. "AZD9291 in EGFR Inhibitor-Resistant Non-Small-Cell Lung Cancer" (2015) The New England Journal of Medicine, vol. 372, No. 18, 1689-1699.
Jia, Yong et al. "EGF816 Exerts Anticancer Effects in Non-Small Cell Lung Cancer by Irreversibly and Selectively Targeting Primary and Acquired Activating Mutations in the EGF Receptor" (2016) Cancer Research, 76(6), 1591-1602.

Juchum, Michael et al. "Trisubstituted Imidazoles with a Rigidized Hinge Binding Motif Act as Single Digit nM Inhibitors of Clinically Relevant EGFR L858R/T790M and L858R/T790M/C797S Mutants: An Example of Target Hopping" (2017) Journal of Medicinal Chemistry, vol. 60, 4636-4656.
Kobayashi, Susumu et al. "EGFR Mutation and Resistance of Non-Small-Cell Lung Cancer to Gefitinib" (2005) New England Journal of Medicine, vol. 352, 8, 786-792.
Konduri, Kartik et al. "EGFR Fusions as Novel Therapeutic Targets in Lung Cancer" (2016) Cancer Discovery, 6, 601-611.
Midha, Anita et al. "EGFR mutation incidence in non-small-cell lung cancer of adenocarcinoma histology: a systematic review and global map by ethnicity (mutMapII)" (2015) Am J Cancer Res, 5(9), 2892-2911.
Mitsudomi, Tetsuya et al. "Gefitinib versus cisplatin plus decetaxel in patients with non-small-cell lung cancer harbouring mutations of the epidermal growth factor receptor (WJT0G3405): an open label, randomised phase 3 trial" (2010) Lancet Oncol., 11, 121-128.
Mok, T.S. et al. "Osimertinib or Platinum—Pemetrexed in EGFR T790M-Positive Lung Cancer" (2017) New England Journal of Medicine, 376 (7), 629-640.
Ortiz-Cuaran, Sandra et al. "Heterogeneous Mechanisms of Primary and Acquired Resistance to Third-Generation EGFR Inhibitors" (2016) Clinical Cancer Research, 22(19), 4837-4847.
Ou, Qiuxiang et al. "Investigating novel resistance mechanisms to third generation EGFR TKI osimertinib in non-small cell lung cancer patients using next generation sequencing" (2017) Journal of Clinical Oncology, vol. 35, Issue 15, Abstract 2572.
Park, Hwangseo et al. "Discovery of EGF Receptor Inhibitors that are Selective for the d746-750/T790M/C797S Mutant through Structure-Based de Novo Design" (2017) Angew Chem. Int. Ed., 56, 7634-7638.
Park, Keunchil et al. "Afatinib versus gefitinib as first-line treatment of patients with EGFR mutation-positive non-small-cell lung cancer (LUX-Lung 7): a phase 2B, open-label, randomised controlled trial" (2016) Lancet Oncol., vol. 17, Issue 5, 577-589.
Patel, Harun M. et al. "Design and synthesis of quinazolinones as EGFR inhibitors to covercome EGFR resistance obstacle" (2017) Bioorganic & Medicinal Chemistry, 25, 2713-2723.
Piotrowska, Z. et al. "Characterizing the Genomic Landscape of EGFR C797S in Lung Cancer Using ctDNA Next-Generation Sequencing" (2017) Presented IASLC 18th World Conference on Lung Cancer, Abstract.
Ramalingam, Suresh S. et al. "Osimertinib as First-Line Treatment of EGFR Mutation-Positive Advanced Non-Small-Cell Lung Cancer" (2018) Journal of Clinical Oncology, vol. 36, No. 9, 841-849.
Song, Haa-Na et al. "Acquired C797S Mutation upon Treatment with a T790M-Specific Third-Generation EGFR Inhibitor (HM61713) in Non-Small Cell Lung Cancer" (2015) Journal of Thoracic Oncology, vol. 11, No. 4, e45-e47.
Soria, J.C. et al. "Osimertinib in Untreated EGFR-Mutated Advanced Non-Small-Cell Lung Cancer" (2018) New England Journal of Medicine, vol. 378, No. 2, 113-125.
Thress, Kenneth S. et al. "Acquired EGFR C797S mediates resistance to AZD9291 in advanced non-small cell lung cancer harboring EGFR T790M" (2015) Nat. Med , 21(6), 560-562.
Wang, Shuhang et al. "Third-generation inhibitors targeting EGFR T790M mutation in advanced non-small cell lung cancer" (2016) Journal of Hematology & Oncology, 9:34, 7 pgs.
Yu, Helena et al. "Acquired Resistance of EGFR-Mutant Lung Cancer to a T790M-Specific EGFR Inhibitor Emergence of a Third Mutation (C797S) in the EGFR Tyrosine Kinase Domain" (2015) JAMA Oncology, vol. 1, No. 7, 982-984.
Zhang, Yaling et al. "Quinazoline-1-deoxynojirimycin hybrids as high active dual inhibitors of EGFR and a-glucosidase" (2017) Bioorganic & Medicinal Chemistry Letters, 27, 4309-4313.
Zhou, Caicun et al. "Erlotinib versus chemotherapy as first-line treatment for patients with advanced EGFR mutationpositive non-small-cell lung cancer (Optimal, CTONG-0802): a multicentre, open-label, randomised, phase 3 study" (2011) Lancet Oncol., 12, 735-742.

BENZIMIDAZOLE COMPOUNDS AND DERIVATIVES AS EGFR INHIBITORS

FIELD OF THE INVENTION

The present invention relates to new substituted benzimidazoles and derivatives of formula (I)

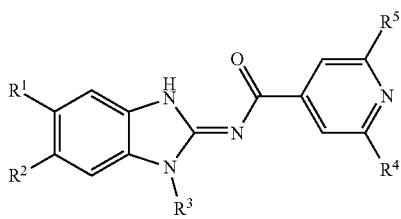

(I)

wherein the groups $R^1$ to $R^5$ have the meanings given in the claims and specification, their use as inhibitors of mutant EGFR, pharmaceutical compositions which contain compounds of this kind and their use as medicaments/medical uses, especially as agents for treatment and/or prevention of oncological diseases.

BACKGROUND OF THE INVENTION

The epidermal growth factor receptor (EGFR) is a receptor tyrosine kinase that transduces mitogenic signals. Mutations in the EGFR gene are found in approximately 12% to 47% of non-small cell lung cancer (NSCLC) tumors with adenocarcinoma histology (Midha, 2015). The two most frequent EGFR alterations found in NSCLC tumors are short in-frame deletions in exon 19 (del19) of the EGFR gene and L858R, a single missense mutation in exon 21 (Konduri, 2016). These two mutations cause ligand-independent EGFR activation and are collectively referred to as EGFR M+. Del19 and L858R mutations in EGFR sensitize NSCLC tumors to the treatment with EGFR tyrosine kinase inhibitors (TKIs). Clinical experience shows an objective response rate of approximately 60-85% in EGFR M+ NSCLC patients treated in $1^{st}$ line with the $1^{st}$, $2^{nd}$ and $3^{rd}$ generation EGFR TKIs erlotinib, gefitinib, afatinib and osimertinib (Mitsudomi, 2010; Park, 2016; Soria, 2017; Zhou, 2011). These responses demonstrate that EGFR M+ NSCLC cells and tumors depend on oncogenic EGFR activity for survival and proliferation, establishing del19 or L858R mutated EGFR as a validated drug target and predictive biomarker for the treatment of NSCLC. The $1^{st}$ generation EGFR TKIs erlotinib and gefitinib as well as the $2^{nd}$ generation TKI afatinib are FDA-approved for the $1^{st}$ line treatment of EGFR M+ NSCLC patients.

While tumor responses are accompanied by marked tumor shrinkage in patients, the response is usually not durable and most patients relapse within 10 to 12 months of treatment with $1^{st}$ and $2^{nd}$ generation EGFR TKIs (Mitsudomi, 2010; Park, 2016; Soria, 2017; Zhou, 2011). The most prominent molecular mechanism underlying progression is the acquisition of a secondary mutation in EGFR, namely T790M (Blakely, 2012; Kobayashi, 2005), in 50% to 70% of patients progressing on $1^{st}$ and $2^{nd}$ generation EGFR inhibitors. This mutation attenuates the inhibitory activity of $1^{st}$ and $2^{nd}$ generation TKIs in cellular assays (see data in Table 13).

Mutant selective and covalent $3^{rd}$ generation EGFR TKIs, such as osimertinib, have been developed that effectively inhibit the primary EGFR mutations del19 and L858R with and without the secondary T790M resistance mutation (Cross, 2014; Wang, 2016). The recently demonstrated efficacy of the $3^{rd}$ generation EGFR TKI osimertinib in the $2^{nd}$ line treatment of EGFR M+ T790M-positive NSCLC demonstrates clinically that tumor cell survival and proliferation is dependent on the mutated EGFR allele (Jänne, 2015; Mok, 2016). Approximately 70% of EGFR M+ T790M-positive patients that were previously treated with earlier generation EGFR TKI respond to osimertinib treatment in $2^{nd}$ line. However, disease progression occurs after an average duration of 10 months (Mok, 2016). The mechanisms underlying acquired resistance to $3^{rd}$ generation EGFR TKIs have been studied in small cohorts of patients and are beginning to emerge (Ou, 2017). Recent data suggest that one major resistance mechanism is the acquisition of the tertiary EGFR mutation C797S in about 20-40% of $2^{nd}$ line patients relapsing on osimertinib TKI (Ortiz-Cuaran, 2016; Ou, 2017; Song, 2016; Thress, 2015; Yu, 2015). $3^{rd}$ generation TKIs, such as osimertinib, covalently attach to EGFR via the residue C797 (Cross, 2014; Wang, 2016). In cellular models the C797S mutation abolishes the activity of $3^{rd}$ generation TKIs tested (Thress, 2015) (see data in Table 13). In $2^{nd}$ line patients, the mutation C797S is preferentially found in conjunction with the EGFR del19 genotype and on the same allele as the T790M mutation (c/'s configuration) (82% of C797S+ patients) (Piotrowska, 2017). Crucially, the EGFR del19/L858R T790M C797S c/'s mutant kinase variant that emerges in $2^{nd}$ line patients progressing on osimertinib (Ortiz-Cuaran, 2016; Ou, 2017; Song, 2016; Thress, 2015; Yu, 2015) can no longer be inhibited by $1^{st}$, $2^{nd}$ or $3^{rd}$ generation EGFR TKIs (Thress, 2015) (see data in Table 13). Based on the fact that the C797S mutation is detected at progression on osimertinib (Ortiz-Cuaran, 2016; Ou, 2017; Song, 2016; Thress, 2015; Yu, 2015), it is likely that tumor cell survival and proliferation in EGFR del19/L858R T790M C797S patients is dependent on this mutant allele and can be inhibited by targeting this allele. Additional EGFR resistance mutations with a lower incidence than C797S were recently described in $2^{nd}$ line EGFR M+ NSCLC patients progressing on osimertinib: L718Q, L792F/H/Y and C797G/N (Bersanelli, 2016; Chen, 2017; Ou, 2017).

The $3^{rd}$ generation EGFR TKI osimertinib has recently also shown efficacy in previously untreated EGFR M+ NSCLC patients (Soria, 2017). Disease progression occurs after an average duration of 19 months. While the EGFR resistance mutation spectrum after $1^{st}$ line osimertinib treatment has not been extensively studied yet, first available data also suggest the emergence of the mutation C797S that abrogates osimertinib activity (Ramalingam, 2017).

The fact that no approved EGFR TKI can inhibit the EGFR del19/L858R T790M C797S variant, an allele occurring after progression of patients on $2^{nd}$ line osimertinib treatment, highlights the medical need for a next generation EGFR TKI, a "$4^{th}$ generation EGFR TKI". This $4^{th}$ generation EGFR TKI should potently inhibit EGFR del19 or L858R irrespective of the presence of the two common resistance mutations T790M and C797S, especially EGFR del19 T790M C797S. The utility of such a $4^{th}$ generation EGFR TKI would be enhanced by activity of the compound on additional resistance mutations, such as the potential osimertinib resistance mutations C797X (X=S, G, N) and L792F/H/Y. The broad activity of the molecule on the EGFR del19 or L858R variants also without T790M and/or C797S mutations would ensure that the new compound can effectively cope with the expected allelic complexity in patient tumors as a monotherapy agent. To facilitate efficacious dosing and reduce EGFR-mediated on-target toxicities, a 4th generation EGFR TKI should not inhibit wild-type EGFR. High selectivity across the human kinome would reduce off-target toxicity of the compound. Another desirable property of a 4th generation EGFR TKI is the ability to efficiently penetrate into the brain (blood-brain barrier penetration) in order to be able to treat brain metastasis and leptomeningeal disease. Lastly, a 4th generation EGFR TKI should display a reduced resistance liability compared to existing EGFR TKIs in order to increase the duration of response in patients.

The aforementioned properties of a 4th generation EGFR TKI would allow to treat patients progressing on 2nd line treatment with a 3rd generation TKI, such as osimertinib, (e.g. with the genotype EGFR del19/L858R T790M C797S), who have currently no targeted therapy treatment option. Furthermore, these properties also have the potential to allow a 4th generation EGFR TKI to provide a longer duration of response in earlier treatment line patients, such as patients progressing on 1st line osimertinib treatment with EGFR C797S mutations as well as 1st line patients. The activity of a 4th generation EGFR TKI on resistance mutations such as T790M, C797X (X=S, G, N) and L792X (X=F, H, Y) has the potential to delay the development of resistance through EGFR intra target mutations in NSCLC tumors. The characteristics outlined above define a 4th generation EGFR TKI as the first EGFR TKI able to effectively target patients with NSCLC tumors carrying the EGFR del19/L858R T790M C797X/L792X variants. Furthermore, a 4th generation EGFR TKI will be the first C797X active compound that also inhibits T790M-positive alleles, possesses EGFR wild-type sparing activity and effectively penetrates into the brain.

The aforementioned characteristics have not been achieved in previously described EGFR inhibitor compounds. Over the past years, selective targeting of mutated EGFR has gained increasing attention. Until today several efforts to identify and optimize inhibitors, which target either the catalytic site of EGFR mutants or an allosteric site of the EGFR protein, have been made with limited success in respect of the above mentioned characteristics.

Recently, a number of EGFR inhibitors which can overcome EGFR resistance mutations including the mutation T790M, as well as the C797S mutation and combinations of both have been published (Zhang, 2017; Park, 2017; Chen, 2017; Bryan 2016; Juchum, 2017; Günther, 2017; WO 2017/004383). Most of the published molecules are non-covalent variants of quinazoline based 2nd generation EGFR inhibitors. (Patel, 2017; Park, 2017; Chen, 2017). However, these published molecules are either weak inhibitors with low selectivity over EGFR wt (Patel, 2017; Chen, 2017) or were designed to specifically bind only to the del19/T790M/C797S mutant without activity to other EGFR variant combinations and mutations (Park, 2017). Other published compound classes show activity only against the T790M and T790M/C797S resistance mutation in the L858R activation background (Bryan 2016; Juchum, 2017; Günther, 2017). However, since these mutations and mutation combinations were only observed in a small fraction of the patient population and since allelic complexity in metastatic tumors is likely high, they are very unlikely to fulfill the necessary criteria in order to be developed towards effective EGFR inhibitors.

The following prior art documents disclose non-covalent compounds as mutant selective EGFR inhibitors with activity toward T790M bearing EGFR: WO 2014/210354; WO 2014/081718; Heald, 2015; Hanan, 2014; Lelais, 2016; Chan, 2016.

Although the compounds from the above mentioned documents are claimed to be active against the two most common EGFR activation/resistance mutation combinations del19/T790M and L858/T790M, most of them display only weak activity against the more prevalent del19/T790M mutation, they also display no affinity towards EGFR harboring the primary activation mutations del19 and L858R alone. Such a selective inhibition of the double mutated EGFR over the activity against the single activation mutations is highly unfavorable due to the heterogeneity of EGFR mutations in patients and would likely lead to a limited efficacy. Additionally, most of the compounds show only a small selectivity towards EGFR wt which is known to be the major factor for common side effects in EGFR targeted therapies (diarrhea, skin-rash) leading to a target specific toxicity. This specific cytotoxic component is undesirable, because it potentially leads to adverse events in treated patients.

The following prior art documents disclose aminobenzimidazole based compounds as EGFR selective inhibitors with activity toward both oncogenic driver mutations L858R and del19 as well as activity against the T790M resistance mutation and combination of them: WO 2013/184757; WO 2013/184766, WO 2015/143148, WO 2015/143161, WO 2016/185333; Lelais, 2016; Jia, 2016.

The following prior art documents disclose further aminobenzimidazole based compounds: WO 2003/030902, WO 2003/041708, WO 2004/014369, WO 2004/014905, WO 2005/079791, WO 2007/133983, WO 2012/018668, WO 2014/036016, WO 2016/176473, WO 2017/049068, WO 2017/049069.

Compounds (I) according to the invention share this basic aminobenzimidazole scaffold with compounds disclosed in these prior art documents. However, the previously published aminobenzimidazoles are designed as covalent EGFR inhibitors bearing a reactive (warhead) group in the molecule. The activity of these inhibitors is mostly driven by a covalent binding to the C797 residue of the EGFR protein and is therefore dependent on the reactive group. This leads to a high susceptibility toward the C797S resistance mutation (Engel, 2016). Corresponding compounds without the reactive (warhead) group derived from these prior art aminobenzimidazoles, however, show only weak remaining activity against EGFR mutants (see data in Table 13). This renders them ineffective as non-covalent EGFR inhibitors and limits their use as broad EGFR mutant inhibitors. Thus, against this background, the skilled person would not have considered the previously known aminobenzimidazole scaffold to be a promising starting point to identify EGFR inhibitors with the profile of a 4th generation EGFR inhibitor as hereinbefore defined.

None of the aforementioned published compounds shows the desired characteristics for an effective and clinically relevant EGFR resistance mutation targeting inhibitor.

In summary, compounds (I) according to the invention show a broad activity on EGFR del19 or EGFR L858R variants, with or without T790M and/or C797S mutations, which ensures that the compounds may effectively cope with the expected allelic complexity in patient tumors as a monotherapy agent. To facilitate efficacious dosing and reduce EGFR-mediated on-target toxicities, the compounds according to the invention have a reduced inhibitory potential regarding wild-type EGFR. Compounds (I) show a high selectivity across the human kinome, which may reduce off-target toxicity of the compounds. Another property of the compounds (I) according to the invention is the ability to potentially penetrate into the brain (blood-brain barrier penetration) in order to be used to treat brain metastasis and leptomeningeal disease. In addition to the inhibitory effect and potency, the compounds disclosed herein show good solubility and fine-tuned DMPK properties.

REFERENCES

Bersanelli, B. et al. (2016). L718Q Mutation as New Mechanism of Acquired Resistance to AZD9291 in EGFR-Mutated NSCLC. Journal of Thoracic Oncology 11, e121-e123.

Blakely, C. M. et al. (2012). Resiliency of lung cancers to EGFR inhibitor treatment unveiled, offering opportunities to divide and conquer EGFR inhibitor resistance. Cancer Discov. 2, 872-875.

Bryan, M. C. et al.; Pyridones as Highly Selective, Noncovalent Inhibitors of T790M Double Mutants of EGFR. *ACS Med. Chem. Lett.* 2016, 7, 100-104.

Bryan, M. C. et al.; Preparation of azaindazole compounds as inhibitors of T790M containing EGFR mutants. WO 2014/210354

Chan, B. K. et al. (2016). Discovery of a Noncovalent, Mutant-Selective Epidermal Growth Factor Receptor Inhibitor. *J. Med. Chem.* 2016, 59, 9080-9093.

Chen, K. et al. (2017). Novel Mutations on EGFR Leu792 Potentially Correlate to Acquired Resistance to Osimertinib in Advanced NSCLC. Journal of Thoracic Oncology 12, e65-e68.

Chen, L. et al.; Novel 4-arylaminoquinazoline derivatives with (E)-propen-1-yl moiety as potent EGFR inhibitors with enhanced antiproliferative activities against tumor cells. *Eu. J. Med. Chem.* 2017, 138, 689-697.

Cross, D. A. E. et al. (2014). AZD9291, an Irreversible EGFR TKI, Overcomes T790M-Mediated Resistance to EGFR Inhibitors in Lung Cancer. Cancer Discovery. 2014 September; 4(9):1046-61. doi: 10.1158/2159-8290.CD-14-0337.

Engel, J. et al.; Insight into the Inhibition of Drug-Resistant Mutants of the Receptor Tyrosine Kinase EGFR. *Angew. Chem. Int. Ed.* 2016, 55, 10909-10912.

Günther, M. et al.; Trisubstituted Pyridinylimidazoles as Potent Inhibitors of the Clinically Resistant L858R/T790M/C797S EGFR Mutant: Targeting of Both Hydrophobic Regions and the Phosphate Binding Site. *J. Med. Chem.* 2017, 60, 5613-5637.

Hanan, E. J. et al.; Discovery of Selective and Noncovalent Diaminopyrimidine-Based Inhibitors of Epidermal Growth Factor Receptor Containing the T790M Resistance Mutation. *J. Med. Chem.* 2014, 57, 10176-10191.

Heald, R. et al. (2015). Noncovalent Mutant Selective Epidermal Growth Factor Receptor Inhibitors: A Lead Optimization Case Study. J. Med. Chem. 58, 8877-8895.

Jänne, P. A et al. (2015). AZD9291 in EGFR Inhibitor-Resistant Non-Small-Cell Lung Cancer. N. Engl. J. Med. 372, 1689-1699.

Jia, Y. et al.; EGF816 Exerts Anticancer Effects in Non-Small Cell Lung Cancer by Irreversibly and Selectively Targeting Primary and Acquired Activating Mutations in the EGF Receptor. *Cancer Research* 2016, 76, 1591-1602.

Juchum, M. et al.; Trisubstituted Imidazoles with a Rigidized Hinge Binding Motif Act As Single Digit nM Inhibitors of Clinically Relevant EGFR L858R/T790M and L858R/T790M/C797S Mutants: An Example of Target Hopping. *J. Med. Chem.* 2017, 60, 4636-4656.

Kobayashi, S. et al. (2005). EGFR mutation and resistance of non-small-cell lung cancer to gefitinib. N. Engl. J. Med. 352, 786-792.

Konduri, K. et al. (2016). EGFR Fusions as Novel Therapeutic Targets in Lung Cancer. Cancer Discovery. 2016 June; 6(6):601-11. doi: 10.1158/2159-8290.CD-16-0075.

Le, N.; Methods for treating epidermal growth factor receptor (EGFR) mutant cancers. WO 2016/185333.

Lelais, G. et al.; Discovery of (R,E)-N-(7-Chloro-1-(1-[4-(dimethylamino)but-2-enoyl]azepan-3-yl)-1H-benzo[d] imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers. *J. Med. Chem.* 2016, 59, 6671-6689.

Lelais, G. et al.; Preparation of fused imidazole compounds and compositions for modulating EGFR activity. WO 2013/184757.

Midha, A. et al. (2015). EGFR mutation incidence in non-small-cell lung cancer of adenocarcinoma histology: a systematic review and global map by ethnicity (mutMapII). Am J Cancer Res. 2015; 5(9): 2892-2911.

Mitsudomi, T. et al. (2010). Gefitinib versus cisplatin plus docetaxel in patients with non-small-cell lung cancer harbouring mutations of the epidermal growth factor receptor (WJTOG3405): an open label, randomised phase 3 trial. Lancet Oncol. 11, 121-128.

Mok, T. S. et al. (2016). Osimertinib or Platinum-Pemetrexed in EGFR T790M-Positive Lung Cancer. N. Engl. J. Med. 367, 629-640.

Ortiz-Cuaran, S. et al. (2016). Heterogeneous Mechanisms of Primary and Acquired Resistance to Third-Generation EGFR Inhibitors. Clin. Cancer Res. 22, 4837-4847.

Ou, Q. et al. (2017). Investigating novel resistance mechanisms to third generation EGFR TKI osimertinib in non-small cell lung cancer patients using next generation sequencing. 2017 ASCO Annual Meeting; Abstract No: 2572; J Clin Oncol 35, 2017 (suppl; abstr 2572)

Park, H. et al.; Discovery of EGF Receptor Inhibitors That Are Selective for the d746-750/T790M/C797S Mutant through Structure-Based de Novo Design. *Angew. Chem. Int. Ed.* 2017, 56, 7634-7638.

Park, K. et al. (2016). Afatinib versus gefitinib as first-line treatment of patients with EGFR mutation-positive non-small-cell lung cancer (LUX-Lung 7): a phase 2B, open-label, randomised controlled trial. Lancet Oncol. 17, 577-589.

Patel, H. M. et al.; Design and synthesis of quinazolinones as EGFR inhibitors to overcome EGFR resistance obstacle. *Biorg. Med. Chem.* 2017, 25, 2713-2723.

Piotrowska, Z. et al. (2017). Characterizing the genomic landscape of EGFR C797S in lung cancer using ctDNA next-generation sequencing. Presented at IASLC 18th World Conference on Lung Cancer.

Ramalingam, S. S. et al. (2017). Osimertinib As First-Line Treatment of EGFR Mutation-Positive Advanced Non-Small-Cell Lung Cancer. Journal of Clinical Oncology, 2017 Aug. 25:JCO2017747576. doi: 10.1200/JC0.2017.74.7576. [Epub ahead of print]

Song, H. N. et al. (2016). Acquired C797S Mutation upon Treatment with a T790M-Specific Third-Generation EGFR Inhibitor (HM61713) in Non-Small Cell Lung Cancer. J. Thorac. Oncol. 11:e45-47.

Soria, J. C. et al. (2017). Osimertinib in Untreated EGFR-Mutated Advanced Non-Small-Cell Lung Cancer. N. Engl. J. Med. 2017 Nov. 18. doi: 10.1056/NEJMoa1713137.

Thress, K. S. et al. (2015). Acquired EGFR C797S mutation mediates resistance to AZD9291 in non-small cell lung cancer harboring EGFR T790M. Nat. Med. 21, 560-562.

Wang, S. et al. (2016). Third-generation inhibitors targeting EGFR T790M mutation in advanced non-small cell lung cancer. J Hematol Oncol. 2016 Apr. 12; 9:34.

Yu, H. A. et al. (2015). Acquired Resistance of EGFR-Mutant Lung Cancer to a T790M-Specific EGFR Inhibitor: Emergence of a Third Mutation (C797S) in the EGFR Tyrosine Kinase Domain. JAMA Oncol. 1, 982-984.

Zhang, Y. et al.; Quinazoline-1-deoxynojirimycin hybrids as high active dual inhibitors of EGFR and α-glucosidase. Bioorg. Med. Chem. Lett. 2017, 27, 4309-4313.

Zhou, C. et al. (2011). Erlotinib versus chemotherapy as first-line treatment for patients with advanced EGFR mutation-positive non-small-cell lung cancer (OPTIMAL, CTONG-0802): a multicentre, open-label, randomised, phase 3 study. Lancet Oncol. 12, 735-742.

DETAILED DESCRIPTION OF THE INVENTION

Compounds

It has now been found that, surprisingly, compounds of formula (I) wherein the groups $R^1$ to $R^5$ have the meanings given hereinafter act as inhibitors of mutant EGFR which is involved in controlling cell proliferation. Thus, the compounds according to the invention may be used for example for the treatment of diseases characterised by excessive or abnormal cell proliferation.

The present invention therefore relates to a compound of formula (I)

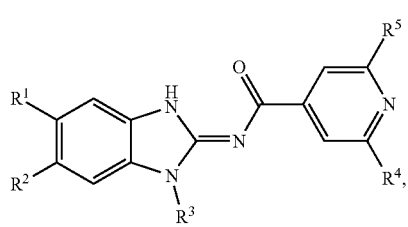

wherein
[A0]
$R^1$ is —$(CH_2)_n$-A;
n is 0 or 1;
A is 3-11 membered heterocyclyl optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)$_2$ and the bivalent substituent =O;
or
$R^1$ is —$NR^AR^A$;
each $R^A$ is independently selected from the group consisting of hydrogen, $C_{1-4}$alkyl, $C_{1-4}$alkoxy-$C_{1-4}$alkyl, $C_{1-4}$alkyl substituted with 4-6 membered heterocyclyl, ($C_{1-4}$alkyl)$_2$amino-$C_{1-4}$alkyl and ($C_{1-4}$alkyl)$_2$amino-$C_{1-4}$alkoxy-$C_{1-4}$alkyl;
or
$R^1$ is $C_{1-6}$alkyl optionally substituted with a substituent selected from the group consisting of ($C_{1-4}$alkyl)$_2$amino, —C(O)NH—$C_{1-4}$alkyl, —C(O)-heterocyclyl with a 5-6 membered heterocyclyl, —OH, —CN and —C(O)O—$C_{1-4}$alkyl;
or
$R^1$ is selected from the group consisting of halogen and hydrogen;
[B0]
$R^2$ is —$(CH_2)_m$—B;
m is 0 or 1;
B is 3-11 membered heterocyclyl optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)$_2$ and the bivalent substituent =O;
or
$R^2$ is —$NR^BR^B$;
each $R^B$ is independently selected from the group consisting of hydrogen, $C_{1-4}$alkyl, $C_{1-4}$alkoxy-$C_{1-4}$alkyl, $C_{1-4}$alkyl substituted with 4-6 membered heterocyclyl, ($C_{1-4}$alkyl)$_2$amino-$C_{1-4}$alkyl and ($C_{1-4}$alkyl)$_2$amino-$C_{1-4}$alkoxy-$C_{1-4}$alkyl;
or
$R^2$ is $C_{1-6}$alkyl optionally substituted with a substituent selected from the group consisting of ($C_{1-4}$alkyl)$_2$amino, —C(O)NH—$C_{1-4}$alkyl, —C(O)-heterocyclyl with a 5-6 membered heterocyclyl, —OH, —CN and —C(O)O—$C_{1-4}$alkyl;
or
$R^2$ is selected from the group consisting of halogen and hydrogen;
[C0]
$R^3$ is selected from the group consisting of $C_{3-6}$alkyl, $C_{3-6}$cycloalkyl and 4-7 membered heterocyclyl, wherein the $C_{3-6}$alkyl, $C_{3-6}$cycloalkyl and 4-7 membered heterocyclyl are all optionally substituted by one or more —OH;
[D0]
$R^4$ is selected from the group consisting of phenyl, 5-6 membered heteroaryl and 9-membered heteroaryl, wherein the phenyl, 5-6 membered heteroaryl and 9-membered heteroaryl are all optionally substituted by one or more, identical or different substituents selected from the group consisting of $C_{1-6}$alkyl, $C_{1-6}$haloalkyl, —O—$C_{1-6}$alkyl, —O—$C_{1-6}$haloalkyl, halogen, hydroxy, —NH—$C_{1-6}$alkyl, —N($C_{1-6}$alkyl)$_2$, —C(O)NH—$C_{1-6}$alkyl, —C(O)N($C_{1-6}$alkyl)$_2$ and ($C_{1-6}$alkyl)$_2$N—$C_{1-6}$alkyl;
[E0]
$R^5$ is selected from the group consisting of hydrogen, $C_{1-4}$alkyl, $C_{1-4}$haloalkyl, $C_{2-4}$alkenyl, $C_{2-4}$alkinyl, halogen, —CN, —$NH_2$, —NH($C_{1-4}$alkyl) and —N($C_{1-4}$alkyl)$_2$;
or a salt thereof.

In one aspect[A1] the invention relates to a compound of formula (I) or a salt thereof, wherein
$R^1$ is —$(CH_2)_n$-A;
n is 0 or 1;
A is 4-6 membered heterocyclyl optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)$_2$ and the bivalent substituent =O.

In another aspect [A2] the invention relates to a compound of formula (I) or a salt thereof, wherein
$R^1$ is —$(CH_2)_n$-A;
n is 0 or 1;

A is selected from the group consisting of piperidinyl, piperazinyl, oxanyl, morpholinyl, pyrrolidinyl, oxolanyl and azetidinyl, wherein the piperidinyl, piperazinyl, oxanyl, morpholinyl, pyrrolidinyl, oxolanyl and azetidinyl are all optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)$_2$ and the bivalent substituent =O.

In another aspect [A3] the invention relates to a compound of formula (I) or a salt thereof, wherein $R^1$ is —(CH$_2$)$_n$-A;

n is 0 or 1;

A is selected from the group consisting of piperidin-1-yl, piperidin-3-yl, piperidin-4-yl, piperazin-1-yl, oxan-2-yl, oxan-3-yl, oxan-4-yl, morpholin-4-yl, pyrrolidin-1-yl, pyrrolidin-3-yl, oxolan-3-yl and azetidin-1-yl, wherein the piperidin-1-yl, piperidin-3-yl, piperidin-4-yl, piperazin-1-yl, oxan-2-yl, oxan-3-yl, oxan-4-yl, morpholin-4-yl, pyrrolidin-1-yl, pyrrolidin-3-yl, oxolan-3-yl and azetidin-1-yl are all optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)$_2$ and the bivalent substituent =O.

In further aspects [A4], [A5], [A6] and [A7], the invention relates to a compound of formula (I) or a salt thereof with structural aspects [A0], [A1], [A2] or [A3], wherein n is 0.

In further aspects [A8], [A9], [A10] and [A11], the invention relates to a compound of formula (I) or a salt thereof with structural aspects [A0], [A1], [A2] or [A3], wherein n is 1.

In another aspect [A12] the invention relates to a compound of formula (I) or a salt thereof, wherein $R^1$ is selected from the group consisting of

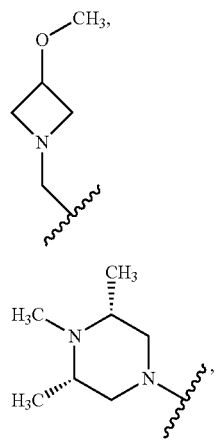

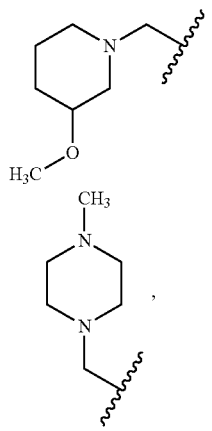

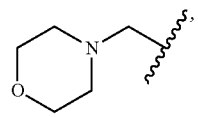

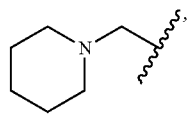

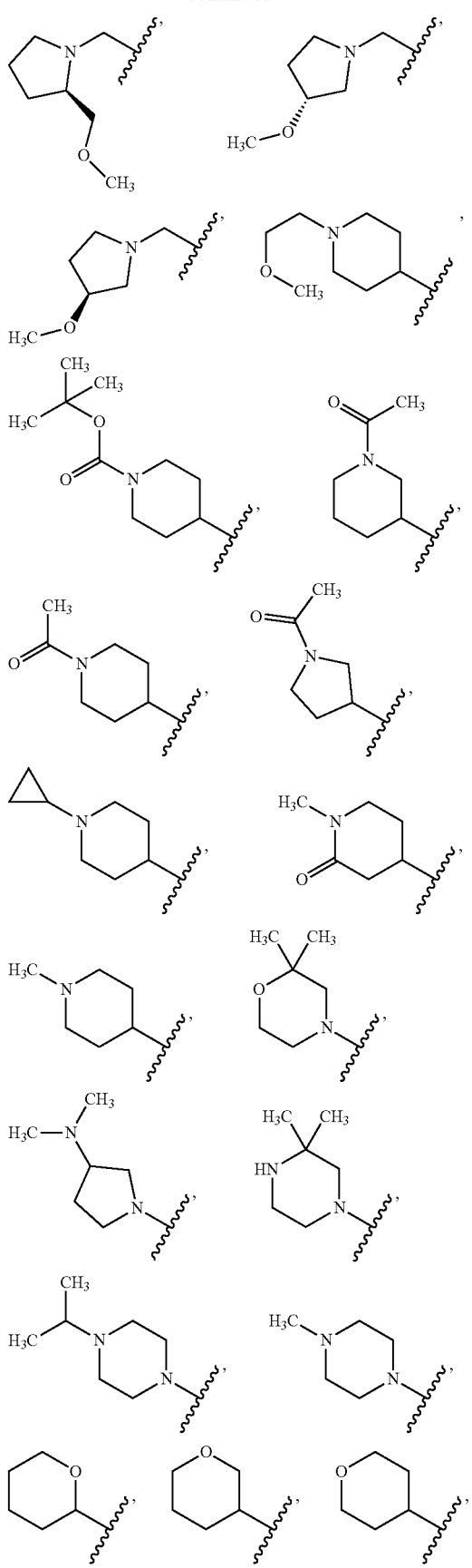

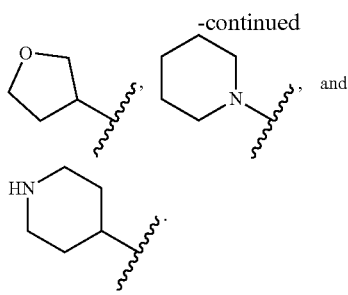

In another aspect [A13] the invention relates to a compound of formula (I) or a salt thereof, wherein
R¹ is selected from the group consisting of

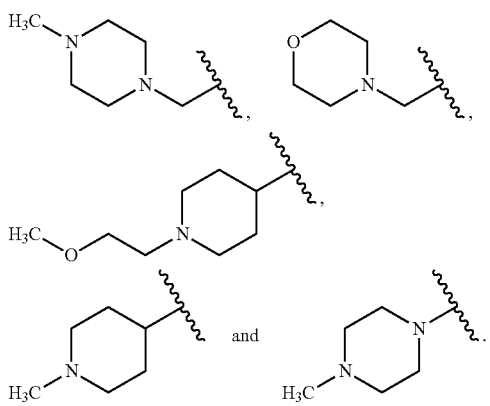

In another aspect [A14] the invention relates to a compound of formula (I) or a salt thereof, wherein
R¹ is $C_{1-4}$alkyl.

In another aspect [A15] the invention relates to a compound of formula (I) or a salt thereof, wherein
R¹ is hydrogen.

In another aspect [A16] the invention relates to a compound of formula (I) or a salt thereof, wherein
R¹ is halogen.

In another aspect [B1] the invention relates to a compound of formula (I) or a salt thereof, wherein
R² is —(CH₂)ₘ—B;
m is 0 or 1;
B is 4-6 membered heterocyclyl optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)₂ and the bivalent substituent =O.

In another aspect [B2] the invention relates to a compound of formula (I) or a salt thereof, wherein
R² is —(CH₂)ₘ—B;
m is 0 or 1;
B is selected from the group consisting of piperidinyl, piperazinyl, oxanyl, morpholinyl, pyrrolidinyl, oxolanyl and azetidinyl, wherein the piperidinyl, piperazinyl, oxanyl, morpholinyl, pyrrolidinyl, oxolanyl and azetidinyl are all optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)₂ and the bivalent substituent =O.

In another aspect [B3] the invention relates to a compound of formula (I) or a salt thereof, wherein
R² is —(CH₂)ₘ—B;
m is 0 or 1;
B is selected from the group consisting of piperidin-1-yl, piperidin-3-yl, piperidin-4-yl, piperazin-1-yl, oxan-2-yl, oxan-3-yl, oxan-4-yl, morpholin-4-yl, pyrrolidin-1-yl, pyrrolidin-3-yl, oxolan-3-yl and azetidin-1-yl, wherein the piperidin-1-yl, piperidin-3-yl, piperidin-4-yl, piperazin-1-yl, oxan-2-yl, oxan-3-yl, oxan-4-yl, morpholin-4-yl, pyrrolidin-1-yl, pyrrolidin-3-yl, oxolan-3-yl and azetidin-1-yl are all optionally substituted by one or more, identical or different substituents selected from the group consisting of $C_{1-4}$alkyl, $C_{1-4}$alkoxy, $C_{1-4}$alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$alkyl)₂ and the bivalent substituent =O.

In further aspects [B4], [B5], [B6] and [B7], the invention relates to a compound of formula (I) or a salt thereof with structural aspects [B0], [B1], [B2] or [B3], wherein
m is 0.

In further aspects [B8], [B9], [B10] and [B11], the invention relates to a compound of formula (I) or a salt thereof with structural aspects [B0], [B1], [B2] or [B3], wherein
m is 1.

In another aspect [B12] the invention relates to a compound of formula (I) or a salt thereof, wherein
R² is selected from the group consisting of

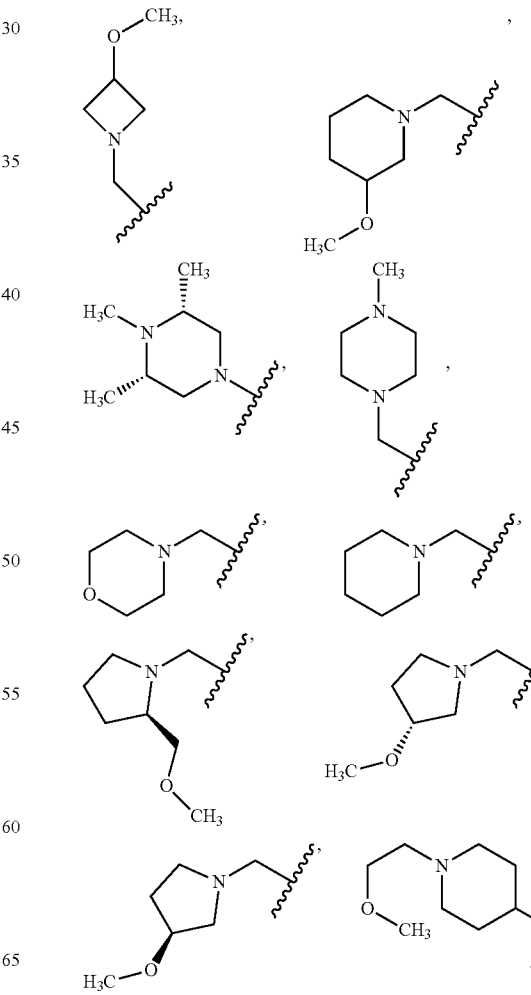

-continued

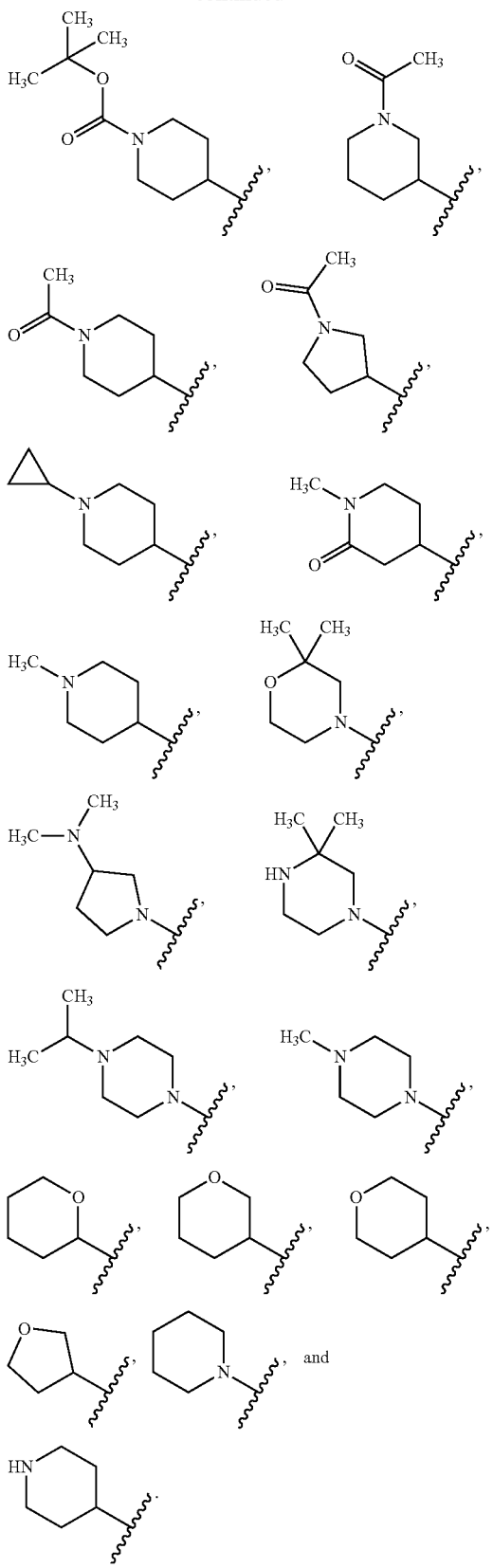

In another aspect [B13] the invention relates to a compound of formula (I) or a salt thereof, wherein $R^2$ is selected from the group consisting of

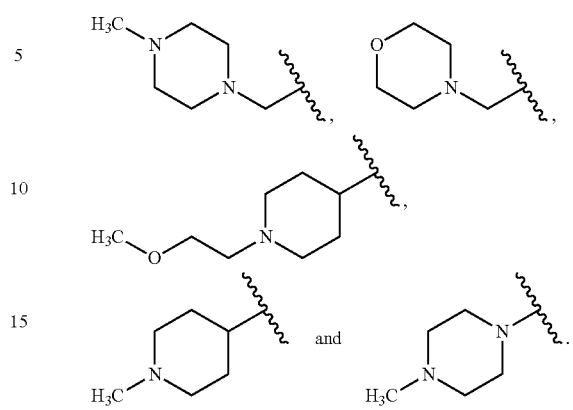

In another aspect [B14] the invention relates to a compound of formula (I) or a salt thereof, wherein
$R^2$ is $C_{1-4}$alkyl.

In another aspect [B15] the invention relates to a compound of formula (I) or a salt thereof, wherein
$R^2$ is hydrogen.

In another aspect [B16] the invention relates to a compound of formula (I) or a salt thereof, wherein
$R^2$ is halogen.

In another aspect [C1] the invention relates to a compound of formula (I) or a salt thereof, wherein
$R^3$ is $C_{3-6}$cycloalkyl.

In another aspect [C2] the invention relates to a compound of formula (I) or a salt thereof, wherein
$R^3$ is cyclohexyl.

In another aspect [C3] the invention relates to a compound of formula (I) or a salt thereof, wherein
$R^3$ is $C_{3-6}$cycloalkyl substituted by —OH;

In another aspect [C4] the invention relates to a compound of formula (I) or a salt thereof, wherein
$R^3$ is

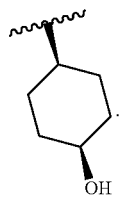 [SMILES: *[C@H]1CC[C@@H](O)CC1]

In another aspect [C5] the invention relates to a compound of formula (I) or a salt thereof, wherein
$R^3$ is $C_{3-6}$alkyl substituted by —OH.

In another aspect [C6] the invention relates to a compound of formula (I) or a salt thereof, wherein
$R^3$ is

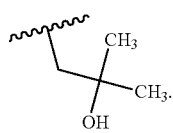

In another aspect [C7] the invention relates to a compound of formula (I) or a salt thereof, R³ is selected from the group consisting of

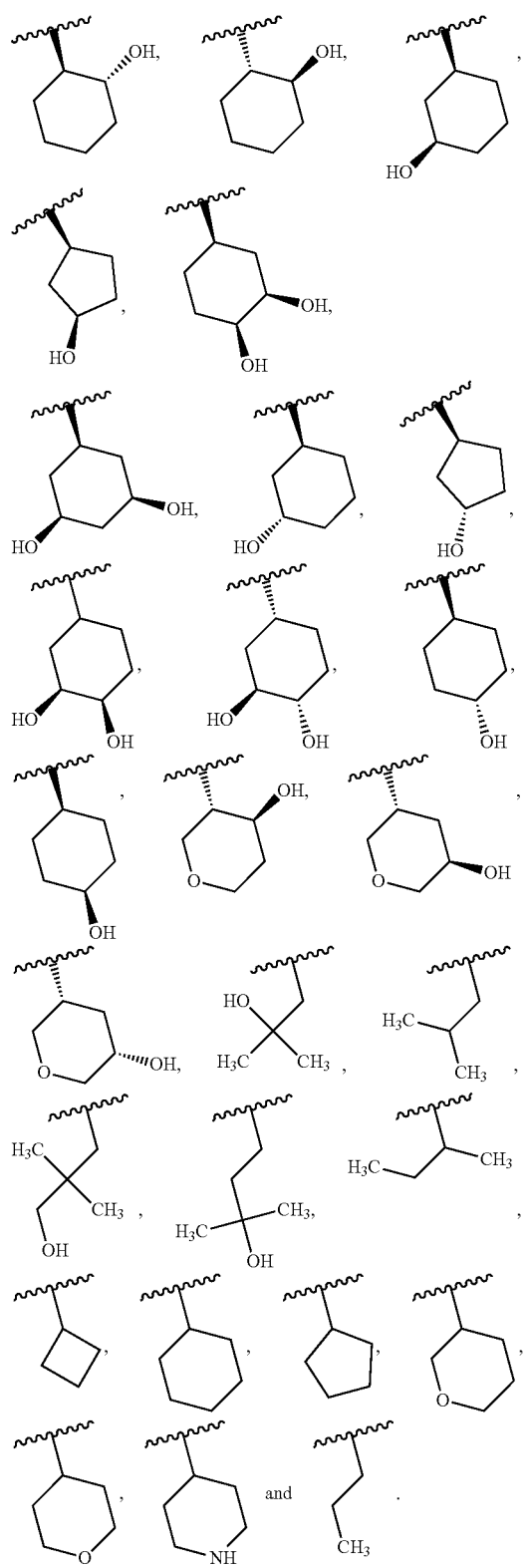

and

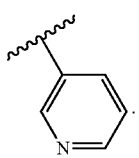

.

In another aspect [D1] the invention relates to a compound of formula (I) or a salt thereof, wherein
R⁴ is selected from the group consisting of phenyl, pyrazolyl and pyridyl, wherein the phenyl, pyrazolyl and pyridyl are all optionally substituted by one or more, identical or different substituents selected from the group consisting of $C_{1-6}$alkyl, $C_{1-6}$haloalkyl, —O—$C_{1-6}$alkyl, —O—$C_{1-6}$haloalkyl, halogen, hydroxy, —NH—$C_{1-6}$alkyl, —N($C_{1-6}$alkyl)₂, —C(O)NH—$C_{1-6}$alkyl, —C(O)N($C_{1-6}$alkyl)₂ and ($C_{1-6}$alkyl)₂N—$C_{1-6}$alkyl.

In another aspect [D2] the invention relates to a compound of formula (I) or a salt thereof, wherein
R⁴ is selected from the group consisting of phenyl, 1H-pyrazol-4-yl and pyridin-3-yl, wherein the phenyl, 1H-pyrazol-4-yl and pyridin-3-yl are all optionally substituted by one or more, identical or different substituents selected from the group consisting of $C_{1-6}$alkyl, $C_{1-6}$haloalkyl, —O—$C_{1-6}$alkyl, —O—$C_{1-6}$haloalkyl, halogen, hydroxy, —NH—$C_{1-6}$alkyl, —N($C_{1-6}$alkyl)₂, —C(O)NH—$C_{1-6}$alkyl, —C(O)N($C_{1-6}$alkyl)₂ and ($C_{1-6}$alkyl)₂N—$C_{1-6}$alkyl.

In another aspect [D3] the invention relates to a compound of formula (I) or a salt thereof, wherein
R⁴ is 1H-pyrazol-4-yl substituted by one or two $C_{1-6}$alkyl.

In another aspect [D4] the invention relates to a compound of formula (I) or a salt thereof, wherein
R⁴ is

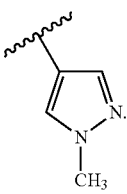

In another aspect [D5] the invention relates to a compound of formula (I) or a salt thereof, wherein
R⁴ is selected from the group consisting phenyl and pyridin-3-yl, both substituted by —O—$C_{1-6}$alkyl.

In another aspect [D6] the invention relates to a compound of formula (I) or a salt thereof, wherein
R⁴ is selected from the group consisting of

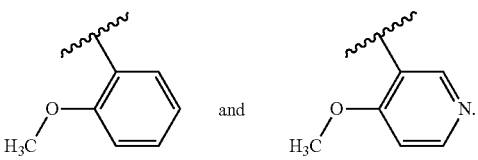

In another aspect [D7] the invention relates to a compound of formula (I) or a salt thereof, wherein
R⁴ is selected from the group consisting of 5-6 heteroaryl and 9-membered heteroaryl.

In another aspect [D8] the invention relates to a compound of formula (I) or a salt thereof, wherein
R⁴ is pyridyl.

In another aspect [D9] the invention relates to a compound of formula (I) or a salt thereof, wherein
R⁴ is In another aspect [E1] the invention relates to a compound of formula (I) or a salt thereof, wherein
$R^5$ is selected from the group consisting of hydrogen, $C_{1-4}$alkyl, $C_{1-4}$haloalkyl, $C_{2-4}$alkinyl, halogen, —CN, —$NH_2$ and —$NH(C_{1-4}$alkyl).

In another aspect [E2] the invention relates to a compound of formula (I) or a salt thereof, wherein
$R^5$ is hydrogen.

In another aspect [E3] the invention relates to a compound of formula (I) or a salt thereof, wherein
$R^5$ is —CN.

In another aspect [E4] the invention relates to a compound of formula (I) or a salt thereof, wherein
$R^5$ is $C_{1-4}$alkyl.

In another aspect [E5] the invention relates to a compound of formula (I) or a salt thereof, wherein
$R^5$ is methyl.

In another aspect [E6] the invention relates to a compound of formula (I) or a salt thereof, wherein
$R^5$ is halogen.

All the above-mentioned structural aspects [A1] to [A16], [B1] to [B16], [C1] to [C7], [D1] to [D9] and [E1] to [E6] are preferred embodiments of the corresponding aspects [A0], [B0], [C0], [D0] and [E0], respectively. The structural aspects [A0] to [A16], [B0] to [B16], [C0] to [C7], [D0] to [D9] and [E0] to [E6] relating to different molecular parts of the compounds (I) according to the invention may be combined with one another as desired in combinations [A][B][C][D][E] to obtain preferred compounds (I). Each combination [A][B][C][D][E] represents and defines individual embodiments or generic subsets of compounds (I) according to the invention.

Preferred embodiments of the invention with structure (I) are example compounds I-1 to I-238 and any subset thereof.

All synthetic intermediates generically defined as well es specifically disclosed herein and their salts are also part of the invention.

All individual synthetic reaction steps as well as reaction sequences comprising these individual synthetic reaction steps, both generically defined or specifically disclosed herein, are also part of the invention.

The present invention further relates to hydrates, solvates, polymorphs, metabolites, derivatives, isomers and prodrugs of a compound of formula (I) (including all individual embodiments and generic subsets disclosed herein).

The present invention further relates to tautomers of a compound of formula (I) (including all individual embodiments and generic subsets disclosed herein).

Specifically, a compound of formula (I) may exist in any of the following tautomeric forms A, B and C, which shall all be part of the invention and shall all be covered by formula (I):

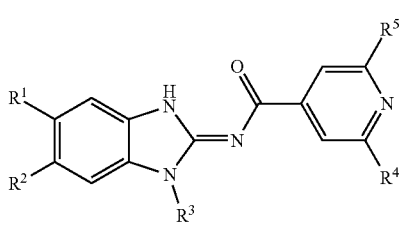

A

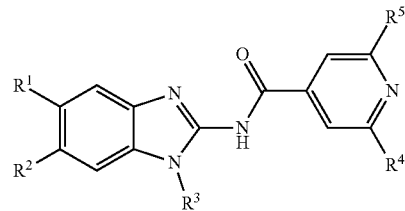

B

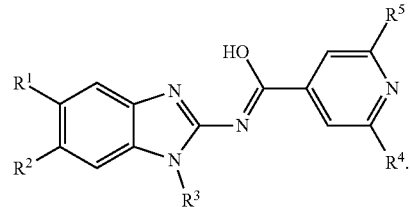

C

The present invention further relates to a hydrate of a compound of formula (I) (including all individual embodiments and generic subsets disclosed herein).

The present invention further relates to a solvate of a compound of formula (I) (including all individual embodiments and generic subsets disclosed herein).

Compounds of formula (I) (including all individual embodiments and generic subsets disclosed herein) which e.g. bear ester groups are potential prodrugs the ester being cleaved under physiological conditions and are also part of the invention.

The present invention further relates to a pharmaceutically acceptable salt of a compound of formula (I) (including all individual embodiments and generic subsets disclosed herein).

The present invention further relates to a pharmaceutically acceptable salt of a compound of formula (I) (including all individual embodiments and generic subsets disclosed herein) with anorganic or organic acids or bases.

Medical Uses-Methods of Treatment

The present invention is directed to compounds of formula (I) (including all individual embodiments and generic subsets disclosed herein), which are useful in the treatment and/or prevention of a disease and/or condition associated with or modulated by mutant EGFR, especially wherein the inhibition of the mutant EGFR is of therapeutic benefit, including but not limited to the treatment and/or prevention of cancer.

In one aspect the invention relates to a compound of formula (I) (including all individual embodiments and generic subsets disclosed herein)- or a pharmaceutically acceptable salt thereof-for use as a medicament.

In another aspect the invention relates to a compound of formula (I) (including all individual embodiments and generic subsets disclosed herein)- or a pharmaceutically acceptable salt thereof-for use in a method of treatment of the human or animal body.

In another aspect the invention relates to a compound of formula (I) (including all individual embodiments and generic subsets disclosed herein)- or a pharmaceutically acceptable salt thereof-for use in the treatment and/or prevention of a disease and/or condition wherein the inhibition of mutant EGFR is of therapeutic benefit, including but not limited to the treatment and/or prevention of cancer.

In another aspect the invention relates to a compound of formula (I) (including all individual embodiments and generic subsets disclosed herein)- or a pharmaceutically acceptable salt thereof-for use in the treatment and/or prevention of cancer.

In another aspect the invention relates to a compound of formula (I) (including all individual embodiments and generic subsets disclosed herein)- or a pharmaceutically acceptable salt thereof-for use in a method of treatment and/or prevention of cancer in the human or animal body.

In another aspect the invention relates to a compound of formula (I) (including all individual embodiments and generic subsets disclosed herein)- or a pharmaceutically acceptable salt thereof-for use in the treatment and/or prevention of cancer.

In another aspect the invention relates to a compound of formula (I) (including all individual embodiments and generic subsets disclosed herein)- or a pharmaceutically acceptable salt thereof-for use in a method of treatment and/or prevention of cancer in the human or animal body.

In another aspect the invention relates to a compound of formula (I) (including all individual embodiments and generic subsets disclosed herein)- or a pharmaceutically acceptable salt thereof-for use as herein defined, wherein said compound is administered before, after or together with at least one other pharmacologically active substance.

In another aspect the invention relates to a compound of formula (I) (including all individual embodiments and generic subsets disclosed herein)- or a pharmaceutically acceptable salt thereof-for use as herein defined, wherein said compound is administered in combination with at least one other pharmacologically active substance.

In another aspect the invention relates to a compound of formula (I) (including all individual embodiments and generic subsets disclosed herein)- or a pharmaceutically acceptable salt thereof-for use in the treatment or in a method of treatment as herein defined.

In another aspect the invention relates to the use of a compound of formula (I) (including all individual embodiments and generic subsets disclosed herein)- or a pharmaceutically acceptable salt thereof-for preparing a pharmaceutical composition for the treatment and/or prevention of cancer.

In another aspect the invention relates to the use of a compound of formula (I) (including all individual embodiments and generic subsets disclosed herein)- or a pharmaceutically acceptable salt thereof-as herein defined wherein said compound is administered before, after or together with at least one other pharmacologically active substance.

In another aspect the invention relates to the use of a compound of formula (I) (including all individual embodiments and generic subsets disclosed herein)- or a pharmaceutically acceptable salt thereof-as herein defined for the treatment.

In another aspect the invention relates to a method for the treatment and/or prevention of a disease and/or condition wherein the inhibition of mutant EGFR is of therapeutic benefit comprising administering a therapeutically effective amount of a compound of formula (I) (including all individual embodiments and generic subsets disclosed herein)- or a pharmaceutically acceptable salt thereof-to a human being.

In another aspect the invention relates to a method for the treatment and/or prevention of cancer comprising administering a therapeutically effective amount of a compound of formula (I) (including all individual embodiments and generic subsets disclosed herein)-or a pharmaceutically acceptable salt thereof-to a human being.

In another aspect the invention relates to a method as herein defined wherein the compound of formula (I) (including all individual embodiments and generic subsets disclosed herein)- or a pharmaceutically acceptable salt thereof-is administered before, after or together with at least one other pharmacologically active substance.

In another aspect the invention relates to a method as herein defined wherein the compound of formula (I) (including all individual embodiments and generic subsets disclosed herein)- or a pharmaceutically acceptable salt thereof-is administered in combination with a therapeutically effective amount of at least one other pharmacologically active substance.

In another aspect the invention relates to a method for the treatment as herein defined.

In another aspect the invention relates to a kit comprising
a first pharmaceutical composition or dosage form comprising a compound of formula (I) (including all individual embodiments and generic subsets disclosed herein) and, optionally, one or more pharmaceutically acceptable carriers, excipients and/or vehicles, and
at least a second pharmaceutical composition or dosage form comprising another pharmacologically active substance and, optionally, one or more pharmaceutically acceptable carriers, excipients and/or vehicles.

In another aspect the invention relates to a pharmaceutical composition comprising at least one (preferably one) compound of formula (I) (including all individual embodiments and generic subsets disclosed herein)- or a pharmaceutically acceptable salt thereof- and one or more pharmaceutically acceptable excipient(s).

In another aspect the invention relates to a pharmaceutical preparation comprising a compound of formula (I) (including all individual embodiments and generic subsets disclosed herein)- or a pharmaceutically acceptable salt thereof- and at least one (preferably one) other pharmacologically active substance.

In one aspect the disease/condition/cancer to be treated/prevented with the compound of formula (I) (including all individual embodiments and generic subsets disclosed herein), or in the medical uses, uses, methods of treatment and/or prevention as herein defined is selected from the group consisting of lung cancer, brain cancers, colorectal cancer, bladder cancer, urothelial cancer, breast cancer, prostate cancer, ovarian cancer, head and neck cancer, pancreatic cancer, gastric cancer and mesothelioma, including metastasis (in particular brain metastasis) of all cancers listed.

In another aspect the disease/condition/cancer to be treated/prevented with the compound of formula (I) (including all individual embodiments and generic subsets disclosed herein), or in the medical uses, uses, methods of treatment and/or prevention as herein defined is lung cancer. Preferably, the lung cancer to be treated is non-small cell lung cancer (NSCLC) including, e.g., locally advanced or metastatic NSCLC, NSCLC adenocarcinoma, NSCLC with squamous histology and NSCLC with non-squamous histology. Most preferably, the lung cancer to be treated is NSCLC adenocarcinoma.

In another aspect the disease/condition/cancer to be treated/prevented with the compound of formula (I) (including all individual embodiments and generic subsets disclosed herein), or in the medical uses, uses, methods of treatment and/or prevention as herein defined is a disease/condition/cancer, preferably cancer (including all embodiments as disclosed herein), with an EGFR genotype selected from genotypes 1 to 16 according to table A (del19=Exon 19 deletion, specifically, e.g., delE746_A750 (most common), delE746_S752insV, delL747_A750insP, delL747_P753insS and delS752_I759):

TABLE A

| # | EGFR genotype |
|---|---|
| 1 | EGFR del19 |
| 2 | EGFR del19 T790M |
| 3 | EGFR del19 C797S |
| 4 | EGFR del19 C797X (preferably C797G or C797N) |
| 5 | EGFR del19 T790M C797S |
| 6 | EGFR del19 T790M C797X (preferably C797G or C797N) |
| 7 | EGFR del19 L792X (preferably L792F, L792H or L792Y) |
| 8 | EGFR del19 T790M L792X (preferably L792F, L792H or L792Y) |
| 9 | EGFR L858R |
| 10 | EGFR L858R T790M |
| 11 | EGFR L858R C797S |
| 12 | EGFR L858R C797X (preferably C797G or C797N) |
| 13 | EGFR L858R T790M C797S |
| 14 | EGFR L858R T790M C797X (preferably C797G or C797N) |
| 15 | EGFR L858R L792X (preferably L792F, L792H or L792Y) |
| 16 | EGFR L858R T790M L792X (preferably L792F, L792H or L792Y) |

Thus, in one aspect the cancer (including all embodiments as disclosed herein) to be treated is a cancer with an EGFR del19 genotype. Preferably, the cancer patients to be treated and suffering from a cancer with an EGFR del19 genotype have the compound of formula (I) (including all individual embodiments and generic subsets disclosed herein) administered as a first line treatment, i.e. the patients are treatment naïve in respect of EGFR TKIs.

In another aspect the cancer (including all embodiments as disclosed herein) to be treated is a cancer with an EGFR del19 T790M genotype. Preferably, the cancer patients to be treated and suffering from a cancer with an EGFR del19 T790M genotype have the compound of formula (I) (including all individual embodiments and generic subsets disclosed herein) administered as a second line treatment, i.e. the patients are progressing on first line therapy with a $1^{st}$ or $2^{nd}$ generation EGFR TKI (i.e. treatment with gefitinib, erlotinib, afatinib or dacomitinib).

In another aspect the cancer (including all embodiments as disclosed herein) to be treated is a cancer with an EGFR del19 C797S genotype. Preferably, the cancer patients to be treated and suffering from a cancer with an EGFR del19 C797S genotype have the compound of formula (I) (including all individual embodiments and generic subsets disclosed herein) administered as a second line treatment, i.e. the patients are progressing on first line therapy with a $3^{rd}$ generation EGFR TKI (i.e. treatment with osimertinib, olmutinib, nazartinib or AC0010).

In another aspect the cancer (including all embodiments as disclosed herein) to be treated is a cancer with an EGFR del19 C797X (preferably C797G or C797N) genotype. Preferably, the cancer patients to be treated and suffering from a cancer with an EGFR del19 C797X (preferably C797G or C797N) genotype have the compound of formula (I) (including all individual embodiments and generic subsets disclosed herein) administered as a second line treatment, i.e. the patients are progressing on first line therapy with a $3^{rd}$ generation EGFR TKI (i.e. treatment with osimertinib, olmutinib, nazartinib or AC0010).

In another aspect the cancer (including all embodiments as disclosed herein) to be treated is a cancer with an EGFR del19 T790M C797S genotype. Preferably, the cancer patients to be treated and suffering from a cancer with an EGFR del19 T790M C797S genotype have the compound of formula (I) (including all individual embodiments and generic subsets disclosed herein) administered as a third line treatment, i.e. the patients progressed on first line therapy with a $1^{st}$ or $2^{nd}$ generation EGFR TKI (i.e. treatment with gefitinib, erlotinib, afatinib or dacomitinib) upon T790M acquisition and are progressing on second line therapy with a $3^{rd}$ generation EGFR TKI (i.e. treatment with osimertinib, olmutinib, nazartinib or AC0010) upon C797S acquisition.

In another aspect the cancer (including all embodiments as disclosed herein) to be treated is a cancer with an EGFR del19 T790M C797X (preferably C797G or C797N) genotype. Preferably, the cancer patients to be treated and suffering from a cancer with an EGFR del19 T790M C797X (preferably C797G or C797N) genotype have the compound of formula (I) (including all individual embodiments and generic subsets disclosed herein) administered as a third line treatment, i.e. the patients progressed on first line therapy with a $1^{st}$ or $2^{nd}$ generation EGFR TKI (i.e. treatment with gefitinib, erlotinib, afatinib or dacomitinib) upon T790M acquisition and are progressing on second line therapy with a $3^{rd}$ generation EGFR TKI (i.e. treatment with osimertinib, olmutinib, nazartinib or AC0010) upon C797X (preferably C797G or C797N) acquisition.

In another aspect the cancer (including all embodiments as disclosed herein) to be treated is a cancer with an EGFR del19 L792X (preferably L792F, L792H or L792Y) genotype. Preferably, the cancer patients to be treated and suffering from a cancer with an EGFR del19 L792X (preferably L792F, L792H or L792Y) genotype have the compound of formula (I) (including all individual embodiments and generic subsets disclosed herein) administered as a second line treatment, i.e. the patients are progressing on first line therapy with a $3^{rd}$ generation EGFR TKI (i.e. treatment with osimertinib, olmutinib, nazartinib or AC0010).

In another aspect the cancer (including all embodiments as disclosed herein) to be treated is a cancer with an EGFR del19 T790M L792X (preferably L792F, L792H or L792Y) genotype. Preferably, the cancer patients to be treated and suffering from a cancer with an EGFR del19 T790M L792X (preferably L792F, L792H or L792Y) genotype have the compound of formula (I) (including all individual embodiments and generic subsets disclosed herein) administered as a third line treatment, i.e. the patients progressed on first line therapy with a $1^{st}$ or $2^{nd}$ generation EGFR TKI (i.e. treatment with gefitinib, erlotinib, afatinib or dacomitinib) upon T790M acquisition and are progressing on second line therapy with a $3^{rd}$ generation EGFR TKI (i.e. treatment with osimertinib, olmutinib, nazartinib or AC0010) upon L792X (preferably L792F, L792H or L792Y) acquisition.

In another aspect the cancer (including all embodiments as disclosed herein) to be treated is a cancer with an EGFR L858R genotype. Preferably, the cancer patients to be treated and suffering from a cancer with an EGFR L858R genotype have the compound of formula (I) (including all individual embodiments and generic subsets disclosed herein) administered as a first line treatment, i.e. the patients are treatment naïve in respect of EGFRTKIs.

In another aspect the cancer (including all embodiments as disclosed herein) to be treated is a cancer with an EGFR L858R T790M genotype. Preferably, the cancer patients to be treated and suffering from a cancer with an EGFR L858R T790M genotype have the compound of formula (I) (including all individual embodiments and generic subsets disclosed herein) administered as a second line treatment, i.e. the patients are progressing on first line therapy with a $1^{st}$ or $2^{nd}$ generation EGFR TKI (i.e. treatment with gefitinib, erlotinib, afatinib or dacomitinib).

In another aspect the cancer (including all embodiments as disclosed herein) to be treated is a cancer with an EGFR L858R C797S genotype. Preferably, the cancer patients to be treated and suffering from a cancer with an EGFR L858R C797S genotype have the compound of formula (I) (including all individual embodiments and generic subsets disclosed herein) administered as a second line treatment, i.e. the patients are progressing on first line therapy with a $3^{rd}$ generation EGFR TKI (i.e. treatment with osimertinib, olmutinib, nazartinib or AC0010).

In another aspect the cancer (including all embodiments as disclosed herein) to be treated is a cancer with an EGFR L858R C797X (preferably C797G or C797N) genotype. Preferably, the cancer patients to be treated and suffering from a cancer with an EGFR L858R C797X (preferably C797G or C797N) genotype have the compound of formula (I) (including all individual embodiments and generic subsets disclosed herein) administered as a second line treatment, i.e. the patients are progressing on first line therapy with a $3^{rd}$ generation EGFR TKI (i.e. treatment with osimertinib, olmutinib, nazartinib or AC0010).

In another aspect the cancer (including all embodiments as disclosed herein) to be treated is a cancer with an EGFR L858R T790M C797S genotype. Preferably, the cancer patients to be treated and suffering from a cancer with an EGFR L858R T790M C797S genotype have the compound of formula (I) (including all individual embodiments and generic subsets disclosed herein) administered as a third line treatment, i.e. the patients progressed on first line therapy with a $1^{st}$ or $2^{nd}$ generation EGFR TKI (i.e. treatment with gefitinib, erlotinib, afatinib or dacomitinib) upon T790M acquisition and are progressing on second line therapy with a $3^{rd}$ generation EGFR TKI (i.e. treatment with osimertinib, olmutinib, nazartinib or AC0010) upon C797S acquisition.

In another aspect the cancer (including all embodiments as disclosed herein) to be treated is a cancer with an EGFR L858R T790M C797X (preferably C797G or C797N) genotype. Preferably, the cancer patients to be treated and suffering from a cancer with an EGFR L858R T790M C797X (preferably C797G or C797N) genotype have the compound of formula (I) (including all individual embodiments and generic subsets disclosed herein) administered as a third line treatment, i.e. the patients progressed on first line therapy with a $1^{st}$ or $2^{nd}$ generation EGFR TKI (i.e. treatment with gefitinib, erlotinib, afatinib or dacomitinib) upon T790M acquisition and are progressing on second line therapy with a $3^{rd}$ generation EGFR TKI (i.e. treatment with osimertinib, olmutinib, nazartinib or AC0010) upon C797X (preferably C797G or C797N) acquisition.

In another aspect the cancer (including all embodiments as disclosed herein) to be treated is a cancer with an EGFR L858R L792X (preferably L792F, L792H or L792Y) genotype. Preferably, the cancer patients to be treated and suffering from a cancer with an EGFR L858R L792X (preferably L792F, L792H or L792Y) genotype have the compound of formula (I) administered as a second line treatment, i.e. the patients are progressing on first line therapy with a $3^{rd}$ generation EGFR TKI (i.e. treatment with osimertinib, olmutinib, nazartinib or AC0010).

In another aspect the cancer (including all embodiments as disclosed herein) to be treated is a cancer with an EGFR L858R T790M L792X (preferably L792F, L792H or L792Y) genotype. Preferably, the cancer patients to be treated and suffering from a cancer with an EGFR L858R T790M L792X (preferably L792F, L792H or L792Y) genotype have the compound of formula (I) (including all individual embodiments and generic subsets disclosed herein) administered as a third line treatment, i.e. the patients progressed on first line therapy with a $1^{st}$ or $2^{nd}$ generation EGFR TKI (i.e. treatment with gefitinib, erlotinib, afatinib or dacomitinib) upon T790M acquisition and are progressing on second line therapy with a $3^{rd}$ generation EGFR TKI (i.e. treatment with osimertinib, olmutinib, nazartinib or AC0010) upon L792X (preferably L792F, L792H or L792Y) acquisition.

In another aspect the pharmacologically active substance to be used together/in combination with the compound of formula (I) (including all individual embodiments and generic subsets disclosed herein), or in the medical uses, uses, methods of treatment and/or prevention as herein defined can be selected from any one or more of the following (preferably there is only one additional pharmacologically active substance used in all these embodiments):

1. inhibitors of EGFR and/or of mutants thereof
   a. EGFR TKIs, e.g. afatinib, erlotinib, gefitinib, lapatinib, dacomitinib, osimertinib, olmutinib, nazartinib, AC0010;
   b. EGFR antibodies, e.g. cetuximab, panitumumab, necitumumab;
2. inhibitors of MEK and/or of mutants thereof
   a. e.g. trametinib, cobimetinib, binimetinib, selumetinib, refametinib;
3. inhibitors of c-MET and/or of mutants thereof
   a. e.g. savolitinib, cabozantinib, foretinib;
   b. MET antibodies, e.g. emibetuzumab;
4. mitotic kinase inhibitors
   a. e.g. CDK4/6 inhibitors
      i. e.g. palbociclib, ribociclib, abemaciclib;
5. immunotherapeutic agents
   a. e.g. immune checkpoint inhibitors
      i. e.g. anti-CTLA4 mAb, anti-PD1 mAb, anti-PD-L1 mAb, anti-PD-L2 mAb, anti-LAG3 mAb, anti-TIM3 mAb;
      ii. preferred are anti-PD1 mAb;
      iii. e.g. ipilimumab, nivolumab, pembrolizumab, atezolizumab, avelumab, durvalumab, pidilizumab, PDR-001 (BAP049-Clone-E disclosed and used in WO 2017/019896);
   b. e.g. immuno modulators
      i. e.g. CD73 inhibitors or CD73 inhibitory antibodies
6. anti-angiogenic agents
   a. e.g. bevacizumab, nintedanib;
7. apoptosis inducers
   a. e.g. Bcl-2 inhibitors
      i. e.g. venetoclax, obatoclax, navitoclax;
   b. e.g. Mcl-1 inhibitors
      i. e.g. AZD-5991, AMG-176, S-64315;
8. mTOR inhibitors
   a. e.g. rapamycin, temsirolimus, everolimus, ridaforolimus;
9. histone deacetylase inhibitors
10. IL6 inhibitors
11. JAK inhibitors Other pharmacologically active substances which may be used in combination with compounds (I) according to the invention (including all individual embodiments and generic subsets disclosed herein) are, e.g., state-of-the-art or standard-of-care compounds, such as e.g. cell proliferation inhibitors, anti-angiogenic substances, steroids or immune modulators/checkpont inhibitors, and the like.

Further examples of pharmacologically active substances which may be administered in combination with the compounds (I) according to the invention (including all individual embodiments and generic subsets disclosed herein), include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARR inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpoint inhibitors (e.g. CTLA4, PD1, PD-L1, PD-L2, LAGS, and TIMS binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

Any disease/condition/cancer, medical use, use, method of treatment and/or prevention as disclosed or defined herein (including molecular/genetic features/genotype) may be treated/performed with any compound of formula (I) as disclosed or defined herein (including all individual embodiments and generic subsets disclosed herein).

Formulations

Suitable preparations for administering the compounds (I) of the invention will be apparent to those with ordinary skill in the art and include for example tablets, pills, capsules, suppositories, lozenges, troches, solutions-particularly solutions for injection (s.c., i.v., i.m.) and infusion (injectables)-elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) of the invention with known excipients, for example inert diluents, carriers, disintegrants, adjuvants, surfactants, binders and/or lubricants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g.

groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 1 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formulae (I) ) | 80 mg |
| | lactose | 55 mg |
| | corn starch | 190 mg |
| | microcrystalline cellulose | 35 mg |
| | polyvinylpyrrolidone | 15 mg |
| | sodiumcarboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Tablets | per tablet |
|---|---|---|
| | active substance according to formulae (I) | 25 mg |
| | lactose | 50 mg |
| | microcrystalline cellulose | 24 mg |
| | magnesium stearate | 1 mg |
| | | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

| D) | Ampoule solution | |
|---|---|---|
| | active substance according to formulae (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like HO, $H_2N$, (O)S, $(O)_2S$, NC (cyano), HOOC, $F_3C$ or the like, the skilled artisan can see the radical attachment point(s) to the molecule from the free valences of the group itself.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)$ $CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH$ $(CH_3)_2$), 2,2-dimethyl-1-propyl (neo-pentyl; —$CH_2C$ $(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$), 2,3-dimethyl-1-butyl (—$CH_2CH(CH_3)CH(CH_3)$ $CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH$ $(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH$ $(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH$ $(CH_3)$—$CH(CH_3))$—, —$(CH_2$—$CH(CH_2CH_3))$—, —$(CH$ $(CH_2CH_3)$—$CH_2)$—, —$(CH(CH_2CH_2CH_3))$—, —$(CH(CH$ $(CH_3))_2)$— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene. The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example—$CH_2F$ and —CHF—, —$CHFCH_2F$ and —CHFCHF- or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms in common. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

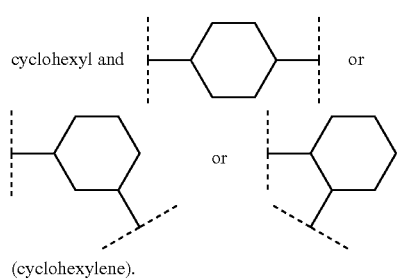

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

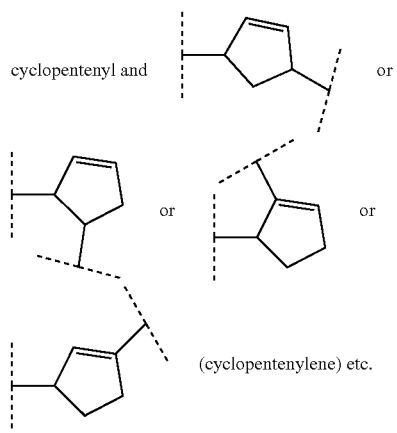

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

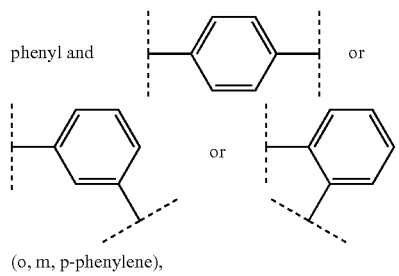

(o, m, p-phenylene),

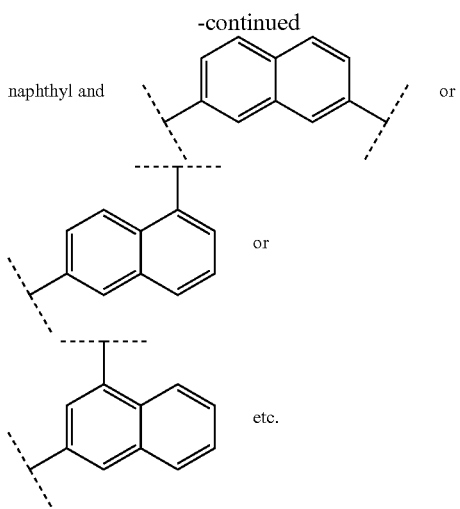

The above definition for arylene also applies if arylene is part of another (combined) group as for example in HO-aryleneamino or H₂N-aryleneoxy.

Heterocyclyl denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide—SO—, sulphone—SO$_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-di-aza-spiro[5.5]undecyl, 2.8-diaza-spiro[4,5]decyl etc.

Further examples are the structures illustrated below, which may be attached via each hydrogen-carrying atom (exchanged for hydrogen):

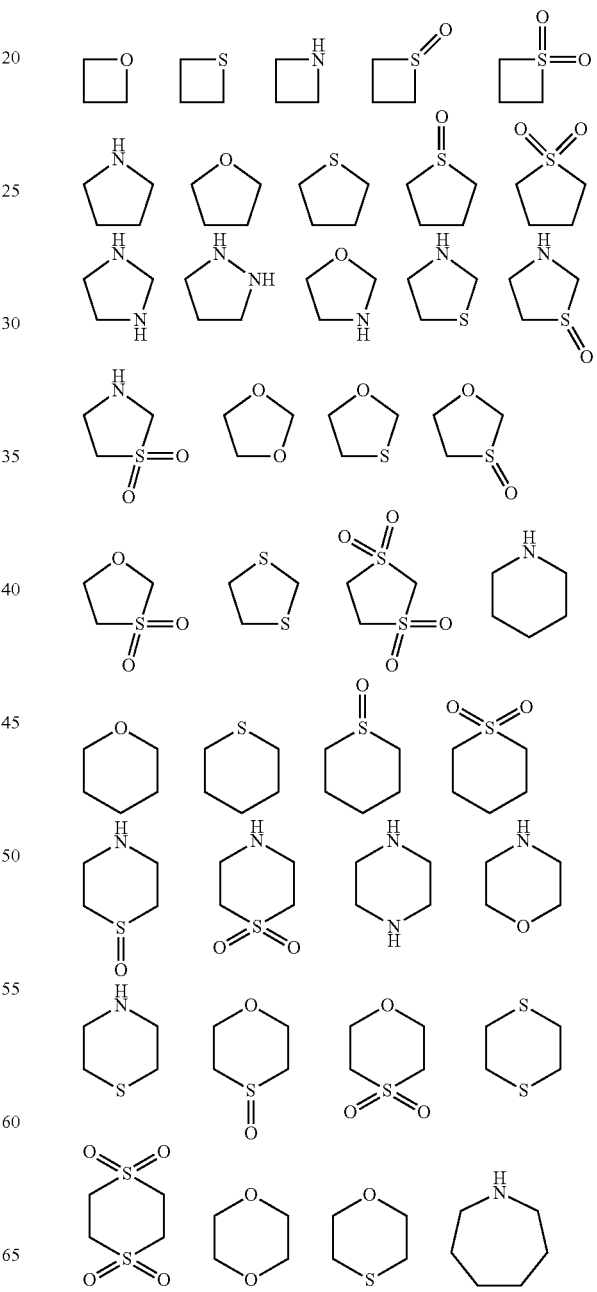

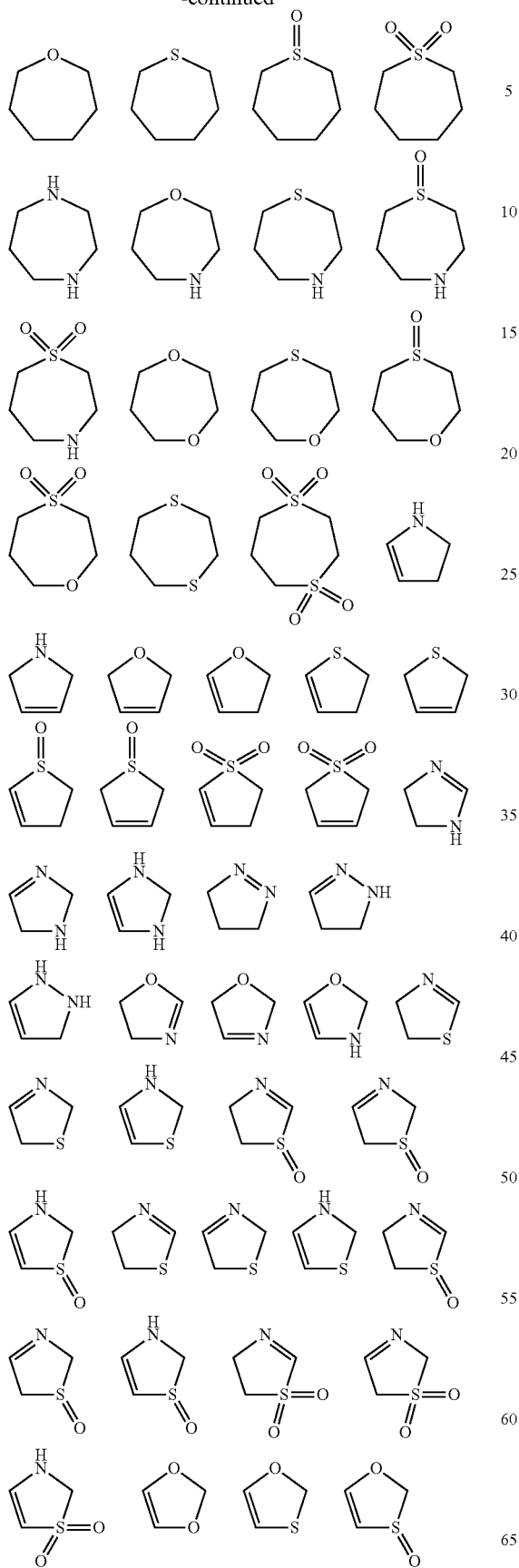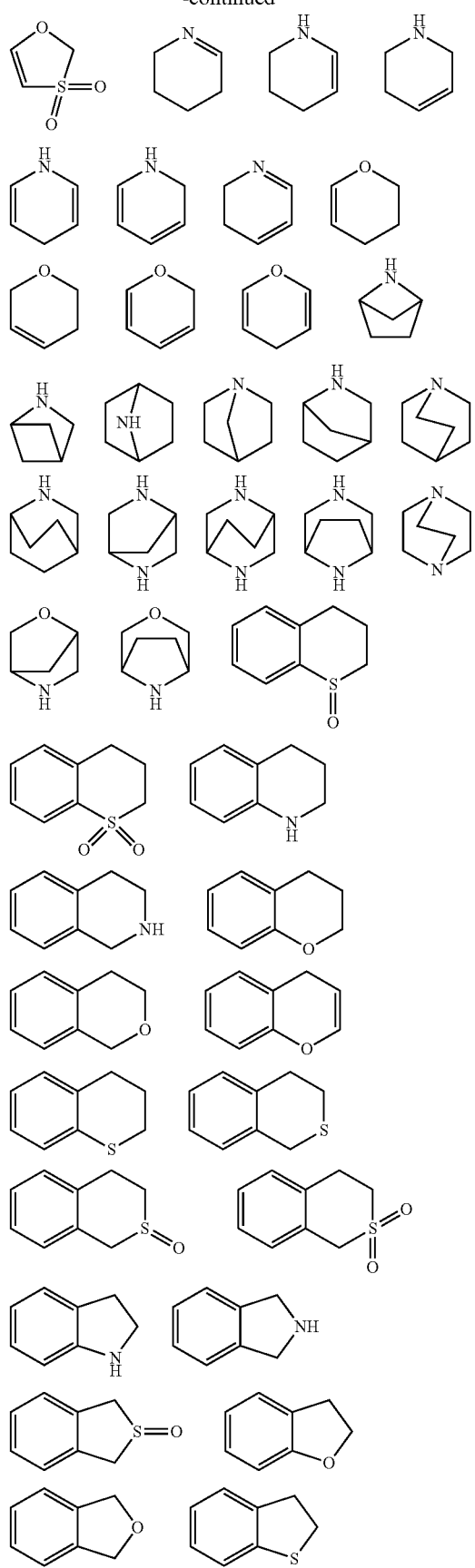

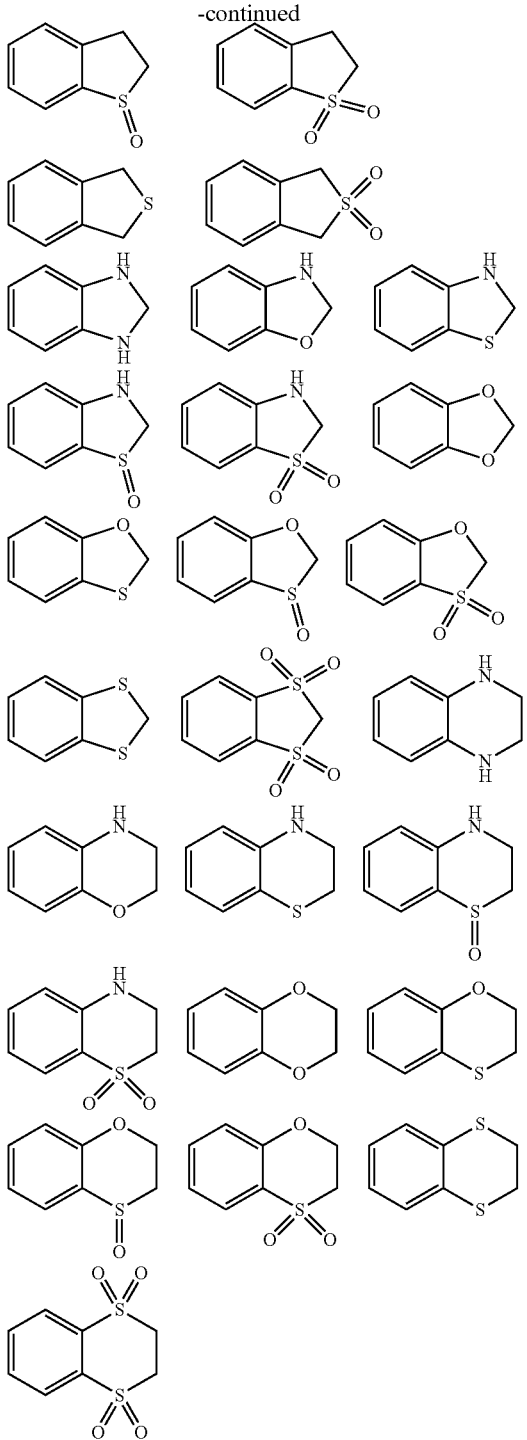

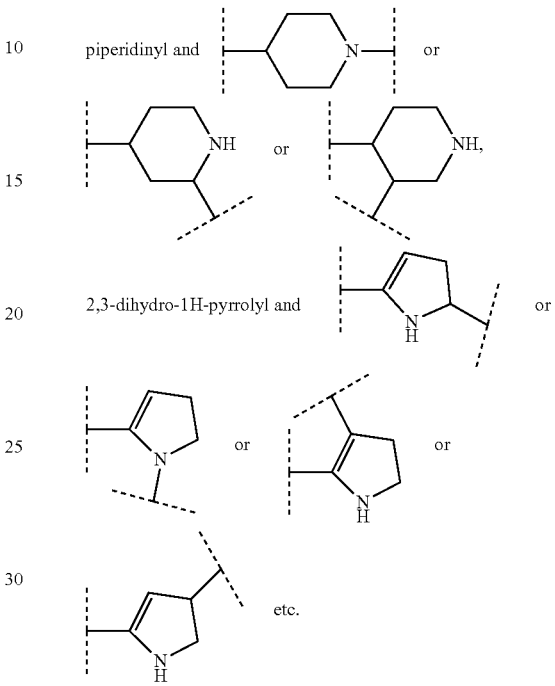

Preferably, heterocyclyls are 4 to 8 membered, monocyclic and have one or two heteroatoms independently selected from oxygen, nitrogen and sulfur. Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

The above definition of heterocyclylene also applies if heterocyclylene is part of another (combined) group as for example in HO-heterocyclyleneamino or $H_2N$-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

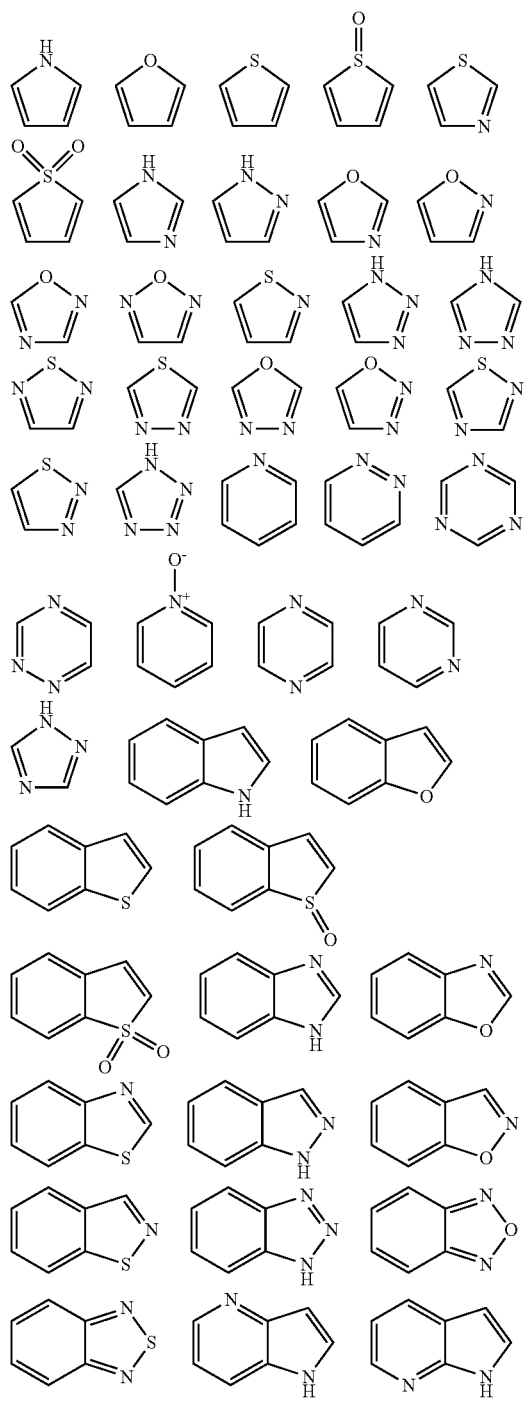

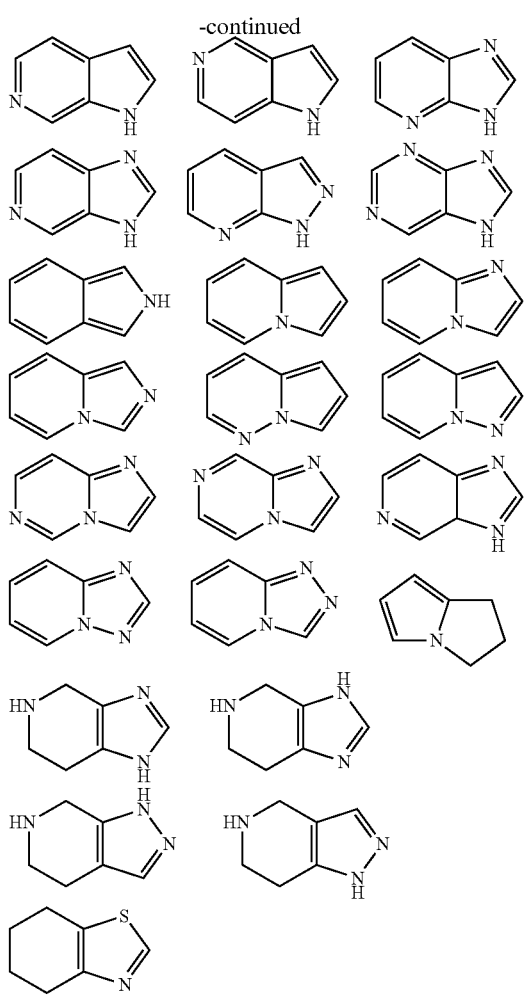

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

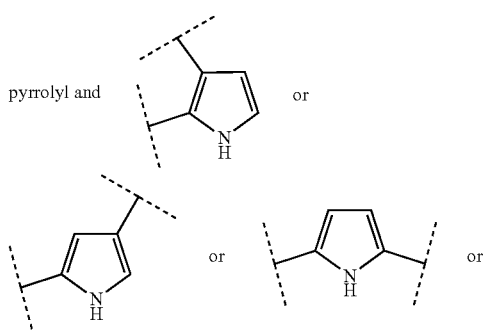

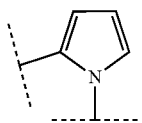

The above definition of heteroarylene also applies if heteroarylene is part of another (combined) group as for example in HO-heteroaryleneamino or H₂N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N₂ or the like, may only be substituents on carbon atoms, whereas the bivalent substituents =O and =NR may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH₂— or sulphur atoms (=O group or =NR group only, one or two =O groups possible or, e.g., one =O group and one =NR group, each group replacing a free electron pair) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries. Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

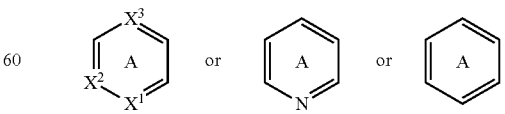

the letter A has the function of a ring designation in order to make it easier, for example, to indicate the attachment of the ring in question to other rings. For bivalent groups in which it is crucial to determine which adjacent groups they bind and with which valency, the corresponding binding partners are indicated in brackets where necessary for clarification purposes, as in the following representations:

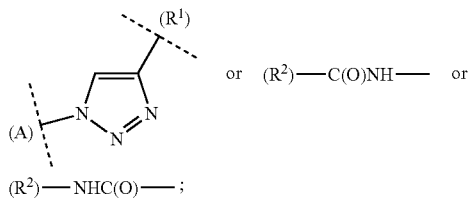

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of Abbreviations

| | |
|---|---|
| Ac | acetyl |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf ($R_f$) | retention factor |
| RP | reversed phase |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula prevails.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18 OBD, 10 µm, 30×100 mm Part. No. 186003971; X-Bridge C18 OBD, 10 µm, 30×100 mm Part. No. 186003930). The compounds are eluted using different gradients of $H_2O$/ACN wherein 0.2% HCOOH is added to the water (acid conditions). For chromatography under basic conditions the water is made basic according to the following recipe: 5 mL of ammonium hydrogen carbonate solution (158 g to 1 L $H_2O$) and 2 mL 32% ammonia$_{(aq)}$ are made up to 1 L with $H_2O$.

The supercritical fluid chromatography (SFC) of the intermediates and example compounds according to the invention is carried out on a JASCO SFC-system with the following columns: Chiralcel OJ (250×20 mm, 5 μm), Chiralpak AD (250×20 mm, 5 μm), Chiralpak AS (250×20 mm, 5 μm), Chiralpak IC (250×20 mm, 5 μm), Chiralpak IA (250×20 mm, 5 μm), Chiralcel OJ (250×20 mm, 5 μm), Chiralcel OD (250×20 mm, 5 μm), Phenomenex Lux C2 (250×20 mm, 5 μm).

The analytical HPLC (reaction monitoring) of intermediate compounds is carried out with columns made by Waters and Phenomenex. The analytical equipment is also provided with a mass detector in each case.

HPLC Mass Spectroscopy/UV Spectrometry

The retention times/MS-ESI$^+$ for characterizing the example compounds according to the invention are produced using an HPLC-MS apparatus (high performance liquid chromatography with mass detector) made by Agilent. Compounds that elute at the injection peak are given the retention time $t_{Ret.}$=0.00.

HPLC-Methods (Preparative)

Prep. HPLC1
- HPLC: 333 and 334 Pumps
- Column: Waters X-Bridge C18 OBD, 10 μm, 30×100 mm, Part. No. 186003930
- Solvent: A: 10 mM $NH_4HCO_3$ in $H_2O$; B: acetonitrile (HPLC grade)
- Detection: UV/Vis-155
- Flow: 50 mL/min
- Gradient: 0.00-1.50 min: 1.5% B
  1.50-7.50 min: varying
  7.50-9.00 min: 100% B Prep. HPLC2
- HPLC: 333 and 334 Pumps
- Column: Waters Sunfire C18 OBD, 10 μm, 30×100 mm, Part. No. 186003971
- Solvent: A: $H_2O$+0.2% HCOOH; B: acetonitrile (HPLC grade)+0.2% HCOOH
- Detection: UV/Vis-155
- Flow: 50 mL/min
- Gradient: 0.00-1.50 min: 1.5% B
  1.50-7.50 min: varying
  7.50-9.00 min: 100% B HPLC-Methods (Analytic)

LCMSBAS
- HPLC: Agilent 1100 Series
- MS: Agilent LC/MSD SL
- Column: Phenomenex Mercury Gemini C18, 3 μm, 2×20 mm, Part. No. 00M-4439-B0-CE
- Solvent: A: 5 mM $NH_4HCO_3$/20 mM $NH_3$ in $H_2O$; B: acetonitrile (HPLC grade)
- Detection: MS: Positive and negative mode
- Mass range: 120-900 m/z
- Flow: 1.00 mL/min
- Column temperature: 40° C.
- Gradient: 0.00-2.50 min: 5%→95% B
  2.50-2.80 min: 95% B
  2.81-3.10 min: 95%→5% B LCMS3, Basisch_1
- HPLC: Agilent 1100 Series
- MS: Agilent LC/MSD (API-ES+/−3000 V, Quadrupol, G6140)
- Column: Waters, Xbridge C18, 2.5 μm, 2.1×20 mm column
- Solvent: A: 20 mM $NH_4HCO_3$/$NH_3$ in $H_2O$ pH 9; B: acetonitrile (HPLC grade)
- Detection: MS: positive and negative mode
- Mass range: 120-900 m/z
- Flow: 1.00 mL/min
- Column temperature: 60° C.
- Gradient: 0.00-1.50 min: 10%→95% B
  1.50-2.00 min: 95% B
  2.00-2.10 min: 95% 10% B Z011_S03
- HPLC: Agilent 1100/1200 Series
- MS: Agilent LC/MSD SL
- Column: Waters XBridge C18_3.0×30 mm_2.5 μm
- Solvent: A: 0.1% $NH_3$ in $H_2O$; B: acetonitrile (HPLC grade)
- Detection: MS: positive and negative mode
- Mass range: 100-1200 m/z
- Column temperature: 60° C.
- Gradient: 0.00-0.20 min: 3% B, flow: 2.2 mL/min
  0.20-1.20 min: 100% B, flow: 2.2 mL/min
  1.20-1.25 min: 100% B, flow: 2.2 mL/min→3.0 mL/min
  1.25-1.40 min: 100% B, flow: 3.0 mL/min Z018_S04
- HPLC: Agilent 1100/1200 Series
- MS: Agilent LC/MSD SL
- Column: Waters Sunfire C18_3.0×30 mm_2.5 μm
- Solvent: A: 0.1% TFA in $H_2O$; B: acetonitrile (HPLC grade)
- Detection: MS: positive and negative mode
- Mass range: 100-1200 m/z
- Column temperature: 60° C.
- Gradient: 0.00-0.20 min: 3% B, flow: 2.2 mL/min
  0.20-1.20 min: 3% B→100% B, flow: 2.2 mL/min
  1.20-1.25 min: 100% B, flow: 2.2 mL/min→3.0 mL/min
  1.25-1.40 min: 100% B, flow: 3.0 mL/min 004_CA10
- HPLC: Agilent 1100/1200 Series
- MS: Agilent LC/MSD SL
- Column: Waters XBridge C18_3.0×30 mm_2.5 μm
- Solvent: A: 0.1% $NH_3$ in $H_2O$; B: acetonitrile (HPLC grade)
- Detection: MS: positive and negative mode
- Mass range: 100-1200 m/z
- Flow: 1.50 mL/min
- Column temperature: 60° C.
- Gradient: 0.00-1.30 min: 5% B→100% B
  1.30-1.50 min: 100% B
  1.50-1.6 min: 100% B→5% B 003_CA11
- HPLC: Waters Acquity, QDa Detector
- MS: Agilent LC/MSD SL
- Column: Waters Sunfire C18_3.0×30 mm_2.5 μm
- Solvent: A: 0.1% TFA in $H_2O$; B: 0.08% TFA in $H_2O$
- Detection: MS: positive and negative mode
- Mass range: 100-1200 m/z
- Flow: 1.50 mL/min
- Column temperature: 60° C.
- Gradient: 0.00-1.30 min: 5% B→100% B
  1.30-1.50 min: 100% B
  1.50-1.6 min: 100% B→5% B MSB
- HPLC: SQD (Waters, Eschborn)
- MS: ZQ (Waters, Eschborn)
- Column: Waters BEH C18, 1.7 µm, 2.1×50 mm
- Solvent: A: 0.1% $NH_4HCO_2$ in $H_2O$ pH 4.5; B: acetonitrile (HPLC grade)
- Detection: MS: positive and negative mode
- Mass range: 50-1200 m/z
- Flow: 0.50 mL/min
- Column temperature: 45° C.
- Gradient: 0.00-1.00 min: 10% B
  - 1.00-4.00 min: 10% B→90% B
  - 4.00-5.10 min: 90% B→10% B
  - 5.10-6.00 min: 10% B VAB
- HPLC: Agilent 1100/1200 Series
- MS: Agilent LC/MSD SL
- Column: Waters X-Bridge BEH C18, 2.5 µm, 2.1×30 mm XP
- Solvent: A: 5 mM $NH_4HCO_3$/19 mM $NH_3$ in $H_2O$; B: acetonitrile (HPLC grade)
- Detection: MS: Positive and negative mode
- Mass range: 100-1200 m/z
- Flow: 1.40 mL/min
- Column temperature: 45° C.
- Gradient: 0.00-1.00 min: 5% B→100% B
  - 1.00-1.37 min: 100% B
  - 1.37-1.40 min: 100%→5% B VAS
- HPLC: Agilent 1100/1200 Series
- MS: Agilent LC/MSD SL
- Column: YMC TriART C18 2.0×30 mm, 3 µm
- Solvent: A: $H_2O$+0.2% formic acid; B: acetonitrile (HPLC grade)
- Detection: MS: positive and negative mode
- Mass range: 105-1200 m/z
- Flow: 1.40 mL/min
- Column temperature: 35° C.
- Gradient: 0.0 min: 5% B
  - 0.0-1.00 min: 5% B→100% B
  - 1.00-1.37 min: 100% B
  - 1.37-1.40 min: 100% B→5% B MONI
- UPLC-MS: Waters Acquity UPLC-integrated with Waters ZQ MS
- Column: YMC TRIART (33×2.1 mm), 3µ
- Solvent: A: 10 mM $NH_4OAc$ in $H_2O$; B: acetonitrile (HPLC grade)
- Detection: MS: Positive and negative mode
- Mass range: 100-800 m/z, Cone Voltage 25 V
- Flow: 1.0 mL/min
- Column temperature: 50° C.
- Gradient: 0.0-0.75 min: 2% B
  - 0.75-1.00 min: 2% B→10% B
  - 1.00-2.00 min: 10% B→98% B
  - 2.00-2.50 min: 98% B
  - 2.50-2.90 min: 98% B→2% B
  - 2.90-3.00 min: 2% B YMC
- UPLC-MS: Waters Acquity UPLC-integrated with Waters ZQ MS
- Column: YMC TRIART (33×2.1 mm), 3µ
- Solvent: A: 10 mM $NH_4OAc$ in $H_2O$; B: acetonitrile (HPLC grade)
- Detection: MS: positive and negative mode
- Mass range: 100-800 m/z, Cone Voltage 30 V
- Flow: 1.0 mL/min
- Column temperature: 50° C.
- Gradient: 0.0-0.75 min: 2% B
  - 0.75-1.00 min: 2% B→10% B
  - 1.00-2.00 min: 10% B→98% B
  - 2.00-2.50 min: 98% B
  - 2.50-2.90 min: 98% B→2% B The compounds according to the invention and intermediates are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein, i.e. it is within the skills of an organic chemist to synthesize these compounds. Substances described in the literature can be prepared according to the published methods of synthesis.

General Reaction Scheme and Summary of the Synthesis Route

Compounds (I) according to the invention can be synthesized using an amide coupling reaction starting from aminobenzimidazoles A-1 and pyridine carboxylic acids B-1 (scheme 1, method A) or of aminobenzimidazoles A-1 and pyridine carboxylic acids B-2 followed by a SUZUKI reaction (see e.g. *J. Org. Chem.*, 2007, 72, 4067-4072; *Org. Lett.*, 2011, 13, 252-255; *J. Org. Chem.*, 2004, 69, 7779-7782) of U-1 thus obtained with coupling reagents H-1 or a BUCHWALD-HARTWIG amination (see e.g. *J. Am. Chem. Soc.*, 2008, 130, 13552-13554; *J. Am. Chem. Soc.*, 2010, 132, 15914-15917) of U-1 with amines H-1 (scheme 1, method B). Additional derivatization steps, e.g. at position $R^1$, $R^2$, $R^3$, $R^4$ and/or $R^5$, like e.g. ester cleavage, carbamate cleavage, reductive amination, double bond hydrogenation, amide coupling, alkylation or reduction of an acid derivative to the corresponding amine or alcohol (not depicted in scheme 1) can be included both for compounds (I) according to the invention and intermediates thereof as described herein.

Scheme 1

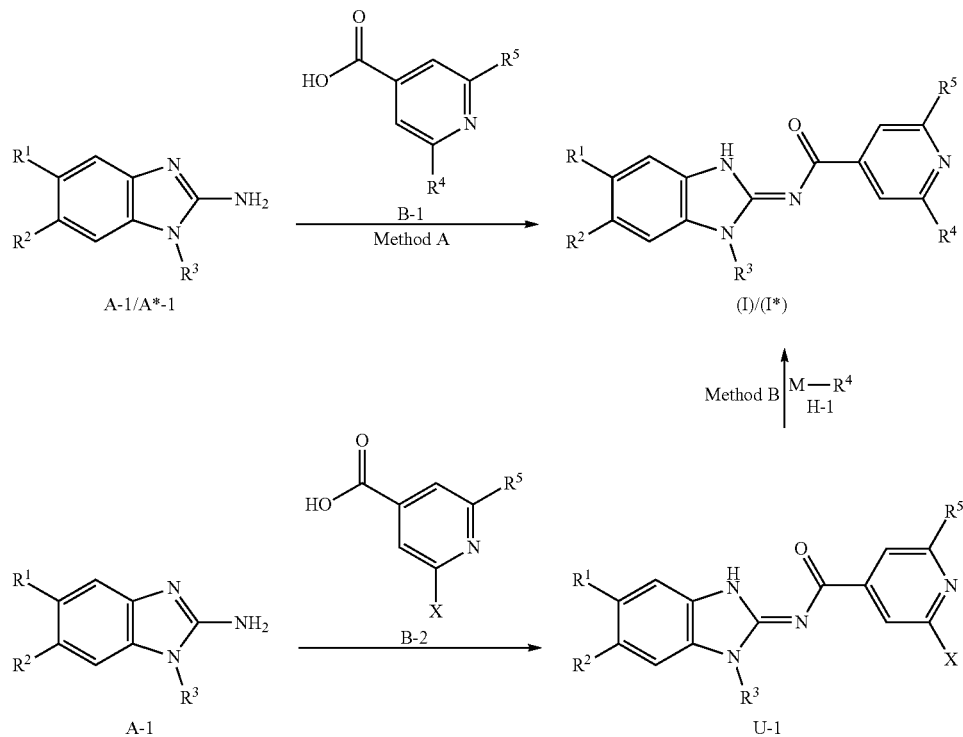

M = hydrogen, boronic acid or boronic acid derivative, e.g. cyclic boronic acid esters but also BF$_3^-$M$^+$;

X = leaving group (e.g. halogen, triflate, mesylate, tosylate), preferably Cl, Br, I Aminobenzimidazoles A-1/A*-1 can be synthesized starting from fluoro nitrobenzenes C-1/C*-1 or starting from C-1/C*-1-precursor fluoro nitrobenzenes S-1/S*-1 or T-1/T*-1 (scheme 2). In the latter approach C-1/C*-1 is synthesized either via a SUZUKI reaction of T-1/T*-1 or S-1/S*-1 with a coupling reagent G-1 (see e.g. *J. Org. Chem.*, 2007, 72, 4067-4072; *Org. Lett*, 2011, 13, 252-255; *J. Org. Chem.*, 2004, 69, 7779-7782) or via a BUCHWALD-HARTWIG amination of T-1/T*-1 or S-1/S*-1 with an amine G-1 (see e.g. *J. Am. Chem. Soc.*, 2008, 130, 13552-13554; *J. Am. Chem. Soc.*, 2010, 132, 15914-15917). C-1/C*-1 thus obtained (or available from other sources) can then undergo a reaction sequence comprising a nucleophilic aromatic substitution with amines D-1, a nitro group reduction of obtained nitro anilines E-1/E*-1 and a cyanogen bromide mediated cyclisation reaction of bisaniline F-1/F*-1 (e.g. WO 2005/079791; WO 2005/070420; WO 2004/014905) to deliver aminobenzimidazoles A-1/A*-1.

Scheme 2

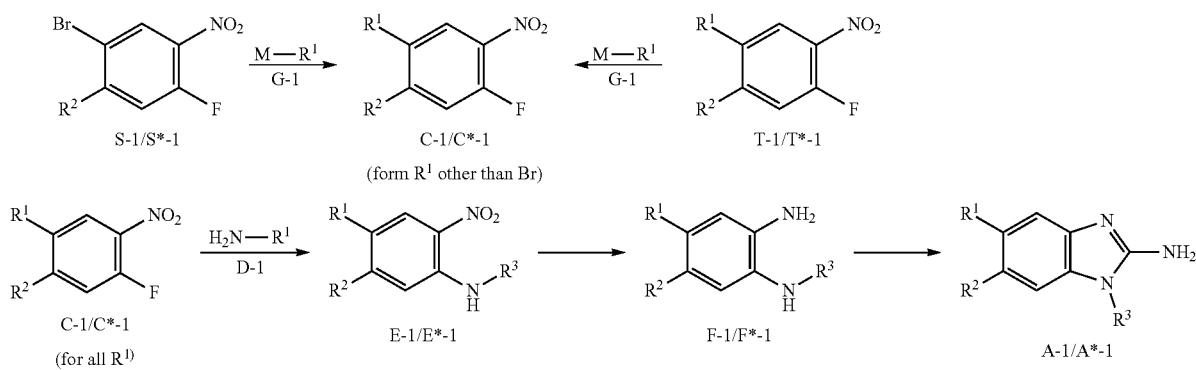

M = hydrogen, boronic acid or boronic acid derivative, e.g. cyclic boronic acid esters but also BF$_3^-$M$^+$ Intermediates A-1/A*-1 thus obtained with $R^1$=Br and/or $R^2$=Br can be further derivatized in these positions either via a SUZUKI reaction with coupling reagent G-1 (see e.g. *J. Org. Chem.*, 2007, 72, 4067-4072; *Org. Lett.*, 2011, 13, 252-255; *J. Org. Chem.*, 2004, 69, 7779-7782) or via a BUCHWALD-HARTWIG amination with amine G-1 (see e.g. *J. Am. Chem. Soc.*, 2008, 130, 13552-13554; *J. Am. Chem. Soc.*, 2010, 132, 15914-15917) (scheme 3). Additional derivatization steps, e.g. at position $R^1$, $R^2$ and/or $R^3$ like e.g. carbamate cleavage, double bond hydrogenation, amide coupling or reduction of an acid derivative to the corresponding amine or alcohol leading to further intermediates A-1/A*-1 (not depicted in scheme 3) can be included.

Scheme 3

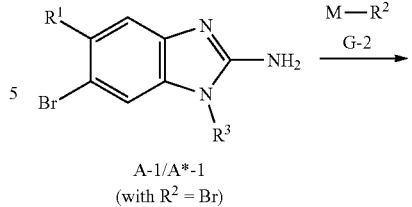

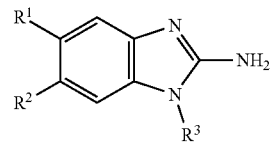

M = hydrogen, boronic acid or boronic acid derivative, e.g. cyclic boronic acid esters but also $BF_3^-M^+$ Pyridine carboxylic acids B-1 and B-2 can be synthesized from ester precursors K-1 (scheme 4). Applying a nucleophilic aromatic substitution reaction of K-1 and H-1 (see e.g. *Helvetica Chimica Acta* 2013, 96, 2160-2172; *Organic Preparations and Procedures Int.* 2004, 36, 76-81) or a SUZUKI reaction (see e.g. *J. Org. Chem.* 2007, 72, 4067-4072; *Org. Lett.* 2011, 13, 252-255; *J. Org. Chem.* 2004, 69, 7779-7782) or a BUCHWALD-HARTWIG amination of K-1 and H-1 (see e.g. *J. Am. Chem. Soc.*, 2008, 130, 13552-13554; *J. Am. Chem. Soc.*, 2010, 132, 15914-15917) the intermediate L-1 can be synthesized. B-1 and B-2 can be obtained from K-1 and L-1, respectively, by saponification. Alternatively, B-1 can be synthesized by a sequence starting from amino pyridine carboxylic esters M-1. Starting with a nucleophilic aromatic substitution reaction of M-1 and fluoro nitro benzenes M-2 (see e.g. *Helvetica Chimica Acta* 2013, 96, 2160-2172; *Organic Preparations and Procedures Int.* 2004, 36, 76-81) the intermediate M-3 can be synthesized. Reduction of the nitro group in M-3 leads to the intermediate M-4. Compound L-1 is then obtained by a cyclocondensation reaction of M-4 (see e.g. *J. Am. Chem. Soc.*, 1951, 73, 5672-5675; *J. Org. Chem.*, 2002, 67, 1708-1711). B-1 is then synthesized by saponification of the esters L-1 under basic or acidic conditions.

Scheme 4

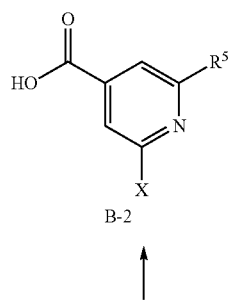

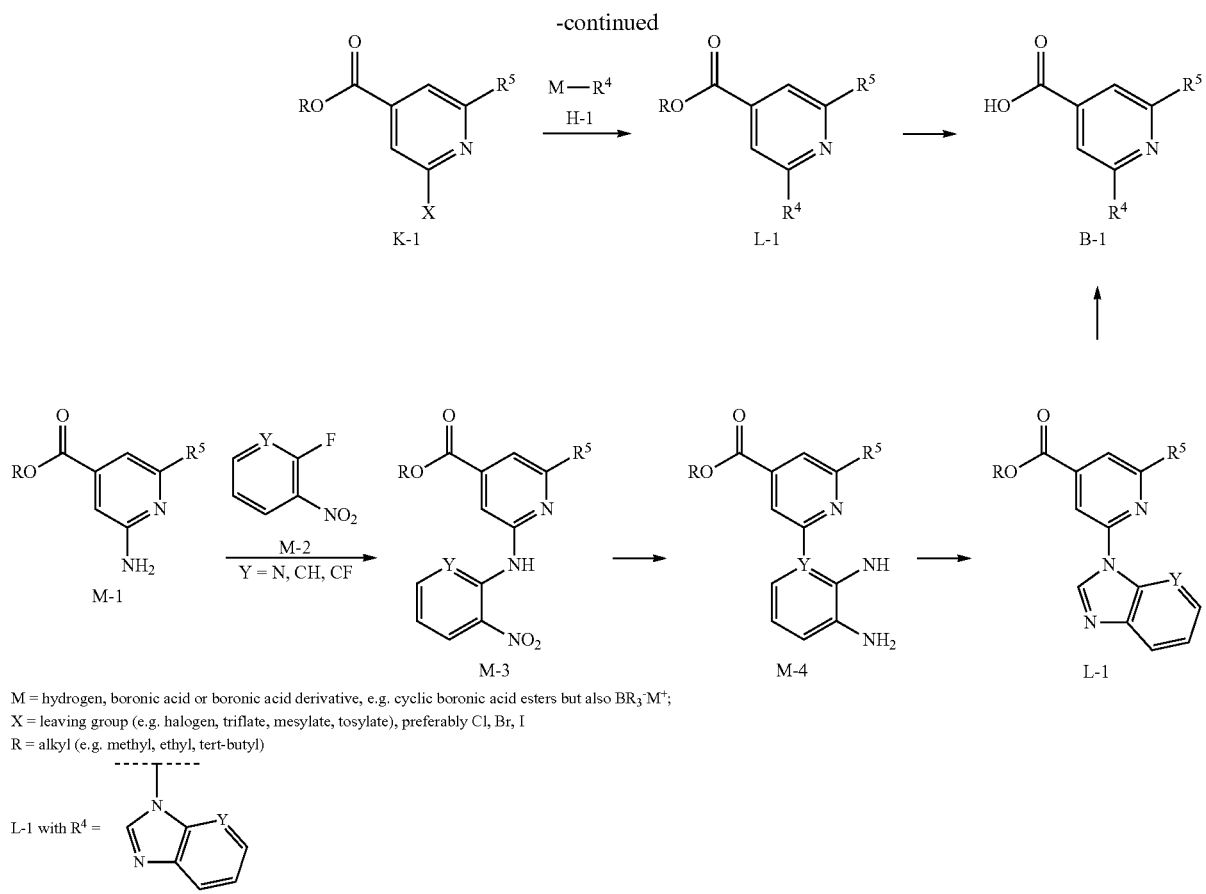

M = hydrogen, boronic acid or boronic acid derivative, e.g. cyclic boronic acid esters but also BR₃⁻M⁺;
X = leaving group (e.g. halogen, triflate, mesylate, tosylate), preferably Cl, Br, I
R = alkyl (e.g. methyl, ethyl, tert-butyl)

Compounds/intermediates marked with an asterisk (*), e.g. E*-1, F*-1, A*-1, L*-1 and (I*) are meant to represent compounds/intermediates where the definition of one or more of the substituents $R^1$ to $R^5$, in particular $R^1$ and $R^2$, differs from the definition of these substituents for compounds (I) according to the invention according to claims and specification. These compounds/intermediates come into existence along the reaction sequence and are derivatized in one or more of $R^1$ to $R^5$ to finally obtain compounds (I) according to the invention.

Synthesis of Intermediates C-1

Experimental Procedure for the Synthesis of C-1a

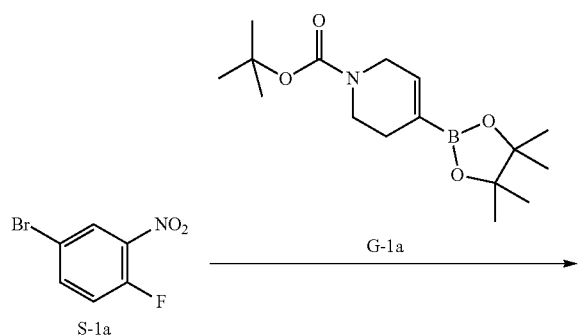

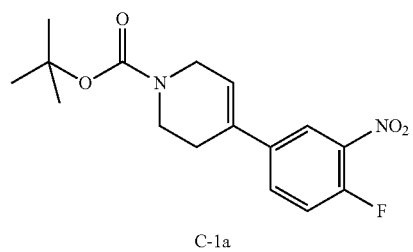

C-1a

To a stirred solution of S-1a (300 mg; 1.4 mmol) in 1,4-dioxane (12.0 mL) is added sodium carbonate (0.43 g; 3.1 mmol; 3.0 eq.) and water (2.0 mL). The mixture is degassed by passing nitrogen through the mixture. Then 1,1'-bis(diphenylphosphino)ferrocene palladium(II)dichloride dichloromethane complex (0.11 g; 0.14 mmol; 0.1 eq.) is added. The reaction mixture is heated at 90° C. for 16 h. After filtering off the reaction mass, the solvent is evaporated. The crude product is purified by normal phase column chromatography using ethyl acetate to afford the desired product C-1a (yield: 91%—400 mg, 1.2 mmol; HPLC-MS: $(M+H)^+=323$, $t_{Ret.}=1.9$ min, method YMC)

Further intermediates C-1 are available in an analogous manner starting from different building blocks S-1 and G-1.

Synthesis of Intermediates E-1 and E*-1
Experimental Procedure for the Synthesis of Intermediate E1-a

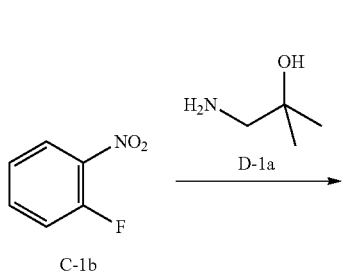

Experimental Procedure for the Synthesis of E-1b

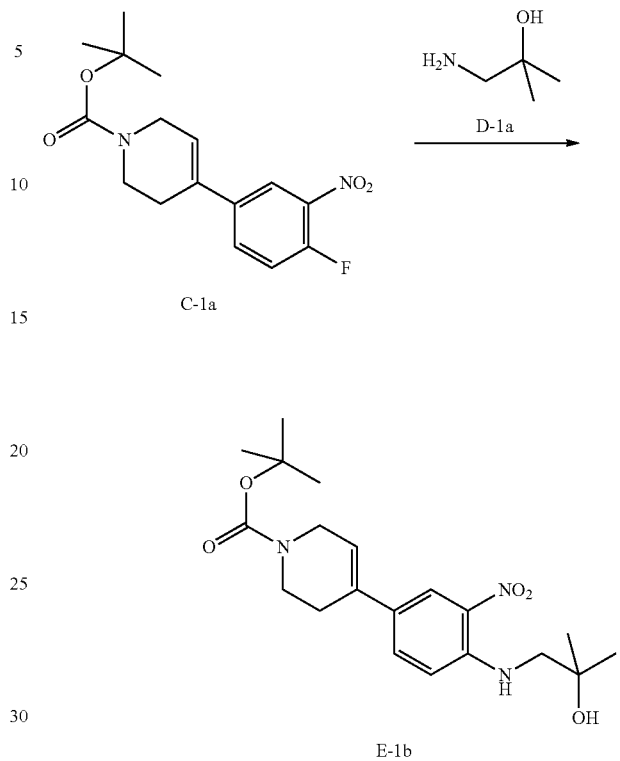

To a suspension of starting material C-1b (13.5 g, 95.5 mmol) and K$_2$CO$_3$ (19.8 g, 143.2 mmol, 1.5 eq.) in DMF (250 mL) is added amine D-1a (10.21 g, 114.5 mmol, 1.2 eq.) in one portion and stirred at 20° C. for 16 h. The solvent is evaporated under reduced pressure and the residue is taken up in 100 mL water. The mixture is extracted with ethyl acetate (3×50 mL) and the combined organic layers are dried over MgSO$_4$ and filtrated. The organic solvent is evaporated under reduced pressure and the crude product is purified using normal phase chromatography (hexane/EtOAc 70:30) to afford pure product E-1a (yield: 95%—19.1 g, 90.5 mmol; HPLC-MS: (M+H)$^+$=211, t$_{Ret.}$=0.9 min, method LCMSBAS).

To a stirred solution of C-1a (0.40 g; 1.24 mmol) in THF (10 mL) at 20° C. is added DIPEA (1.0 mL; 6.2 mmol; 5.0 eq.) and D-1a (0.14 mL; 1.49 mmol; 1.2 eq.). The reaction mixture is stirred for 18 h at 60° C. The reaction mixture is diluted with water (10 mL) and extracted with ethyl acetate (3×10 mL). The combined organic layers are dried over MgSO$_4$ and filtrated. The organic solvent is evaporated under reduced pressure and the crude product is purified using normal phase chromatography (hexane/EtOAc 70:30) to afford pure product E-1b (yield: 82%—0.40 g, 1.0 mmol; HPLC-MS: (M+H)$^+$=392, t$_{Ret.}$=1.9 min, method MONI).

The following intermediates E-1 and E*-1 (table 1) are available in an analogous manner starting from different building blocks C-1, C*-1 and D-1.

TABLE 1

| # | Structure | MS (M + H)$^+$; t$_{Ret.}$ HPLC [min] | HPLC-MS method |
|---|---|---|---|
| E-1a | (structure) | (M + H)$^+$ = 211; t$_{Ret.}$ = 0.9 | LCMSBAS |

TABLE 1-continued

| # | Structure | MS (M + H)+; t_Ret. HPLC [min] | HPLC-MS method |
|---|---|---|---|
| E-1b | 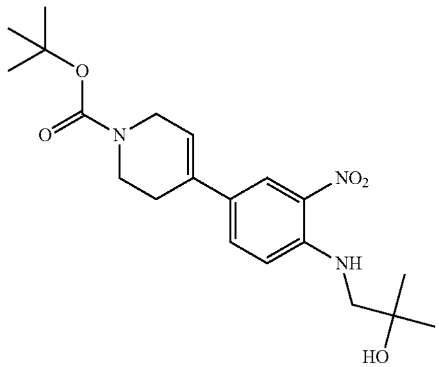 [SMILES: CC(C)(O)CNc1ccc(C2=CCN(C(=O)OC(C)(C)C)CC2)cc1[N+](=O)[O-]] | (M + H)+ = 392; t_Ret. = 1.9 | MONI |
| E-1c | 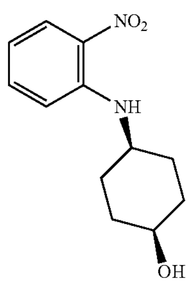 | (M + H)+ = 237; t_Ret. = 0.9 | VAB |
| E-1d | 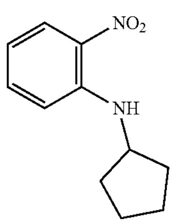 [SMILES: O=[N+]([O-])c1ccccc1NC1CCCC1] | (M + H)+ = 207; t_Ret. = 0.9 | VAB |
| E-1e | 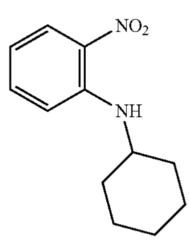 | (M + H)+ = 221; t_Ret. = 1.23 | VAB |
| E-1f | 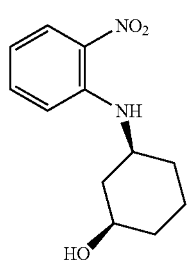 | (M + H)+ = 237; t_Ret. = 0.9 | VAB |

TABLE 1-continued

| # | Structure | MS (M + H)+; t_Ret. HPLC [min] | HPLC-MS method |
|---|---|---|---|
| E-1g | 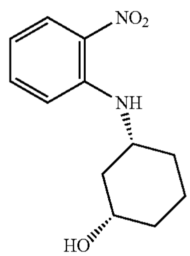 | (M + H)+ = 237; t_Ret. = 0.9 | VAB |
| E-1h | 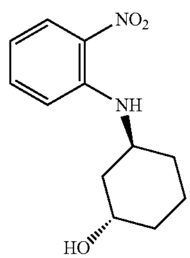 | (M + H)+ = 237; t_Ret. = 0.9 | VAB |
| E-1i | 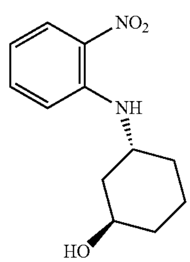 | (M + H)+ = 237; t_Ret. = 0.9 | VAB |
| E-1j | 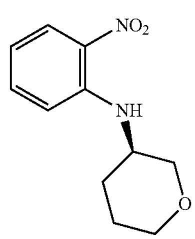 [SMILES: O=[N+]([O-])c1ccccc1N[C@@H]1CCCOC1] | (M + H)+ = 193; t_Ret. = 1.5 | MONI |
| E-1k | 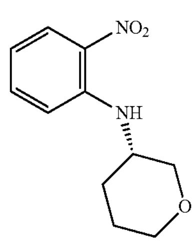 [SMILES: O=[N+]([O-])c1ccccc1N[C@H]1CCCOC1] | (M + H)+ = 193; t_Ret. = 1.5 | MONI |
| E-1l | 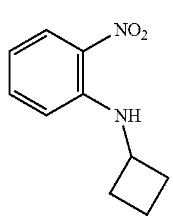 [SMILES: O=[N+]([O-])c1ccccc1NC1CCC1] | (M + H)+ = 193; t_Ret. = 4.1 | MONI |

TABLE 1-continued

| # | Structure | MS (M + H)+; t_Ret. HPLC [min] | HPLC-MS method |
|---|---|---|---|
| E-1m | 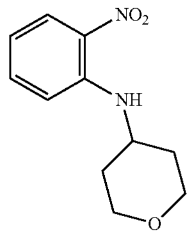 [SMILES: O=[N+]([O-])c1ccccc1NC1CCOCC1] | (M + H)+ = 223; t_Ret. = 1.8 | MONI |
| E-1n | 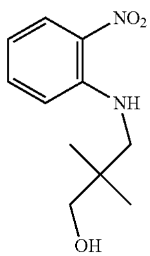 | (M + H)+ = 225; t_Ret. = 1.1 | LCMSBAS |
| E-1o | 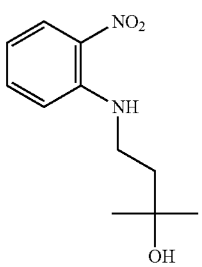 [SMILES: CC(C)(O)CCNc1ccccc1[N+](=O)[O-]] | (M + H)+ = 225; t_Ret. = 1.1 | LCMSBAS |
| E-1p | 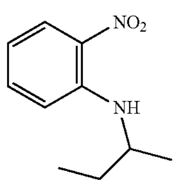 | (M + H)+ = 195; t_Ret. = 3.7 | MONI |
| E-1q | 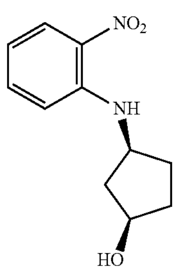 [SMILES: O=[N+]([O-])c1ccccc1N[C@H]1CC[C@@H](O)C1] | (M + H)+ = 223; t_Ret. = 0.8 | VAB |
| E-1r | 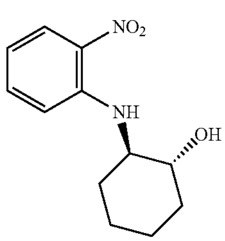 [SMILES: O=[N+]([O-])c1ccccc1N[C@@H]1CCCC[C@H]1O] | (M + H)+ = 237; t_Ret. = 3.2 | MONI |

TABLE 1-continued

| # | Structure | MS (M + H)+; t_Ret. HPLC [min] | HPLC-MS method |
|---|---|---|---|
| E-1s | 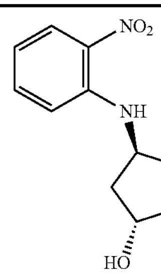 | (M + H)+ = 223; t_Ret. = 0.8 | VAB |
| E-1t | 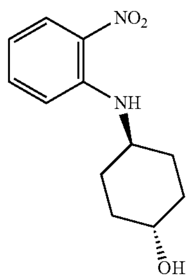 [SMILES: O=[N+]([O-])c1ccccc1N[C@H]1CC[C@H](O)CC1] | (M + H)+ = 237; t_Ret. = 1.6 | MONI |
| E-1u | 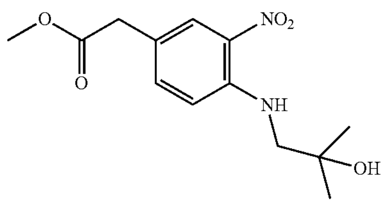 | (M + H)+ = 283; t_Ret. = 1.0 | LCMSBAS |
| E-1v | 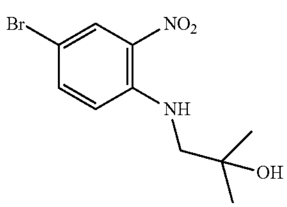 | (M + H)+ = 290; t_Ret. = 1.2 | LCMSBAS |
| E-1w | 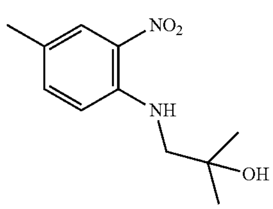 [SMILES: Cc1ccc(NCC(C)(C)O)c([N+](=O)[O-])c1] | commercially available | |
| E-1x | 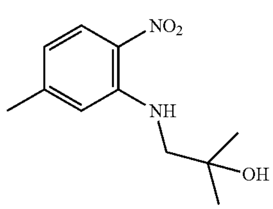 | commercially available | |
| E-1y | 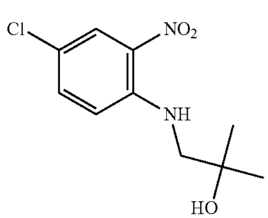 [SMILES: CC(C)(O)CNc1ccc(Cl)cc1[N+](=O)[O-]] | (M + H)+ = 245; t_Ret. = 1.8 | MONI |

TABLE 1-continued

| # | Structure | MS (M + H)+; t_Ret. HPLC [min] | HPLC-MS method |
|---|---|---|---|
| E-1z | 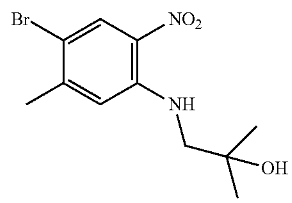 | (M + H)+ = 304; t_Ret. = 1.9 | YMC |
| E-1aa | 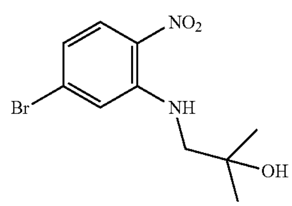 | commercially available | |
| E-1ab | 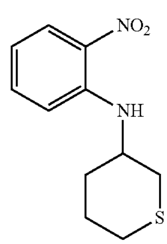 [SMILES: O=[N+]([O-])c1ccccc1NC1CCCSC1] | (M + H)+ = 239; t_Ret. = 2.2 | YMC |
| E-1ac | 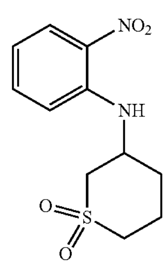 [SMILES: O=[N+]([O-])c1ccccc1NC1CCCS(=O)(=O)C1] | (M + H)+ = 271; t_Ret. = 1.7 | YMC |
| E-1ad | 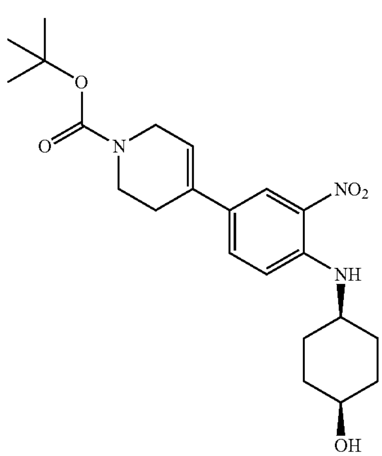 | (M + H)+ = 291; t_Ret. = 3.6 | MONI |

TABLE 1-continued

| # | Structure | MS (M + H)+; t_Ret. HPLC [min] | HPLC-MS method |
|---|---|---|---|
| E-1ae | 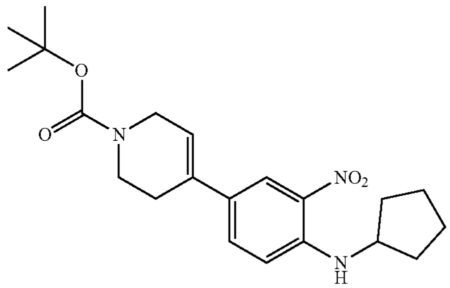 [SMILES: CC(C)(C)OC(=O)N1CC=C(c2ccc(NC3CCCC3)c([N+](=O)[O-])c2)CC1] | (M + H)+ = 388; t_Ret. = 2.1 | YMC |
| E-1af | 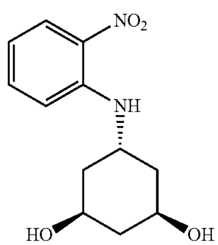 | (M + H)+ = 253; t_Ret. = 2.6 | MONI |
| E-1ag | 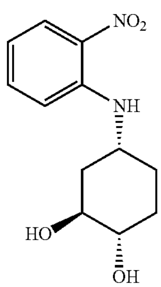 | (M + H)+ = 253; t_Ret. = 0.7 | VAB |
| E-1ah | 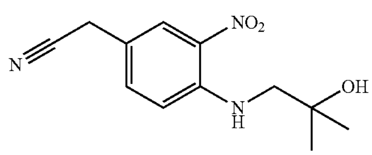 [SMILES: CC(C)(O)CNc1ccc(CC#N)cc1[N+](=O)[O-]] | (M + H)+ = 250; t_Ret. = 2.0 | YMC |
| E*-1a | 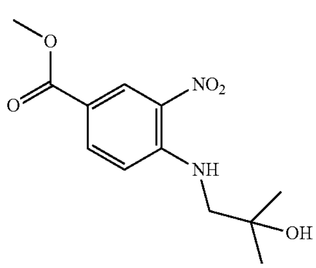 | (M + H)+ = 269; t_Ret. = 1.0 | LCMSBAS |
| E*-1b | 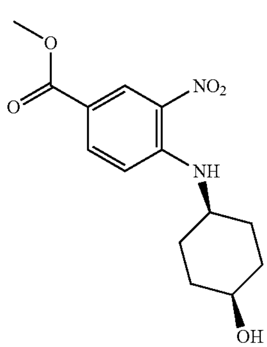 [SMILES: COC(=O)c1ccc(N[C@H]2CC[C@@H](O)CC2)c([N+](=O)[O-])c1] | (M + H)+ = 295; t_Ret. = 3.3 | MONI |

TABLE 1-continued

| # | Structure | MS (M + H)+; t_Ret. HPLC [min] | HPLC-MS method |
|---|---|---|---|
| E*-1c | 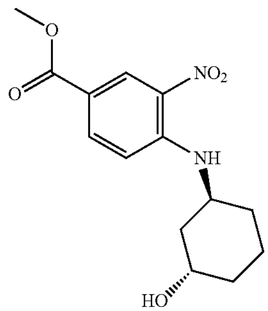 [SMILES: COC(=O)c1ccc(N[C@H]2CCC[C@H](O)C2)c([N+](=O)[O-])c1] | (M + H)+ = 295; t_Ret. = 3.2 | MONI |
| E*-1d | 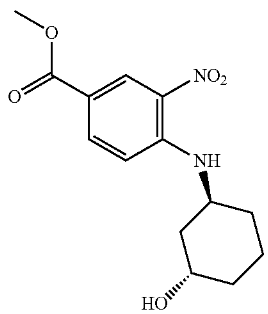 [SMILES: COC(=O)c1ccc(N[C@H]2CCC[C@H](O)C2)c([N+](=O)[O-])c1] | (M + H)+ = 295; t_Ret. = 1.4 | LCMSBAS |
| E*-1e | 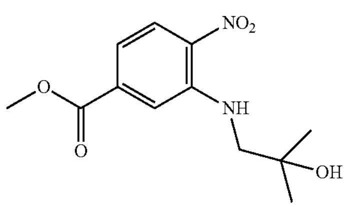 [SMILES: COC(=O)c1ccc([N+](=O)[O-])c(NCC(C)(C)O)c1] | (M + H)+ = 269; t_Ret. = 1.0 | LCMSBAS |
| E*-1f | 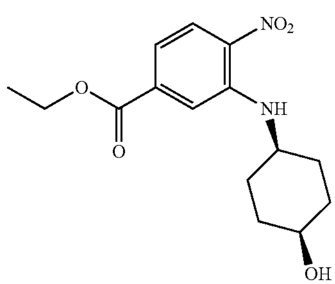 | (M + H)+ = 279; t_Ret. = 2.7 | MONI |
| E*-1g | 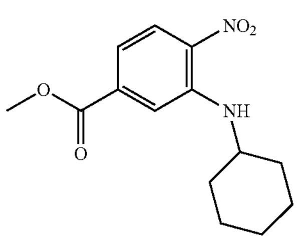 | (M + H)+ = 293; t_Ret. = 2.2 | YMC |

Experimental Procedure for the Synthesis of E-1ai

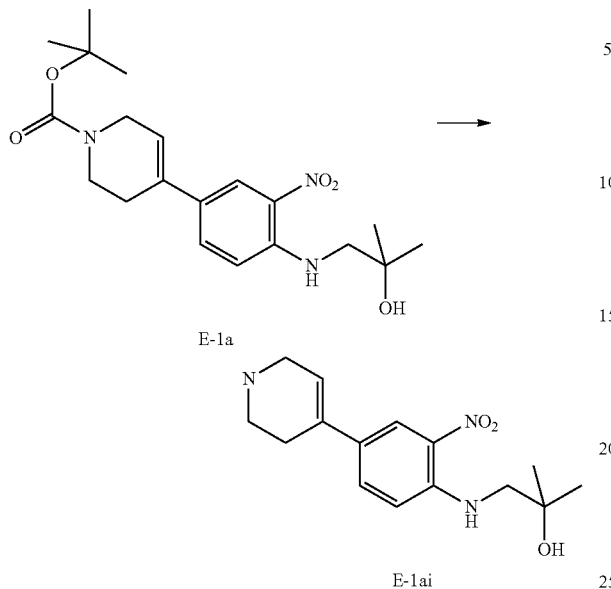

To a stirred solution of E-1a (0.40 g; 1.0 mmol) in methanol is added HCl in 1,4-dioxane (4.0 M; 20.0 mL; 80 eq.) at 20° C. The reaction mixture is stirred for 3 h at 20° C., then the solvent is evaporated. The crude product is taken up in sat. NaHCO$_3$ solution and extracted with ethyl acetate (3×30 mL), the combined organic layers are dried over MgSO$_4$ and filtrated. Evaporation of the solvent under reduced pressure yields the pure product E-1ai (yield: 86%—0.25 g, 0.86 mmol; HPLC-MS: (M+H)$^+$=292, t$_{Ret.}$=1.4 min, method MONI).

Experimental Procedure for the Synthesis of E-1ai

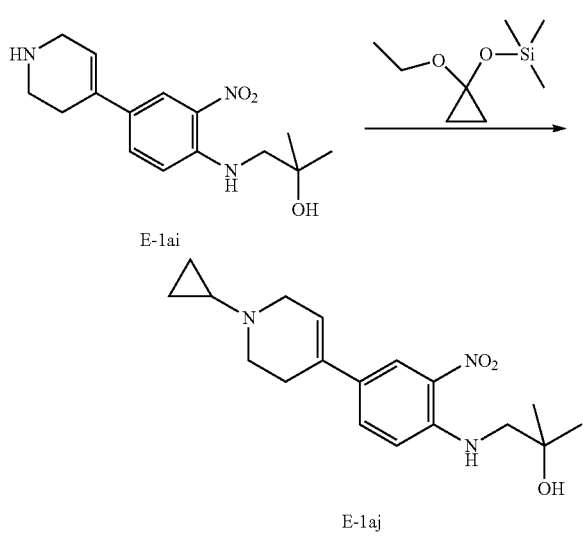

To a stirred solution of E-1ai (0.20 g; 0.69 mmol) in methanol (10.0 mL) is added (1-ethoxy-cyclopropoxy)-trimethylsilane (0.24 g, 1.37 mmol, 2.0 eq.), AcOH (0.59 mL; 10.30 mmol; 1.5 eq.), molecular sieves (1 g) and NaCNBH$_3$ (0.13 g; 2.06 mmol; 3.0 eq.). The reaction mixture is stirred for 18 h at 80° C., then the reaction is quenched by addition of an aqueous K$_2$CO$_3$ solution. The mixture is extracted with ethyl acetate (3×30 mL). The combined organic layers are dried over MgSO$_4$ and filtrated. The organic solvent is evaporated under reduced pressure and the crude product is purified using normal phase chromatography (hexane/EtOAc 80:20) to afford pure product E-1aj (yield: 44%—0.10 g, 0.23 mmol; HPLC-MS: (M+H)$^+$=332, t$_{Ret.}$=1.8 min, method MONI).

Experimental Procedure for the Synthesis of E-1ak

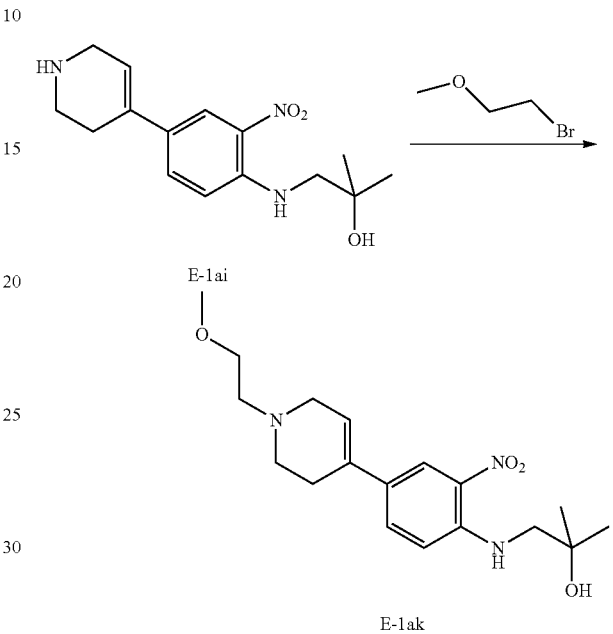

To a stirred solution of E-1ai (0.30 g; 1.03 mmol) in THF (10 mL) is added DIPEA (0.83 mL; 5.15 mmol; 5.0 eq.) followed by 1-bromo-2-methoxy-ethane (0.11 mL; 1.24 mmol; 1.2 eq.) at 20° C. The reaction mixture is stirred for 48 h at 20° C., then the reaction mixture is diluted with water (20 mL) and extracted with ethyl acetate (3×30 mL). The combined organic layers are dried over MgSO$_4$ and filtrated. The organic solvent is evaporated under reduced pressure and the crude product is purified using normal phase chromatography (hexane/EtOAc 80:20) to afford pure product E-ak (yield: 42%—0.15 g, 0.43 mmol; HPLC-MS: (M+H)$^+$=350, t$_{Ret.}$=1.5 min, method MONI).

Synthesis of Intermediates F-1 and F*-1

Experimental Procedure for the Synthesis of F-1a

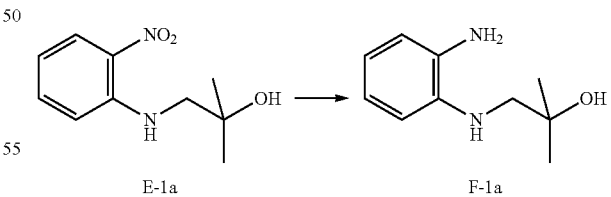

Starting material E-1a (19.3 g, 92.1 mmol) is dissolved in a MeOH/DCM mixture (1:1, 300 mL) and after addition of Pd/C (2.5 g, 3 mol %) the reaction mixture is stirred at 20° C. under a pressure of 5 bar hydrogen for 16 h. After full conversion the reaction mixture is filtrated over Celite® and the solvent is evaporated under reduced pressure. The intermediate F-1a is used for further synthesis without any additional purification (yield: 99%—16.3 g, 90.5 mmol; HPLC-MS: (M+H)$^+$=181, t$_{Ret.}$=1.5 min, method MONI).

The following intermediates F-1 and F*-1 (table 2) are available in an analogous manner starting from different nitro precursors E-1 and E*-1.

TABLE 2

| # | Structure | MS (M + H)+; $t_{Ret}$ HPLC [min] | HPLC-MS method |
|---|---|---|---|
| F-1a | 2-aminophenyl-NH-CH2-C(CH3)2-OH | (M + H)+ = 181; $t_{Ret.}$ = 1.5 | MONI |
| F-1b | 2-aminophenyl-NH-(trans-4-hydroxycyclohexyl) | (M + H)+ = 207; $t_{Ret.}$ = 0.7 | VAB |
| F-1c | 2-aminophenyl-NH-cyclopentyl | (M + H)+ = 177; $t_{Ret.}$ = 1.9 | MONI |
| F-1d | 2-aminophenyl-NH-cyclohexyl | commercially available | |
| F-1e | 2-aminophenyl-NH-(cis-3-hydroxycyclohexyl) | (M + H)+ = 207; $t_{Ret}$ = 0.7 | VAB |

TABLE 2-continued

| # | Structure | MS (M + H)+; $t_{Ret}$ HPLC [min] | HPLC-MS method |
|---|---|---|---|
| F-1f | *2-aminophenyl-NH-(1S,3S)-3-hydroxycyclohexyl* | (M + H)+ = 207; $t_{Ret.}$ = 0.7 | VAB |
| F-1g | *2-aminophenyl-NH-(1R,3S)-3-hydroxycyclohexyl* | (M + H)+ = 207; $t_{Ret}$ = 0.6 | VAB |
| F-1h | *2-aminophenyl-NH-(1R,3R)-3-hydroxycyclohexyl* | (M + H)+ = 207; $t_{Ret.}$ = 0.6 | VAB |
| F-1i | *2-aminophenyl-NH-(3S)-tetrahydropyran-3-yl* | (M + H)+ = 193; $t_{Ret.}$ = 1.5 | MONI |
| F-1j | *2-aminophenyl-NH-(3R)-tetrahydropyran-3-yl* | (M + H)+ = 193; $t_{Ret}$ = 1.5 | MONI |
| F-1k | *2-aminophenyl-NH-cyclobutyl* | (M + H)+ = 163; $t_{Ret.}$ = 1.7 | MONI |

TABLE 2-continued

| # | Structure | MS (M + H)+; t_Ret HPLC [min] | HPLC-MS method |
|---|---|---|---|
| F-1l | 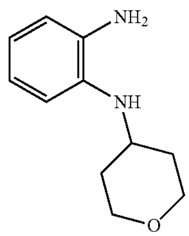 [SMILES: Nc1ccccc1NC1CCOCC1] | (M + H)+ = 193; t_Ret. = 1.5 | MONI |
| F-1m | 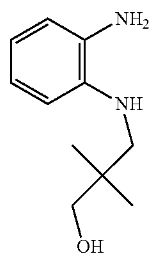 | (M + H)+ = 195; t_Ret. = 0.8 | LCMSBAS |
| F-1n | 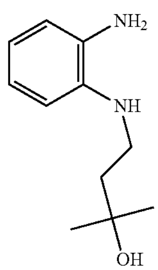 | (M + H)+ = 195; t_Ret. = 0.8 | LCMSBAS |
| F-1o | 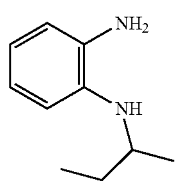 | (M + H)+ = 165; t_Ret. = 3.3 | MONI |
| F-1p | 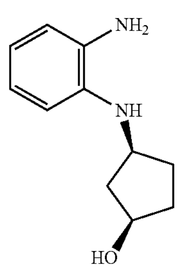 [SMILES: Nc1ccccc1N[C@H]1CC[C@@H](O)C1] | (M + H)+ = 193; t_Ret. = 0.7 | VAB |
| F-1q | 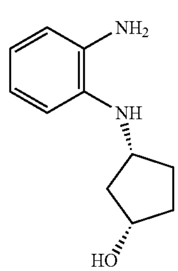 [SMILES: Nc1ccccc1N[C@@H]1CC[C@H](O)C1] | (M + H)+ = 193; t_Ret. = 0.7 | VAB |

TABLE 2-continued

| # | Structure | MS (M + H)+; $t_{Ret}$ HPLC [min] | HPLC-MS method |
|---|---|---|---|
| F-1r | 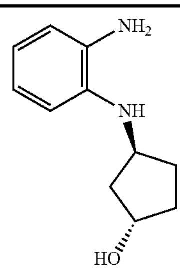 | (M + H)+ = 193; $t_{Ret.}$ = 0.6 | VAB |
| F-1s | 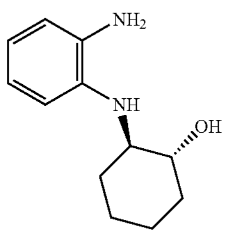 [SMILES: Nc1ccccc1N[C@@H]1CCCC[C@H]1O] | (M + H)+ = 207; $t_{Ret.}$ = 1.5 | YMC |
| F-1t | 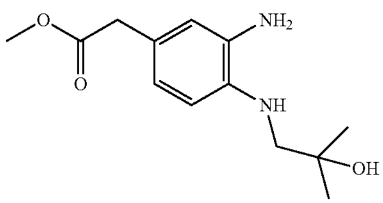 [SMILES: COC(=O)Cc1ccc(NCC(C)(C)O)c(N)c1] | (M + H)+ = 253; $t_{Ret.}$ = 0.8 | LCMSBAS |
| F-1u | 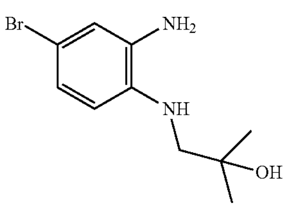 | (M + H)+ = 259/261; $t_{Ret.}$ = 1.6 | MONI |
| F-1v | 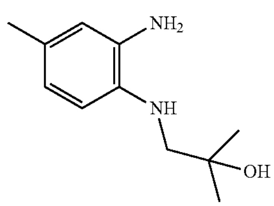 | (M + H)+ = 195; $t_{Ret.}$ = 3.1 | MONI |
| F-1w | 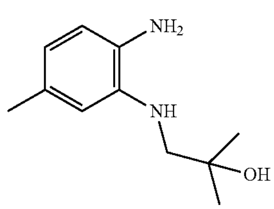 | (M + H)+ = 195; $t_{Ret.}$ = 1.5 | MONI |
| F-1x | 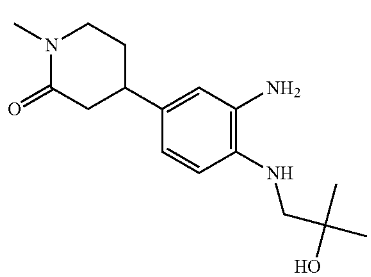 [SMILES: CN1CCC(c2ccc(NCC(C)(C)O)c(N)c2)CC1=O] | (M + H)+ = 292; $t_{Ret.}$ = 1.4 | MONI |

TABLE 2-continued

| # | Structure | MS (M + H)+; $t_{Ret}$ HPLC [min] | HPLC-MS method |
|---|---|---|---|
| F-1y | 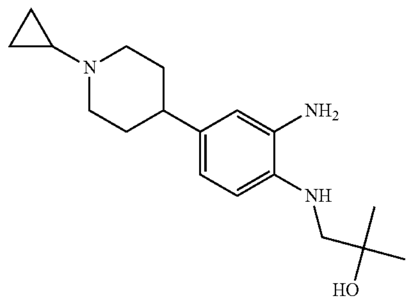 [SMILES: CC(C)(O)CNc1ccc(C2CCN(C3CC3)CC2)cc1N] | (M + H)+ = 304; $t_{Ret.}$ = 1.5 | MONI |
| F-1z | 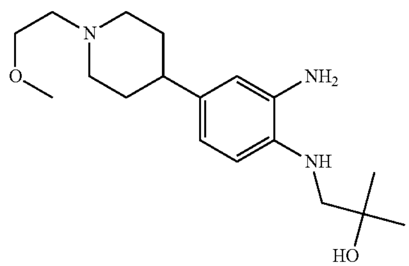 [SMILES: COCCN1CCC(c2ccc(NCC(C)(C)O)c(N)c2)CC1] | (M + H)+ = 322; $t_{Ret.}$ = 1.4 | MONI |
| F-1aa | 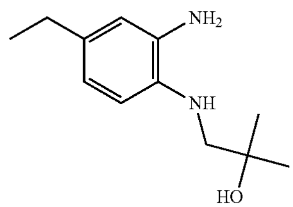 | (M + H)+ = 209; $t_{Ret.}$ = 3.0 | MONI |
| F-1ab | 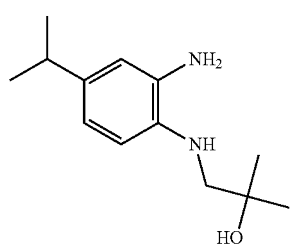 [SMILES: CC(C)c1ccc(NCC(C)(C)O)c(N)c1] | (M + H)+ = 223; $t_{Ret.}$ = 1.7 | MONI |
| F-1ac | 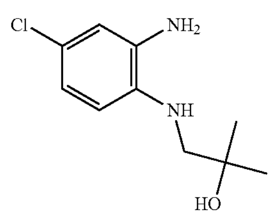 | (M + H)+ = 215; $t_{Ret.}$ = 1.6 | MONI |
| F-1ad | 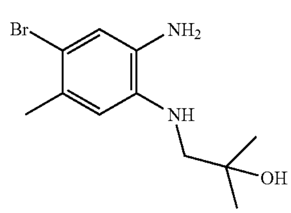 | (M + H)+ = 273/275; $t_{Ret.}$ = 1.6 | MONI |

TABLE 2-continued

| # | Structure | MS (M + H)+; t_Ret HPLC [min] | HPLC-MS method |
|---|---|---|---|
| F-1ae | 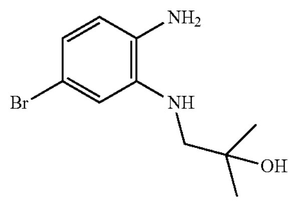 | (M + H)+ = 259/261; t_Ret. = 1.6 | MONI |
| F-1af | 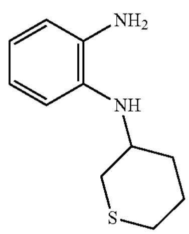 [SMILES: Nc1ccccc1NC1CCCSC1] | (M + H)+ = 209; t_Ret. = 1.4 | YMC |
| F-1ag | 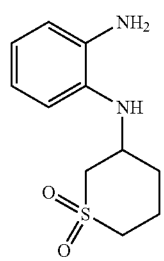 [SMILES: Nc1ccccc1NC1CCCS(=O)(=O)C1] | (M + H)+ = 241; t_Ret. = 1.5 | YMC |
| F-1ah | 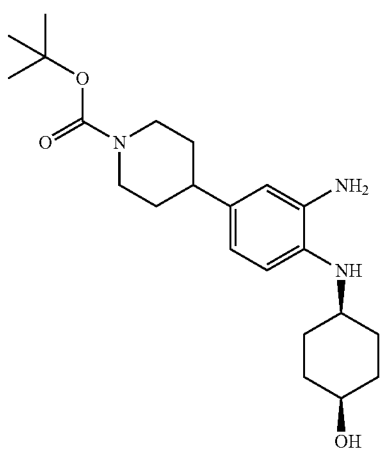 [SMILES: CC(C)(C)OC(=O)N1CCC(c2ccc(N[C@H]3CC[C@@H](O)CC3)c(N)c2)CC1] | (M + H)+ = 390; t_Ret. = 1.8 | YMC |
| F-1ai | 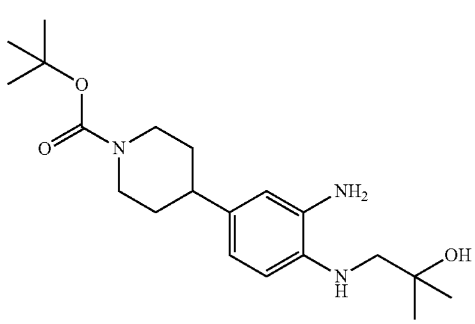 [SMILES: CC(C)(O)CNc1ccc(C2CCN(C(=O)OC(C)(C)C)CC2)cc1N] | (M + H)+ = 364; t_Ret. = 0.9 | VAB |

TABLE 2-continued

| # | Structure | MS (M + H)+; t_Ret HPLC [min] | HPLC-MS method |
|---|---|---|---|
| F-1aj | 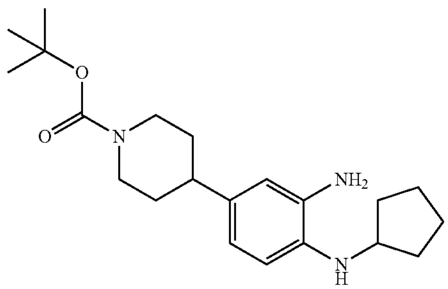 [SMILES: CC(C)(C)OC(=O)N1CCC(c2ccc(NC3CCCC3)c(N)c2)CC1] | (M + H)+ = 360; t_Ret. = 2.0 | YMC |
| F-1ak | 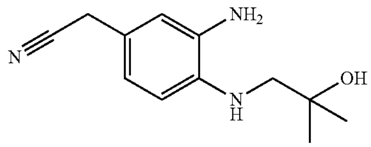 [SMILES: CC(C)(O)CNc1ccc(CC#N)cc1N] | (M + H)+ = 220; t_Ret. = 1.8 | YMC |
| F-1al | 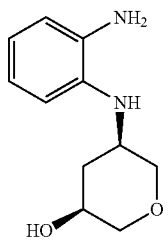 [SMILES: Nc1ccccc1N[C@H]1COC[C@@H](O)C1] | (M + H)+ = 209; t_Ret. = 1.4 | YMC |
| F-1am | 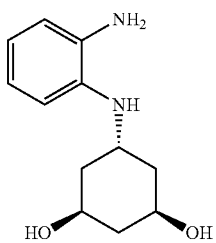 | (M + H)+ = 223; t_Ret. = 2.0 | MONI |
| F-1an | 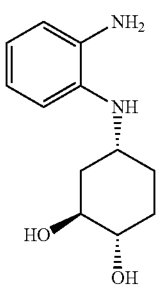 [SMILES: Nc1ccccc1N[C@@H]1CC[C@H](O)[C@@H](O)C1] | (M + H)+ = 223; t_Ret. = 0.6 | VAB |
| F*-1a | 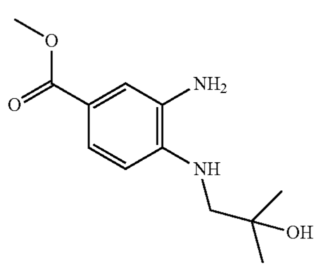 [SMILES: COC(=O)c1ccc(NCC(C)(C)O)c(N)c1] | (M + H)+ = 239; t_Ret. = 0.3 | MONI |

TABLE 2-continued

| # | Structure | MS (M + H)+; t_Ret HPLC [min] | HPLC-MS method |
|---|---|---|---|
| F*-1b | methyl 3-amino-4-((trans-4-hydroxycyclohexyl)amino)benzoate | (M + H)+ = 265; t_Ret. = 1.5 | YMC |
| F*-1c | methyl 3-amino-4-((cis-3-hydroxycyclohexyl)amino)benzoate | (M + H)+ = 265; t_Ret. = 1.5 | YMC |
| F*-1d | methyl 3-amino-4-((trans-3-hydroxycyclohexyl)amino)benzoate | (M + H)+ = 265; t_Ret. = 1.5 | YMC |
| F*-1e | ethyl 4-amino-3-((trans-4-hydroxycyclohexyl)amino)benzoate | (M + H)+ = 279; t_Ret. = 2.8 | MONI |
| F*-1f | ethyl 4-amino-3-(cyclohexylamino)benzoate | (M + H)+ = 263; t_Ret. = 1.3 | YMC |

TABLE 2-continued

| # | Structure | MS (M + H)+; $t_{Ret}$ HPLC [min] | HPLC-MS method |
|---|---|---|---|
| F*-1g | ![structure] | (M + H)+ = 239; $t_{Ret.}$ = 1.5 | YMC |
| F*-1h | ![structure] | (M + H)+ = 223; $t_{Ret.}$ = 0.8 | LCMSBAS |

Synthesis of Intermediates A-1 and A*-1
Procedure for the Synthesis of Intermediate A-1

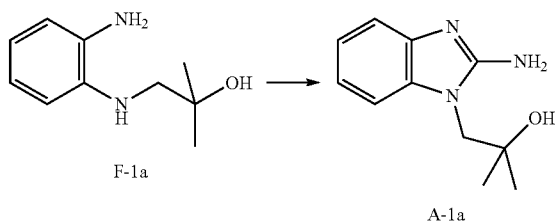

In a three-necked round bottom flask equipped with addition funnel and a thermometer starting material F-1a (16.3 g, 90.5 mmol) is dissolved in a mixture of EtOH and DCM (1:1, 300 mL). To this reaction mixture a solution of cyanogen bromide in DCM (3 M, 30.8 mL, 1.0 eq.) is added slowly via the addition funnel. The reaction temperature is maintained below 20° C. and the reaction is stirred for 16 h. After full conversion, the reaction is diluted with DCM and extracted with a 2 M NaOH solution. The organic phase is dried over MgSO$_4$, filtrated and the solvent is evaporated under reduced pressure. The crude product is purified using normal phase chromatography (DCM/MeOH, 95:5) to afford pure product A-1a (yield: 80%—14.8 g, 72.4 mmol; HPLC-MS: (M+H)+=206, $t_{Ret.}$=0.7 min, method LCMS-BAS).

The following intermediates A-1 and A*-1 (table 3) are available in an analogous manner starting from different anilines F-1 and F*-1.

TABLE 3

| # | Structure | MS (M + H)+; $t_{Ret}$ HPLC [min] | HPLC-MS method |
|---|---|---|---|
| A-1a | ![structure] | (M + H)+ = 206; $t_{Ret.}$ = 0.7 | LCMSBAS |
| A-1b | ![structure] | (M + H)+ = 232; $t_{Ret.}$ = 0.8 | LCMSBAS |

TABLE 3-continued
| # | Structure | MS (M + H)⁺; $t_{Ret}$ HPLC [min] | HPLC-MS method |
|---|---|---|---|
| A-1c | 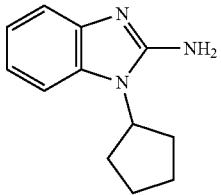 [SMILES: Nc1nc2ccccc2n1C1CCCC1] | commercially available | |
| A-1d | 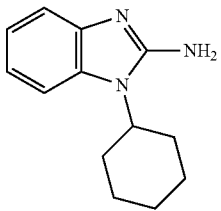 [SMILES: Nc1nc2ccccc2n1C1CCCCC1] | commercially available | |
| A-1e | 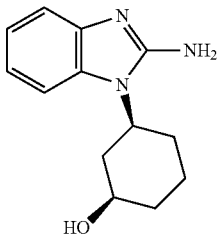 [SMILES: Nc1nc2ccccc2n1[C@H]1CCC[C@@H](O)C1] | (M + H)⁺ = 232; $t_{Ret.}$ = 0.8 | LCMSBAS |
| A-1f | 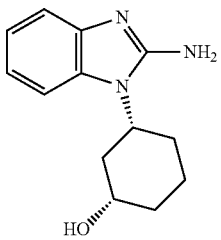 [SMILES: Nc1nc2ccccc2n1[C@@H]1CCC[C@H](O)C1] | (M + H)⁺ = 232; $t_{Ret.}$ = 0.8 | LCMSBAS |
| A-1g | 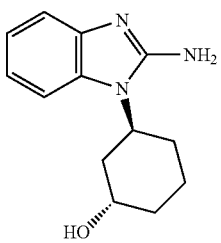 [SMILES: Nc1nc2ccccc2n1[C@H]1CCC[C@H](O)C1] | (M + H)⁺ = 232; $t_{Ret.}$ = 0.7 | VAB |
| A-1h | 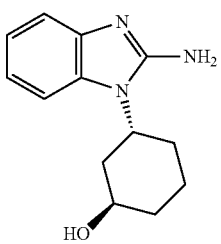 [SMILES: Nc1nc2ccccc2n1[C@@H]1CCC[C@@H](O)C1] | (M + H)⁺ = 232; $t_{Ret.}$ = 0.7 | VAB |

TABLE 3-continued

| # | Structure | MS (M + H)+; $t_{Ret}$ HPLC [min] | HPLC-MS method |
|---|---|---|---|
| A-1i | (benzimidazol-2-amine with (R)-tetrahydropyran-3-yl) | (M + H)+ = 218; $t_{Ret.}$ = 1.4 | MONI |
| A-1j | (benzimidazol-2-amine with (S)-tetrahydropyran-3-yl) | (M + H)+ = 218; $t_{Ret.}$ = 1.4 | MONI |
| A-1k | (benzimidazol-2-amine with cyclobutyl) | (M + H)+ = 188; $t_{Ret.}$ = 1.5 | MONI |
| A-1l | (benzimidazol-2-amine with tetrahydropyran-4-yl) | (M + H)+ = 218; $t_{Ret.}$ = 1.4 | MONI |
| A-1m | (benzimidazol-2-amine with 3-hydroxy-2,2-dimethylpropyl) | (M + H)+ = 220; $t_{Ret.}$ = 0.8 | LCMSBAS |
| A-1n | (benzimidazol-2-amine with 3-hydroxy-3-methylbutyl) | (M + H)+ = 220; $t_{Ret.}$ = 0.8 | LCMSBAS |
| A-1o | (benzimidazol-2-amine with isobutyl) | (M + H)+ = 190; $t_{Ret.}$ = 2.9 | MONI |

TABLE 3-continued
| # | Structure | MS (M + H)+; $t_{Ret}$ HPLC [min] | HPLC-MS method |
|---|---|---|---|
| A-1p | 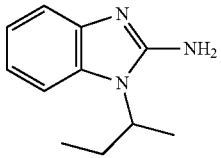 | (M + H)+ = 190; $t_{Ret.}$ = 2.9 | MONI |
| A-1q | 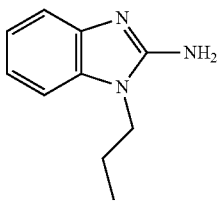 | commercially available | |
| A-1r | 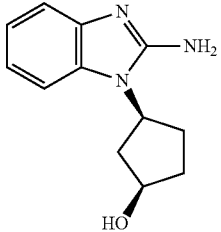 [SMILES: Nc1nc2ccccc2n1[C@H]1CC[C@@H](O)C1] | (M + H)+ = 218; $t_{Ret.}$ = 0.6 | VAB |
| A-1s | 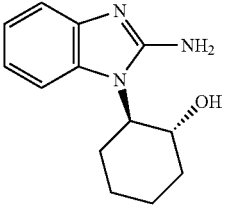 [SMILES: Nc1nc2ccccc2n1[C@@H]1CCCC[C@H]1O] | (M + H)+ = 231; $t_{Ret.}$ = 2.8 | MONI |
| A-1t | 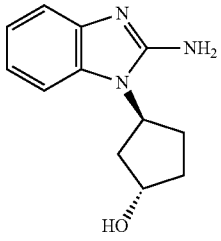 [SMILES: Nc1nc2ccccc2n1[C@H]1CC[C@H](O)C1] | (M + H)+ = 218; $t_{Ret.}$ = 0.b | VAB |
| A-1u | 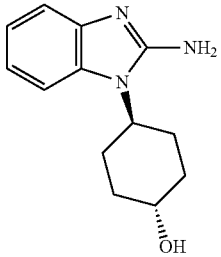 [SMILES: Nc1nc2ccccc2n1[C@H]1CC[C@H](O)CC1] | (M + H)+ = 232; $t_{Ret.}$ = 1.5 | MONI |

TABLE 3-continued

| # | Structure | MS (M + H)+; $t_{Ret}$ HPLC [min] | HPLC-MS method |
|---|---|---|---|
| A-1v | 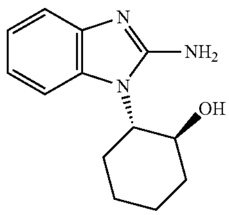 [SMILES: Nc1nc2ccccc2n1[C@H]1CCCC[C@@H]1O] | (M + H)+ = 232; $t_{Ret.}$ = 1.5 | MONI |
| A-1w | 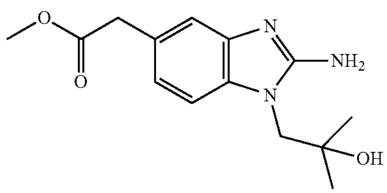 [SMILES: COC(=O)Cc1ccc2c(c1)nc(N)n2CC(C)(C)O] | (M + H)+ = 278; $t_{Ret.}$ = 0.8 | LCMSBAS |
| A-1x | 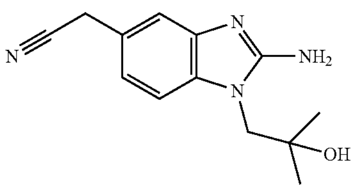 [SMILES: CC(C)(O)Cn1c(N)nc2cc(CC#N)ccc21] | (M + H)+ = 245; $t_{Ret.}$ = 1.4 | YMC |
| A-1y | 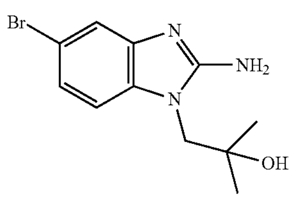 | (M + H)+ = 284/286; $t_{Ret.}$ = 1.6 | MONI |
| A-1z | 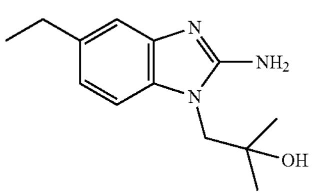 [SMILES: CCc1ccc2c(c1)nc(N)n2CC(C)(C)O] | (M + H)+ = 234; $t_{Ret.}$ = 2.7 | MONI |
| A-1aa | 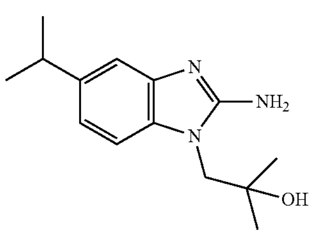 [SMILES: CC(C)c1ccc2c(c1)nc(N)n2CC(C)(C)O] | (M + H)+ = 248; $t_{Ret.}$ = 2.6 | MONI |
| A-1ab | 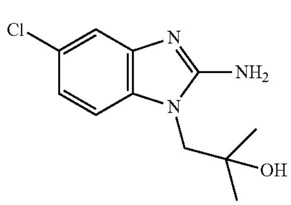 [SMILES: CC(C)(O)Cn1c(N)nc2cc(Cl)ccc21] | (M + H)+ = 240; $t_{Ret.}$ = 2.6 | YMC |

TABLE 3-continued

| # | Structure | MS (M + H)+; t_Ret HPLC [min] | HPLC-MS method |
|---|---|---|---|
| A-1ac | 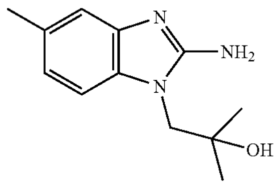 [SMILES: Cc1ccc2c(c1)nc(N)n2CC(C)(C)O] | (M + H)+ = 220; t_Ret. = 2.6 | MONI |
| A-1ad | 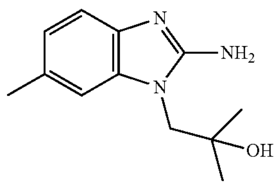 [SMILES: Cc1ccc2nc(N)n(CC(C)(C)O)c2c1] | (M + H)+ = 220; t_Ret. = 3.7 | MONI |
| A-1ae | 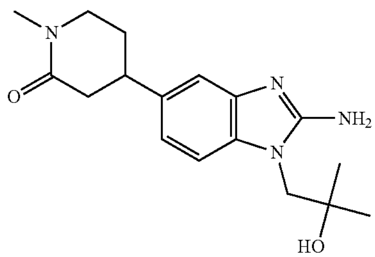 [SMILES: CN1CCC(c2ccc3c(c2)nc(N)n3CC(C)(C)O)CC1=O] | (M + H)+ = 317; t_Ret. = 1.4 | MONI |
| A-1af | 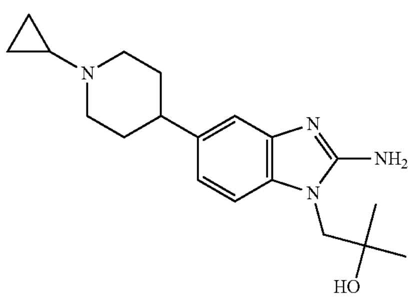 [SMILES: CC(C)(O)Cn1c(N)nc2cc(C3CCN(C4CC4)CC3)ccc21] | (M + H)+ = 329; t_Ret. = 1.5 | MONI |
| A-1ag | 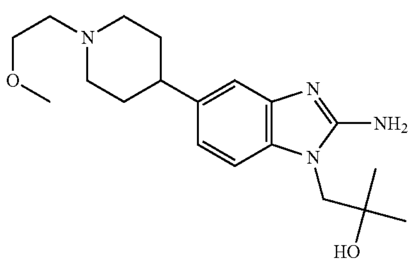 [SMILES: COCCN1CCC(c2ccc3c(c2)nc(N)n3CC(C)(C)O)CC1] | (M + H)+ = 347; t_Ret. = 1.4 | MONI |
| A-1ah | 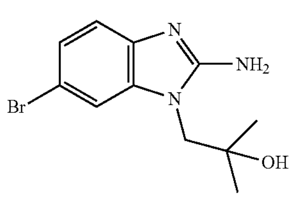 [SMILES: CC(C)(O)Cn1c(N)nc2ccc(Br)cc21] | (M + H)+ = 284/286; t_Ret. = 1.6 | MONI |
| A-1ai | 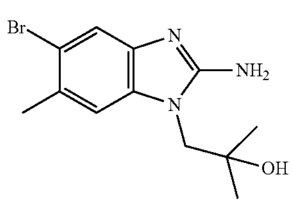 [SMILES: Cc1cc2c(cc1Br)nc(N)n2CC(C)(C)O] | (M + H)+ = 298/300; t_Ret. = 1.6 | MONI |

TABLE 3-continued

| # | Structure | MS (M + H)+; t_Ret HPLC [min] | HPLC-MS method |
|---|---|---|---|
| A-1aj | 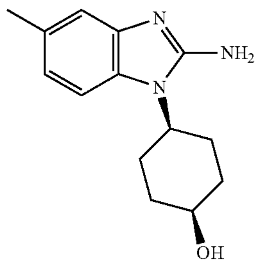 [SMILES: Cc1ccc2c(c1)nc(N)n2[C@H]1CC[C@@H](O)CC1] | (M + H)+ = 246; t_Ret. = 0.7 | VAB |
| A-1ak | 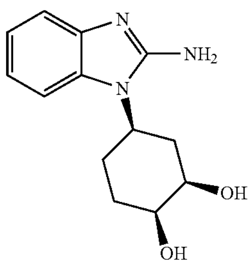 [SMILES: Nc1nc2ccccc2n1[C@@H]1CC[C@H](O)[C@H](O)C1] | (M + H)+ = 248; t_Ret. = 0.4 | LCMSBAS |
| A-1al | 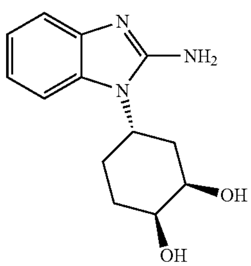 [SMILES: Nc1nc2ccccc2n1[C@H]1CC[C@H](O)[C@H](O)C1] | (M + H)+ = 248; t_Ret. = 0.6 | LCMSBAS |
| A-1am | 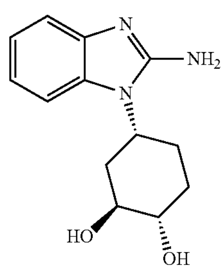 [SMILES: Nc1nc2ccccc2n1[C@@H]1CC[C@H](O)[C@@H](O)C1] | (M + H)+ = 248; t_Ret. = 0.6 | LCMSBAS |
| A-1an | 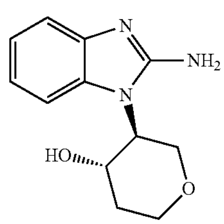 [SMILES: Nc1nc2ccccc2n1[C@H]1COCC[C@@H]1O] | (M + H)+ = 233; t_Ret. = 1.3 | YMC |
| A-1ao | 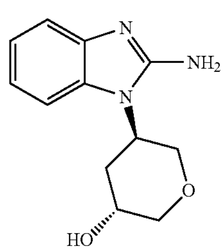 [SMILES: Nc1nc2ccccc2n1[C@H]1COC[C@H](O)C1] | (M + H)+ = 234; t_Ret. = 1.3 | YMC |

TABLE 3-continued

| # | Structure | MS (M + H)+; $t_{Ret}$ HPLC [min] | HPLC-MS method |
|---|---|---|---|
| A-1ap | 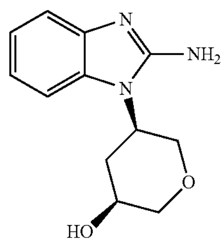 [SMILES: Nc1nc2ccccc2n1[C@H]1COC[C@@H](O)C1] | (M + H)+ = 234; $t_{Ret.}$ = 1.3 | YMC |
| A-1aq | 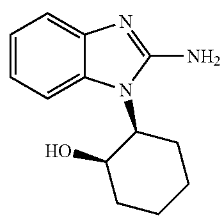 [SMILES: Nc1nc2ccccc2n1[C@H]1CCCC[C@H]1O] | (M + H)+ = 232; $t_{Ret.}$ = 1.5 | YMC |
| A-1ar | 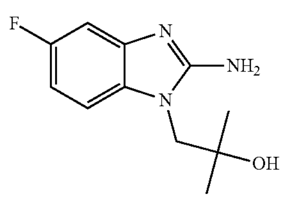 [SMILES: CC(C)(O)Cn1c(N)nc2cc(F)ccc21] | (M + H)+ = 224; $t_{Ret.}$ = 1.5 | YMC |
| A-1as | 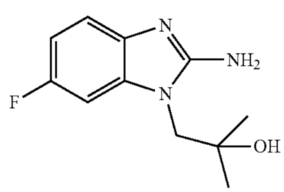 [SMILES: CC(C)(O)Cn1c(N)nc2ccc(F)cc21] | (M + H)+ = 224; $t_{Ret.}$ = 1.5 | YMC |
| A-1at | 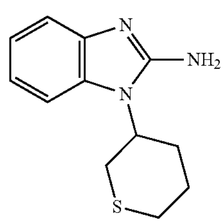 [SMILES: Nc1nc2ccccc2n1C1CCCSC1] | (M + H)+ = 234; $t_{Ret.}$ = 1.4 | YMC |
| A-1au | 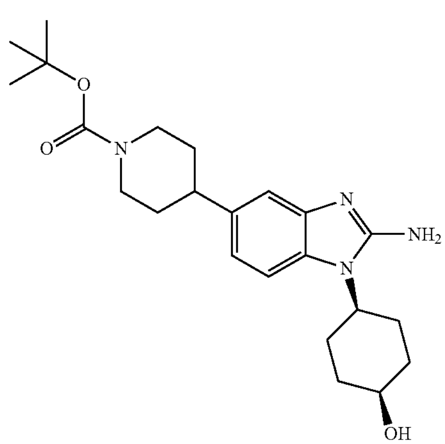 [SMILES: CC(C)(C)OC(=O)N1CCC(c2ccc3c(c2)nc(N)n3[C@H]2CC[C@@H](O)CC2)CC1] | (M + H)+ = 415; $t_{Ret.}$ = 1.6 | YMC |

TABLE 3-continued

| # | Structure | MS (M + H)+; t_Ret HPLC [min] | HPLC-MS method |
|---|---|---|---|
| A-1av | 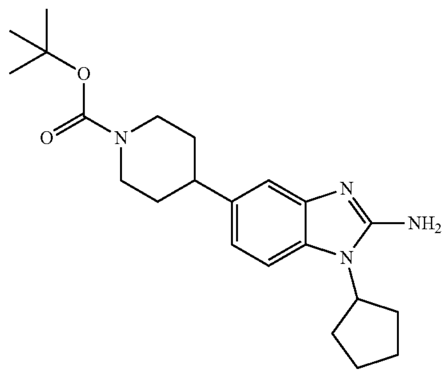 [SMILES: CC(C)(C)OC(=O)N1CCC(c2ccc3c(c2)nc(N)n3C2CCCC2)CC1] | (M + H)+ = 385; t_Ret. = 1.8 | YMC |
| A-1aw | 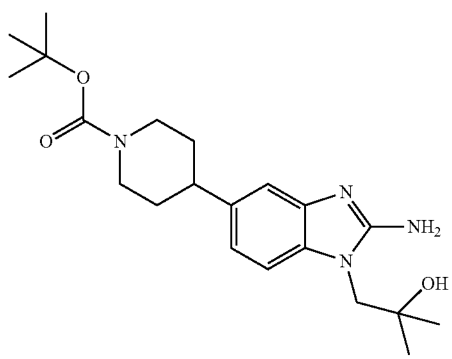 [SMILES: CC(C)(O)Cn1c(N)nc2cc(C3CCN(C(=O)OC(C)(C)C)CC3)ccc21] | (M + H)+ = 389; t_Ret. = 0.9 | VAB |
| A-1ax | 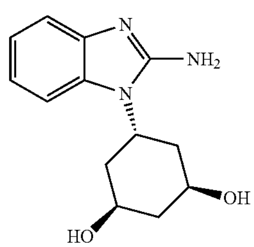 [SMILES: Nc1nc2ccccc2n1[C@H]1C[C@H](O)C[C@H](O)C1] | (M + H)+ = 248; t_Ret. = 2.1 | MONI |
| A*-1a | 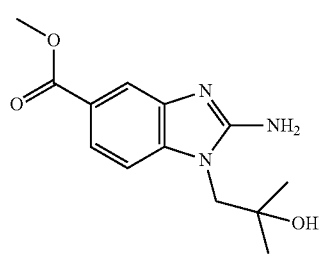 [SMILES: COC(=O)c1ccc2c(c1)nc(N)n2CC(C)(C)O] | (M + H)+ = 264; t_Ret. = 0.8 | LCMSBAS |
| A*-1b | 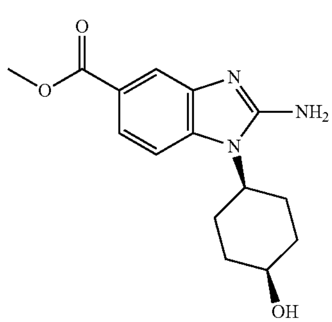 [SMILES: COC(=O)c1ccc2c(c1)nc(N)n2[C@H]1CC[C@@H](O)CC1] | (M + H)+ = 290; t_Ret. = 1.4 | YMC |

TABLE 3-continued

| # | Structure | MS (M + H)+; $t_{Ret}$ HPLC [min] | HPLC-MS method |
|---|---|---|---|
| A*-1c | 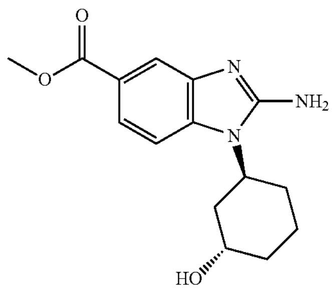 [SMILES: COC(=O)c1ccc2c(c1)nc(N)n2[C@H]1CCC[C@H](O)C1] | (M + H)+ = 290; $t_{Ret.}$ = 1.4 | YMC |
| A*-1d | 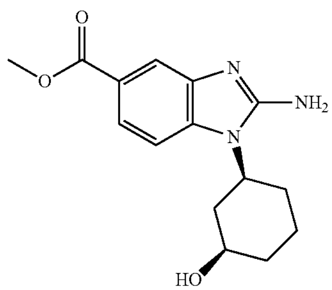 [SMILES: COC(=O)c1ccc2c(c1)nc(N)n2[C@H]1CCC[C@@H](O)C1] | (M + H)+ = 290; $t_{Ret.}$ = 1.4 | YMC |
| A*-1e | 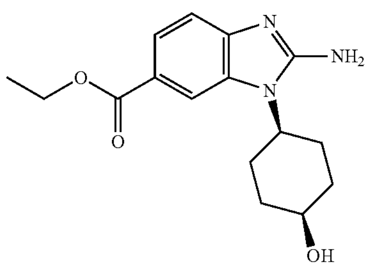 [SMILES: CCOC(=O)c1ccc2nc(N)n([C@H]3CC[C@@H](O)CC3)c2c1] | (M + H)+ = 304; $t_{Ret.}$ = 2.6 | MONI |
| A*-1f | 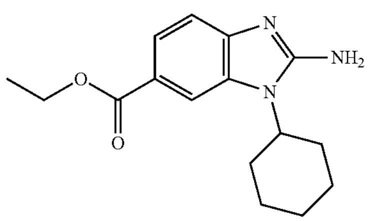 [SMILES: CCOC(=O)c1ccc2nc(N)n(C3CCCCC3)c2c1] | (M + H)+ = 290; $t_{Ret.}$ = 1.8 | YMC |
| A*-1g | 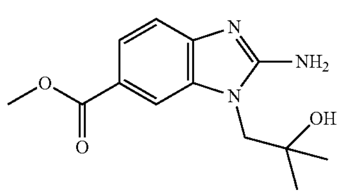 | (M + H)+ = 364; $t_{Ret.}$ = 1.5 | YMC |
| A*-1h | 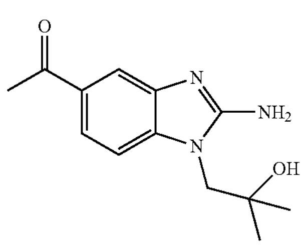 [SMILES: CC(=O)c1ccc2c(c1)nc(N)n2CC(C)(C)O] | (M + H)+ = 248; $t_{Ret.}$ = 1.0 | LCMSBAS |

Experimental Procedure for the Synthesis of A-1ay

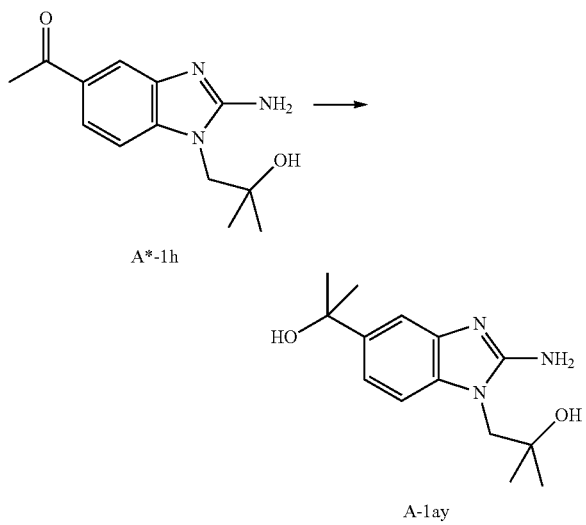

A*-1h

A-1ay

To a well stirred solution of A*-1h (3.6 g, 14.6 mmol) in dry THF (100 mL) is added a solution of MeMgCl (38.8 mL, 38.8 mmol, 2.7 equiv.) at 0° C. The resultant reaction mixture is then allowed to stir for 4 h. To the reaction mixture is added a NH$_4$Cl solution (20 mL) and the mixture is extracted with EtOAc (3×250 mL). The combined organic phases are washed sequentially with water (2×500 mL) and brine (500 mL). The organic extract is dried (Na$_2$SO$_4$), filtered and the filtrate is concentrated under reduced pressure to provide the crude product which is separated by normal phase column chromatography using ethyl acetate to afford the desired product A-1ay (yield: 34%—1.3 g, 4.9 mmol; HPLC-MS: (M+H)$^+$=264, t$_{Ret.}$=1.8 min, method YMC).

Experimental Procedure for the Synthesis of A-1az

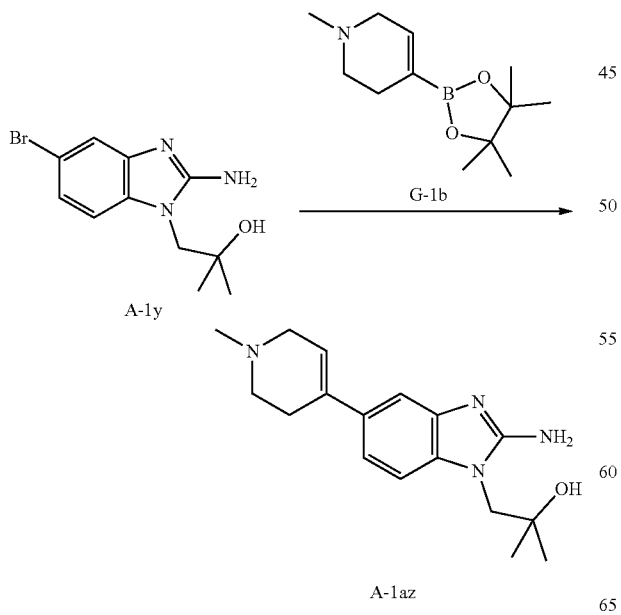

A-1y

A-1az

To a well stirred solution of A-1y (10.0 g, 35.0 mmol), G-1b (8.6 g, 39.1 mmol, 1.1 eq.) and Cs$_2$CO$_3$ (28.7 g, 88.3 mmol, 2.5 eq.) in a solvent mixture of degassed 1,4-dioxane (120 mL) and water (12 mL) at 20° C. under Ar-atmosphere is added [1,1-bis(diphenylphosphino)ferrocene]dichloropalladium(II) complex with dichloromethane (2.9 g, 4.2 mol, 12 mol %) portion wise. The resultant reaction mixture is then allowed to stir at 100° C. for 18 h. The reaction mixture is cooled to 20° C., diluted with water (250 mL) and extracted with EtOAc (3×250 mL). The combined organic phases are washed sequentially with water (2×500 mL) and brine (500 mL). The organic extract is dried (Na$_2$SO$_4$), filtered and the filtrate is concentrated under reduced pressure to provide the crude product which on trituration with a solvent mixture of hexane/DCM (3:1) and drying furnishes the desired product A-1az which is used directly for next step (yield: 66%—6.9 g, 23.1 mmol; HPLC-MS: (M+H)$^+$=301, t$_{Ret.}$=1.3 min, method MONI)

Experimental Procedure for the Synthesis of A-1ba

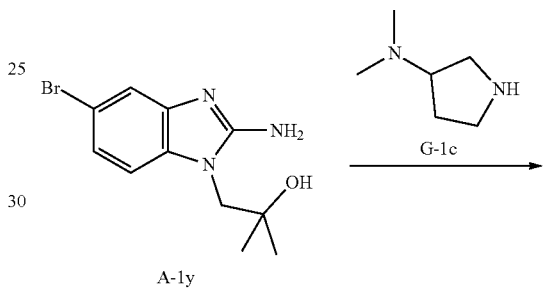

A-1y

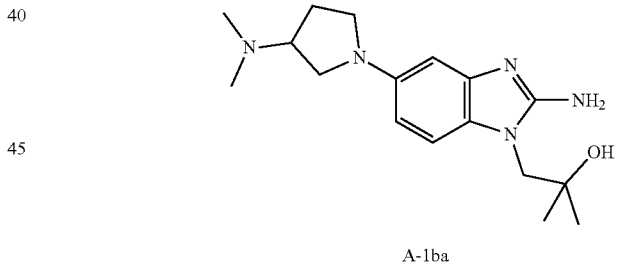

A-1ba

To a well stirred solution of A-1y (850 mg, 3.0 mmol), G-1c (3.5 g, 30.0 mmol, 10 eq.) and KO$^t$Bu (1.35 g, 12 mmol, 4.0 eq.) in degassed f-amyl alcohol (20 mL) at 20° C. under Ar-atmosphere is added 2-(di-f-butylphosphino)biphenyl (90 mg, 0.3 mmol, 10 mol %) and tris(dlbenzylideneacetone)dipalladium(0) (137 mg, 0.15 mmol, 5 mol %). The resultant reaction mixture is then allowed to stir at 100° C. for 5 h. The reaction mixture is cooled to 20° C., filtrated and the crude product A-1ba is purified using reversed phase chromatography (method: prep. HPLC1) (yield: 51%—487 mg, 1.53 mmol; HPLC-MS: (M+H)$^+$=318, t$_{Ret.}$=0.82 min, method Z011_S03)

The following intermediates A-1 and A*-1 (table 4) are available in an analogous manner starting from different precursors A-1 and A*-1 previously obtained.

TABLE 4

| # | Structure | MS (M + H)⁺; t_Ret HPLC [min] | HPLC-MS method |
|---|---|---|---|
| A-1az | 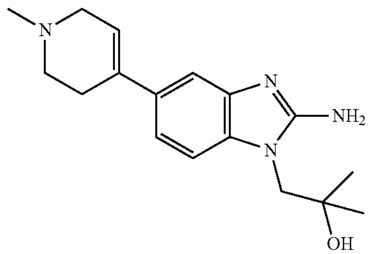 [SMILES: CN1CC=C(c2ccc3c(c2)nc(N)n3CC(C)(C)O)CC1] | (M + H)⁺ = 301; t_Ret. = 1.3 | MONI |
| A-1ba | 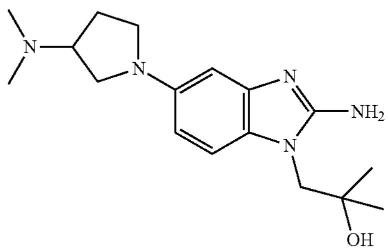 [SMILES: CN(C)C1CCN(c2ccc3c(c2)nc(N)n3CC(C)(C)O)C1] | (M + H)⁺ = 318; t_Ret. = 0.8 | Z011_S03 |
| A-1bb | 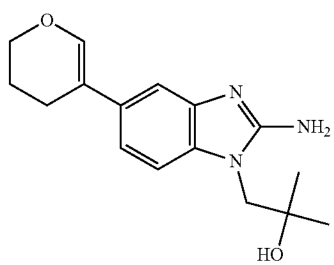 [SMILES: CC(C)(O)Cn1c(N)nc2cc(C3=COCCC3)ccc21] | (M + H)⁺ = 288; t_Ret. = 0.9 | Z011-S03 |
| A-1bc | 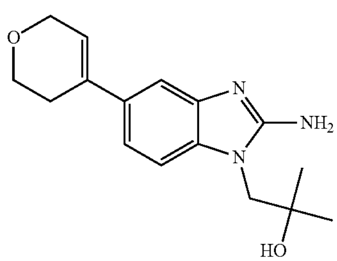 [SMILES: CC(C)(O)Cn1c(N)nc2cc(C3=CCOCC3)ccc21] | (M + H)⁺ 288; t_Ret. = 0.8 | Z011-S03 |
| A-1bd | 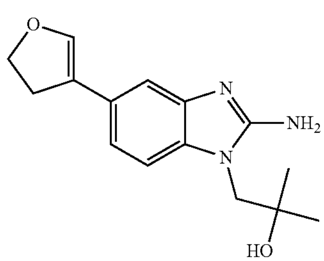 [SMILES: CC(C)(O)Cn1c(N)nc2cc(C3=COCC3)ccc21] | (M + H)⁺ = 274; t_Ret. = 0.8 | Z011-S03 |
| A-1be | 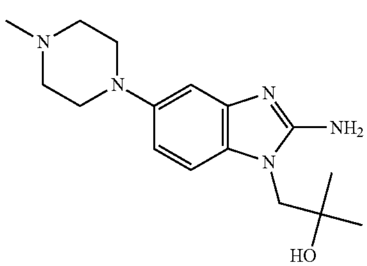 [SMILES: CN1CCN(c2ccc3c(c2)nc(N)n3CC(C)(C)O)CC1] | (M + H)⁺ = 304; t_Ret. = 0.8 | Z011_S03 |

TABLE 4-continued

| # | Structure | MS (M + H)+; t_Ret HPLC [min] | HPLC-MS method |
|---|---|---|---|
| A-1bf | 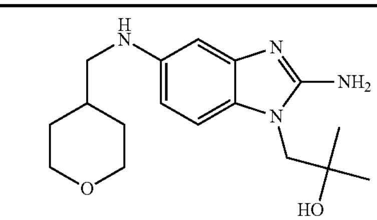 | (M + H)+ = 319; t_Ret. = 0.8 | Z011_S03 |
| A-1bg | 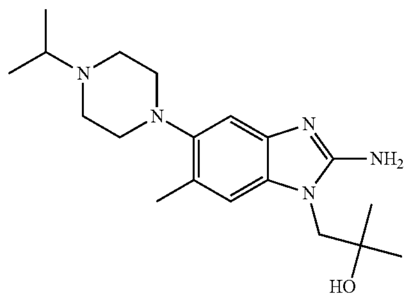 [SMILES: Cc1cc2c(cc1N1CCN(C(C)C)CC1)nc(N)n2CC(C)(C)O] | (M + H)+ = 346; t_Ret. = 1.0 | Z011_S03 |
| A-1bh | 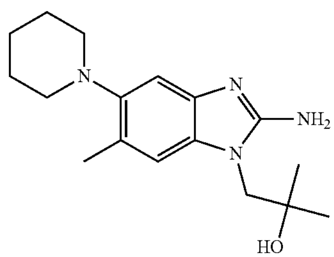 [SMILES: Cc1cc2c(cc1N1CCCCC1)nc(N)n2CC(C)(C)O] | (M + H)+ = 303; t_Ret. = 1.0 | Z011_S03 |
| A-1bi | 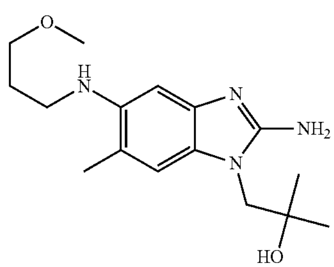 [SMILES: COCCCNc1cc2nc(N)n(CC(C)(C)O)c2cc1C] | (M + H)+ = 307; t_Ret. = 0.8 | Z011_S03 |
| A-1bj | 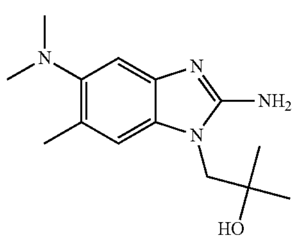 [SMILES: Cc1cc2c(cc1N(C)C)nc(N)n2CC(C)(C)O] | (M + H)+ = 263; t_Ret. = 0.8 | Z011_S03 |
| A-1bk | 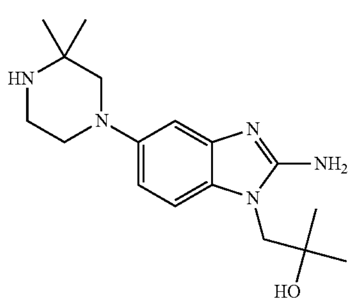 [SMILES: CC(C)(O)Cn1c(N)nc2cc(N3CCNC(C)(C)C3)ccc21] | (M + H)+ = 318; t_Ret. = 0.8 | Z011_S03 |

TABLE 4-continued

| # | Structure | MS (M + H)+; t_Ret HPLC [min] | HPLC-MS method |
|---|---|---|---|
| A-1bl | 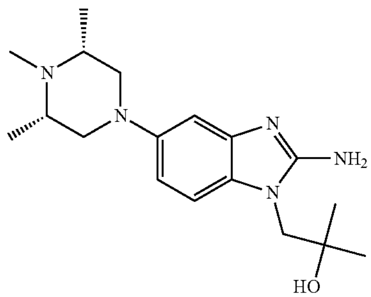 [SMILES: C[C@@H]1CN(c2ccc3c(c2)nc(N)n3CC(C)(C)O)C[C@H](C)N1C] | (M + H)+ = 332; t_Ret. = 0.8 | Z011_S03 |
| A-1bm | 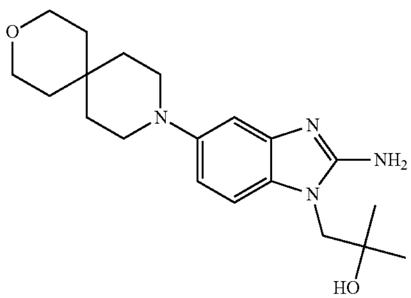 [SMILES: CC(C)(O)Cn1c(N)nc2cc(N3CCC4(CCOCC4)CC3)ccc21] | (M + H)+ = 359; t_Ret. = 0.8 | Z011_S03 |
| A-1bn | 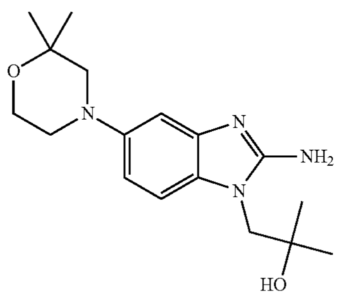 [SMILES: CC(C)(O)Cn1c(N)nc2cc(N3CCOC(C)(C)C3)ccc21] | (M + H)+ = 319; t_Ret. = 0.9 | Z011_S03 |
| A-1bo | 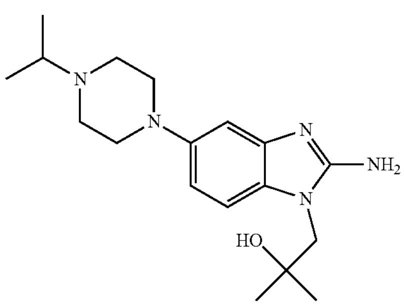 [SMILES: CC(C)N1CCN(c2ccc3c(c2)nc(N)n3CC(C)(C)O)CC1] | (M + H)+ = 332; t_Ret. = 0.9 | Z011_S03 |
| A-1bp | 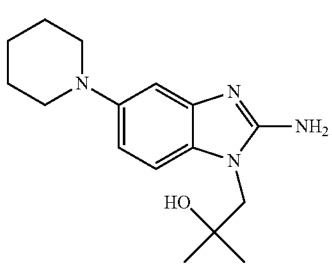 [SMILES: CC(C)(O)Cn1c(N)nc2cc(N3CCCCC3)ccc21] | (M + H)+ = 289; t_Ret. = 0.9 | Z011_S03 |

TABLE 4-continued

| # | Structure | MS (M + H)+; $t_{Ret}$ HPLC [min] | HPLC-MS method |
|---|---|---|---|
| A-1bq | 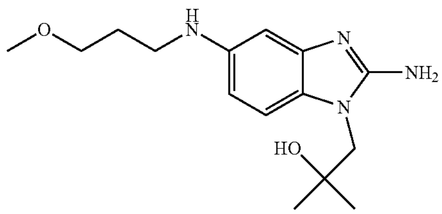 [SMILES: COCCCNc1ccc2c(c1)nc(N)n2CC(C)(C)O] | (M + H)+ = 293; $t_{Ret.}$ = 0.8 | Z011_S03 |
| A-1br | 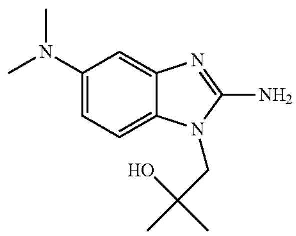 [SMILES: CN(C)c1ccc2c(c1)nc(N)n2CC(C)(C)O] | (MH)+ = 249; $t_{Ret.}$ = 0.8 | Z011_S03 |
| A-1bs | 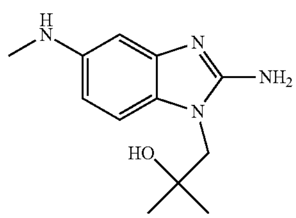 [SMILES: CNc1ccc2c(c1)nc(N)n2CC(C)(C)O] | (M + H)+ = 235; $t_{Ret.}$ = 0.7 | Z011_S03 |
| A-1bt | 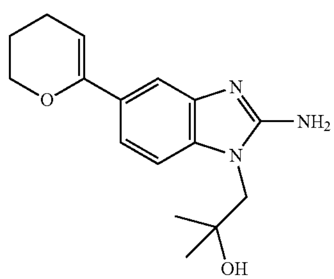 [SMILES: CC(C)(O)Cn1c(N)nc2cc(C3=CCCCO3)ccc21] | (M + H)+ = 288; $t_{Ret.}$ = 1.1 | LCMSBAS |
| A-1bu | 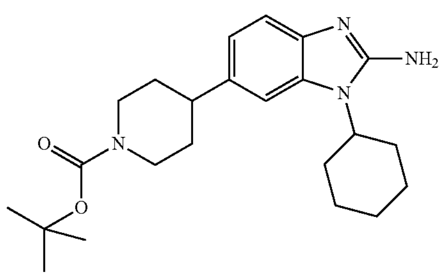 [SMILES: CC(C)(C)OC(=O)N1CCC(c2ccc3nc(N)n(C4CCCCC4)c3c2)CC1] | (M + H)+ = 399; $t_{Ret.}$ = 1.0 | VAB |
| A-1bv | 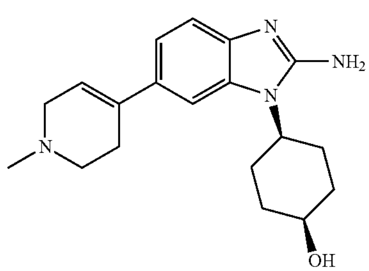 [SMILES: CN1CC=C(c2ccc3nc(N)n([C@H]4CC[C@@H](O)CC4)c3c2)CC1] | (M + H)+ = 327; $t_{Ret.}$ = 1.4 | YMC |

TABLE 4-continued

| # | Structure | MS (M + H)+; t_Ret HPLC [min] | HPLC-MS method |
|---|---|---|---|
| A-1bw | 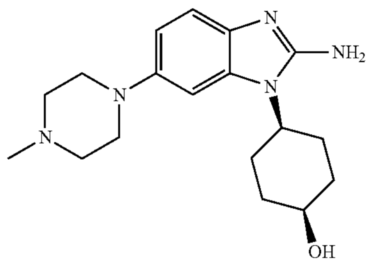 | (M + H)+ = 314; t_Ret. = 0.4 | LCMSBAS |
| A-1bx | 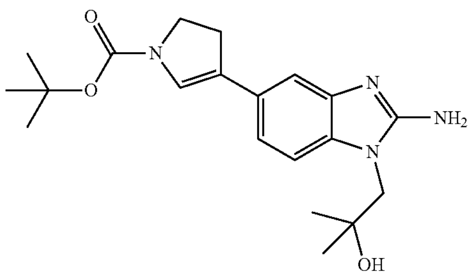 [SMILES: CC(C)(O)Cn1c(N)nc2cc(C3=CN(C(=O)OC(C)(C)C)CC3)ccc21] | (M + H)+ = 373; t_Ret. = 1.2 | LCMSBAS |
| A-1by | 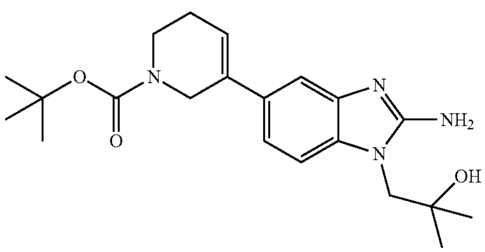 [SMILES: CC(C)(O)Cn1c(N)nc2cc(C3=CCCN(C(=O)OC(C)(C)C)C3)ccc21] | (M + H)+ = 387; t_Ret. = 1.6 | YMC |
| A-1bz | 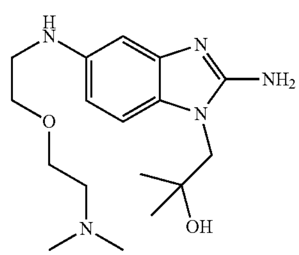 [SMILES: CN(C)CCOCCNc1ccc2c(c1)nc(N)n2CC(C)(C)O] | (M + H)+ = 336; t_Ret. = 0.8 | Z011_S03 |
| A-1ca | 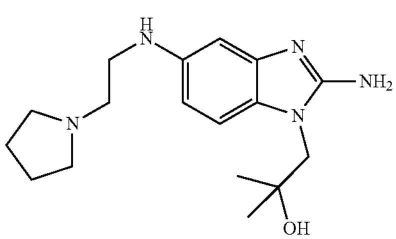 [SMILES: CC(C)(O)Cn1c(N)nc2cc(NCCN3CCCC3)ccc21] | (M + H)+ = 318; t_Ret. = 0.8 | Z011_S03 |
| A-1cb | 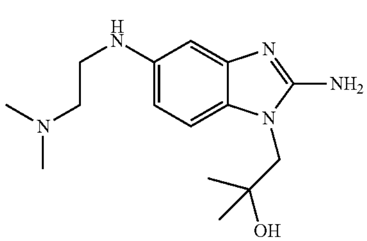 [SMILES: CN(C)CCNc1ccc2c(c1)nc(N)n2CC(C)(C)O] | (M + H)+ = 292; t_Ret. = 0.8 | Z011_S03 |

TABLE 4-continued

| # | Structure | MS (M + H)+; t_Ret HPLC [min] | HPLC-MS method |
|---|---|---|---|
| A-1cd | 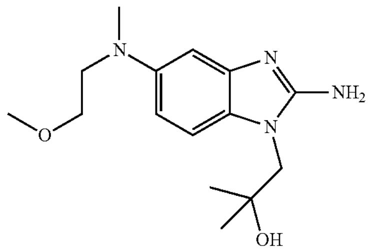 [SMILES: COCCN(C)c1ccc2c(c1)nc(N)n2CC(C)(C)O] | (M + H)+ = 293; t_Ret. = 0.8 | Z011_S03 |
| A-1ce | 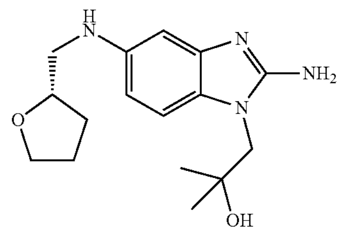 [SMILES: CC(C)(O)Cn1c(N)nc2cc(NC[C@@H]3CCCO3)ccc21] | (M + H)+ = 305; t_Ret. = 0.8 | Z011_S03 |
| A*-1i | 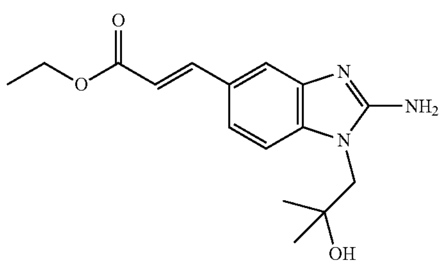 [SMILES: CCOC(=O)/C=C/c1ccc2c(c1)nc(N)n2CC(C)(C)O] | (M + H)+ = 304; t_Ret. = 1.0 | LCMSBAS |
| A*-1j | 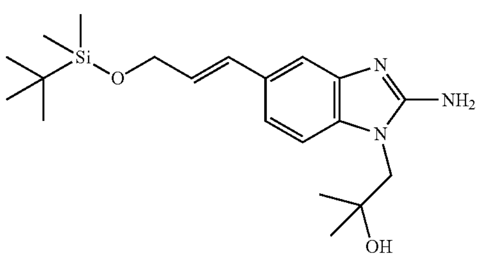 [SMILES: CC(C)(O)Cn1c(N)nc2cc(/C=C/CO[Si](C)(C)C(C)(C)C)ccc21] | (M + H)+ = 376; t_Ret. = 1.5 | LCMSBAS |
| A*-1k | 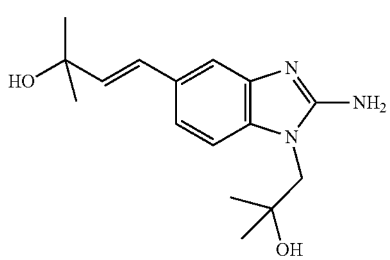 [SMILES: CC(C)(O)/C=C/c1ccc2c(c1)nc(N)n2CC(C)(C)O] | (M + H)+ = 290; t_Ret. = 0.9 | LCMSBAS |

Experimental Procedure for the Synthesis of A-1cf

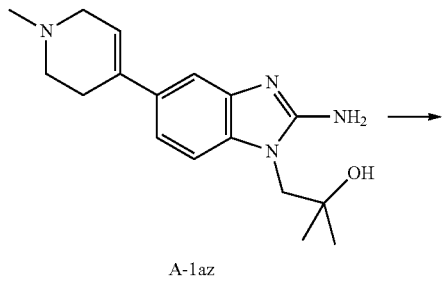

A-1az

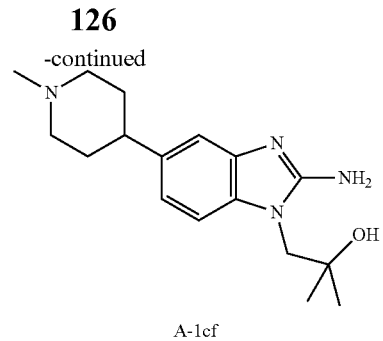

A-1cf

Starting material A-1az (5.0 g, 16.6 mmol) is dissolved in methanol (150.0 mL) and the reaction mass is degassed with argon. Palladium hydroxide (2.3 g, 6.7 mmol; 40 mol %) is added and the reaction mass is placed in parr-shaker with 50 psi $H_2$ for 24 h After full conversion the reaction mixture is filtered over Celite® and concentrated under reduced pressure. The crude product is purified using normal phase chromatography (DCM/MeOH/EtsN, 95:5:0.2) to afford pure product A-1cf (yield: 80%—4.0 g, 13.2 mmol; HPLC-MS: $(M+H)^+$=303, $t_{Ret.}$=0.9 min, method Z011-S03).

The following intermediates A-1 and A*-1 (table 5) are available in an analogous manner starting from different precursors A-1 and A*-1 previously obtained.

TABLE 5

| # | Structure | MS (M + H)⁺; $t_{Ret}$ HPLC [min] | HPLC-MS method |
|---|---|---|---|
| A-1cf | ![structure] | (M + H)⁺ = 303; $t_{Ret.}$ = 0.9 | Z011-S03 |
| A-1cg | ![structure] | (M + H)⁺ = 290; $t_{Ret.}$ = 0.8 | Z011-S03 |
| A-1ch | ![structure] | (M + H)⁺ = 290; $t_{Ret.}$ = 0.8 | Z011-S03 |

TABLE 5-continued

| # | Structure | MS (M + H)+; $t_{Ret}$ HPLC [min] | HPLC-MS method |
|---|---|---|---|
| A-1ci | 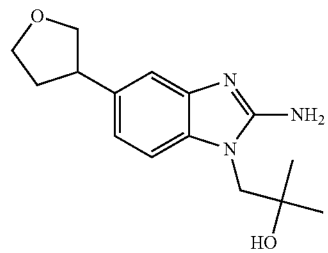 [SMILES: CC(C)(O)Cn1c(N)nc2cc(C3CCOC3)ccc21] | (M + H)+ = 276; $t_{Ret.}$ = 0.8 | Z011-S03 |
| A-1cj | 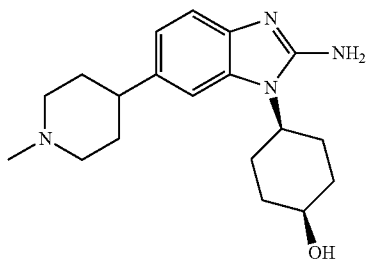 [SMILES: CN1CCC(c2ccc3nc(N)n([C@H]4CC[C@@H](O)CC4)c3c2)CC1] | (M + H)+ = 329; $t_{Ret.}$ = 1.3 | YMC |
| A-1ck | 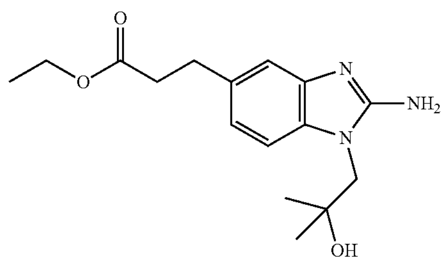 [SMILES: CCOC(=O)CCc1ccc2c(c1)nc(N)n2CC(C)(C)O] | (M + H)+ = 306; $t_{Ret.}$ = 0.4 | LCMSBAS |
| A-1cl | 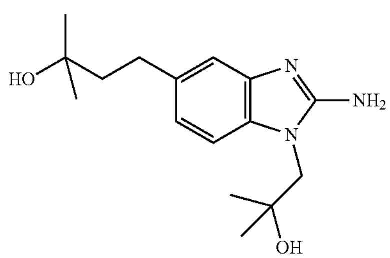 [SMILES: CC(C)(O)CCc1ccc2c(c1)nc(N)n2CC(C)(C)O] | (M + H)+ = 292; $t_{Ret.}$ = 0.6 | LCMSBAS |
| A-1cm | 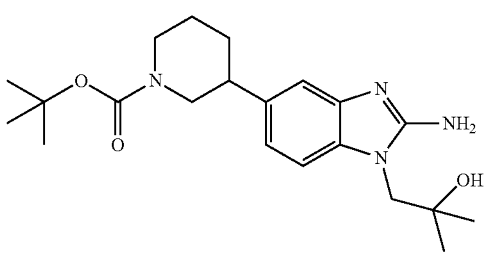 [SMILES: CC(C)(O)Cn1c(N)nc2cc(C3CCCN(C(=O)OC(C)(C)C)C3)ccc21] | (M + H)+ = 389; $t_{Ret.}$ = 0.9 | LCMSBAS |
| A-1cn | 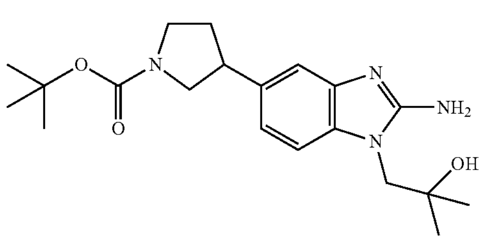 [SMILES: CC(C)(O)Cn1c(N)nc2cc(C3CCN(C(=O)OC(C)(C)C)C3)ccc21] | (M + H)+ = 375; $t_{Ret.}$ = 0.9 | LCMSBAS |

TABLE 5-continued

| # | Structure | MS (M + H)+; $t_{Ret}$ HPLC [min] | HPLC-MS method |
|---|---|---|---|
| A-1co | 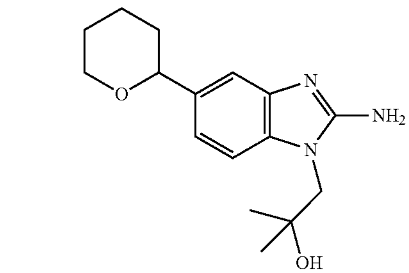 [SMILES: CC(C)(O)Cn1c(N)nc2cc(C3CCCCO3)ccc21] | (M + H)+ = 290; $t_{Ret.}$ = 0.5 | LCMSBAS |
| A*-1l | 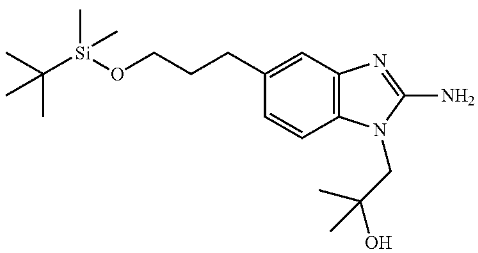 [SMILES: CC(C)(O)Cn1c(N)nc2cc(CCCO[Si](C)(C)C(C)(C)C)ccc21] | (M + H)+ = 378; $t_{Ret.}$ = 0.4 | LCMSBAS |

Experimental procedure for the synthesis of A-1cp and A*-1m

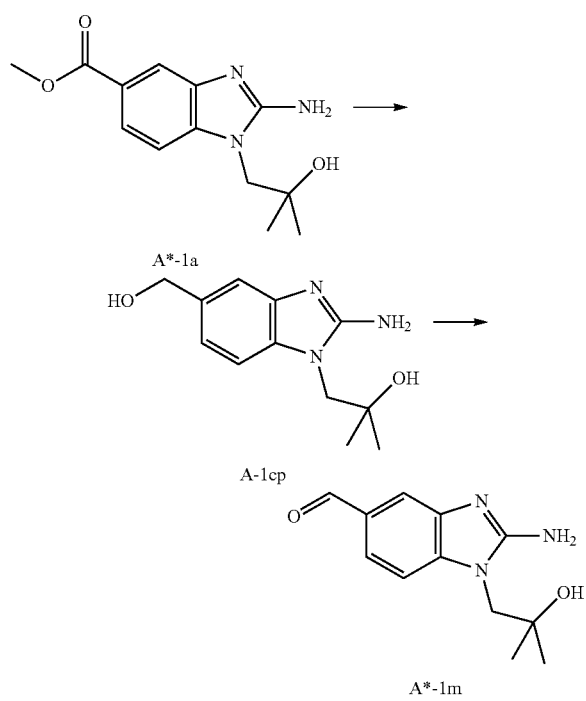

A*-1a (1.00 g, 3.8 mmol, 1.0 eq.) is dissolved in dry THF (30.0 mL) and cooled to 0° C. Then LiAlH₄ (1 M in Et₂O, 5.7 mL, 5.7 mmol, 1.5 eq.) is added. The reaction is stirred over night at 20° C. and after full conversion isopropanol (30 mL) is added to quench the reaction. Celite® is added and the solvents are evaporated under reduced pressure. The crude product is purified using normal phase chromatography (DCM/MeOH, 95:5) to afford pure product A-1cp (yield: 72%—0.64 g, 2.7 mmol; HPLC-MS: (M+H)+=236, $t_{Ret.}$=0.29 min, method LCMSBAS).

A-1cp thus obtained (600 mg, 2.5 mmol, 1.0 eq.) is dissolved in acetonitrile (80 mL) and DCM (16 mL), then activated MnO₂ (985 mg, 10.2 mmol, 4.0 eq.) is added. The reaction is stirred over night at 20° C. Then activated MnO₂ (493 mg, 5.1 mmol, 2.0 eq.) is added again and the reaction is stirred for additional 4 h. After full conversion the reaction mixture is filtered over Celite® and the solvents are evaporated under reduced pressure. The crude product is purified using normal phase chromatography (DCM/MeOH, 95:5) to afford pure product A*-1m (yield: 87%—0.52 g, 2.2 mmol; HPLC-MS: (M+H)+=234, $t_{Ret.}$=0.74 min, method LCMSBAS).

The following intermediates A-1 and A*-1 (table 6) are available in an analogous manner starting from different precursors A*-1 previously obtained.

TABLE 6

| # | Structure | MS (M + H)+; $t_{Ret.}$ HPLC [min] | HPLC-MS method |
|---|---|---|---|
| A-1cp | 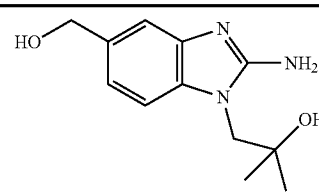 | (M + H)+ = 236; $t_{Ret.}$ = 0.29 | LCMSBAS |
| A*-1m | 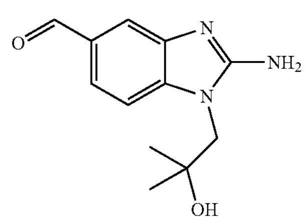 [SMILES: CC(C)(O)Cn1c(N)nc2cc(C=O)ccc21] | (M + H)+ = 234; $t_{Ret.}$ = 0.7 | LCMSBAS |

TABLE 6-continued

| # | Structure | MS (M + H)+; $t_{Ret.}$ HPLC [min] | HPLC-MS method |
|---|---|---|---|
| A*-1n | 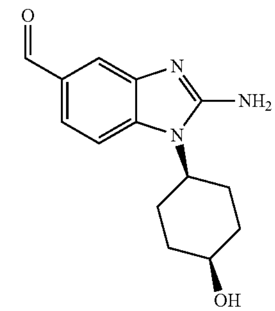 [SMILES: Nc1nc2cc(C=O)ccc2n1[C@H]1CC[C@@H](O)CC1] | (M + H)+ = 260; $t_{Ret.}$ = 1.9 | MONI |
| A*-1o | 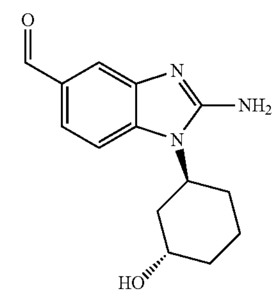 [SMILES: Nc1nc2cc(C=O)ccc2n1[C@H]1CCC[C@H](O)C1] | (M + H)+ = 260; $t_{Ret.}$ = 2.2 | MONI |
| A*-1p | 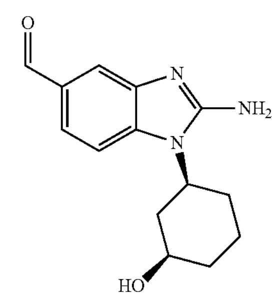 [SMILES: Nc1nc2cc(C=O)ccc2n1[C@H]1CCC[C@@H](O)C1] | (M + H)+ = 260; $t_{Ret.}$ = 2.2 | MONI |
| A*-1q | 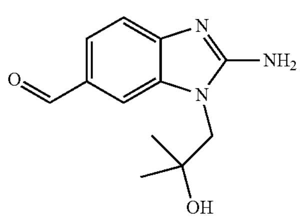 [SMILES: CC(C)(O)Cn1c(N)nc2ccc(C=O)cc21] | (M + H)+ = 234; $t_{Ret.}$ = 0.6 | LCMSBAS |
| A*-1r | 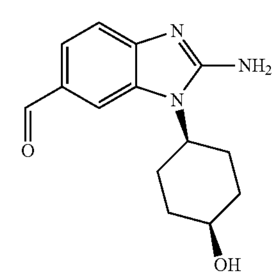 [SMILES: Nc1nc2ccc(C=O)cc2n1[C@H]1CC[C@@H](O)CC1] | (M + H)+ = 260; $t_{Ret.}$ = 1.9 | MONI |
| A*-1s | | (M + H)+ = 244; $t_{Ret.}$ = 1.6 | YMC |

Experimental Procedure for the Synthesis of Intermediate A-1cq

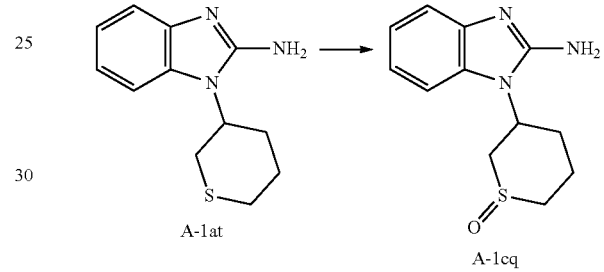

A-1at (900 mg, 3.86 mmol) is dissolved in DCM (40 mL) and the mixture is cooled to 0° C. m-CPBA (666 mg, 3.86 mmol, 1.0 eq.) is added and the reaction is stirred at 0° C. for 4 h. The reaction is quenched with a sat. aq. sol. of $Na_2S_2O_3$ and basified with sat. aq. $NaHCO_3$ sol. The mixture is extracted with DCM, the combined organic phases are dried over $MgSO_4$, filtrated and the solvents are evaporated. The residue is purified by normal phase chromatography (eluent: DCM/MeOH, 95:5) yielding A-1cq (yield: 70%—670 mg, 2.69 mmol; HPLC-MS: (M+H)+=250, $t_{Ret.}$=1.17 min, method: YMC).

Synthesis of Intermediates L-1 and L*-1

Experimental Procedure for the Synthesis of L-1a

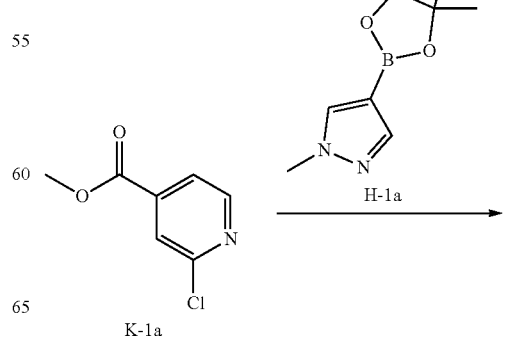

-continued

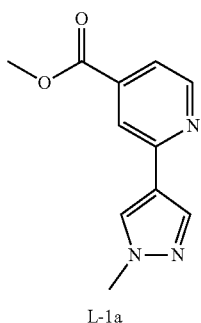

L-1a

To a stirred suspension of K-1a (60 mg, 3.43 mmol), H-1a (840 mg, 3.96 mmol, 1.15 eq.) and $Cs_2CO_3$ (3.3 g, 10.1 mmol, 2.9 eq.) in a DME/water mixture (3:1, 16 mL) is added [1,1'-bis(diphenylphosphino)ferrocene]dichloropalladium(II) complex with dichloromethane (150 mg, 0.2 mmol, 5 mol %). The reaction mixture is stirred under microwave irradiation at 90° C. for 30 min. After full conversion the solvents are evaporated under reduced pressure and taken up in water. The mixture is extracted with DCM, the combined organic phases are dried over $MgSO_4$, filtrated and the solvent is evaporated under reduced pressure. The crude product is purified using normal phase chromatography (DCM/MeOH/$NH_3$, 100:10:1) to afford pure product L-1a (yield: 61%—455 mg, 2.1 mmol; HPLC-MS: $(M+H)^+$=218, $t_{Ret.}$=0.72 min, method VAB).

The following intermediates L-1 and L*-1 (table 7) are available in an analogous manner starting from precursors K-1 and K*-1.

TABLE 7

| # | Structure | MS $(M + H)^+$; $t_{Ret.}$ HPLC [min] | HPLC-MS method |
|---|---|---|---|
| L-1a | 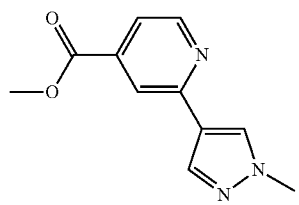 | $(M + H)^+ = 218$; $t_{Ret.} = 0.7$ | VAB |
| L-1b | 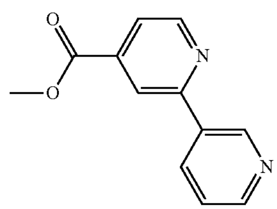 [SMILES: COC(=O)c1ccnc(-c2cccnc2)c1] | $(M + H)^+ = 215$; $t_{Ret.} = 2.7$ | MONI |
| L-1c | 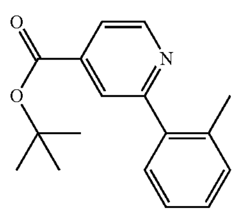 | $(M + H)^+ = 220$; $t_{Ret.} = 1.1$ | VAS |
| L-1d | 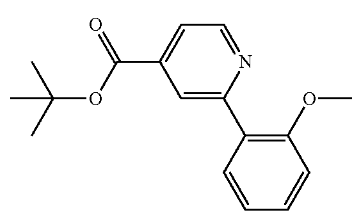 [SMILES: COc1ccccc1-c1cc(C(=O)OC(C)(C)C)ccn1] | $(M + H)^+ = 286$; $t_{Ret.} = 1.1$ | VAB |
| L-1e | 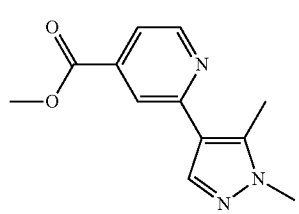 | $(M + H)^+ = 232$; $t_{Ret.} = 0.8$ | VAB |

TABLE 7-continued
| # | Structure | MS (M + H)+; $t_{Ret.}$ HPLC [min] | HPLC-MS method |
|---|---|---|---|
| L-1f | 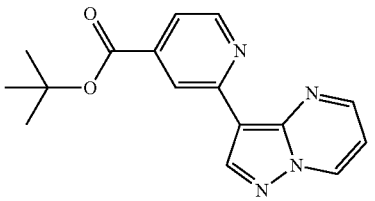 [SMILES: CC(C)(C)OC(=O)c1ccnc(-c2cnn3cccnc23)c1] | (M + H)+ = 297; $t_{Ret.}$ = 1.1 | VAB |
| L-1g | 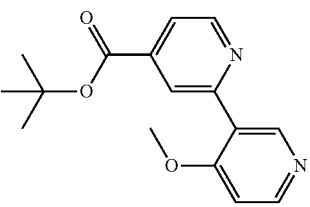 [SMILES: COc1ccncc1-c1cc(C(=O)OC(C)(C)C)ccn1] | (M + H)+ = 287; $t_{Ret.}$ = 0.9 | VAB |
| L-1h | 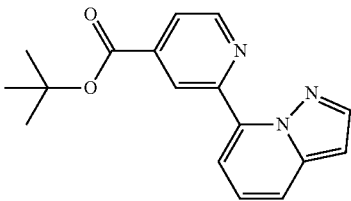 [SMILES: CC(C)(C)OC(=O)c1ccnc(-c2cccc3ccnn23)c1] | (M + H)+ = 296; $t_{Ret.}$ = 1.1 | VAB |
| L-1i | 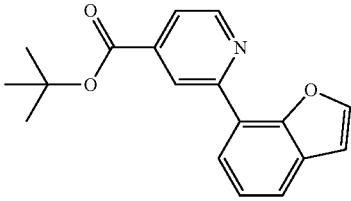 [SMILES: CC(C)(C)OC(=O)c1ccnc(-c2cccc3ccoc23)c1] | (M + H)+ = 296; $t_{Ret.}$ = 1.3 | VAB |
| L-1j | 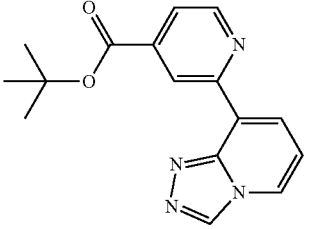 [SMILES: CC(C)(C)OC(=O)c1ccnc(-c2cccn3cnnc23)c1] | (M + H)+ = 297; $t_{Ret.}$ = 1.1 | LCMSBAS |
| L-1k | 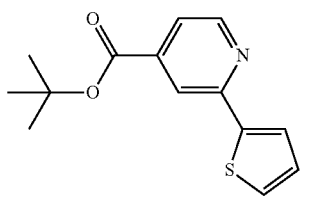 [SMILES: CC(C)(C)OC(=O)c1ccnc(-c2cccs2)c1] | (M + H)+ = 262; $t_{Ret.}$ = 1.3 | VAB |
| L-1l | 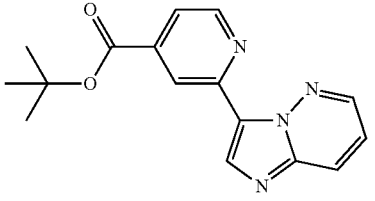 [SMILES: CC(C)(C)OC(=O)c1ccnc(-c2cnc3cccnn23)c1] | (M + H)+ = 297; $t_{Ret.}$ = 0.9 | VAB |

TABLE 7-continued

| # | Structure | MS (M + H)+; t_Ret. HPLC [min] | HPLC-MS method |
|---|---|---|---|
| L-1m | 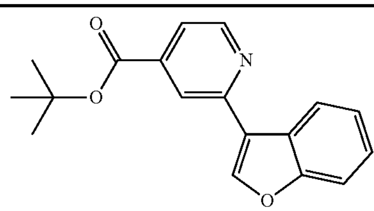 | (M + H)+ = 296; t_Ret. = 1.2 | VAB |
| L-1n | 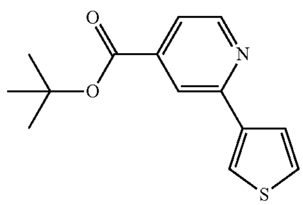 | (M + H)+ = 272; t_Ret. = 1.2 | VAB |
| L-1o | 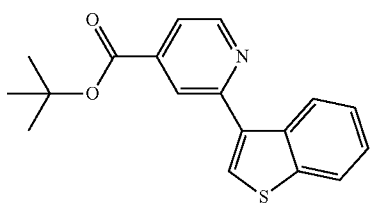 [SMILES: CC(C)(C)OC(=O)c1ccnc(-c2csc3ccccc23)c1] | (M + H)+ = 312; t_Ret. = 1.1 | VAB |
| L-1p | 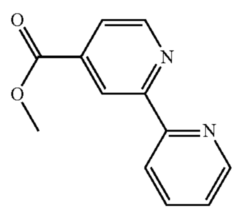 | (M + H)+ = 257; t_Ret. = 1.0 | VAB |
| L-1q | 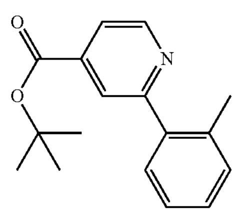 [SMILES: Cc1ccccc1-c1cc(C(=O)OC(C)(C)C)ccn1] | (M + H)+ = 270; t_Ret. = 1.1 | VAB |
| L-1r | 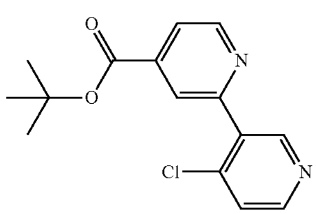 [SMILES: CC(C)(C)OC(=O)c1ccnc(-c2cnccc2Cl)c1] | (M + H)+ = 291/293; t_Ret. = 1.0 | VAB |
| L-1s | 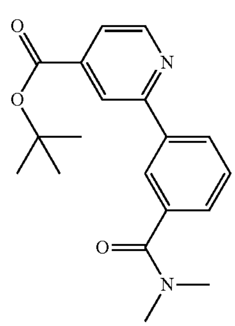 [SMILES: CN(C)C(=O)c1cccc(-c2cc(C(=O)OC(C)(C)C)ccn2)c1] | (M + H)+ = 327; t_Ret. = 0.9 | VAB |

TABLE 7-continued

| # | Structure | MS (M + H)+; $t_{Ret.}$ HPLC [min] | HPLC-MS method |
|---|---|---|---|
| L-1t | 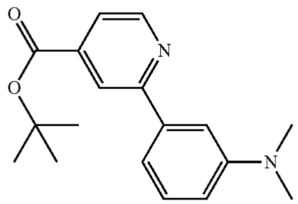 [SMILES: CN(C)c1cccc(-c2cc(C(=O)OC(C)(C)C)ccn2)c1] | (M + H)+ = 299; $t_{Ret.}$ = 1.1 | VAS |
| L-1u | 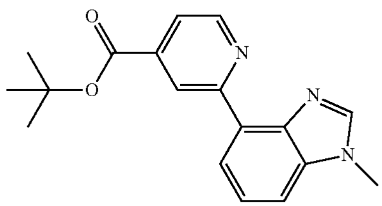 [SMILES: Cn1cnc2c(-c3cc(C(=O)OC(C)(C)C)ccn3)cccc21] | (M + H)+ = 310; $t_{Ret.}$ = 0.7 | VAS |
| L-1v | 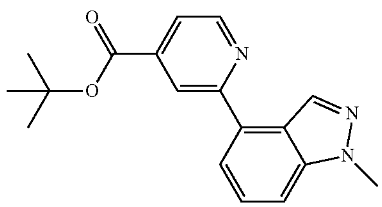 [SMILES: Cn1ncc2c(-c3cc(C(=O)OC(C)(C)C)ccn3)cccc21] | (M + H)+ = 310; $t_{Ret.}$ = 1.4 | LCMSBAS |
| L-1w | 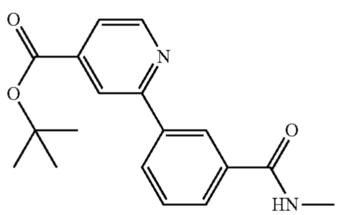 [SMILES: CNC(=O)c1cccc(-c2cc(C(=O)OC(C)(C)C)ccn2)c1] | (M + H)+ = 313; $t_{Ret.}$ = 0.9 | VAB |
| L-1x | 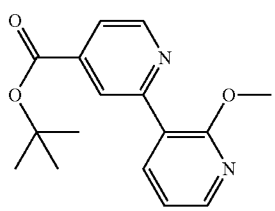 [SMILES: COc1ncccc1-c1cc(C(=O)OC(C)(C)C)ccn1] | (M + H)+ = 287; $t_{Ret.}$ = 1.1 | VAS |
| L-1y | 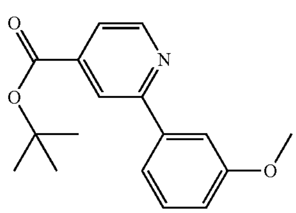 [SMILES: COc1cccc(-c2cc(C(=O)OC(C)(C)C)ccn2)c1] | (M + H)+ = 286; $t_{Ret.}$ = 1.1 | VAB |
| L-1z | 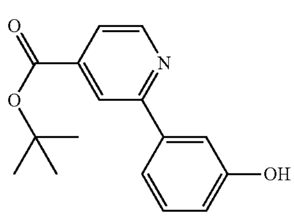 [SMILES: CC(C)(C)OC(=O)c1ccnc(-c2cccc(O)c2)c1] | (M + H)+ = 272; $t_{Ret.}$ = 0.9 | VAB |

TABLE 7-continued

| # | Structure | MS (M + H)+; $t_{Ret.}$ HPLC [min] | HPLC-MS method |
|---|---|---|---|
| L-1aa | 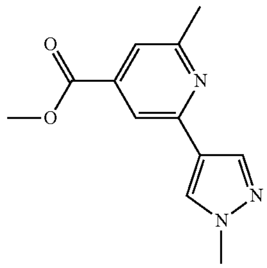 [SMILES: COC(=O)c1cc(C)nc(-c2cnn(C)c2)c1] | (M + H)+ = 232; $t_{Ret.}$ = 0.7 | VAB |
| L-1ab | 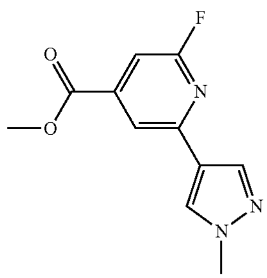 [SMILES: COC(=O)c1cc(F)nc(-c2cnn(C)c2)c1] | (M + H)+ = 236; $t_{Ret.}$ = 0.8 | VAB |
| L-1ac | 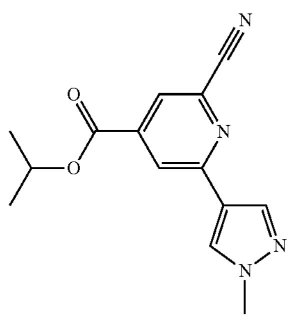 [SMILES: CC(C)OC(=O)c1cc(C#N)nc(-c2cnn(C)c2)c1] | (M + H)+ = 271; $t_{Ret.}$ = 0.9 | VAB |
| L-1ad | 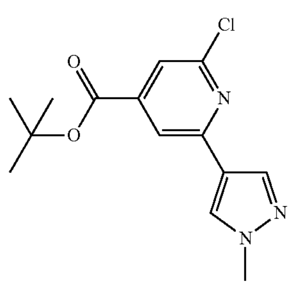 [SMILES: Cn1cc(-c2cc(C(=O)OC(C)(C)C)cc(Cl)n2)cn1] | (M + H)+ = 294; $t_{Ret.}$ = 1.0 | VAB |
| L-1ae | 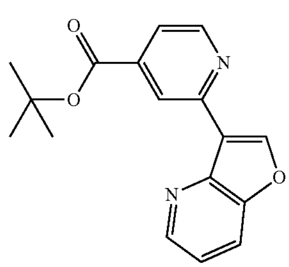 [SMILES: CC(C)(C)OC(=O)c1ccnc(-c2coc3cccnc23)c1] | (M + H)+ = 241; $t_{Ret.}$ = 0.2 | VAB |

TABLE 7-continued

| # | Structure | MS (M + H)+; t_Ret. HPLC [min] | HPLC-MS method |
|---|---|---|---|
| L-1af | 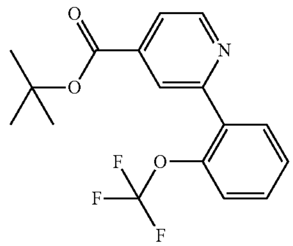 [SMILES: CC(C)(C)OC(=O)c1ccnc(-c2ccccc2OC(F)(F)F)c1] | (M + H)+ = 340; t_Ret. = 0.6 | VAB |
| L-1ag | 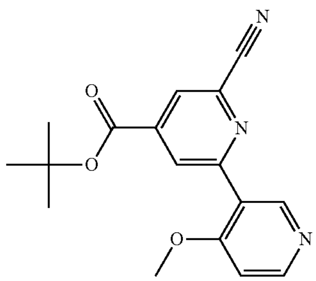 [SMILES: COc1ccncc1-c1cc(C(=O)OC(C)(C)C)cc(C#N)n1] | (M + H)+ = 312; t_Ret. = 0.8 | VAS |
| L-1ah | 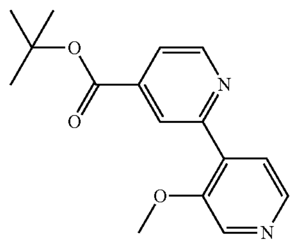 [SMILES: COc1cnccc1-c1cc(C(=O)OC(C)(C)C)ccn1] | (M + H)+ = 231; t_Ret. = 0.3 | VAS |
| L-1ai | 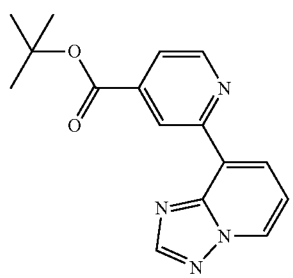 [SMILES: CC(C)(C)OC(=O)c1ccnc(-c2cccn3ncnc23)c1] | (M + H)+ = 241; t_Ret. = 0.6 | VAS |
| L-1aj | 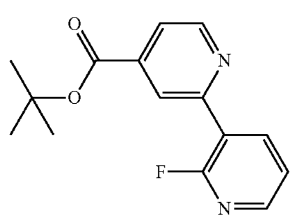 [SMILES: CC(C)(C)OC(=O)c1ccnc(-c2cccnc2F)c1] | (M + H)+ = 275; t_Ret. = 1.0 | VAB |
| L-1ak | 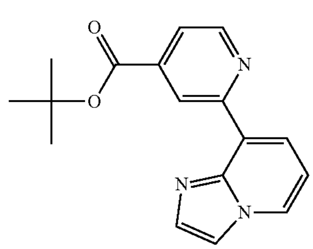 [SMILES: CC(C)(C)OC(=O)c1ccnc(-c2cccn3ccnc23)c1] | (M + H)+ = 296; t_Ret. = 1.1 | VAB |

TABLE 7-continued

| # | Structure | MS (M + H)+; $t_{Ret.}$ HPLC [min] | HPLC-MS method |
|---|---|---|---|
| L-1al | 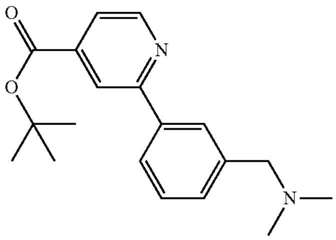 [SMILES: CN(C)Cc1cccc(-c2cc(C(=O)OC(C)(C)C)ccn2)c1] | (M + H)+ = 313; $t_{Ret.}$ = 1.1 | VAB |
| L-1am | 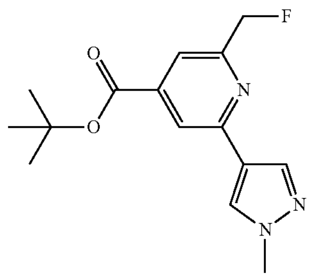 [SMILES: Cn1cc(-c2cc(C(=O)OC(C)(C)C)cc(CF)n2)cn1] | (M + H)+ = 292; $t_{Ret.}$ = 0.9 | VAB |
| L*-1a | 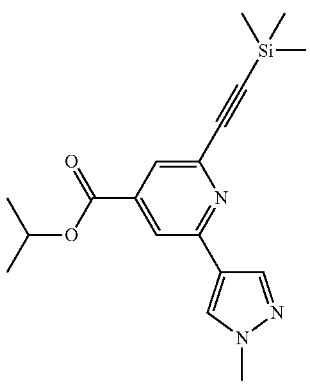 [SMILES: CC(C)OC(=O)c1cc(C#C[Si](C)(C)C)nc(-c2cnn(C)c2)c1] | (M + H)+ = 342; $t_{Ret.}$ = 1.1 | VAB |

Experimental Procedure for the Synthesis of L-1an

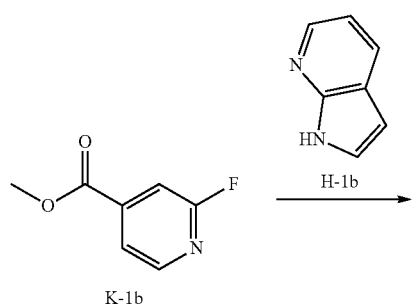

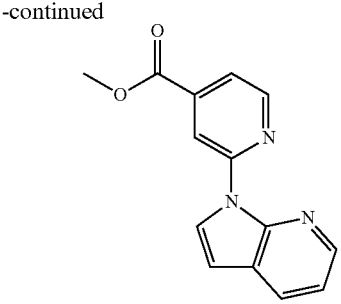

L-1an

To a stirred suspension of H-1b (100 mg, 0.83 mmol) and $Cs_2CO_3$ (405 mg, 1.24 mmol, 1.5 eq.) in NMP (1.0 mL) is added K-1b (263 mg, 1.66 mmol, 2.0 eq.). The reaction mixture is stirred at 100° C. for 18 h. After full conversion the reaction mixture is taken up in water. The mixture is extracted with DCM, the combined organic phases are dried over $MgSO_4$, filtrated and the solvent is evaporated under reduced pressure. The crude product is purified using reverse phase chromatography to afford pure product L-1an (yield: 25%—52 mg, 0.21 mmol; HPLC-MS: (M+H)+=254, $t_{Ret.}$=1.00 min, method VAS).

The following intermediates L-1 (table 8) are available in an analogous manner starting from different precursors K-1.

TABLE 8

| # | Structure | MS (M + H)+; $t_{Ret.}$ HPLC [min] | HPLC-MS method |
|---|-----------|-----------------------------------|----------------|
| L-1an | 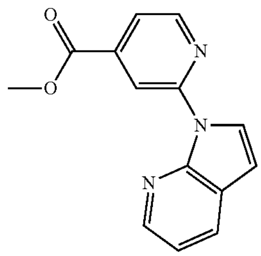 [SMILES: COC(=O)c1ccnc(-n2ccc3cccnc32)c1] | (M + H)+ = 254; $t_{Ret.}$ = 1.0 | VAS |
| L-1ao | 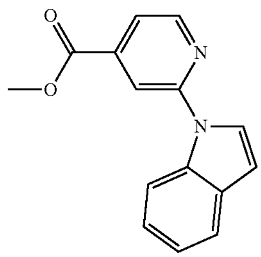 [SMILES: COC(=O)c1ccnc(-n2ccc3ccccc32)c1] | (M + H)+ = 253; $t_{Ret.}$ = 1.0 | VAB |
| L-1ap | 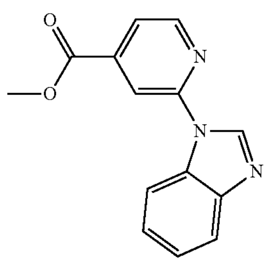 [SMILES: COC(=O)c1ccnc(-n2cnc3ccccc32)c1] | (M + H)+ = 254; $t_{Ret.}$ = 0.8 | VAB |

Experimental Procedure for the Synthesis of L-1aq

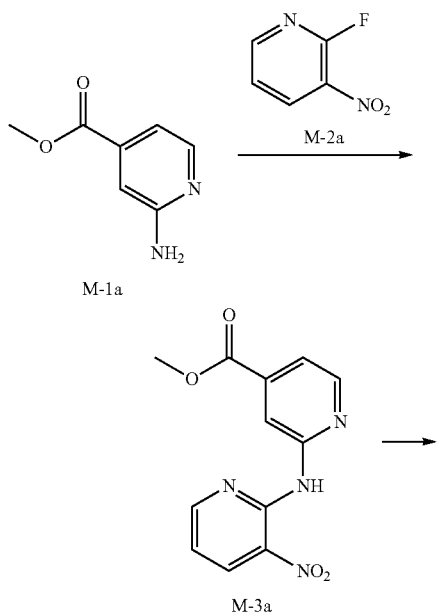

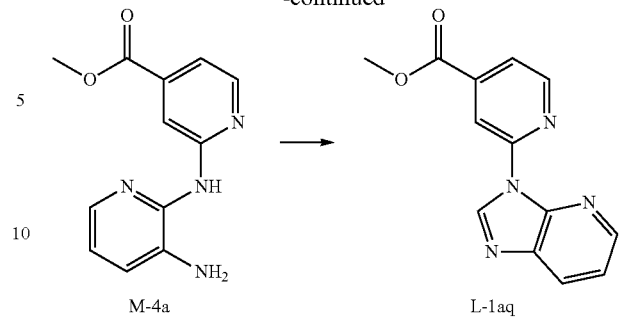

M-2a (200 mg, 1.41 mmol) and M-1a (257 mg, 1.69 mmol, 1.2 eq.) are dissolved in THF (3 mL). Then the reaction mixture is cooled to −20° C. and potassium tert-butoxide (331 mg, 2.96 mmol, 2.1 eq.) is added. The mixture is stirred at −20° C. for 1 h. The solvents are evaporated and the residue is purified by reverse phase chromatography (method: basic prep. HPLC1) yielding M-3a (yield: 17%—65 mg, 0.24 mmol; HPLC-MS: (M+H)+=275, $t_{Ret.}$=0.95 min, method: VAB).

In a Büchi-reactor M-3a thus obtained (65 mg, 0.24 mmol) is dissolved in MeOH (50 mL) and Raney-Nickel is added. Then a pressure of 5 bar of hydrogen is applied. The mixture is stirred at 20° C. for 3 h. The reaction mixture is filtrated, the solvents are evaporated and the product M-4a is used without further purification for the next step (yield: 100%—58 mg, 0.24 mmol; HPLC-MS: (M+H)+=245, $t_{Ret.}$=0.65 min, method: VAB).

M-4a (58 mg, 0.24 mmol) is dissolved in THF (1.0 mL), p-toluenesulfonic acid (25 mg, 0.14 mmol, 0.58 eq.) and trimethyl orthoformate (155 mg, 1.44 mmol, 6.1 eq.) are added. The mixture is stirred at 75° C. for 24 h. The solvents are evaporated and the residue is purified by reverse phase chromatography (method: basic prep. HPLC1) yielding L-1aq (yield: 30%—18 mg, 0.07 mmol; HPLC-MS: (M+H)+= 255, $t_{Ret.}$=0.78 min, method: VAB).

The following intermediates L-1 (table 9) are available in an analogous manner starting from precursors M-1 and M-2.

TABLE 9

| # | Structure | MS (M + H)+; $t_{Ret.}$ HPLC [min] | HPLC-MS method |
|---|-----------|-----------------------------------|----------------|
| L-1aq | 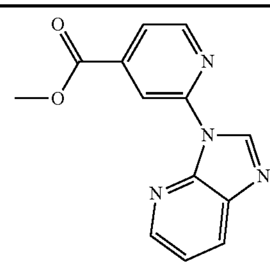 | (M + H)+ = 255; $t_{Ret.}$ = 0.8 | VAB |
| L-1ar | 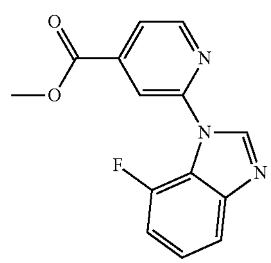 [SMILES: COC(=O)c1ccnc(-n2cnc3cccc(F)c32)c1] | (M + H)+ = 272; $t_{Ret.}$ = 0.9 | VAB |

Experimental Procedure for the Synthesis of L-1as and L-1at

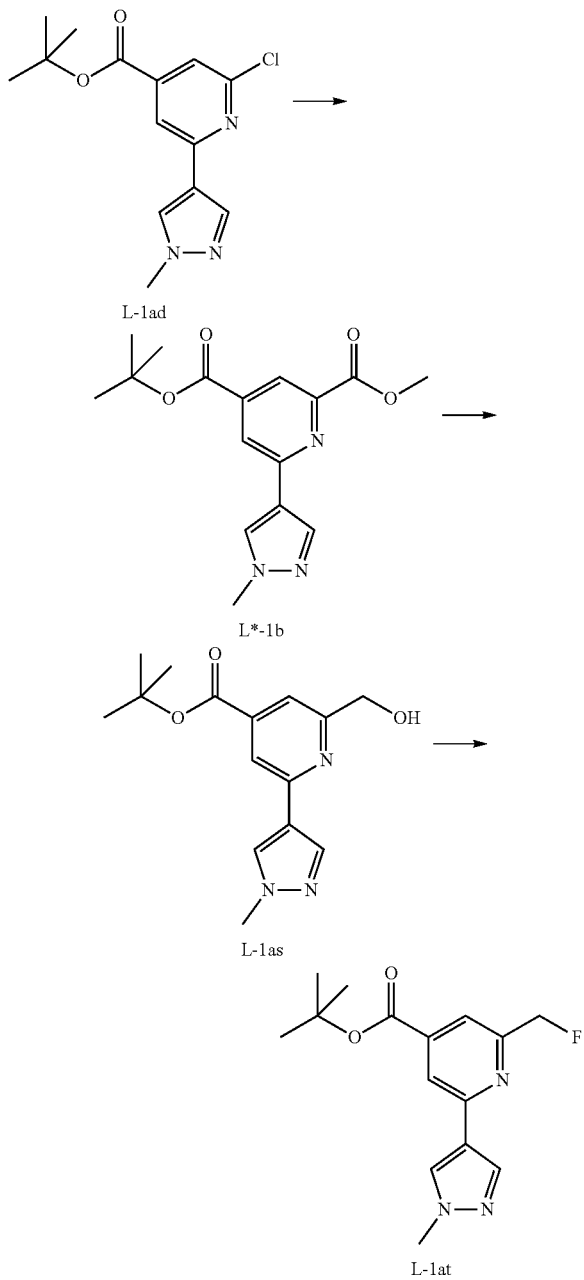

In a high pressure reactor L-1ad (550 mg, 1.87 mmol), DIPEA (1.0 mL, 5.76 mmol, 3.1 eq.) and [1,1'-bis(diphenylphosphino)ferrocene] dichloropalladium(II) complex with dichloromethane (20 mg, 0.02 mmol, 0.01 eq.) are dissolved in MeOH (50 mL). Then a pressure of 5 bar of carbon monoxide is applied and the reaction is stirred at 70° C. for 16 h. The solvents are evaporated and the residue is purified by reverse phase chromatography (method: prep. HPLC1) yielding L*-1b (yield: 98%—580 mg, 1.83 mmol; HPLC-MS: (M+H)$^+$=378, $t_{Ret.}$=0.91 min, method: VAB).

L*-1b thus obtained (200 mg, 0.60 mmol) is dissolved in EtOH (5 mL) and DCM (5 mL). Then NaBH$_4$ (100 mg, 2.62 mmol, 4.37 eq.) is added and the reaction is stirred at 20° C. for 20 h. The reaction is quenched with aq. HCl, neutralized with aq. sat. NaHCO$_3$ sol. The aqueous phase is extracted with DCM, the combined organic phases are dried over MgSO$_4$, filtrated, the solvents are evaporated and the residue is purified by normal phase chromatography (eluent: DCM/MeOH/NH$_3$; 100:10:1) yielding L-1as (yield: 87%—150 mg, 0.52 mmol; HPLC-MS: (M+H)$^+$=290, $t_{Ret.}$=0.82 min, method: VAB).

L-1as thus obtained (45 mg, 0.16 mmol) is dissolved in DCM (5 mL). Then diethylaminosulfur trifluoride (40 μL, 0.29 mmol, 1.86 eq.) is added and the reaction is stirred at 20° C. for 1 h. The solvent is evaporated and the residue is purified by reverse phase chromatography (method: prep. HPLC1) yielding L-1 at (yield: 44%—20 mg, 0.07 mmol; HPLC-MS: (M+H)$^+$=292, $t_{Ret.}$=1.21 min, method: LCMSBAS).

Synthesis of Intermediates B-1 and B-2
Experimental Procedure for the Synthesis of B-1a

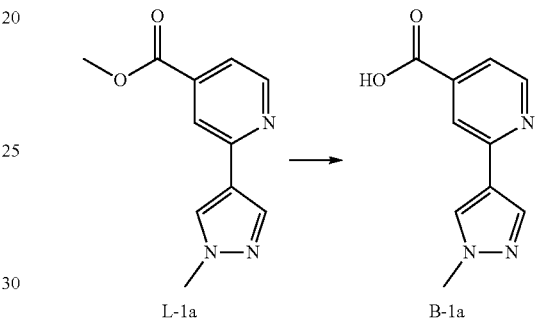

L-1a (4.4 g, 20.4 mmol) is dissolved in water (50.0 mL) and LiOH (732 mg, 1.47 eq.) is added. The reaction mixture is stirred at 20° C. for 4 h. After full conversion the pH is adjusted to pH 3-4. The resulting precipitate is filtered off, washed with water, dried and the solvents are evaporated under reduced pressure to afford the pure product B-1a (yield: 75%—3.1 g, 15.2 mmol; HPLC-MS: (M+H)$^+$=204, $t_{Ret.}$=0.0 min, method LCMSBAS).

Experimental Procedure for the Synthesis of B-1ba

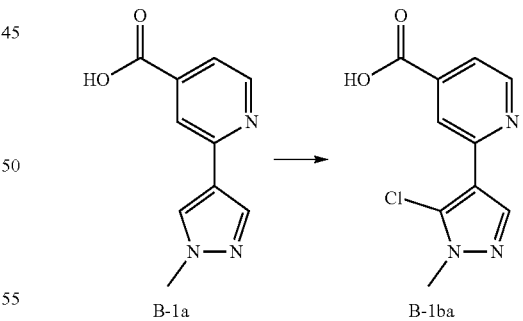

B-1a (200 mg, 0.98 mmol) is dissolved in ACN (5 mL) and NCS (402 mg, 2.95 mmol, 3 eq.) is added. The reaction is stirred at 70° C. for 2 h. The solvents are evaporated and the residue is purified by reverse phase chromatography (method: prep. HPLC1) yielding B-1ba (yield: 25%—59 mg, 0.25 mmol; HPLC-MS: (M+H)$^+$=238, $t_{Ret.}$=0.10 min, method: LCMSBAS).

The following intermediates B-1 and B-2 (table 10) can be synthesized analogously to B-1a (also acidic cleavage for tert-butyl esters) and B-1ba.

TABLE 10

| # | Structure | MS (M + H)+; $t_{Ret.}$ HPLC [min] | HPLC-MS method |
|---|---|---|---|
| B-1a | 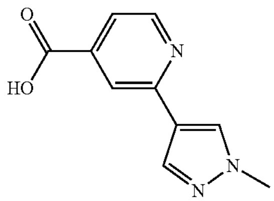 | (M + H)+ = 204; $t_{Ret.}$ = 0.3 | VAB |
| B-1b | 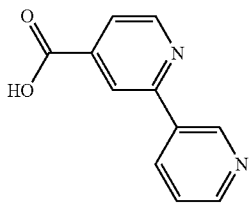 [SMILES: O=C(O)c1ccnc(-c2cccnc2)c1] | (M + H)+ = 201; $t_{Ret.}$ = 1.1 | MONI |
| B-1c | 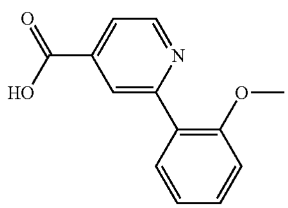 [SMILES: COc1ccccc1-c1cc(C(=O)O)ccn1] | (M + H)+ = 230; $t_{Ret.}$ = 0.6 | VAS |
| B-1d | 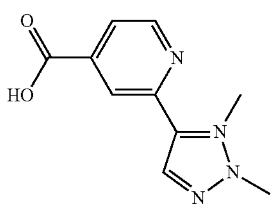 | (M + H)+ = 218; $t_{Ret.}$ = 0.4 | VAS |
| B-1e | 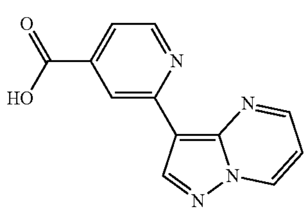 [SMILES: O=C(O)c1ccnc(-c2cnn3cccnc23)c1] | (M + H)+ = 241; $t_{Ret.}$ = 0.4 | VAS |
| B-1f | 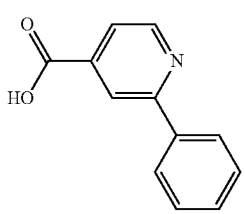 [SMILES: O=C(O)c1ccnc(-c2ccccc2)c1] | (M + H)+ = 200; $t_{Ret.}$ = 0.5 | VAB |
| B-1g | 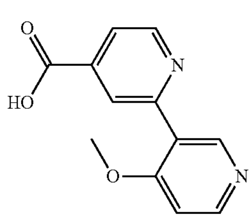 [SMILES: COc1ccncc1-c1cc(C(=O)O)ccn1] | (M + H)+ = 231; $t_{Ret.}$ = 0.2 | VAS |

TABLE 10-continued

| # | Structure | MS (M + H)⁺; t$_{Ret.}$ HPLC [min] | HPLC-MS method |
|---|---|---|---|
| B-1h | 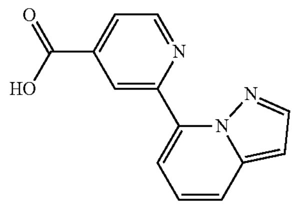 [SMILES: O=C(O)c1ccnc(-c2cccc3ccnn23)c1] | (M + H)⁺ = 240; t$_{Ret.}$ = 0.5 | VAB |
| B-1i | 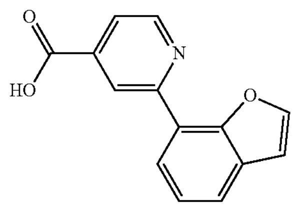 [SMILES: O=C(O)c1ccnc(-c2cccc3ccoc23)c1] | (M + H)⁺ = 240; t$_{Ret.}$ = 0.6 | VAB |
| B-1j | 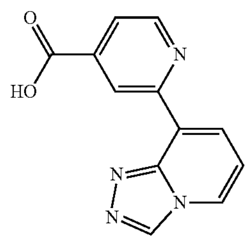 [SMILES: O=C(O)c1ccnc(-c2cccn3cnnc23)c1] | (M + H)⁺ = 241; t$_{Ret.}$ = 0.0 | LCMBAS1 |
| B-1k | 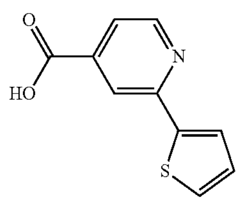 [SMILES: O=C(O)c1ccnc(-c2cccs2)c1] | (M + H)⁺ = 206; t$_{Ret.}$ = 0.6 | VAB |
| B-1l | 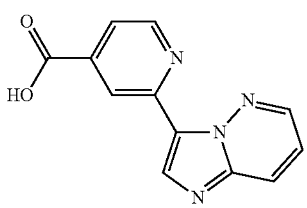 [SMILES: O=C(O)c1ccnc(-c2cnc3cccnn23)c1] | (M + H)⁺ = 241; t$_{Ret.}$ = 0.7 | VAS |
| B-1m | 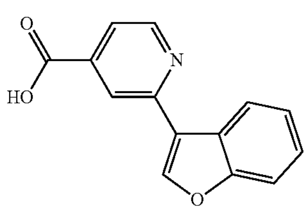 [SMILES: O=C(O)c1ccnc(-c2coc3ccccc23)c1] | (M + H)⁺ = 240; t$_{Ret.}$ = 0.9 | VAS |
| B-1n | 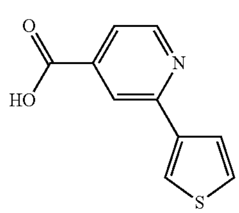 [SMILES: O=C(O)c1ccnc(-c2ccsc2)c1] | (M + H)⁺ = 206; t$_{Ret.}$ = 0.6 | VAB |

TABLE 10-continued

| # | Structure | MS (M + H)+; t_Ret. HPLC [min] | HPLC-MS method |
|---|---|---|---|
| B-1o | 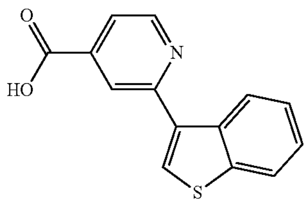 [SMILES: O=C(O)c1ccnc(-c2csc3ccccc23)c1] | (M + H)+ = 256; t_Ret. = 0.9 | VAS |
| B-1p | 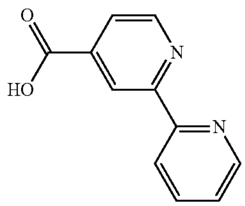 [SMILES: O=C(O)c1ccnc(-c2ccccn2)c1] | (M + H)+ = 201; t_Ret. = 0.4 | VAB |
| B-1q | 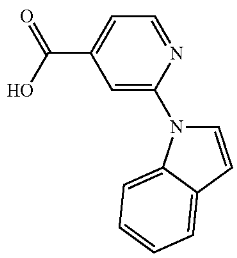 [SMILES: O=C(O)c1ccnc(-n2ccc3ccccc32)c1] | (M + H)+ = 239; t_Ret. = 1.0 | VAS |
| B-1r | 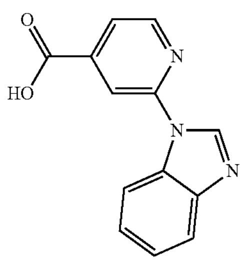 [SMILES: O=C(O)c1ccnc(-n2cnc3ccccc32)c1] | (M + H)+ = 240; t_Ret. = 0.7 | VAS |
| B-1s | 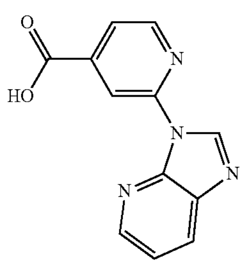 [SMILES: O=C(O)c1ccnc(-n2cnc3cccnc32)c1] | (M + H)+ = 241; t_Ret. = 0.7 | VAS |
| B-1t | 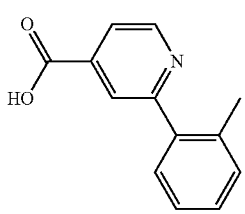 [SMILES: Cc1ccccc1-c1cc(C(=O)O)ccn1] | (M + H)+ = 214; t_Ret. = 0.7 | VAS |

TABLE 10-continued

| # | Structure | MS (M + H)+; t_Ret. HPLC [min] | HPLC-MS method |
|---|---|---|---|
| B-1u | 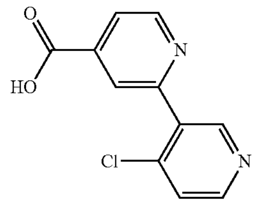 [SMILES: O=C(O)c1ccnc(-c2cnccc2Cl)c1] | (M + H)+ = 235/237; t_Ret. = 0.2 | VAB |
| B-1v | 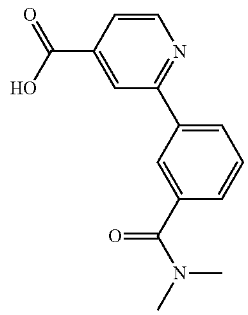 [SMILES: CN(C)C(=O)c1cccc(-c2cc(C(=O)O)ccn2)c1] | (M + H)+ = 271; t_Ret. = 0.6 | VAS |
| B-1w | 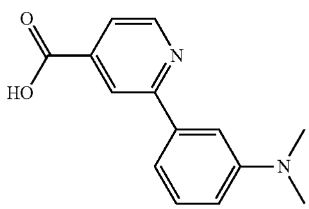 [SMILES: CN(C)c1cccc(-c2cc(C(=O)O)ccn2)c1] | (M + H)+ = 243; t_Ret. = 0.6 | VAS |
| B-1x | 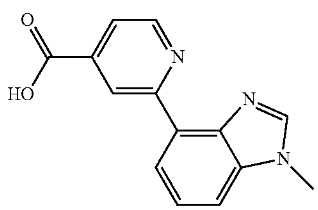 [SMILES: Cn1cnc2c(-c3cc(C(=O)O)ccn3)cccc21] | (M + H)+ = 254; t_Ret. = 0.5 | VAS |
| B-1y | 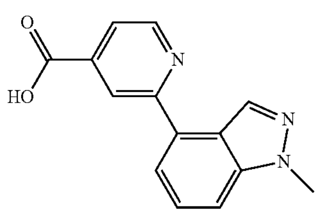 [SMILES: Cn1ncc2c(-c3cc(C(=O)O)ccn3)cccc21] | (M + H)+ = 254; t_Ret. = 0.2 | LCMSBAS |
| B-1z | 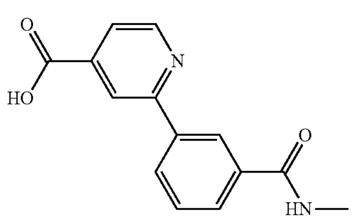 [SMILES: CNC(=O)c1cccc(-c2cc(C(=O)O)ccn2)c1] | (M + H)+ = 257; t_Ret. = 0.5 | VAS |
| B-1aa | 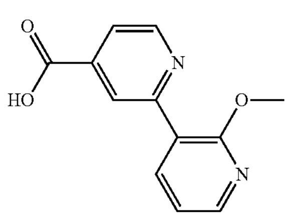 [SMILES: COc1ncccc1-c1cc(C(=O)O)ccn1] | (M + H)+ = 231; t_Ret. = 0.6 | VAS |

TABLE 10-continued

| # | Structure | MS (M + H)+; $t_{Ret.}$ HPLC [min] | HPLC-MS method |
|---|---|---|---|
| B-1ab | 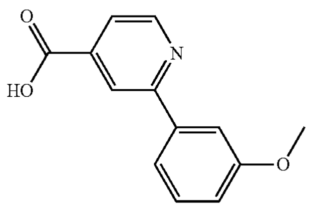 [SMILES: COc1cccc(-c2cc(C(=O)O)ccn2)c1] | (M + H)+ = 230; $t_{Ret.}$ = 0.8 | VAS |
| B-1ac | 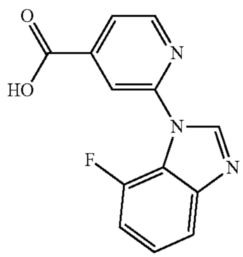 [SMILES: O=C(O)c1ccnc(-n2cnc3cccc(F)c32)c1] | (M + H)+ = 258; $t_{Ret.}$ = 0.8 | VAS |
| B-1ad | 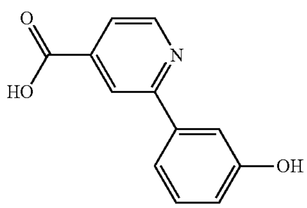 [SMILES: O=C(O)c1ccnc(-c2cccc(O)c2)c1] | (M + H)+ = 216; $t_{Ret.}$ = 0.5 | VAS |
| B-1ae | 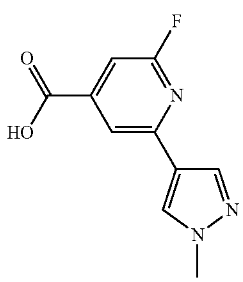 | (M + H)+ = 236; $t_{Ret.}$ = 0.8 | VAB |
| B-1af | 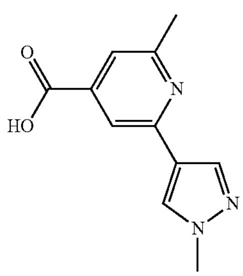 [SMILES: Cc1cc(C(=O)O)cc(-c2cnn(C)c2)n1] | (M + H)+ = 218; $t_{Ret.}$ = 0.1 | VAB |
| B-1ag | 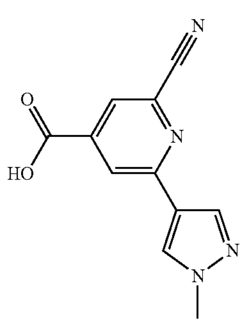 [SMILES: Cn1cc(-c2cc(C(=O)O)cc(C#N)n2)cn1] | (M + H)+ = 229; $t_{Ret.}$ = 0.5 | VAB |

TABLE 10-continued

| # | Structure | MS (M + H)+; $t_{Ret.}$ HPLC [min] | HPLC-MS method |
|---|---|---|---|
| B-1ah | 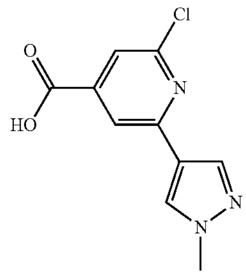 | (M + H)+ = 238/240; $t_{Ret.}$ = 0.4 | VAB |
| B-1ai | 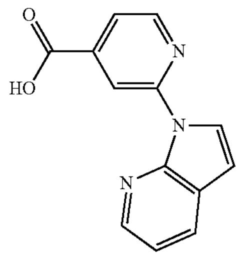 [SMILES: O=C(O)c1ccnc(-n2ccc3cccnc32)c1] | (M + H)+ = 240; $t_{Ret.}$ = 0.8 | VAS |
| B-1aj | 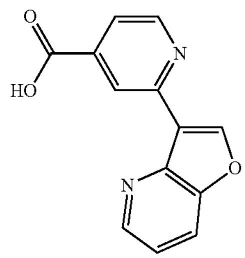 [SMILES: O=C(O)c1ccnc(-c2coc3cccnc23)c1] | (M + H)+ = XXX; $t_{Ret.}$ = X.X | LCMSBAS |
| B-1ak | 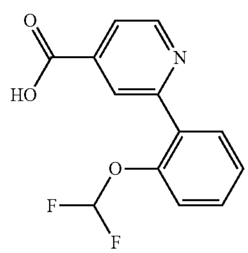 [SMILES: O=C(O)c1ccnc(-c2ccccc2OC(F)F)c1] | (M + H)+ = 284; $t_{Ret.}$ = 0.6 | VAB |
| B-1al | 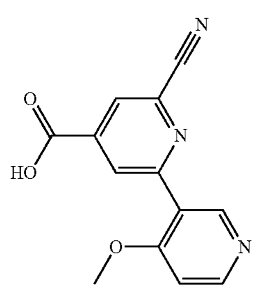 [SMILES: COc1ccncc1-c1cc(C(=O)O)cc(C#N)n1] | (M + H)+ = 256; $t_{Ret.}$ = 0.7 | VAB |
| B-1am | 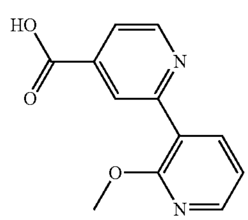 [SMILES: COc1ncccc1-c1cc(C(=O)O)ccn1] | (M + H)+ = 231; $t_{Ret.}$ = 0.6 | VAS |

TABLE 10-continued

| # | Structure | MS (M + H)+; t_Ret. HPLC [min] | HPLC-MS method |
|---|---|---|---|
| B-1an | 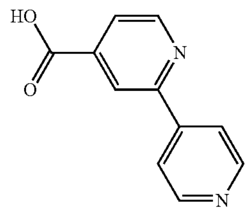 [SMILES: O=C(O)c1ccnc(-c2ccncc2)c1] | (M + H)+ = 231; t_Ret. = 0.3 | VAS |
| B-1ao | 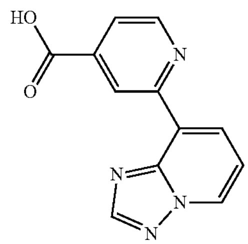 [SMILES: O=C(O)c1ccnc(-c2cccn3ncnc23)c1] | (M + H)+ = 241; t_Ret. = 0.6 | VAS |
| B-1ap | 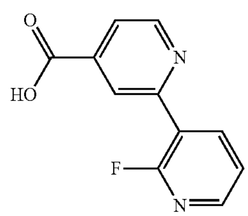 [SMILES: O=C(O)c1ccnc(-c2cccnc2F)c1] | (M + H)+ = 275; t_Ret. = 1.0 | VAS |
| B-1aq | 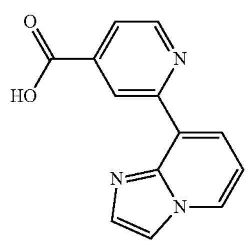 [SMILES: O=C(O)c1ccnc(-c2cccn3ccnc23)c1] | (M + H)+ = 240; t_Ret. = 0.9 | VAS |
| B-1ar | 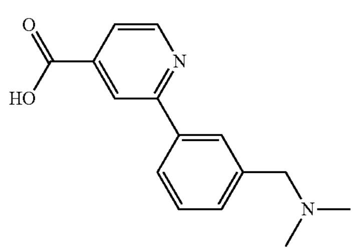 [SMILES: CN(C)Cc1cccc(-c2cc(C(=O)O)ccn2)c1] | (M + H)+ = 257; t_Ret. = 0.24 | VAS |
| B-1as | 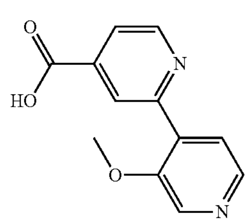 [SMILES: COc1cnccc1-c1cc(C(=O)O)ccn1] | (M + H)+ = 231; t_Ret. = 0.3 | VAS |

TABLE 10-continued

| # | Structure | MS (M + H)+; $t_{Ret.}$ HPLC [min] | HPLC-MS method |
|---|---|---|---|
| B-1at | 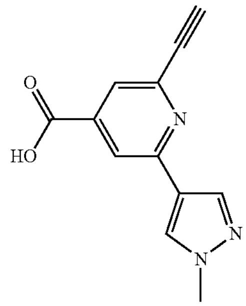 [SMILES: C#Cc1cc(C(=O)O)cc(-c2cnn(C)c2)n1] | (M + H)+ = 228; $t_{Ret.}$ = 0.1 | LCMSBAS |
| B-1au | 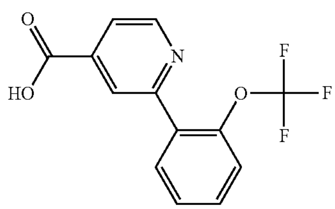 [SMILES: O=C(O)c1ccnc(-c2ccccc2OC(F)(F)F)c1] | (M + H)+ = 284; $t_{Ret.}$ = 0.6 | VAB |
| B-1ay | 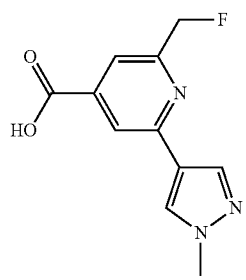 | (M + H)+ = 272; $t_{Ret.}$ = 0.3 | VAB |
| B-1aw | 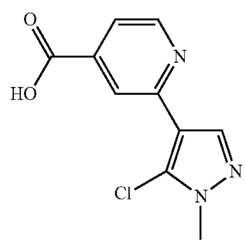 [SMILES: Cn1ncc(-c2cc(C(=O)O)ccn2)c1Cl] | (M + H)+ = 238; $t_{Ret.}$ = 0.1 | LCMSBAS |
| B-1ax | 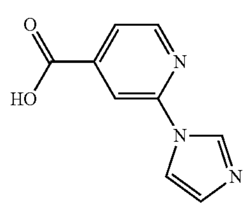 [SMILES: O=C(O)c1ccnc(-n2ccnc2)c1] | commercially available | |
| B-2a | 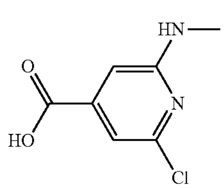 | commercially available | |

TABLE 10-continued

| # | Structure | MS (M + H)+; t_Ret. HPLC [min] | HPLC-MS method |
|---|---|---|---|
| B-2b | ![structure] | commercially available | |
| B-2c | ![structure] | commercially available | |

Synthesis of Intermediates U-1

Experimental Procedure for the Synthesis of U-1a

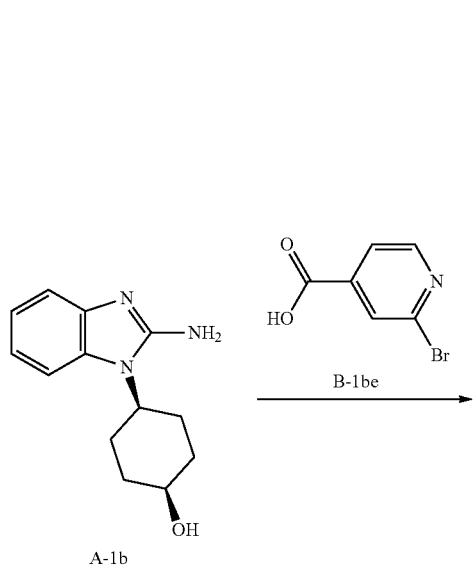

B-1be (720.5 mg; 3.6 mmol) is dissolved in DCM (50.0 mL). DIPEA (1.6 mL, 9.7 mmol) and HATU (1357.6 mg, 3.6 mmol) are added. The reaction mixture is stirred at 20° C. for 5 min, then A-1b (750 mg, 3.2 mmol) is added and stirring is continued over a period of 18 h. The reaction mixture is evaporated to dryness, the remaining residue is dissolved in DMSO, filtered and purified by reverse phase chromatography (method: prep. HPLC1) yielding U-1a (yield: 61%—415 mg, 1.99 mmol; HPLC-MS: (M+H)+ = 416, $t_{Ret.}$=0.9 min, method: VAB).

The following intermediates U-1 (table 11) can be synthesized analogously to U-1a.

TABLE 11

| # | Structure | MS (M + H)+; t_Ret. HPLC [min] | HPLC-MS method |
|---|---|---|---|
| U-1a | ![structure] | (M + H)+ = 416; $t_{Ret.}$ = 0.9 | VAB |

TABLE 11-continued

| # | Structure | MS (M + H)+; $t_{Ret.}$ HPLC [min] | HPLC-MS method |
|---|---|---|---|
| U-1b | 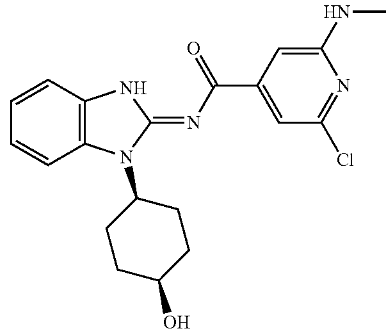 [SMILES: CNc1cc(C(=O)/N=c2\[nH]c3ccccc3n2[C@H]2CC[C@@H](O)CC2)cc(Cl)n1] | (M + H)+ = 400; $t_{Ret.}$ = 0.9 | VAB |
| U-1c | 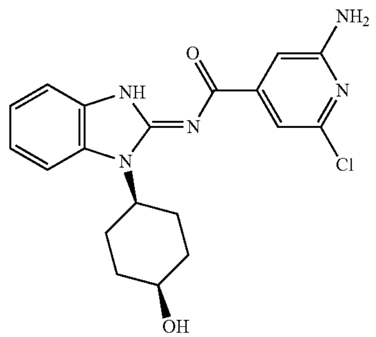 [SMILES: Nc1cc(C(=O)/N=c2\[nH]c3ccccc3n2[C@H]2CC[C@@H](O)CC2)cc(Cl)n1] | (M + H)+ = 432; $t_{Ret.}$ = 1.0 | LCMSBAS |
| U-1d | 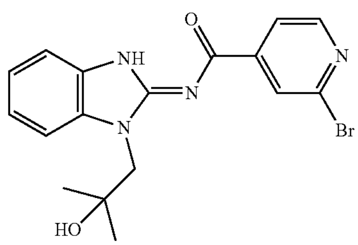 [SMILES: CC(C)(O)Cn1/c(=N/C(=O)c2ccnc(Br)c2)[nH]c2ccccc21] | (M + H)+ = 389; $t_{Ret.}$ = 0.9 | VAB |

Preparation of Compounds (I) According to the Invention
Experimental Procedure for the Synthesis of I-001 (Synthesis Method A)

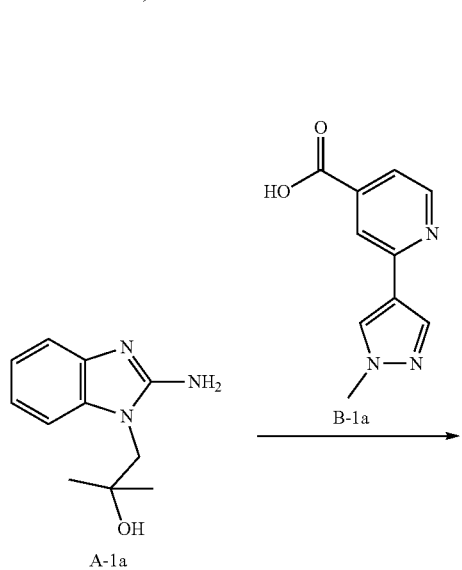

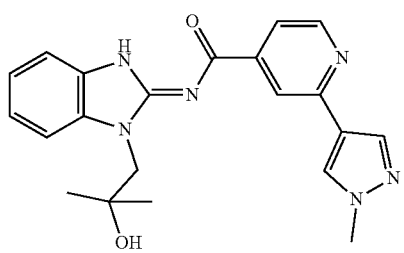

I-001

A-1a (20 mg, 0.09 mmol), HATU (45 mg, 0.12 mmol, 1.2 eq.) and DIPEA (100 μL, 0.59 mmol, 6.3 eq.) are dissolved in DCM (2.0 mL) at 20° C. After 15 min acid B-1a is added and the reaction is stirred at 20° C. for 1 h. After full conversion the solvent is evaporated and the residue is purified by reverse phase chromatography (method: prep. HPLC1) yielding pure I-001 (yield: 55%—20 mg, 0.05 mmol; HPLC-MS: (M+H)+=391, $t_{Ret.}$=0.82 min, method VAB).

Experimental Procedure for the Synthesis of I-230 (Synthesis Method A)

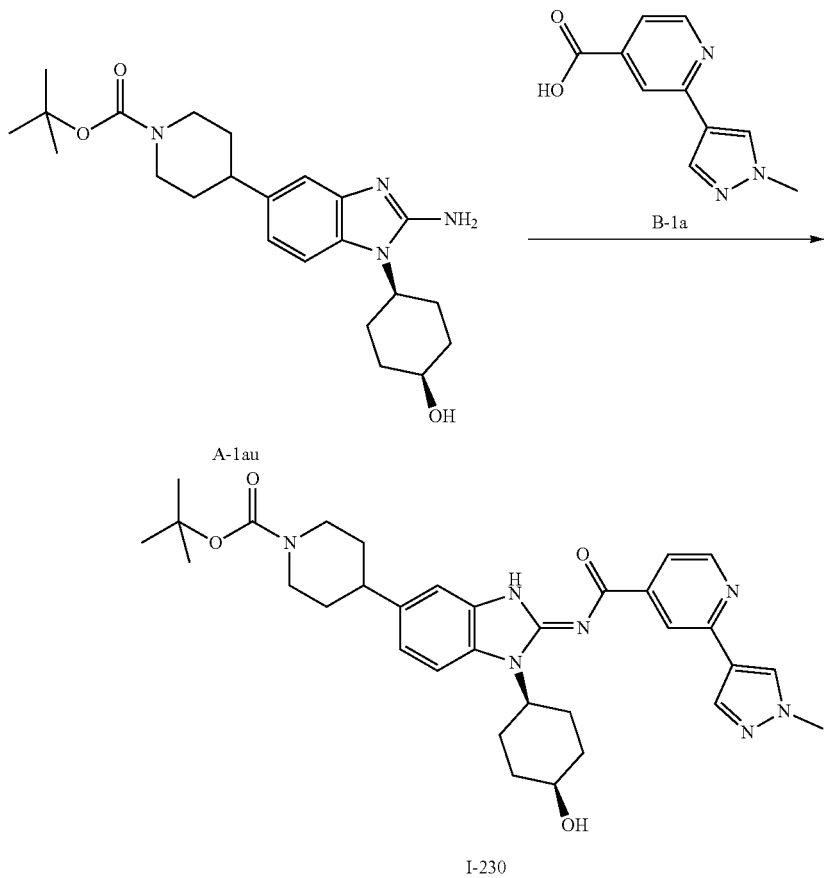

A-1au (200 mg, 0.48 mmol) and B-1a (108 mg, 0.53 mmol, 1.1 eq.) are dissolved in 1,4-dioxane (1.0 mL). DIPEA (165 μL, 0.96 mmol, 2.0 eq.) and HATU (220 mg, 0.58 mmol, 1.2 eq.) are added. The reaction mixture is stirred at 20° C. for 16 h. The reaction mixture is evaporated to dryness, the remaining residue is dissolved in DMSO, filtered and purified by reverse phase chromatography (method: prep. HPLC1) yielding I-230 (yield: 47%—136 mg, 0.23 mmol; HPLC-MS: (M+H)$^+$=600, $t_{Ret.}$=0.99 min, method: LCMSBAS).

Experimental Procedure for the Synthesis of I-141 (Synthesis Method B)

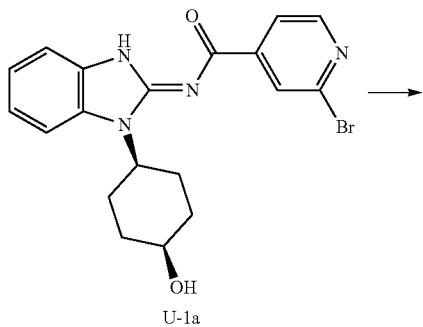

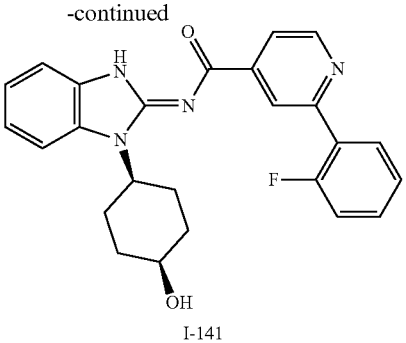

U-1a (30 mg, 0.07 mmol), 2-fluorophenylboronic acid (13 mg, 0.09 mmol, 1.3 eq.), Cs$_2$CO$_3$ (80 mg, 0.24 mmol, 3.4 eq.) and LiBF$_4$ (8 mg, 0.9 mmol, 1.2 eq.) are dissolved/suspended in a DME/water mixture (3:1, 3 mL) and [1,1'-bis(diphenylphosphino)ferrocene] dichloropalladium(II) complex with dichloromethane (5 mg, 0.01 mmol, 0.1 eq.) is added. The reaction is stirred at 130° C. for 1 h, the solvents are evaporated and the residue is purified by reverse phase chromatography (method: prep. HPLC1) yielding I-141 (yield: 32%—10 mg, 0.02 mmol; HPLC-MS: (M+H)$^+$= 431, $t_{Ret.}$=1.28 min, method: LCMSBAS).

Experimental Procedure for the Synthesis of I-058 (Derivatization (C) of Compound Obtained after Method A with an Intermediate A*-1)

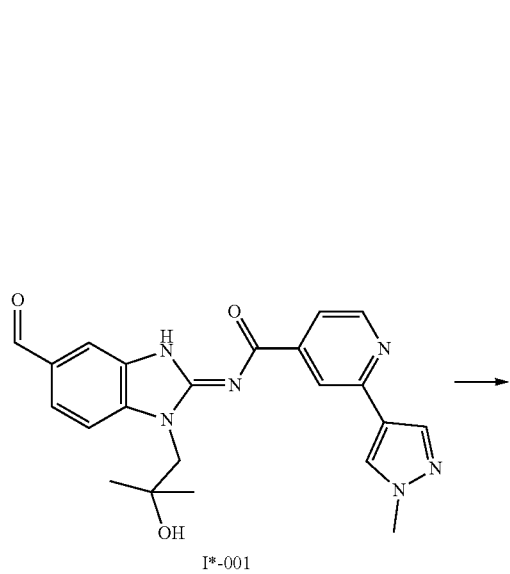
I*-001

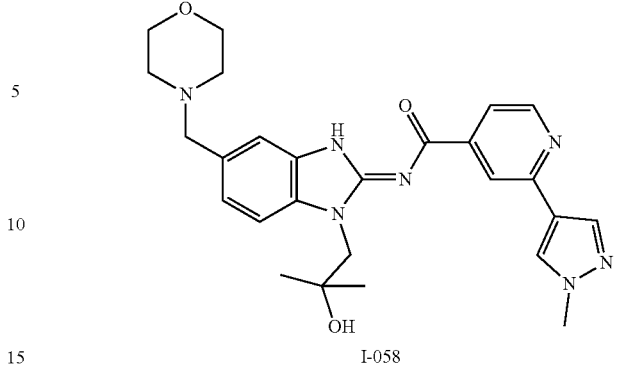
I-058

I*-001 (100 mg, 0.24 mmol) is dissolved in dry THF (10 mL), morpholine (31 mg, 0.36 mmol, 1.5 eq.), acetic acid (139 µL, 10 eq.) and NaBH(OAc)$_3$ are added at 20° C. and the reaction is stirred for 16 h. After full conversion the reaction is quenched with methanol, the solvents are evaporated and the residue is purified by reverse phase chromatography (method: prep. HPLC1) yielding pure I-058 (yield: 38%—45 mg, 0.09 mmol); HPLC-MS: (M+H)$^+$=490, $t_{Ret.}$=1.02 min, method: LCMSBAS)

Experimental Procedure for the Synthesis of I-218 and I-219 (Derivatization (C) of Previously Obtained Compound (I))

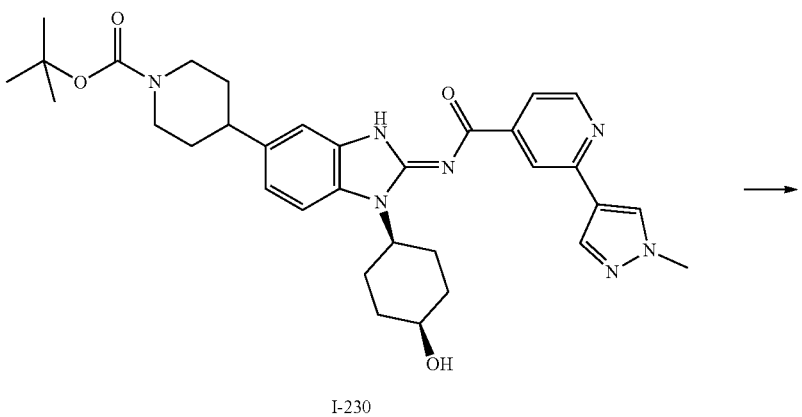
I-230

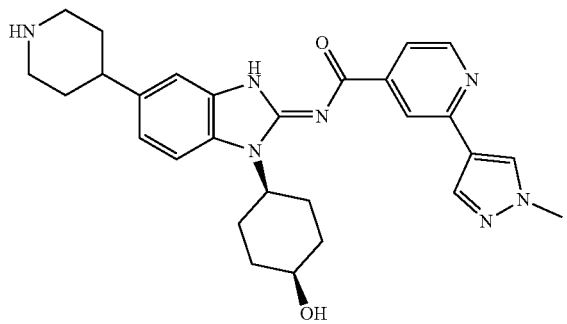
I-218

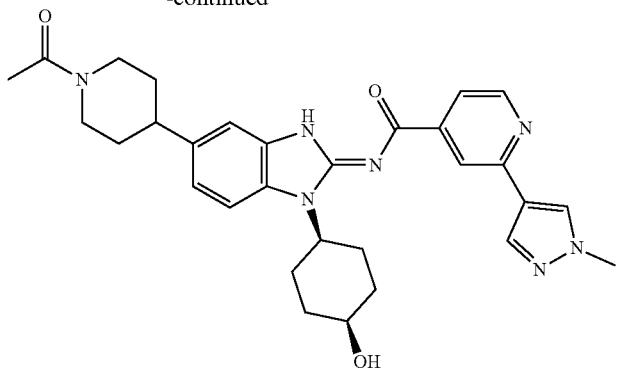

I-219

I-230 (136 mg, 0.23 mmol) is dissolved in MeOH (2 mL) and HCl in dioxane (1 mL, 4.0 M, 4 mmol, 17.6 equiv.) is added. The reaction is stirred at 20° C. for 16 h. The reaction mixture is neutralized with aq. sat. NaHCO$_3$ solution and the mixture is extracted with EtOAc. The solvent is evaporated and the residue is treated with water. The formed precipitate is filtered off, redissolved in ACN/water (1:1) and the solvents are evaporated yielding I-218 (yield: 57%—65 mg, 0.13 mmol); HPLC-MS: (M+H)$^+$=500, $t_{Ret.}$=1.08 min, method: LCMSBAS).

I-218 thus obtained (50 mg, 0.10 mmol) is dissolved in DCM (2 mL), DIPEA (67 µL, 0.40 mmol, 4.0 eq.) and acetyl chloride (9 µL, 0.13 mmol, 1.3 equiv.) are added. The reaction is stirred at 20° C. for 30 min. The solvents are evaporated and the residue is purified by reverse phase chromatography (method: prep. HPLC1) yielding I-219 (yield: 72%—39 mg, 0.07 mmol; HPLC-MS: (M+H)$^+$=542, $t_{Ret.}$=1.04 min, method: LCMSBAS).

Experimental Procedure for the Synthesis of I*-002 and I-130 (Derivatization (C) of Previously Obtained Compound (I))

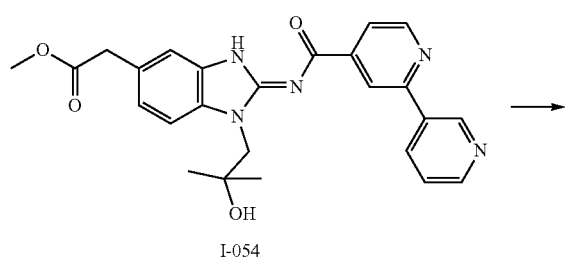

I-054

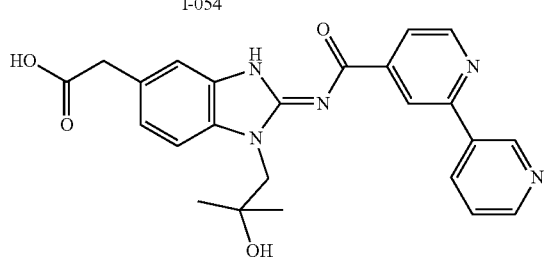

I*-002

↓

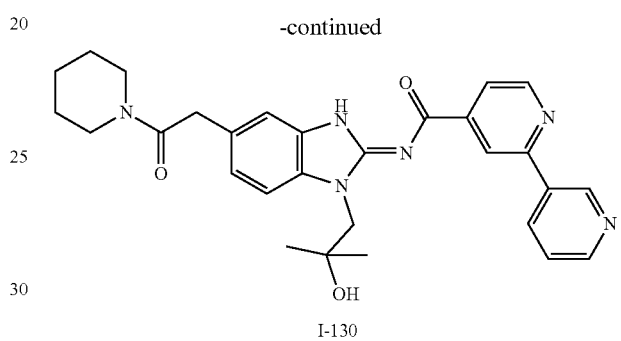

I-130

I-054 (400 mg, 0.87 mmol) is dissolved in dioxane (1 mL) and water (1 mL) and LiOH (208 mg, 8.71 mmol, 10 eq.) is added. The reaction is stirred at 20° C. for 16 h. The organic solvent is evaporated and the aq. solution is acidified with HCl (pH=3). The precipitated product is filtered off and dried yielding I*-002 (yield: 75%—290 mg, 0.65 mmol); HPLC-MS: (M+H)$^+$=546, $t_{Ret.}$=0.73 min, method: LCMSBAS).

I*-002 thus obtained (70 mg, 0.16 mmol) is dissolved in DCM (2 mL), HATU (94 mg, 0.24 mmol, 1.5 equiv.), DIPEA (61 mg, 0.47 mmol, 3.0 eq.) and piperidine (16 mg, 0.19 mmol, 1.2 equiv.) are added. The reaction is stirred at 20° C. for 16 h. The solvents are evaporated and the residue is purified by reverse phase chromatography (method: prep. HPLC1) yielding I-130 (yield: 63%—51 mg, 0.10 mmol; HPLC-MS: (M+H)$^+$=513, $t_{Ret.}$=1.06 min, method: LCMSBAS).

Experimental Procedure for the Synthesis of I-056 (Derivatization (C) of Previously Obtained Compound (0)

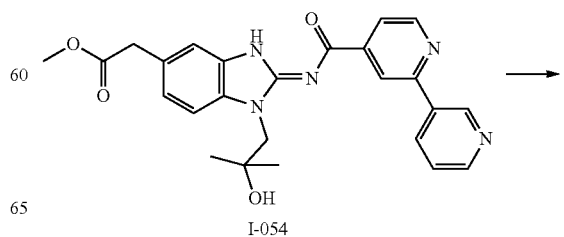

I-054

-continued

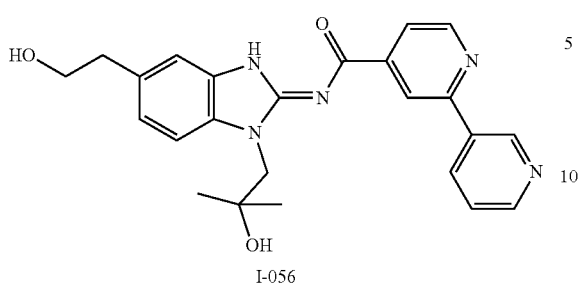

I-056

I-054 (840 mg, 1.83 mmol) is dissolved in THF (5 mL) and a LiAlH$_4$ solution (2.74 mL, 2.74 mmol, 1.5 eq.) is added. The reaction is stirred at 20° C. for 16 h before iPrOH (5 mL) is added. The organic solvent is evaporated and the residue is purified by normal phase chromatography (eluent: DCM/MeOH; 100:10) yielding I-056 (yield: 22%—170 mg, 0.39 mmol); HPLC-MS: (M+H)$^+$=432, $t_{Ret.}$=0.93 min, method: LCMSBAS).

Experimental Procedure for the Synthesis of I-184 (Derivatization (C) of Compound Obtained after Method a with an Intermediate a*-1)

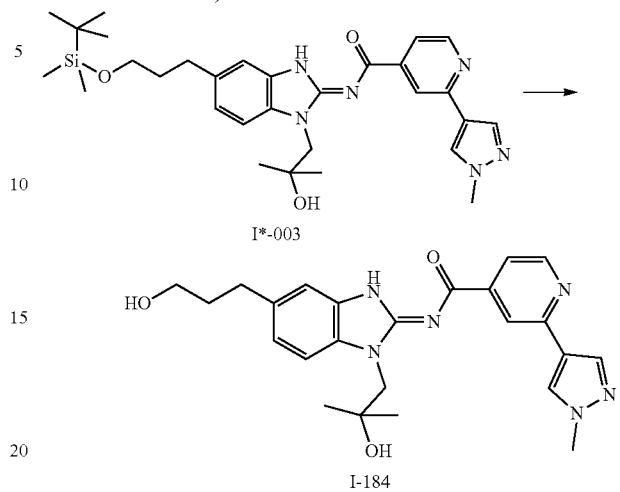

I*-003

I-184

I*-003 (60 mg, 0.11 mmol) is dissolved in THF (1 mL) and TBAF (106 mg, 0.12 mmol, 1.1 eq.) is added. The reaction is stirred at 20° C. for 16 h before iPrOH (5 mL) is added. The solvents are evaporated and the residue is purified by reverse phase chromatography (method: prep. HPLC1) yielding I-184 (yield: 25%—12 mg, 0.03 mmol); HPLC-MS: (M+H)$^+$=449, $t_{Ret.}$=1.0 min, method: LCMSBAS).

TABLE 12

| # | Structure | method | IC$_{50}$ [nM] | MS (M + H)$^+$ $t_{Ret}$ HPLC [min] | HPLC-MS method |
|---|---|---|---|---|---|
| I-001 | 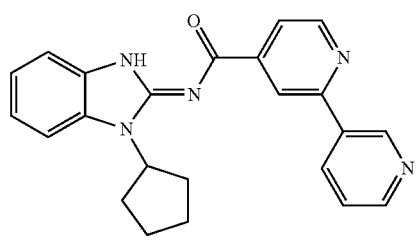 | A | 43 | (M + H)$^+$ = 301, $t_{Ret.}$ = 1.0 | LCMSBAS |
| I-002 | 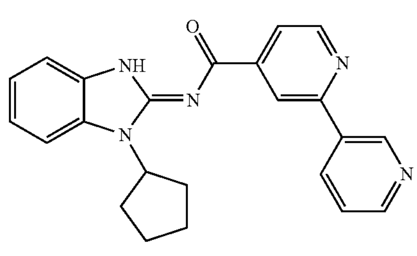 [SMILES: O=C(/N=c1\[nH]c2ccccc2n1C1CCCC1)c1ccnc(-c2cccnc2)c1] | A | 9 | (M + H)$^+$ = 384, $t_{Ret.}$ = 1.3 | LCMSBAS |

TABLE 12-continued
| # | Structure | method | IC$_{50}$ [nM] | MS (M + H)$^+$ t$_{Ret}$ HPLC [min] | HPLC-MS method |
|---|---|---|---|---|---|
| I-003 | 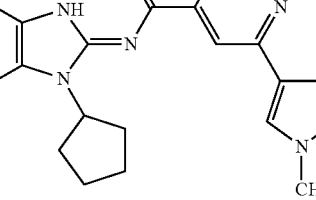 | A | 29 | (M + H)$^+$ = 387, t$_{Ret.}$ = 1.01 | LCMSBAS |
| I-004 | 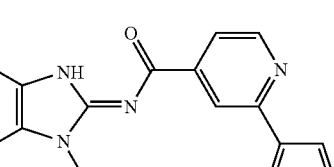 | A | 13 | (M + H)$^+$ = 401, t$_{Ret.}$ = 1.3 | LCMSBAS |
| I-005 | 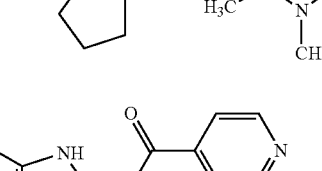 | B | 11 | (M + H)$^+$ = 401, t$_{Ret.}$ = 1.29 | LCMSBAS |
| I-006 | 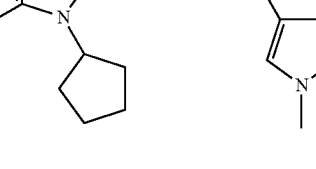 | C | 35 | (M + H)$^+$ = 388, t$_{Ret.}$ = 1.02 | LCMSBAS |
| I-007 | 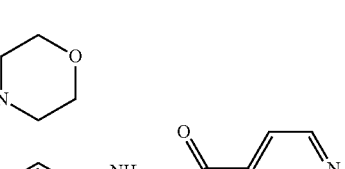 | A | 15 | (M + H)$^+$ = 500, t$_{Ret.}$ = 1.25 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-008 | 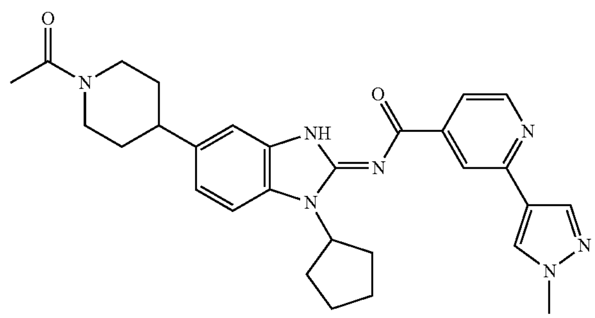 [SMILES: CC(=O)N1CCC(c2ccc3c(c2)[nH]/c(=N\C(=O)c2ccnc(-c4cnn(C)c4)c2)n3C2CCCC2)CC1] | A | 6 | (M + H)$^+$ = 512, t$_{Ret.}$ = 1.18 | LCMSBAS |
| I-009 | 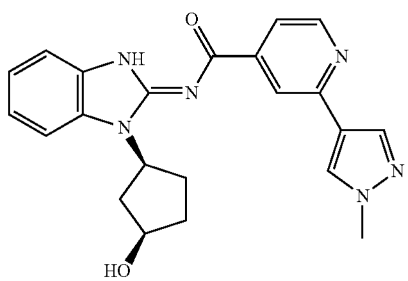 [SMILES: Cn1cc(-c2cc(C(=O)/N=c3\[nH]c4ccccc4n3[C@H]3CC[C@@H](O)C3)ccn2)cn1] | A | 30 | (M + H)$^+$ = 403, t$_{Ret.}$ = 0.97 | LCMSBAS |
| I-010 | 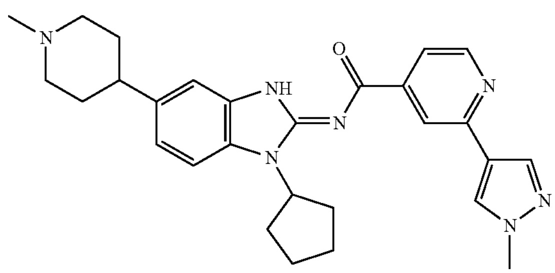 [SMILES: CN1CCC(c2ccc3c(c2)[nH]/c(=N\C(=O)c2ccnc(-c4cnn(C)c4)c2)n3C2CCCC2)CC1] | A | 20 | (M + H)$^+$ = 484, t$_{Ret.}$ = 1.39 | LCMSBAS |
| I-011 | 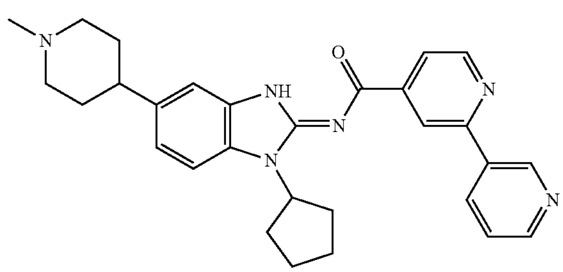 [SMILES: CN1CCC(c2ccc3c(c2)[nH]/c(=N\C(=O)c2ccnc(-c4cccnc4)c2)n3C2CCCC2)CC1] | A | 77 | (M + H)$^+$ = 481, t$_{Ret.}$ = 1.51 | LCMSBAS |
| I-012 | 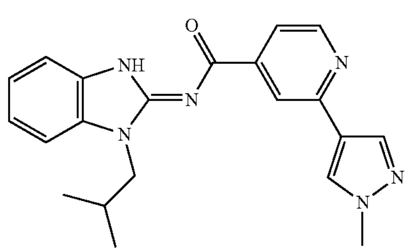 [SMILES: CC(C)Cn1/c(=N/C(=O)c2ccnc(-c3cnn(C)c3)c2)[nH]c2ccccc21] | A | 25 | (M + H)$^+$ = 375, t$_{Ret.}$ = 1.22 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-013 | 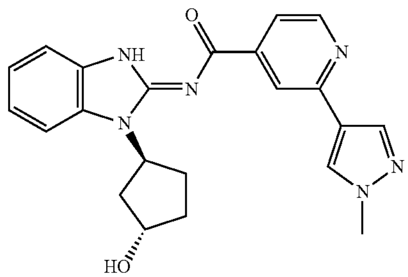 [SMILES: Cn1cc(-c2cc(C(=O)/N=c3\[nH]c4ccccc4n3[C@H]3CC[C@H](O)C3)ccn2)cn1] | A | 13 | (M + H)$^+$ = 403, t$_{Ret.}$ = 0.97 | LCMSBAS |
| I-014 | 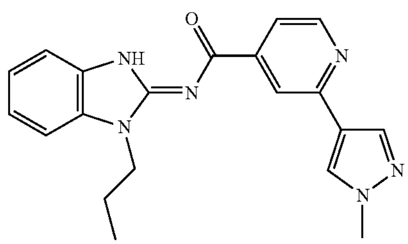 [SMILES: CCCn1/c(=N/C(=O)c2ccnc(-c3cnn(C)c3)c2)[nH]c2ccccc21] | A | 94 | (M + H)$^+$ = 361, t$_{Ret.}$ = 1.15 | LCMSBAS |
| I-015 | 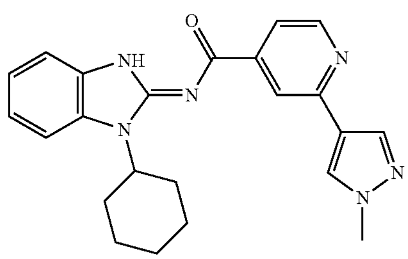 | A | 9 | (M + H)$^+$ = 401, t$_{Ret.}$ = 1.3 | LCMSBAS |
| I-016 | 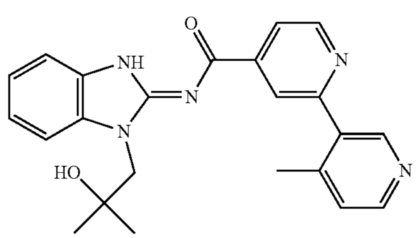 [SMILES: Cc1ccncc1-c1cc(C(=O)/N=c2\[nH]c3ccccc3n2CC(C)(C)O)ccn1] | B | 58 | (M + H)$^+$ = 402, t$_{Ret.}$ = 1.04 | LCMSBAS |
| I-017 | 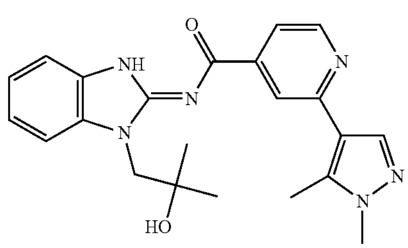 [SMILES: Cc1c(-c2cc(C(=O)/N=c3\[nH]c4ccccc4n3CC(C)(C)O)ccn2)cnn1C] | A | 7 | (M + H)$^+$ = 405, t$_{Ret.}$ = 1.05 | LCMSBAS |
| I-018 | 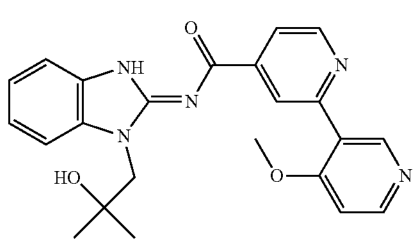 [SMILES: COc1ccncc1-c1cc(C(=O)/N=c2\[nH]c3ccccc3n2CC(C)(C)O)ccn1] | A | 1 | (M + H)$^+$ = 418, t$_{Ret.}$ = 1 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-019 | 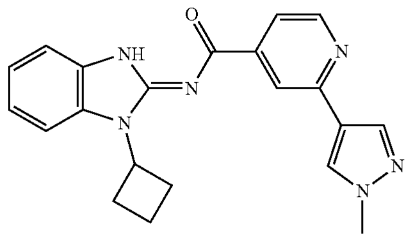 [SMILES: Cn1cc(-c2cc(C(=O)/N=c3\[nH]c4ccccc4n3C3CCC3)ccn2)cn1] | A | 37 | (M + H)$^+$ = 373, t$_{Ret.}$ = 1.19 | LCMSBAS |
| I-020 | 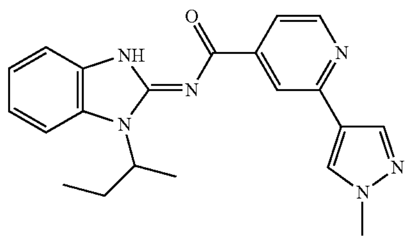 [SMILES: CCC(C)n1/c(=N/C(=O)c2ccnc(-c3cnn(C)c3)c2)[nH]c2ccccc21] | A | 41 | (M + H)$^+$ = 375, t$_{Ret.}$ = 1.21 | LCMSBAS |
| I-021 | 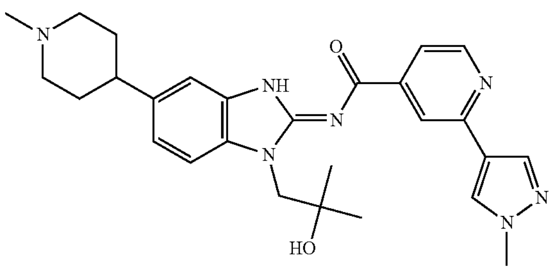 [SMILES: CN1CCC(c2ccc3c(c2)[nH]/c(=N\C(=O)c2ccnc(-c4cnn(C)c4)c2)n3CC(C)(C)O)CC1] | A | 4 | (M + H)$^+$ = 488, t$_{Ret.}$ = 1.03 | LCMSBAS |
| I-022 | 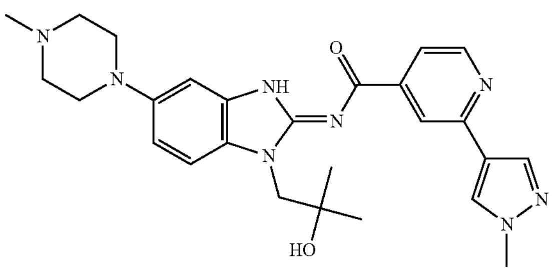 [SMILES: CN1CCN(c2ccc3c(c2)[nH]/c(=N\C(=O)c2ccnc(-c4cnn(C)c4)c2)n3CC(C)(C)O)CC1] | A | 71 | (M + H)$^+$ = 489, t$_{Ret.}$ = 0.97 | LCMSBAS |
| I-023 | 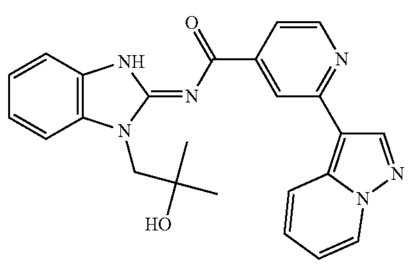 [SMILES: CC(C)(O)Cn1/c(=N/C(=O)c2ccnc(-c3cnn4ccccc34)c2)[nH]c2ccccc21] | B | 7 | (M + H)$^+$ = 427, t$_{Ret.}$ = 1.16 | LCMSBAS |
| I-024 | 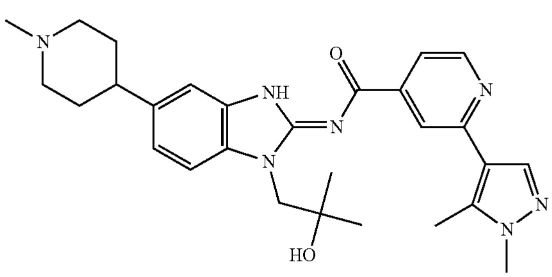 | A | 2 | (M + H)$^+$ = 502, t$_{Ret.}$ = 1.1 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-025 | 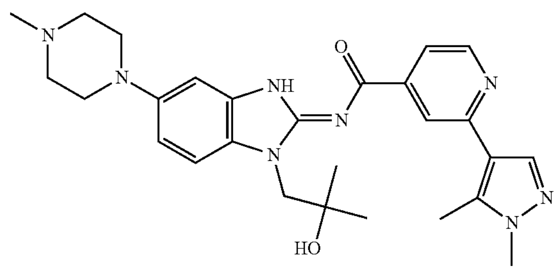 [SMILES: Cc1c(-c2cc(C(=O)/N=c3\[nH]c4cc(N5CCN(C)CC5)ccc4n3CC(C)(C)O)ccn2)cnn1C] | A | 28 | (M + H)$^+$ = 503, t$_{Ret.}$ = 1.01 | LCMSBAS |
| I-026 | 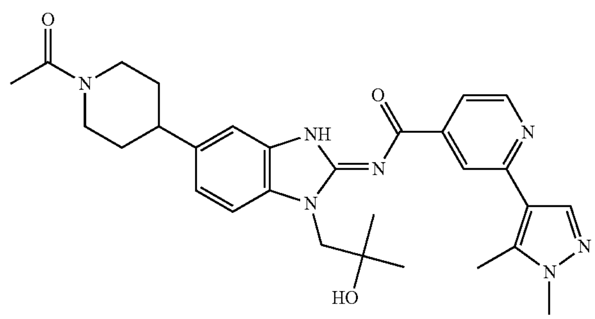 [SMILES: CC(=O)N1CCC(c2ccc3c(c2)[nH]/c(=N\C(=O)c2ccnc(-c4cnn(C)c4C)c2)n3CC(C)(C)O)CC1] | A | 7 | (M + H)$^+$ = 530, t$_{Ret.}$ = 1.02 | LCMSBAS |
| I-027 | 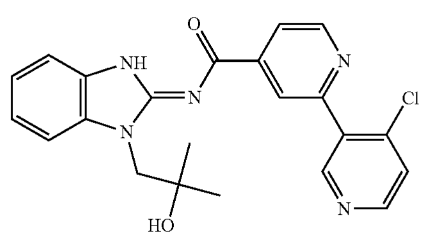 [SMILES: CC(C)(O)Cn1/c(=N/C(=O)c2ccnc(-c3cnccc3Cl)c2)[nH]c2ccccc21] | A | 55 | (M + H)$^+$ = 422, t$_{Ret.}$ = 1.07 | LCMSBAS |
| I-028 | 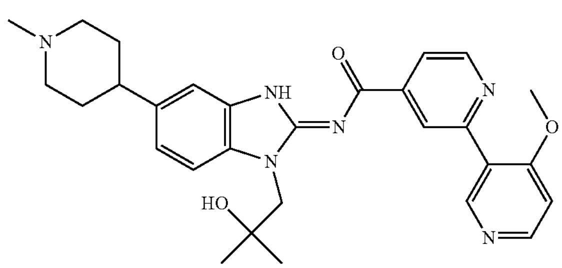 [SMILES: COc1ccncc1-c1cc(C(=O)/N=c2\[nH]c3cc(C4CCN(C)CC4)ccc3n2CC(C)(C)O)ccn1] | A | 1 | (M + H)$^+$ = 515, t$_{Ret.}$ = 1.04 | LCMSBAS |
| I-029 | 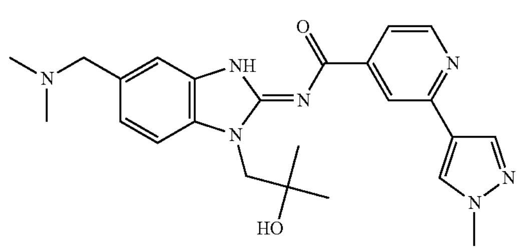 [SMILES: CN(C)Cc1ccc2c(c1)[nH]/c(=N\C(=O)c1ccnc(-c3cnn(C)c3)c1)n2CC(C)(C)O] | C | 58 | (M + H)$^+$ = 448, t$_{Ret.}$ = 0.98 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-030 | 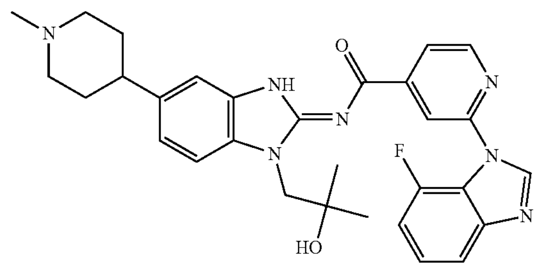 [SMILES: CN1CCC(c2ccc3c(c2)[nH]/c(=N\C(=O)c2ccnc(-n4cnc5cccc(F)c54)c2)n3CC(C)(C)O)CC1] | A | 6 | (M + 2H)$^+$ = 272, t$_{Ret.}$ = 1.23 | LCMSBAS |
| I-031 | 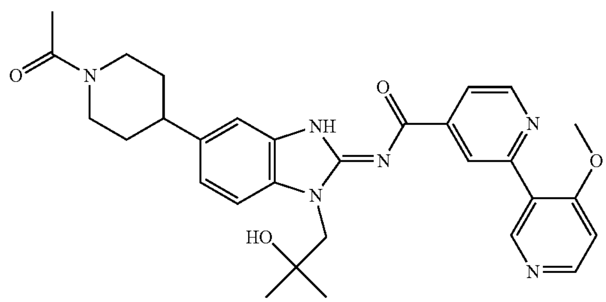 | A | 1 | (M + H)$^+$ = 453, t$_{Ret.}$ = 1 | LCMSBAS |
| I-032 | 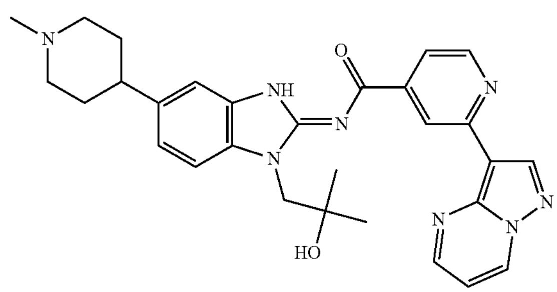 [SMILES: CN1CCC(c2ccc3c(c2)[nH]/c(=N\C(=O)c2ccnc(-c4cnn5cccnc45)c2)n3CC(C)(C)O)CC1] | A | 1 | (M + H)$^+$ = 525, t$_{Ret.}$ = 1.08 | LCMSBAS |
| I-033 | 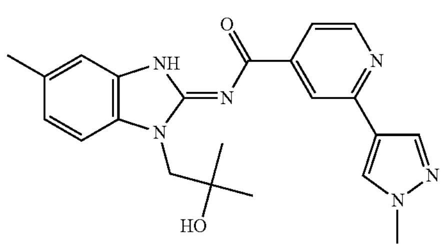 [SMILES: Cc1ccc2c(c1)[nH]/c(=N\C(=O)c1ccnc(-c3cnn(C)c3)c1)n2CC(C)(C)O] | A | 9 | (M + H)$^+$ = 405, t$_{Ret.}$ = 1.1 | LCMSBAS |
| I-034 | 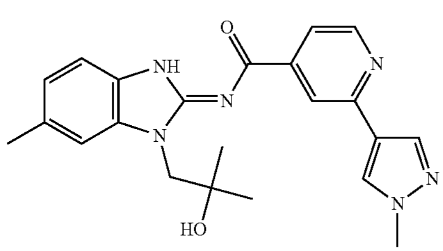 [SMILES: Cc1ccc2[nH]/c(=N\C(=O)c3ccnc(-c4cnn(C)c4)c3)n(CC(C)(C)O)c2c1] | A | 21 | (M + H)$^+$ = 405, t$_{Ret.}$ = 1.1 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-035 | 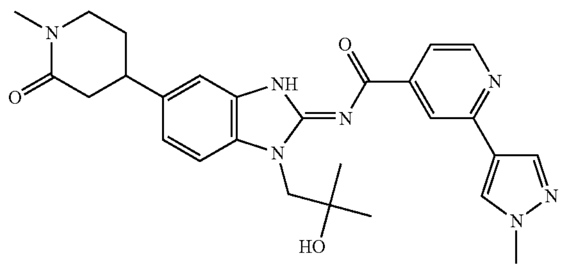 [SMILES: CN1CCC(c2ccc3c(c2)[nH]/c(=N\C(=O)c2ccnc(-c4cnn(C)c4)c2)n3CC(C)(C)O)CC1=O] | A | 79 | (M + H)$^+$ = 502, t$_{Ret.}$ = 0.96 | LCMSBAS |
| I-036 | 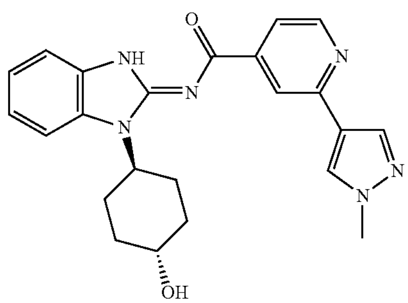 [SMILES: Cn1cc(-c2cc(C(=O)/N=c3\[nH]c4ccccc4n3[C@H]3CC[C@H](O)CC3)ccn2)cn1] | A | 3 | (M + H)$^+$ = 417, t$_{Ret.}$ = 1 | LCMSBAS |
| I-037 | 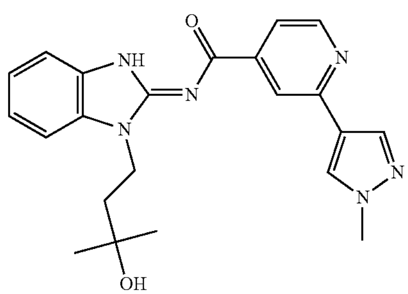 [SMILES: Cn1cc(-c2cc(C(=O)/N=c3\[nH]c4ccccc4n3CCC(C)(C)O)ccn2)cn1] | A | 15 | (M + H)$^+$ = 405, t$_{Ret.}$ = 1.0 | LCMSBAS |
| I-038 | 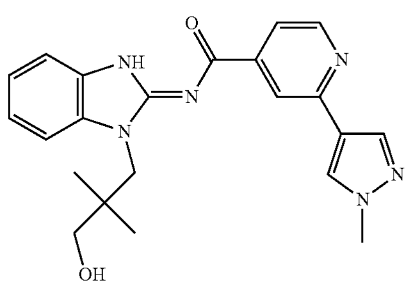 [SMILES: Cn1cc(-c2cc(C(=O)/N=c3\[nH]c4ccccc4n3CC(C)(C)CO)ccn2)cn1] | A | 27 | (M + H)$^+$ = 405, t$_{Ret.}$ = 1.1 | LCMSBAS |
| I-039 | 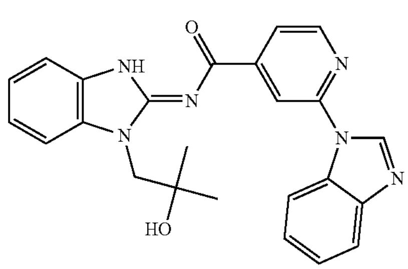 [SMILES: CC(C)(O)Cn1/c(=N/C(=O)c2ccnc(-n3cnc4ccccc43)c2)[nH]c2ccccc21] | A | 9 | (M + H)$^+$ = 427, t$_{Ret.}$ = 1.15 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-040 | 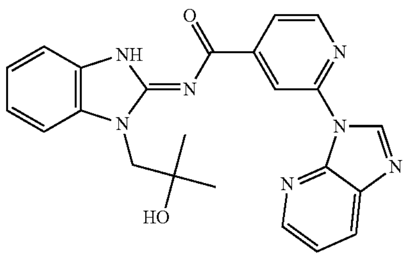 [SMILES: CC(C)(O)Cn1/c(=N/C(=O)c2ccnc(-n3cnc4cccnc43)c2)[nH]c2ccccc21] | A | 3 | (M + H)$^+$ = 428, t$_{Ret.}$ = 1.09 | LCMSBAS |
| I-041 | 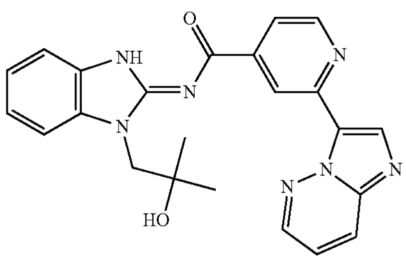 [SMILES: CC(C)(O)Cn1/c(=N/C(=O)c2ccnc(-c3cnc4cccnn34)c2)[nH]c2ccccc21] | A | 1 | (M + H)$^+$ = 428, t$_{Ret.}$ = 1.01 | LCMSBAS |
| I-042 | 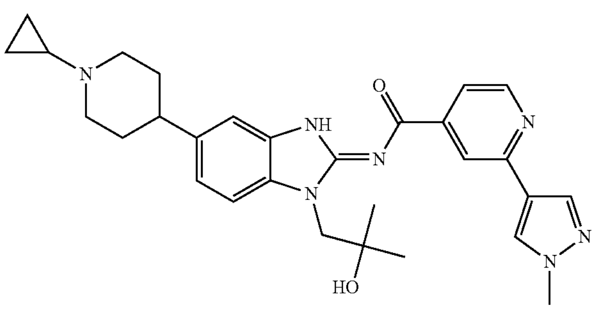 [SMILES: Cn1cc(-c2cc(C(=O)/N=c3\[nH]c4cc(C5CCN(C6CC6)CC5)ccc4n3CC(C)(C)O)ccn2)cn1] | A | 3 | (M + H)$^+$ = 514, t$_{Ret.}$ = 1.21 | LCMSBAS |
| I-043 | 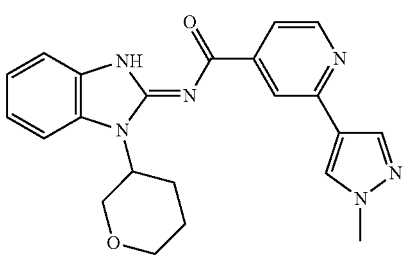 [SMILES: Cn1cc(-c2cc(C(=O)/N=c3\[nH]c4ccccc4n3C3CCCOC3)ccn2)cn1] | A | 6 | (M + H)$^+$ = 403, t$_{Ret.}$ = 1.07 | LCMSBAS |
| I-044 | 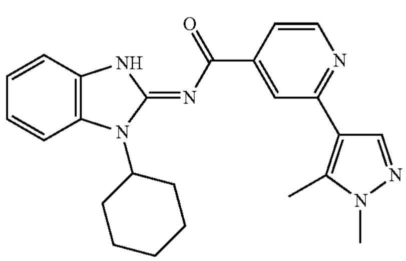 [SMILES: Cc1c(-c2cc(C(=O)/N=c3\[nH]c4ccccc4n3C3CCCCC3)ccn2)cnn1C] | A | 2 | (M + H)$^+$ = 415, t$_{Ret.}$ = 1.36 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-045 | 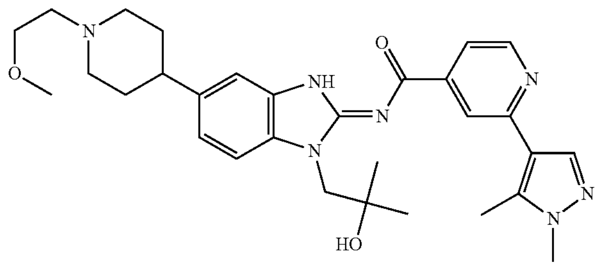 [SMILES: COCCN1CCC(c2ccc3c(c2)[nH]/c(=N\C(=O)c2ccnc(-c4cnn(C)c4C)c2)n3CC(C)(C)O)CC1] | A | 2 | (M + H)$^+$ = 546, t$_{Ret.}$ = 1.11 | LCMSBAS |
| I-046 | 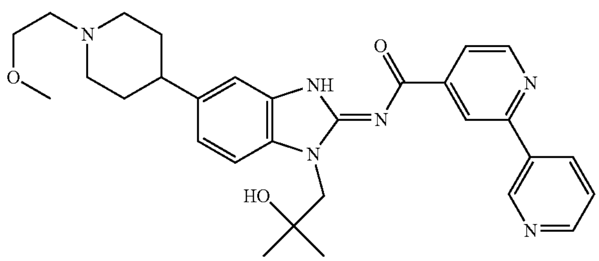 [SMILES: COCCN1CCC(c2ccc3c(c2)[nH]/c(=N\C(=O)c2ccnc(-c4cccnc4)c2)n3CC(C)(C)O)CC1] | A | 2 | (M + H)$^+$ = 529, t$_{Ret.}$ = 1.11 | LCMSBAS |
| I-047 | 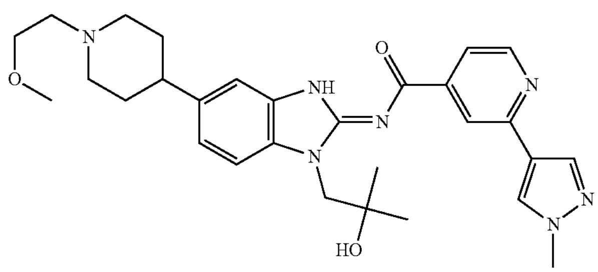 [SMILES: COCCN1CCC(c2ccc3c(c2)[nH]/c(=N\C(=O)c2ccnc(-c4cnn(C)c4)c2)n3CC(C)(C)O)CC1] | A | 3 | (M + H)$^+$ = 532, t$_{Ret.}$ = 1.06 | LCMSBAS |
| I-048 | 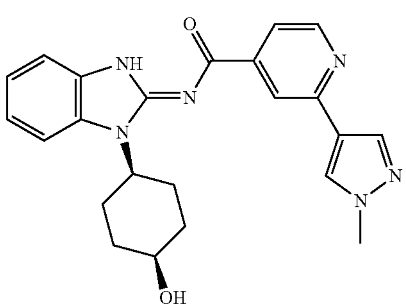 [SMILES: Cn1cc(-c2cc(C(=O)/N=c3\[nH]c4ccccc4n3[C@H]3CC[C@@H](O)CC3)ccn2)cn1] | A | 1 | (M + H)$^+$ = 417, t$_{Ret.}$ = 1.08 | LCMSBAS |
| I-049 | 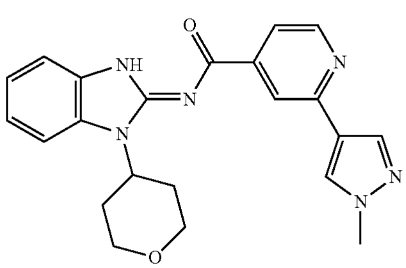 [SMILES: Cn1cc(-c2cc(C(=O)/N=c3\[nH]c4ccccc4n3C3CCOCC3)ccn2)cn1] | A | 7 | (M + H)$^+$ = 403, t$_{Ret.}$ = 1.03 | LCMSBAS |

TABLE 12-continued
| # | Structure | method | IC$_{50}$ [nM] | MS (M + H)$^+$ t$_{Ret}$ HPLC [min] | HPLC-MS method |
|---|---|---|---|---|---|
| I-050 | 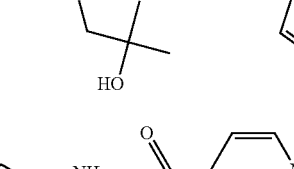 | A | 24 | (M + H)$^+$ = 393, t$_{Ret.}$ = 1.2 | LCMSBAS |
| I-051 | 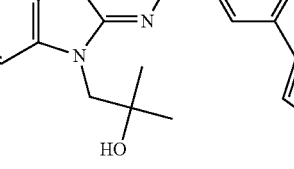 | A | 27 | (M + H)$^+$ = 393, t$_{Ret.}$ = 1.21 | LCMSBAS |
| I-052 | 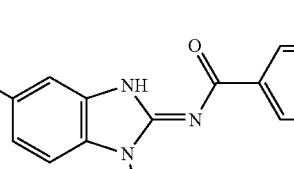 | A | 6 | (M + H)$^+$ = 472, t$_{Ret.}$ = 1.11 | LCMSBAS |
| I-053 | 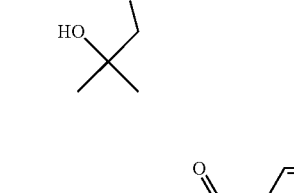 | A | 2 | (M + H)$^+$ = 475, t$_{Ret.}$ = 1.07 | LCMSBAS |
| I-054 | 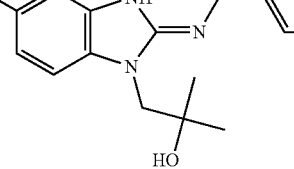 | A | 7 | (M + H)$^+$ = 460, t$_{Ret.}$ = 1.04 | LCMSBAS |
| I-055 | 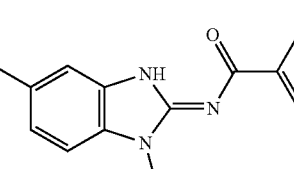 | A | 10 | (M + H)$^+$ = 463, t$_{Ret.}$ = 0.99 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-056 | 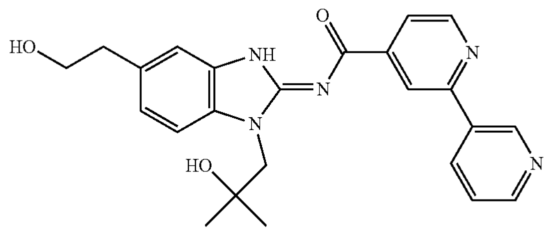 [SMILES: CC(C)(O)Cn1/c(=N/C(=O)c2ccnc(-c3cccnc3)c2)[nH]c2cc(CCO)ccc21] | A | 5 | (M + H)$^+$ = 432, t$_{Ret}$ = 0.93 | LCMSBAS |
| I-057 | 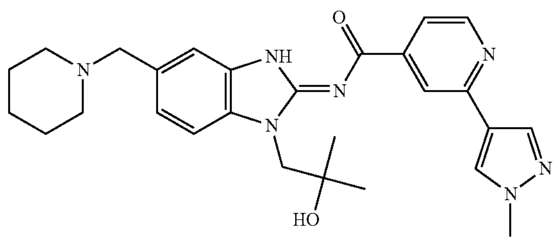 [SMILES: Cn1cc(-c2cc(C(=O)/N=c3\[nH]c4cc(CN5CCCCC5)ccc4n3CC(C)(C)O)ccn2)cn1] | C | 27 | (M + H)$^+$ = 488, t$_{Ret}$ = 1.19 | LCMSBAS |
| I-058 | 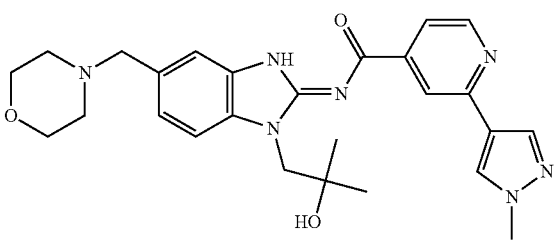 [SMILES: Cn1cc(-c2cc(C(=O)/N=c3\[nH]c4cc(CN5CCOCC5)ccc4n3CC(C)(C)O)ccn2)cn1] | C | 93 | (M + H)$^+$ = 490, t$_{Ret}$ = 1.03 | LCMSBAS |
| I-059 | 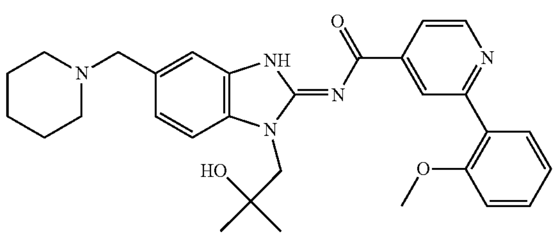 [SMILES: COc1ccccc1-c1cc(C(=O)/N=c2\[nH]c3cc(CN4CCCCC4)ccc3n2CC(C)(C)O)ccn1] | C | 3 | (M + H)$^+$ = 514, t$_{Ret}$ = 1.37 | LCMSBAS |
| I-060 | 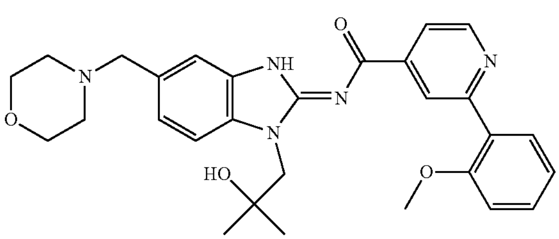 [SMILES: COc1ccccc1-c1cc(C(=O)/N=c2\[nH]c3cc(CN4CCOCC4)ccc3n2CC(C)(C)O)ccn1] | C | 1 | (M + H)$^+$ = 516, t$_{Ret}$ = 1.21 | LCMSBAS |
| I-061 | 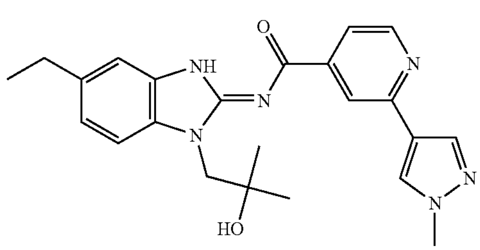 [SMILES: CCc1ccc2c(c1)[nH]/c(=N\C(=O)c1ccnc(-c3cnn(C)c3)c1)n2CC(C)(C)O] | A | 7 | (M + H)$^+$ = 419, t$_{Ret}$ = 1.19 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-062 | 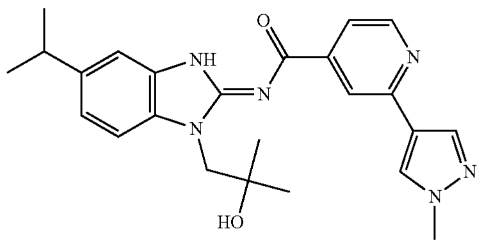 [SMILES: CC(C)c1ccc2c(c1)[nH]/c(=N\C(=O)c1ccnc(-c3cnn(C)c3)c1)n2CC(C)(C)O] | A | 9 | (M + H)$^+$ = 433, t$_{Ret}$ = 1.25 | LCMSBAS |
| I-063 | 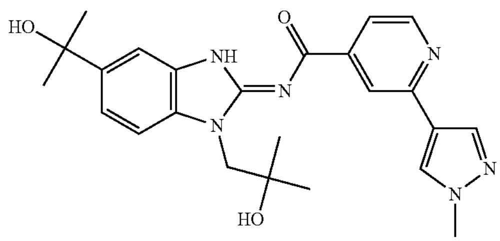 [SMILES: Cn1cc(-c2cc(C(=O)/N=c3\[nH]c4cc(C(C)(C)O)ccc4n3CC(C)(C)O)ccn2)cn1] | A | 74 | (M + H)$^+$ = 449, t$_{Ret}$ = 1.01 | LCMSBAS |
| I-064 | 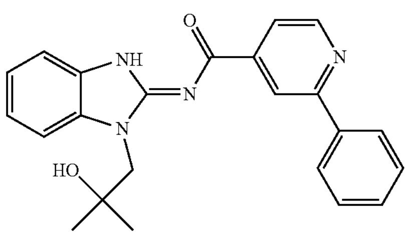 [SMILES: CC(C)(O)Cn1/c(=N/C(=O)c2ccnc(-c3ccccc3)c2)[nH]c2ccccc21] | A | 9 | (M + H)$^+$ = 387, t$_{Ret}$ = 1.23 | LCMSBAS |
| I-065 | 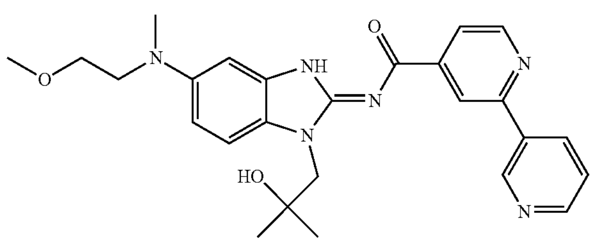 [SMILES: COCCN(C)c1ccc2c(c1)[nH]/c(=N\C(=O)c1ccnc(-c3cccnc3)c1)n2CC(C)(C)O] | A | 30 | (M + H)$^+$ = 475, t$_{Ret}$ = | MSB |
| I-066 | 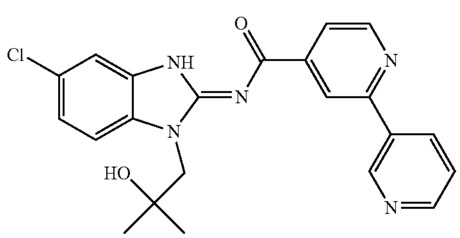 [SMILES: CC(C)(O)Cn1/c(=N/C(=O)c2ccnc(-c3cccnc3)c2)[nH]c2cc(Cl)ccc21] | A | 23 | (M + H)$^+$ = 422, t$_{Ret}$ = 0.58 | 003_CA11 |
| I-067 | 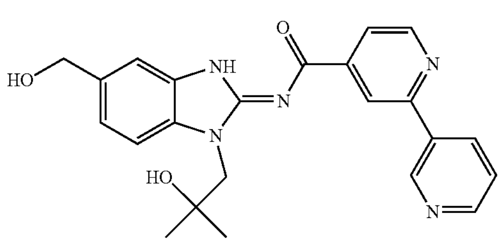 [SMILES: CC(C)(O)Cn1/c(=N/C(=O)c2ccnc(-c3cccnc3)c2)[nH]c2cc(CO)ccc21] | A | 16 | (M + H)$^+$ = 418, t$_{Ret}$ = 0.51 | 003_CA11 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-68 | 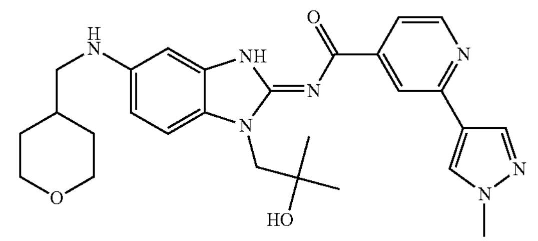 [SMILES: Cn1cc(-c2cc(C(=O)/N=c3\[nH]c4cc(NCC5CCOCC5)ccc4n3CC(C)(C)O)ccn2)cn1] | A | 14 | (M + H)$^+$ = 504, t$_{Ret}$ = 0.91 | Z011_S03 |
| I-69 | 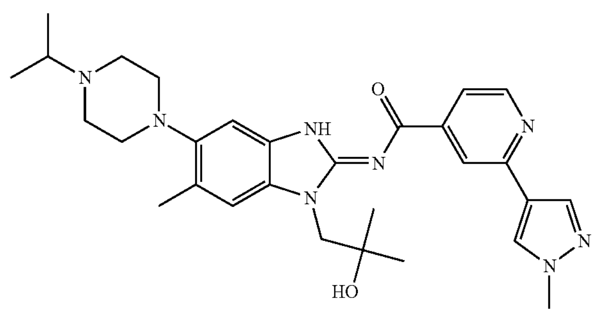 [SMILES: Cc1cc2c(cc1N1CCN(C(C)C)CC1)[nH]/c(=N\C(=O)c1ccnc(-c3cnn(C)c3)c1)n2CC(C)(C)O] | A | 26 | (M + H)$^+$ = 531, t$_{Ret}$ = 1.06 | Z011_S03 |
| I-70 | 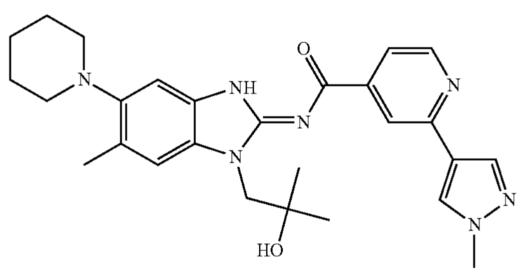 [SMILES: Cc1cc2c(cc1N1CCCCC1)[nH]/c(=N\C(=O)c1ccnc(-c3cnn(C)c3)c1)n2CC(C)(C)O] | A | 94 | (M + H)$^+$ = 488, t$_{Ret}$ = 1.13 | Z011_S03 |
| I-71 | 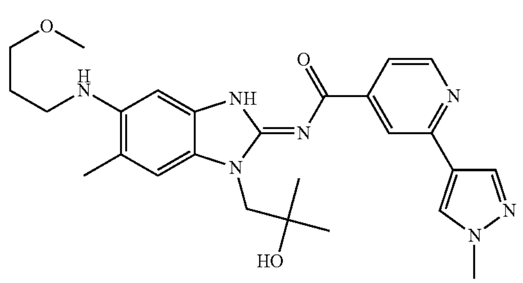 [SMILES: COCCCNc1cc2[nH]/c(=N\C(=O)c3ccnc(-c4cnn(C)c4)c3)n(CC(C)(C)O)c2cc1C] | A | 86 | (M + H)$^+$ = 492, t$_{Ret}$ = 0.95 | Z011_S03 |
| I-72 | 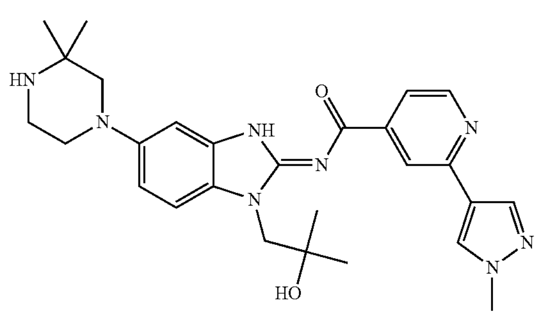 | A | 71 | (M + H)$^+$ = 593, t$_{Ret}$ = 0.73 | Z018_S04 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-73 | 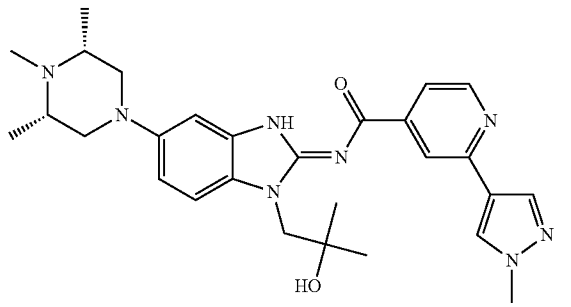 [SMILES: C[C@@H]1CN(c2ccc3c(c2)[nH]/c(=N\C(=O)c2ccnc(-c4cnn(C)c4)c2)n3CC(C)(C)O)C[C@H](C)N1C] | A | 81 | (M + H)$^+$ = 517, t$_{Ret}$ = 0.91 | Z011_S03 |
| I-74 | 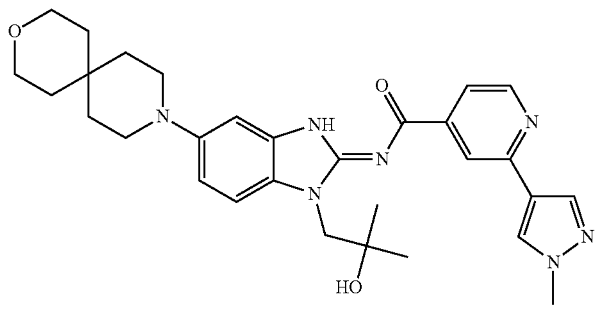 [SMILES: Cn1cc(-c2cc(C(=O)/N=c3\[nH]c4cc(N5CCC6(CCOCC6)CC5)ccc4n3CC(C)(C)O)ccn2)cn1] | A | 71 | (M + H)$^+$ = 544, t$_{Ret}$ = | MSB |
| I-75 | 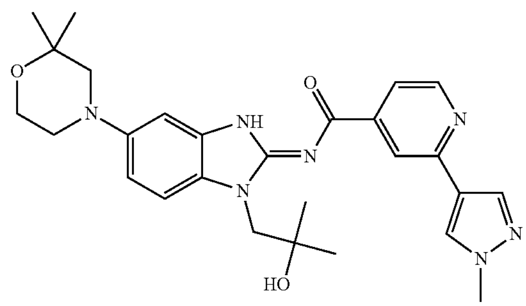 [SMILES: Cn1cc(-c2cc(C(=O)/N=c3\[nH]c4cc(N5CCOC(C)(C)C5)ccc4n3CC(C)(C)O)ccn2)cn1] | A | 54 | (M + H)$^+$ = 504, t$_{Ret}$ = 0.86 | Z018_S04 |
| I-76 | 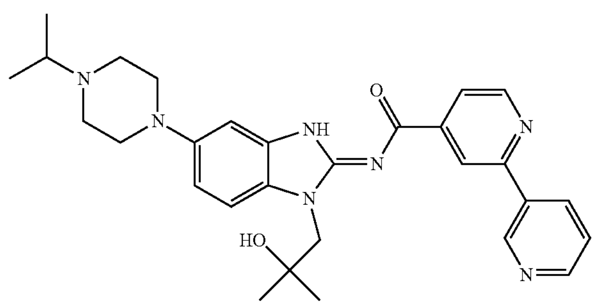 | A | 17 | (M + H)$^+$ = 428, t$_{Ret}$ = 0.99 | Z011_S03 |
| I-77 | 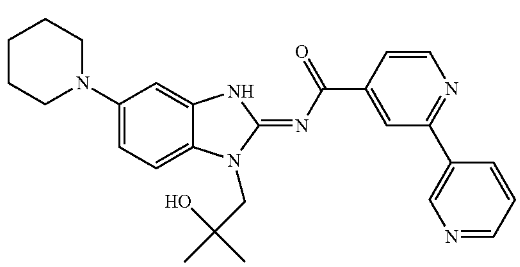 [SMILES: CC(C)(O)Cn1/c(=N/C(=O)c2ccnc(-c3cccnc3)c2)[nH]c2cc(N3CCCCC3)ccc21] | A | 76 | (M + H)$^+$ = 471, t$_{Ret}$ = 0.82 | 003_CA11 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-78 | 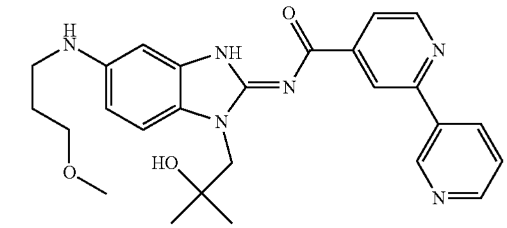 [SMILES: COCCCNc1ccc2c(c1)[nH]/c(=N\C(=O)c1ccnc(-c3cccnc3)c1)n2CC(C)(C)O] | A | 5 | (M + H)$^+$ = 475, t$_{Ret}$ = 0.67 | 003_CA11 |
| I-79 | 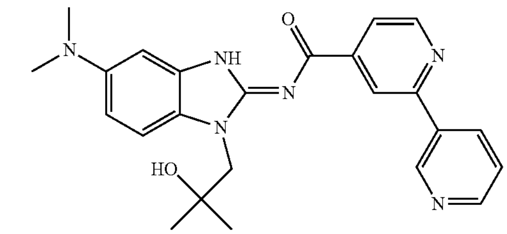 [SMILES: CN(C)c1ccc2c(c1)[nH]/c(=N\C(=O)c1ccnc(-c3cccnc3)c1)n2CC(C)(C)O] | A | 42 | (M + H)$^+$ = 431, t$_{Ret}$ = 0.71 | 003_CA11 |
| I-80 | 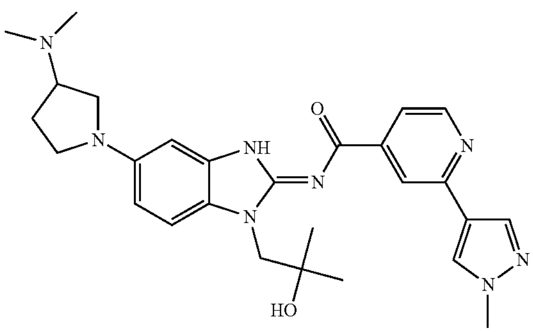 [SMILES: CN(C)C1CCN(c2ccc3c(c2)[nH]/c(=N\C(=O)c2ccnc(-c4cnn(C)c4)c2)n3CC(C)(C)O)C1] | A | 89 | (M + H)$^+$ = 503, t$_{Ret}$ = 0.4 | 003_CA11 |
| I-81 | 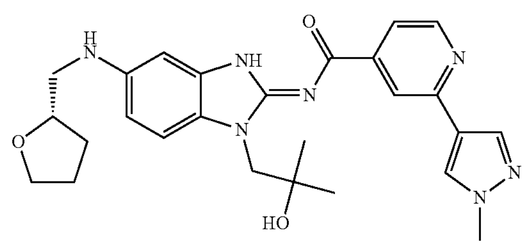 [SMILES: Cn1cc(-c2cc(C(=O)/N=c3\[nH]c4cc(NC[C@@H]5CCCO5)ccc4n3CC(C)(C)O)ccn2)cn1] | A | 9 | (M + H)$^+$ = 490, t$_{Ret}$ = 0.45 | 003_CA11 |
| I-82 | 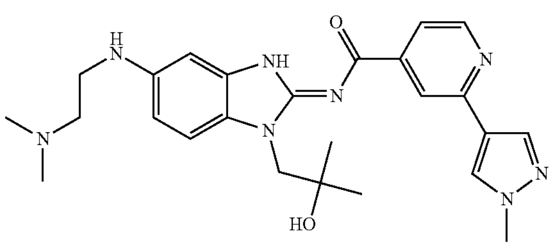 [SMILES: CN(C)CCNc1ccc2c(c1)[nH]/c(=N\C(=O)c1ccnc(-c3cnn(C)c3)c1)n2CC(C)(C)O] | A | 14 | (M + H)$^+$ = 477, t$_{Ret}$ = 0.37 | 003_CA11 |
| I-83 | 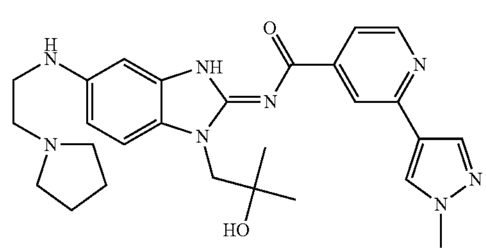 [SMILES: Cn1cc(-c2cc(C(=O)/N=c3\[nH]c4cc(NCCN5CCCC5)ccc4n3CC(C)(C)O)ccn2)cn1] | A | 14 | (M + H)$^+$ = 503, t$_{Ret}$ = 0.39 | 003_CA11 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-84 | 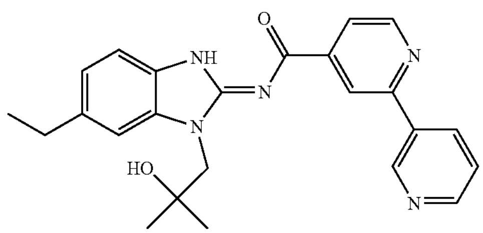 [SMILES: CCc1ccc2[nH]/c(=N\C(=O)c3ccnc(-c4cccnc4)c3)n(CC(C)(C)O)c2c1] | A | 21 | (M + H)$^+$ = 416, t$_{Ret}$ = 0.79 | 003_CA11 |
| I-85 | 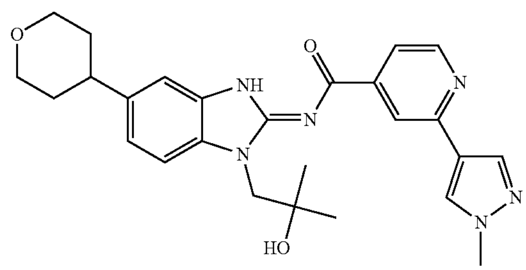 [SMILES: Cn1cc(-c2cc(C(=O)/N=c3\[nH]c4cc(C5CCOCC5)ccc4n3CC(C)(C)O)ccn2)cn1] | A | 3 | (M + H)$^+$ = 475, t$_{Ret}$ = 0.91 | Z011_S03 |
| I-86 | 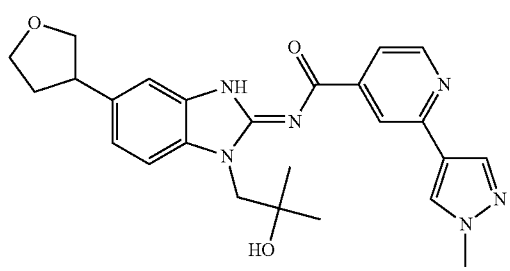 [SMILES: Cn1cc(-c2cc(C(=O)/N=c3\[nH]c4cc(C5CCOC5)ccc4n3CC(C)(C)O)ccn2)cn1] | A | 5 | (M + H)$^+$ = 461, t$_{Ret}$ = 0.87 | Z011_S03 |
| I-87 | 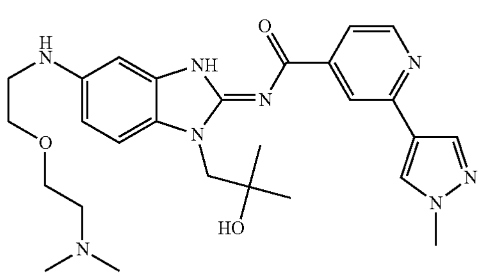 [SMILES: CN(C)CCOCCNc1ccc2c(c1)[nH]/c(=N\C(=O)c1ccnc(-c3cnn(C)c3)c1)n2CC(C)(C)O] | A | 81 | (M + H)$^+$ = 521, t$_{Ret}$ = 0.34 | Z011_S03 |
| I-88 | 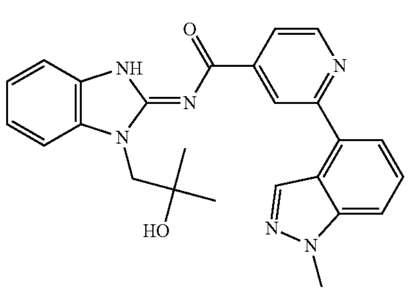 [SMILES: Cn1ncc2c(-c3cc(C(=O)/N=c4\[nH]c5ccccc5n4CC(C)(C)O)ccn3)cccc21] | A | 11 | (M + H)$^+$ = 441, t$_{Ret}$ = 1.23 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-89 | 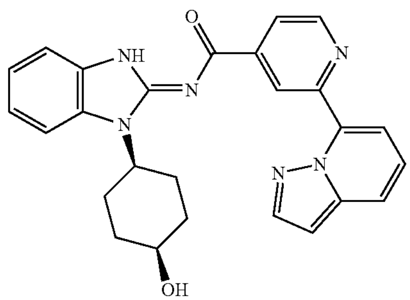 [SMILES: O=C(/N=c1\[nH]c2ccccc2n1[C@H]1CC[C@@H](O)CC1)c1ccnc(-c2cccc3ccnn23)c1] | A | 8 | (M + H)$^+$ = 453, t$_{Ret}$ = 1.21 | LCMSBAS |
| I-90 | 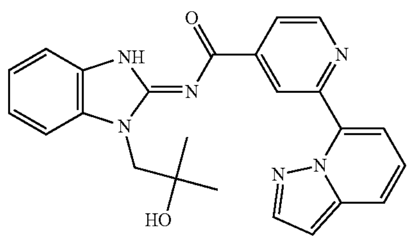 [SMILES: CC(C)(O)Cn1/c(=N/C(=O)c2ccnc(-c3cccc4ccnn34)c2)[nH]c2ccccc21] | A | 12 | (M + H)$^+$ = 427, t$_{Ret}$ = 1.22 | LCMSBAS |
| I-91 | 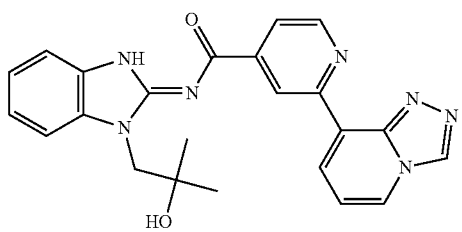 [SMILES: CC(C)(O)Cn1/c(=N/C(=O)c2ccnc(-c3cccn4cnnc34)c2)[nH]c2ccccc21] | A | 16 | (M + H)$^+$ = 428, t$_{Ret}$ = 1.03 | LCMSBAS |
| I-92 | 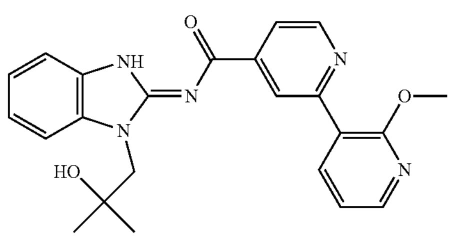 | A | 20 | (M + H)$^+$ = 418, t$_{Ret}$ = 1.19 | LCMSBAS |
| I-93 | 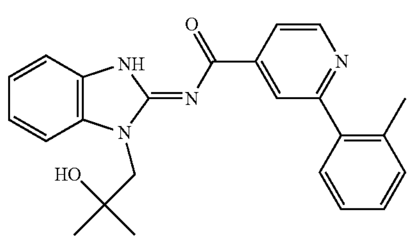 | A | 57 | (M + H)$^+$ = 410, t$_{Ret}$ = 1.29 | LCMSBAS |
| I-94 | 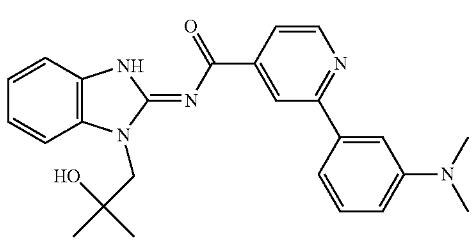 [SMILES: CN(C)c1cccc(-c2cc(C(=O)/N=c3\[nH]c4ccccc4n3CC(C)(C)O)ccn2)c1] | A | 99 | (M + H)$^+$ = 430, t$_{Ret}$ = 1.33 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-95 | 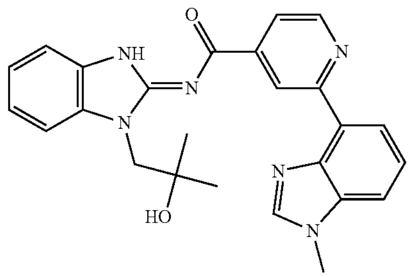 [SMILES: Cn1cnc2c(-c3cc(C(=O)/N=c4\[nH]c5ccccc5n4CC(C)(C)O)ccn3)cccc21] | A | 74 | (M + H)$^+$ = 441, t$_{Ret}$ = 1.15 | LCMSBAS |
| I-96 | 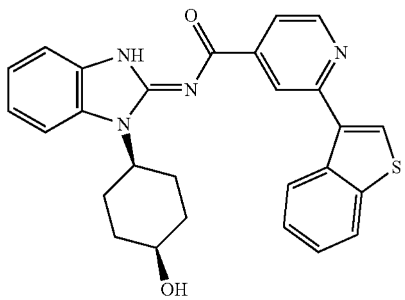 [SMILES: O=C(/N=c1\[nH]c2ccccc2n1[C@H]1CC[C@@H](O)CC1)c1ccnc(-c2csc3ccccc23)c1] | A | 39 | (M + H)$^+$ = 469, t$_{Ret}$ = 1.35 | LCMSBAS |
| I-97 | 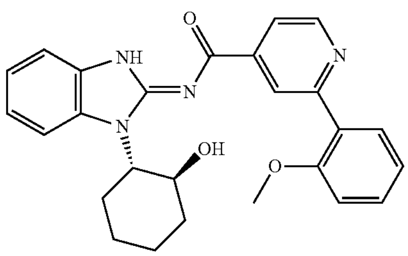 [SMILES: COc1ccccc1-c1cc(C(=O)/N=c2\[nH]c3ccccc3n2[C@H]2CCCC[C@@H]2O)ccn1] | A | 14 | (M + H)$^+$ = 443, t$_{Ret}$ = 1.31 | LCMSBAS |
| I-98 | 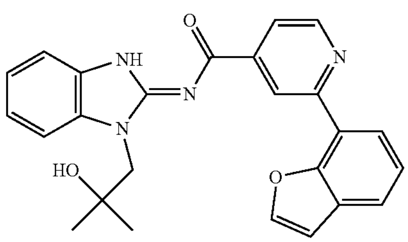 [SMILES: CC(C)(O)Cn1/c(=N/C(=O)c2ccnc(-c3cccc4ccoc34)c2)[nH]c2ccccc21] | A | 6 | (M + H)$^+$ = 427, t$_{Ret}$ = 1.32 | LCMSBAS |
| I-99 | 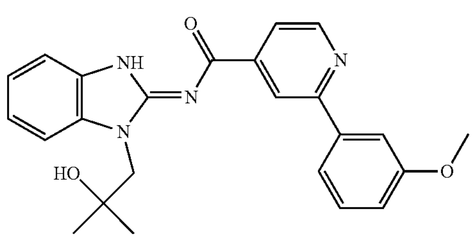 | A | 42 | (M + H)$^+$ = 417, t$_{Ret}$ = 1.29 | LCMSBAS |
| I-100 | 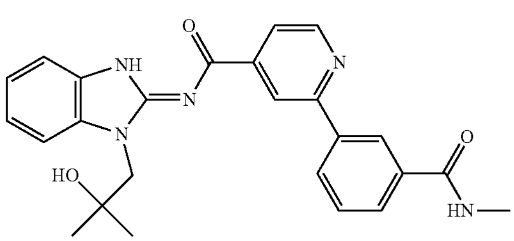 [SMILES: CNC(=O)c1cccc(-c2cc(C(=O)/N=c3\[nH]c4ccccc4n3CC(C)(C)O)ccn2)c1] | A | 76 | (M + H)$^+$ = 444, t$_{Ret}$ = 1.1 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-101 | 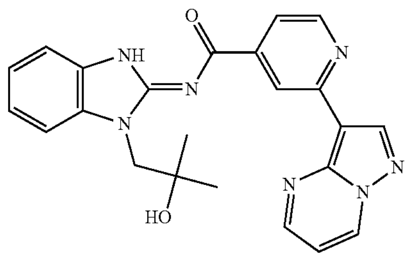 [SMILES: CC(C)(O)Cn1/c(=N/C(=O)c2ccnc(-c3cnn4cccnc34)c2)[nH]c2ccccc21] | A | 1 | (M + H)$^+$ = 428, t$_{Ret}$ = 1.09 | LCMSBAS |
| I-102 | 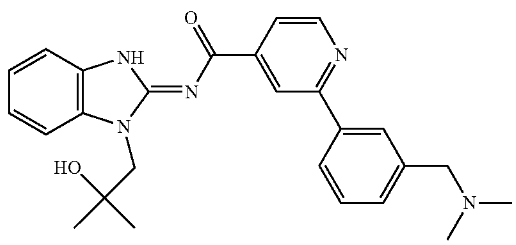 [SMILES: CN(C)Cc1cccc(-c2cc(C(=O)/N=c3\[nH]c4ccccc4n3CC(C)(C)O)ccn2)c1] | A | 2 | (M + H)$^+$ = 444, t$_{Ret}$ = 1.26 | LCMSBAS |
| I-103 | 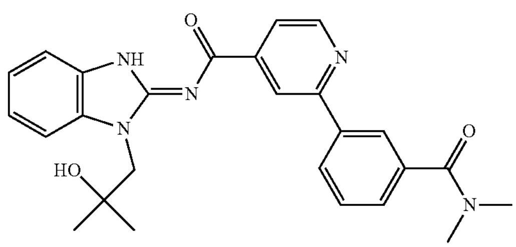 [SMILES: CN(C)C(=O)c1cccc(-c2cc(C(=O)/N=c3\[nH]c4ccccc4n3CC(C)(C)O)ccn2)c1] | A | 43 | (M + H)$^+$ = 458, t$_{Ret}$ = 1.14 | LCMSBAS |
| I-104 | 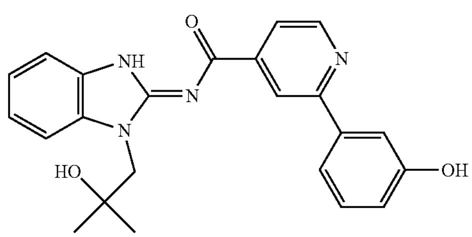 [SMILES: CC(C)(O)Cn1/c(=N/C(=O)c2ccnc(-c3cccc(O)c3)c2)[nH]c2ccccc21] | A | 12 | (M + H)$^+$ = 403, t$_{Ret}$ = 1.13 | LCMSBAS |
| I-105 | 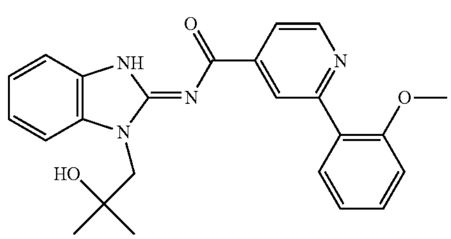 | A | 2 | (M + H)$^+$ = 417, t$_{Ret}$ = 1.24 | LCMSBAS |
| I-106 | 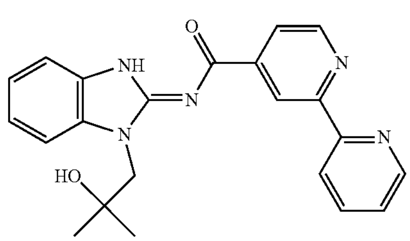 [SMILES: CC(C)(O)Cn1/c(=N/C(=O)c2ccnc(-c3ccccn3)c2)[nH]c2ccccc21] | A | 97 | (M + H)$^+$ = 388, t$_{Ret}$ = 1.16 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-107 | 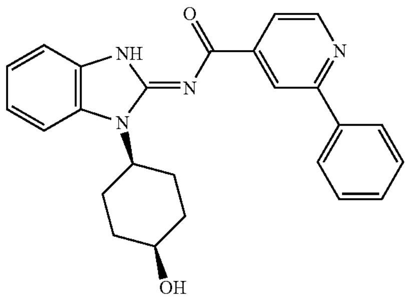 [SMILES: O=C(/N=c1\[nH]c2ccccc2n1[C@H]1CC[C@@H](O)CC1)c1ccnc(-c2ccccc2)c1] | A | 4 | (M + H)$^+$ = 413, t$_{Ret}$ = 1.29 | LCMSBAS |
| I-108 | 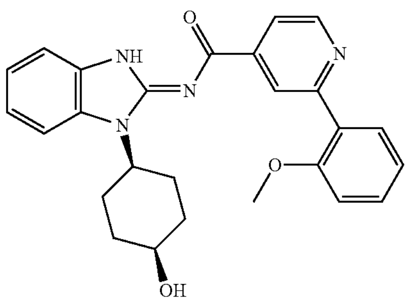 [SMILES: COc1ccccc1-c1cc(C(=O)/N=c2\[nH]c3ccccc3n2[C@H]2CC[C@@H](O)CC2)ccn1] | A | 3 | (M + H)$^+$ = 443, t$_{Ret}$ = 1.27 | LCMSBAS |
| I-109 | 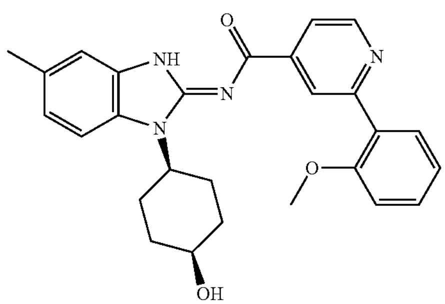 [SMILES: COc1ccccc1-c1cc(C(=O)/N=c2\[nH]c3cc(C)ccc3n2[C@H]2CC[C@@H](O)CC2)ccn1] | A | 4 | (M + H)$^+$ = 457, t$_{Ret}$ = 1.33 | LCMSBAS |
| I-110 | 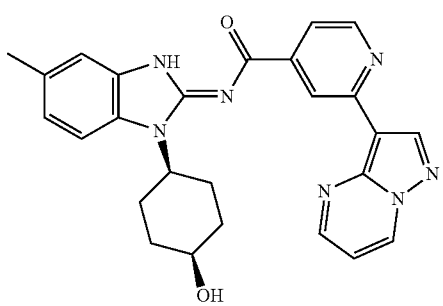 [SMILES: Cc1ccc2c(c1)[nH]/c(=N\C(=O)c1ccnc(-c3cnn4cccnc34)c1)n2[C@H]1CC[C@@H](O)CC1] | A | 1 | (M + H)$^+$ = 468, t$_{Ret}$ = 1.2 | LCMSBAS |
| I-111 | 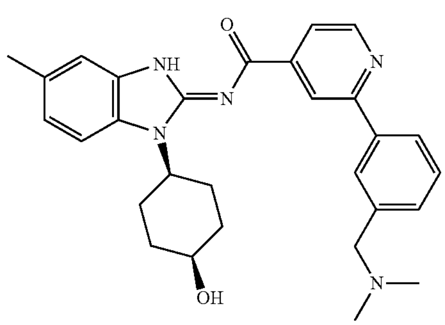 [SMILES: Cc1ccc2c(c1)[nH]/c(=N\C(=O)c1ccnc(-c3cccc(CN(C)C)c3)c1)n2[C@H]1CC[C@@H](O)CC1] | A | 4 | (M + H)$^+$ = 484, t$_{Ret}$ = 1.49 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-112 | 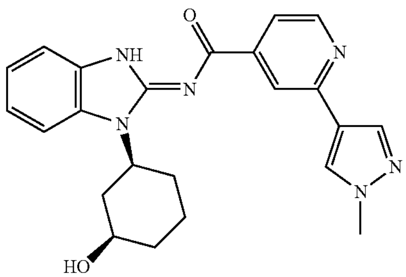 [SMILES: Cn1cc(-c2cc(C(=O)/N=c3\[nH]c4ccccc4n3[C@H]3CCC[C@@H](O)C3)ccn2)cn1] | A | 13 | (M + H)$^+$ = 417, t$_{Ret}$ = 1.07 | LCMSBAS |
| I-113 | 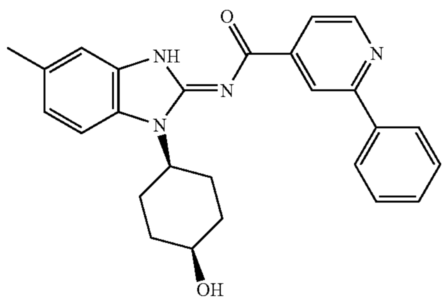 [SMILES: Cc1ccc2c(c1)[nH]/c(=N\C(=O)c1ccnc(-c3ccccc3)c1)n2[C@H]1CC[C@@H](O)CC1] | A | 5 | (M + H)$^+$ = 427, t$_{Ret}$ = 1.35 | LCMSBAS |
| I-114 | 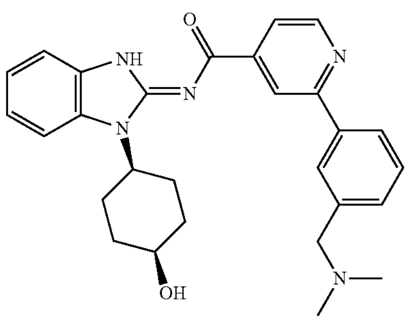 [SMILES: CN(C)Cc1cccc(-c2cc(C(=O)/N=c3\[nH]c4ccccc4n3[C@H]3CC[C@@H](O)CC3)ccn2)c1] | A | 2 | (M + H)$^+$ = 470, t$_{Ret}$ = 1.33 | LCMSBAS |
| I-115 | 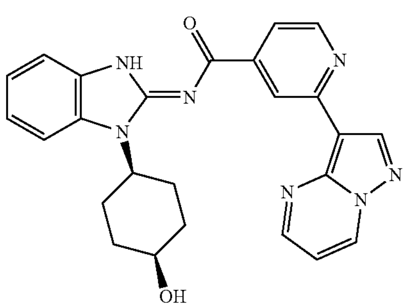 [SMILES: O=C(/N=c1\[nH]c2ccccc2n1[C@H]1CC[C@@H](O)CC1)c1ccnc(-c2cnn3cccnc23)c1] | A | 1 | (M + H)$^+$ = 454, t$_{Ret}$ = 1.09 | LCMSBAS |
| I-116 | 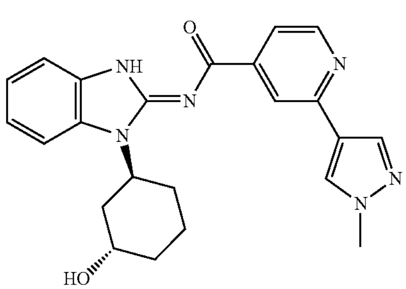 [SMILES: Cn1cc(-c2cc(C(=O)/N=c3\[nH]c4ccccc4n3[C@H]3CCC[C@H](O)C3)ccn2)cn1] | A | 1 | (M + H)$^+$ = 417, t$_{Ret}$ = 1.1 | LCMSBAS |

TABLE 12-continued
| # | Structure | method | IC$_{50}$ [nM] | MS (M + H)$^+$ t$_{Ret}$ HPLC [min] | HPLC-MS method |
|---|---|---|---|---|---|
| I-117 | 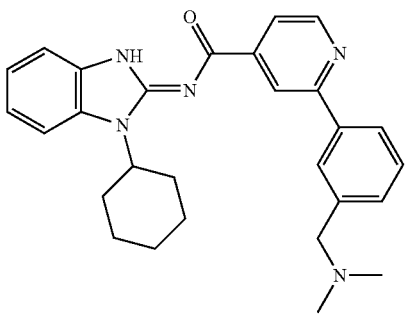 | A | 12 | (M + H)$^+$ = 464, t$_{Ret}$ = 1.61 | LCMSBAS |
| I-118 | 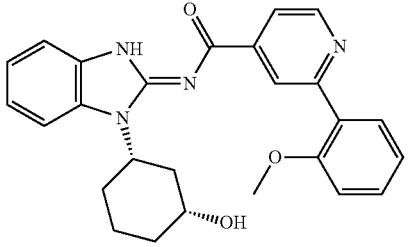 [SMILES: COc1ccccc1-c1cc(C(=O)/N=c2\[nH]c3ccccc3n2[C@H]2CCC[C@@H](O)C2)ccn1] | A | 3 | (M + H)$^+$ = 443, t$_{Ret}$ = 1.23 | LCMSBAS |
| I-119 | 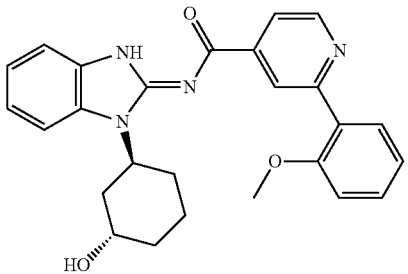 [SMILES: COc1ccccc1-c1cc(C(=O)/N=c2\[nH]c3ccccc3n2[C@H]2CCC[C@H](O)C2)ccn1] | A | 3 | (M + H)$^+$ = 442, t$_{Ret}$ = 1.26 | LCMSBAS |
| I-120 | 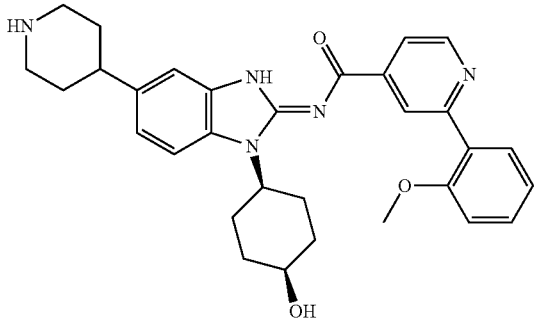 [SMILES: COc1ccccc1-c1cc(C(=O)/N=c2\[nH]c3cc(C4CCNCC4)ccc3n2[C@H]2CC[C@@H](O)CC2)ccn1] | A | 3 | (M + H)$^+$ = 526, t$_{Ret}$ = 1.15 | LCMSBAS |
| I-121 | 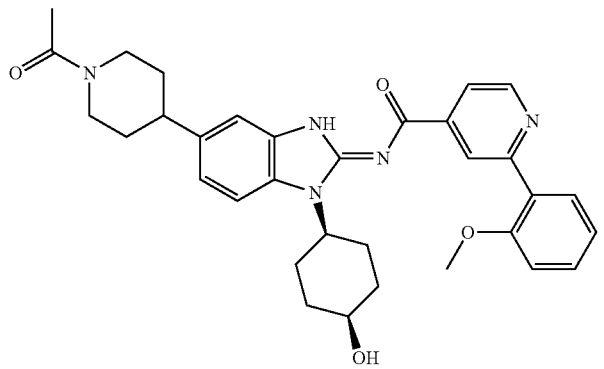 [SMILES: COc1ccccc1-c1cc(C(=O)/N=c2\[nH]c3cc(C4CCN(C(C)=O)CC4)ccc3n2[C@H]2CC[C@@H](O)CC2)ccn1] | A | 2 | (M + H)$^+$ = 568, t$_{Ret}$ = 1.19 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-122 | 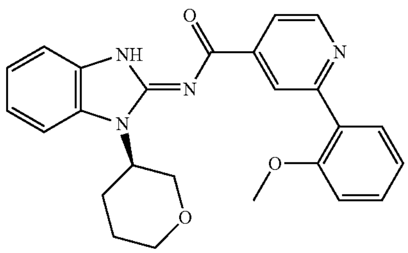 [SMILES: COc1ccccc1-c1cc(C(=O)/N=c2\[nH]c3ccccc3n2[C@@H]2CCCOC2)ccn1] | A | 2 | (M + H)$^+$ = 429, t$_{Ret}$ = 1.32 | LCMSBAS |
| I-123 | 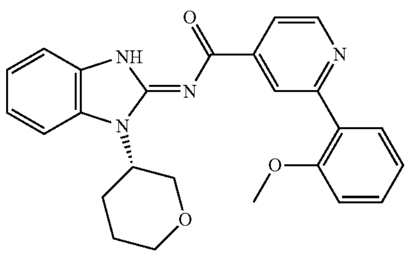 [SMILES: COc1ccccc1-c1cc(C(=O)/N=c2\[nH]c3ccccc3n2[C@H]2CCCOC2)ccn1] | A | 2 | (M + H)$^+$ = 429, t$_{Ret}$ = 1.32 | LCMSBAS |
| I-124 | 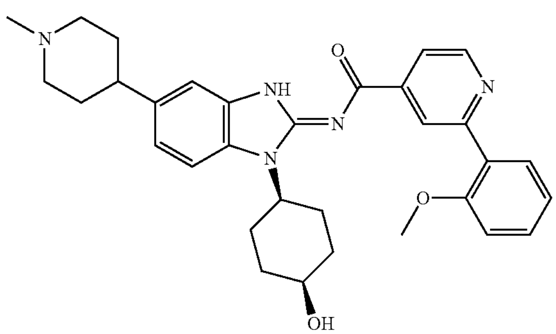 [SMILES: COc1ccccc1-c1cc(C(=O)/N=c2\[nH]c3cc(C4CCN(C)CC4)ccc3n2[C@H]2CC[C@@H](O)CC2)ccn1] | A | 2 | (M + H)$^+$ = 540, t$_{Ret}$ = 1.27 | LCMSBAS |
| I-125 | 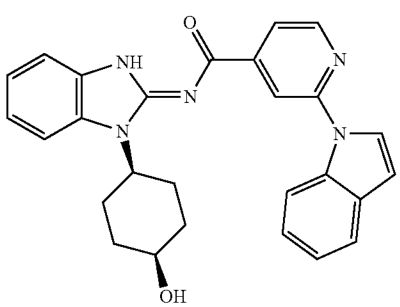 [SMILES: O=C(/N=c1\[nH]c2ccccc2n1[C@H]1CC[C@@H](O)CC1)c1ccnc(-n2ccc3ccccc32)c1] | A | 11 | (M + H)$^+$ = 452, t$_{Ret}$ = 1.42 | LCMSBAS |
| I-126 | 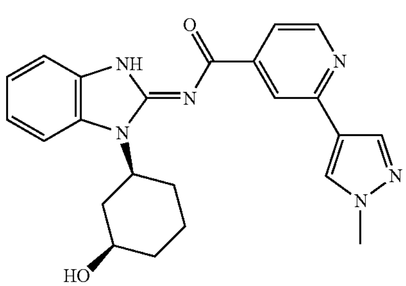 [SMILES: Cn1cc(-c2cc(C(=O)/N=c3\[nH]c4ccccc4n3[C@H]3CCC[C@@H](O)C3)ccn2)cn1] | A | 6 | (M + H)$^+$ = 417, t$_{Ret}$ = 1.07 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-127 | 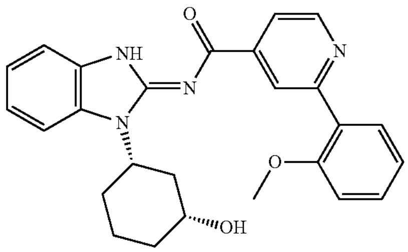 [SMILES: COc1ccccc1-c1cc(C(=O)/N=c2\[nH]c3ccccc3n2[C@H]2CCC[C@@H](O)C2)ccn1] | A | 2 | (M + H)$^+$ = 443, t$_{Ret}$ = 1.23 | LCMSBAS |
| I-128 | 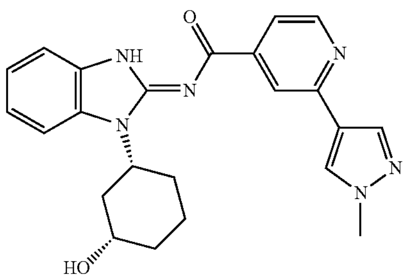 [SMILES: Cn1cc(-c2cc(C(=O)/N=c3\[nH]c4ccccc4n3[C@@H]3CCC[C@H](O)C3)ccn2)cn1] | A | 7 | (M + H)$^+$ = 417, t$_{Ret}$ = 1.07 | LCMSBAS |
| I-129 | 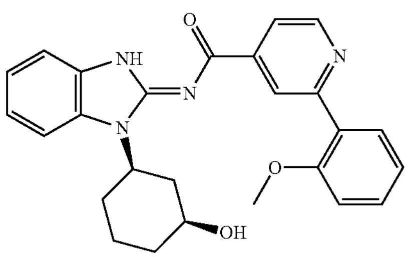 [SMILES: COc1ccccc1-c1cc(C(=O)/N=c2\[nH]c3ccccc3n2[C@@H]2CCC[C@H](O)C2)ccn1] | A | 5 | (M + H)$^+$ = 443, t$_{Ret}$ = 1.23 | LCMSBAS |
| I-130 | 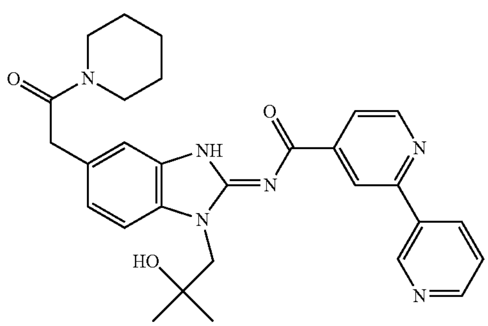 [SMILES: CC(C)(O)Cn1/c(=N/C(=O)c2ccnc(-c3cccnc3)c2)[nH]c2cc(CC(=O)N3CCCCC3)ccc21] | C | 5 | (M + H)$^+$ = 513, t$_{Ret}$ = 1.06 | LCMSBAS |
| I-131 | 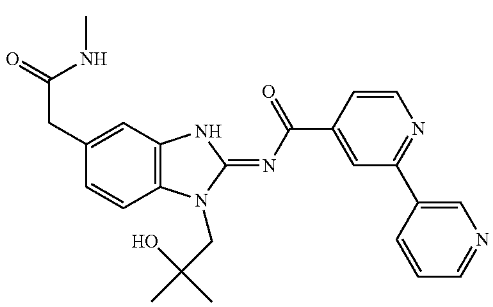 [SMILES: CNC(=O)Cc1ccc2c(c1)[nH]/c(=N\C(=O)c1ccnc(-c3cccnc3)c1)n2CC(C)(C)O] | C | 92 | (M + H)$^+$ = 459, t$_{Ret}$ = 9.88 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-132 | 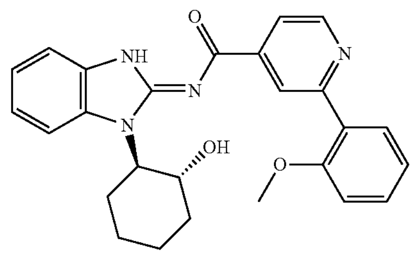 [SMILES: COc1ccccc1-c1cc(C(=O)/N=c2\[nH]c3ccccc3n2[C@@H]2CCCC[C@H]2O)ccn1] | A | 7 | (M + H)$^+$ = 443, t$_{Ret}$ = 1.31 | LCMSBAS |
| I-133 | 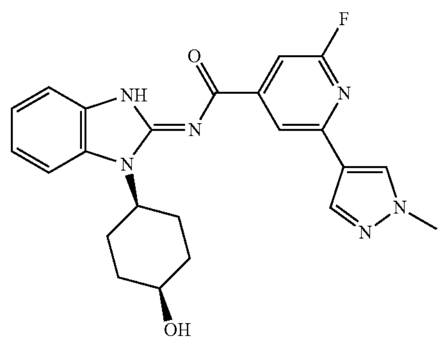 [SMILES: Cn1cc(-c2cc(C(=O)/N=c3\[nH]c4ccccc4n3[C@H]3CC[C@@H](O)CC3)cc(F)n2)cn1] | A | 1 | (M + H)$^+$ = 435, t$_{Ret}$ = 1.19 | LCMSBAS |
| I-134 | 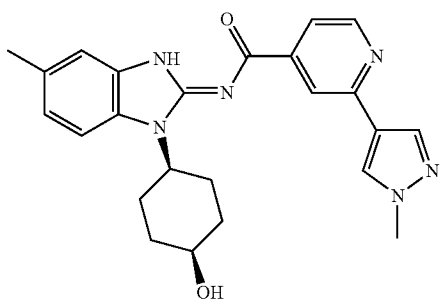 [SMILES: Cc1ccc2c(c1)[nH]/c(=N\C(=O)c1ccnc(-c3cnn(C)c3)c1)n2[C@H]1CC[C@@H](O)CC1] | A | 1 | (M + H)$^+$ = 431, t$_{Ret}$ = 1.15 | LCMSBAS |
| I-135 | 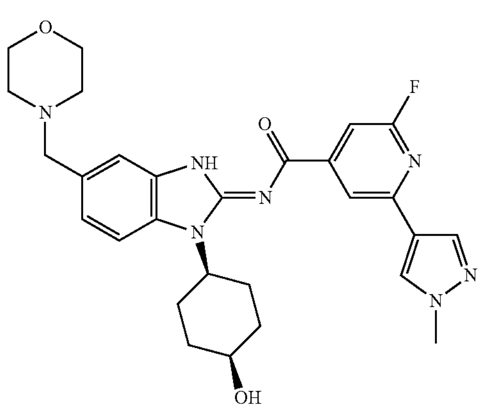 [SMILES: Cn1cc(-c2cc(C(=O)/N=c3\[nH]c4cc(CN5CCOCC5)ccc4n3[C@H]3CC[C@@H](O)CC3)cc(F)n2)cn1] | C | 2 | (M + H)$^+$ = 534, t$_{Ret}$ = 1.14 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-136 | 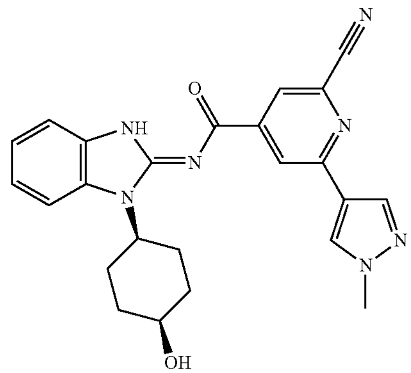 [SMILES: Cn1cc(-c2cc(C(=O)/N=c3\[nH]c4ccccc4n3[C@H]3CC[C@@H](O)CC3)cc(C#N)n2)cn1] | A | 2 | (M + H)$^+$ = 442, t$_{Ret}$ = 1.20 | LCMSBAS |
| I-137 | 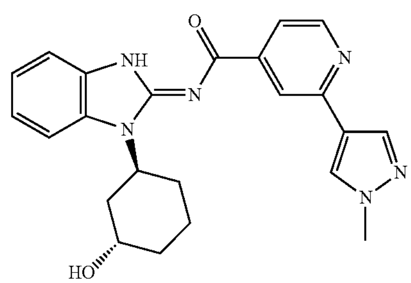 [SMILES: Cn1cc(-c2cc(C(=O)/N=c3\[nH]c4ccccc4n3[C@H]3CCC[C@H](O)C3)ccn2)cn1] | A | 2 | (M + H)$^+$ = 417, t$_{Ret}$ = 1.11 | LCMSBAS |
| I-138 | 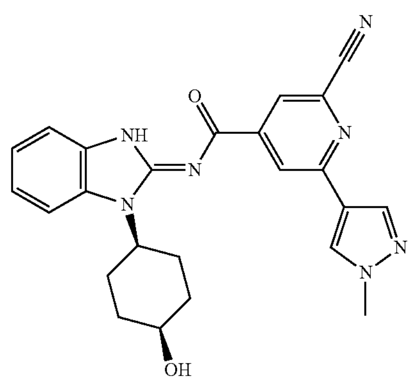 | A | 2 | (M + H)$^+$ = 417, t$_{Ret}$ = 1.11 | LCMSBAS |
| I-139 | 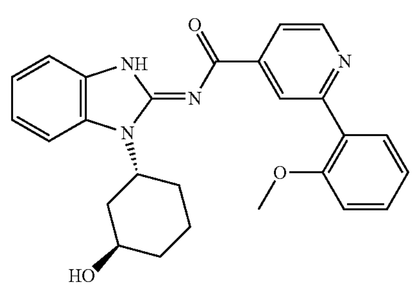 [SMILES: COc1ccccc1-c1cc(C(=O)/N=c2\[nH]c3ccccc3n2[C@@H]2CCC[C@@H](O)C2)ccn1] | A | 2 | (M + H)$^+$ = 443, t$_{Ret}$ = 1.27 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-140 | 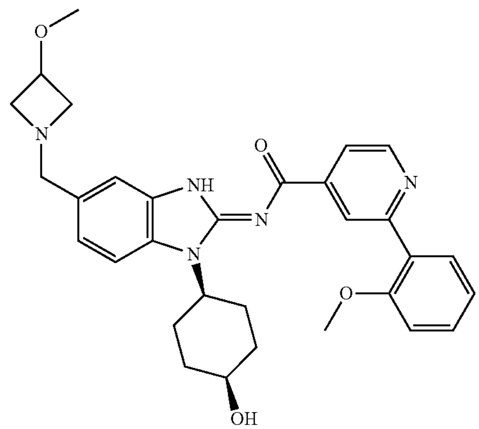 [SMILES: COc1ccccc1-c1cc(C(=O)/N=c2\[nH]c3cc(CN4CC(OC)C4)ccc3n2[C@H]2CC[C@@H](O)CC2)ccn1] | C | 2 | (M + H)$^+$ = 542, t$_{Ret}$ = 1.19 | LCMSBAS |
| I-141 | 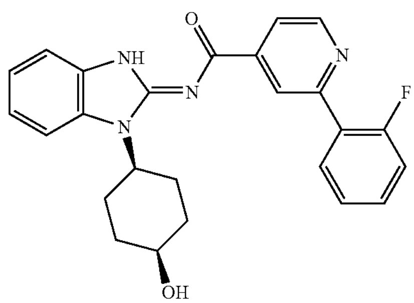 [SMILES: O=C(/N=c1\[nH]c2ccccc2n1[C@H]1CC[C@@H](O)CC1)c1ccnc(-c2ccccc2F)c1] | B | 2 | (M + H)$^+$ = 431, t$_{Ret}$ = 1.28 | LCMSBAS |
| I-142 | 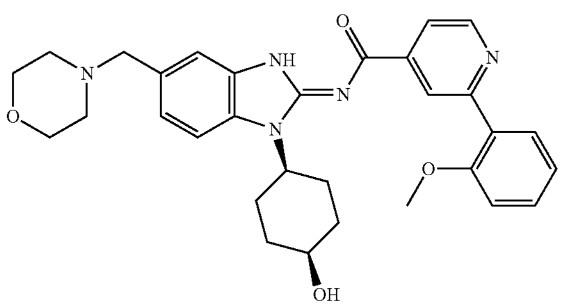 [SMILES: COc1ccccc1-c1cc(C(=O)/N=c2\[nH]c3cc(CN4CCOCC4)ccc3n2[C@H]2CC[C@@H](O)CC2)ccn1] | C | 3 | (M + H)$^+$ = 542, t$_{Ret}$ = 1.19 | LCMSBAS |
| I-143 | 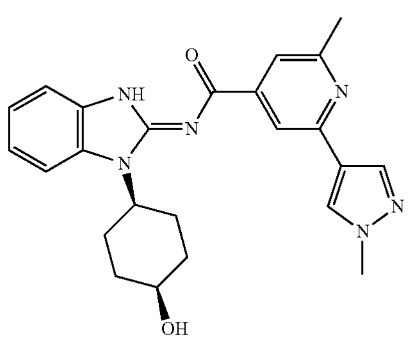 [SMILES: Cc1cc(C(=O)/N=c2\[nH]c3ccccc3n2[C@H]2CC[C@@H](O)CC2)cc(-c2cnn(C)c2)n1] | A | 3 | (M + H)$^+$ = 431, t$_{Ret}$ = 1.13 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-144 | 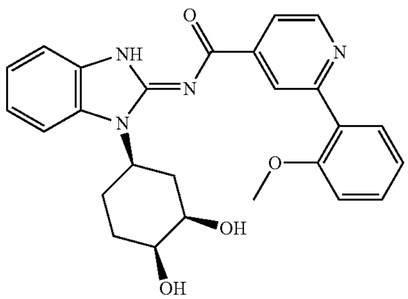 [SMILES: COc1ccccc1-c1cc(C(=O)/N=c2\[nH]c3ccccc3n2[C@@H]2CC[C@H](O)[C@H](O)C2)ccn1] | A | 3 | (M + H)$^+$ = 459, t$_{Ret}$ = 1.11 | LCMSBAS |
| I-145 | 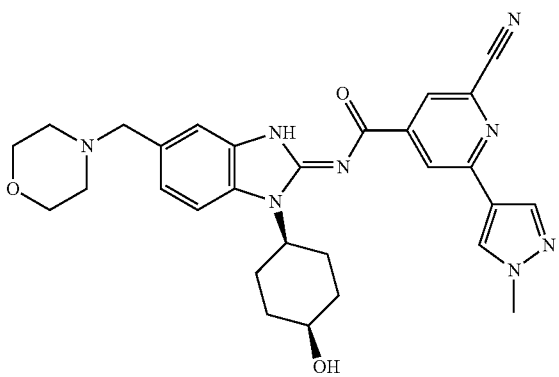 [SMILES: Cn1cc(-c2cc(C(=O)/N=c3\[nH]c4cc(CN5CCOCC5)ccc4n3[C@H]3CC[C@@H](O)CC3)cc(C#N)n2)cn1] | C | 3 | (M + H)$^+$ = 541, t$_{Ret}$ = 1.16 | LCMSBAS |
| I-146 | 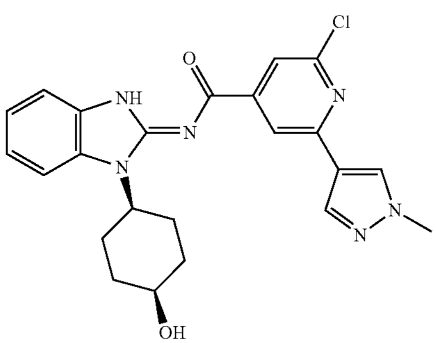 [SMILES: Cn1cc(-c2cc(C(=O)/N=c3\[nH]c4ccccc4n3[C@H]3CC[C@@H](O)CC3)cc(Cl)n2)cn1] | A | 5 | (M + H)$^+$ = 451, t$_{Ret}$ = 1.23 | LCMSBAS |
| I-147 | 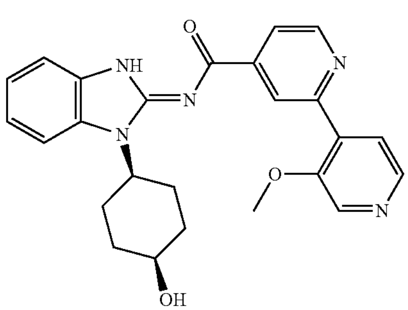 [SMILES: COc1cnccc1-c1cc(C(=O)/N=c2\[nH]c3ccccc3n2[C@H]2CC[C@@H](O)CC2)ccn1] | A | 4 | (M + H)$^+$ = 444, t$_{Ret}$ = 1.10 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-148 | 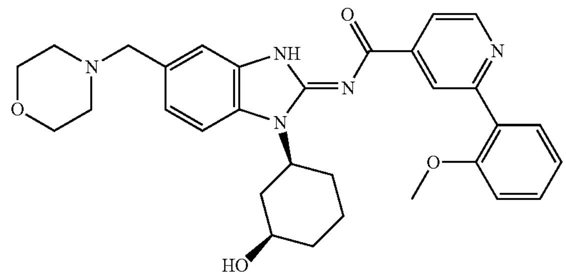 [SMILES: COc1ccccc1-c1cc(C(=O)/N=c2\[nH]c3cc(CN4CCOCC4)ccc3n2[C@H]2CCC[C@@H](O)C2)ccn1] | C | 4 | (M + H)$^+$ = 542, t$_{Ret}$ = 1.20 | LCMSBAS |
| I-149 | 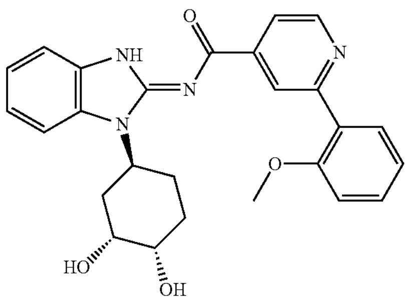 [SMILES: COc1ccccc1-c1cc(C(=O)/N=c2\[nH]c3ccccc3n2[C@H]2CC[C@H](O)[C@H](O)C2)ccn1] | A | 4 | (M + H)$^+$ = 459, t$_{Ret}$ = 1.12 | LCMSBAS |
| I-150 | 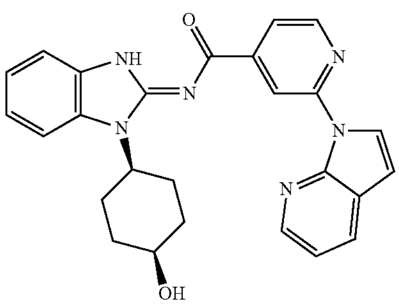 [SMILES: O=C(/N=c1\[nH]c2ccccc2n1[C@H]1CC[C@@H](O)CC1)c1ccnc(-n2ccc3cccnc32)c1] | A | 4 | (M + H)$^+$ = 453, t$_{Ret}$ = 1.34 | LCMSBAS |
| I-151 | 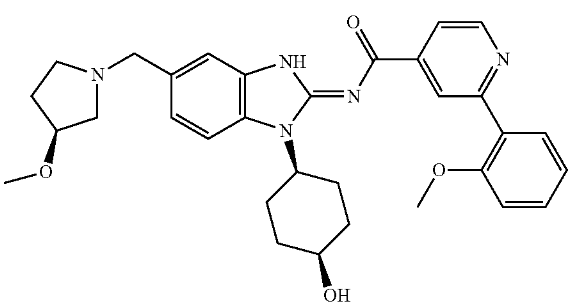 [SMILES: COc1ccccc1-c1cc(C(=O)/N=c2\[nH]c3cc(CN4CC[C@H](OC)C4)ccc3n2[C@H]2CC[C@@H](O)CC2)ccn1] | C | 4 | (M + H)$^+$ = 556, t$_{Ret}$ = 1.24 | LCMSBAS |
| I-152 | 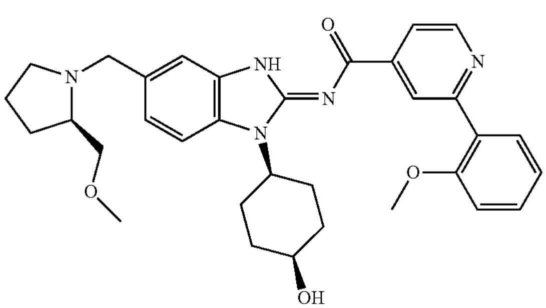 [SMILES: COC[C@H]1CCCN1Cc1ccc2c(c1)[nH]/c(=N\C(=O)c1ccnc(-c3ccccc3OC)c1)n2[C@H]1CC[C@@H](O)CC1] | C | 4 | (M + H)$^+$ = 570, t$_{Ret}$ = 1.32 | LCMSBAS |

TABLE 12-continued
| # | Structure | method | IC$_{50}$ [nM] | MS (M + H)$^+$ t$_{Ret}$ HPLC [min] | HPLC-MS method |
|---|---|---|---|---|---|
| I-153 | 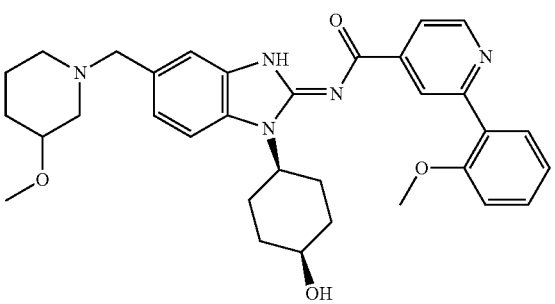 [SMILES: COc1ccccc1-c1cc(C(=O)/N=c2\[nH]c3cc(CN4CCCC(OC)C4)ccc3n2[C@H]2CC[C@@H](O)CC2)ccn1] | C | 4 | (M + H)$^+$ = 570, t$_{Ret}$ = 1.29 | LCMSBAS |
| I-154 | 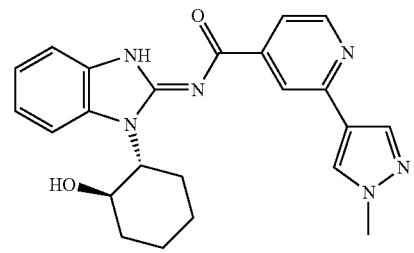 [SMILES: Cn1cc(-c2cc(C(=O)/N=c3\[nH]c4ccccc4n3[C@@H]3CCCC[C@H]3O)ccn2)cn1] | A | 9 | (M + H)$^+$ = 417, t$_{Ret}$ = 1.13 | LCMSBAS |
| I-155 | 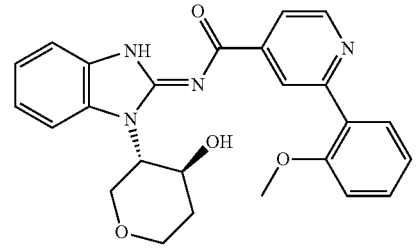 [SMILES: COc1ccccc1-c1cc(C(=O)/N=c2\[nH]c3ccccc3n2[C@H]2COCC[C@@H]2O)ccn1] | A | 5 | (M + H)$^+$ = 445, t$_{Ret}$ = 1.15 | LCMSBAS |
| I-156 | 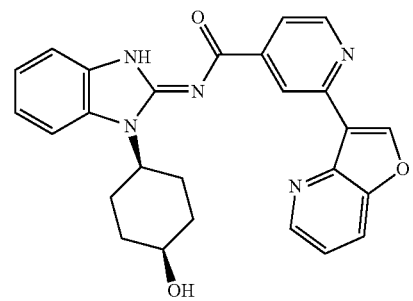 [SMILES: O=C(/N=c1\[nH]c2ccccc2n1[C@H]1CC[C@@H](O)CC1)c1ccnc(-c2coc3cccnc23)c1] | A | 5 | (M + H)$^+$ = 454, t$_{Ret}$ = 1.15 | LCMSBAS |
| I-157 | 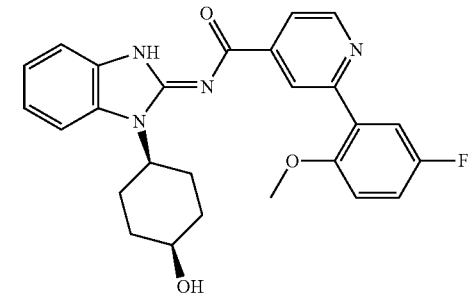 [SMILES: COc1ccc(F)cc1-c1cc(C(=O)/N=c2\[nH]c3ccccc3n2[C@H]2CC[C@@H](O)CC2)ccn1] | B | 5 | (M + H)$^+$ = 461, t$_{Ret}$ = 1.29 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-158 | 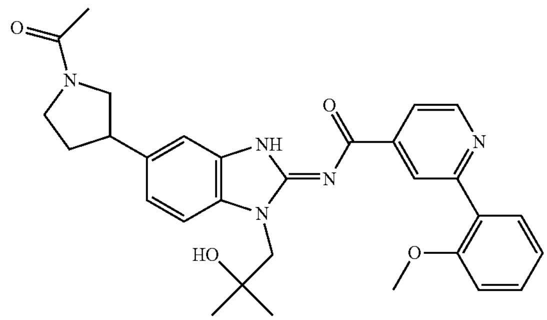 [SMILES: COc1ccccc1-c1cc(C(=O)/N=c2\[nH]c3cc(C4CCN(C(C)=O)C4)ccc3n2CC(C)(C)O)ccn1] | C | 6 | (M + H)$^+$ = 528, t$_{Ret}$ = 1.17 | LCMSBAS |
| I-159 | 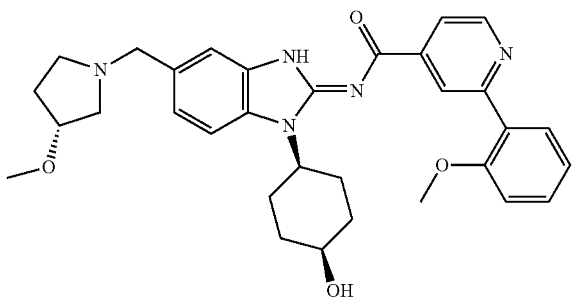 [SMILES: COc1ccccc1-c1cc(C(=O)/N=c2\[nH]c3cc(CN4CC[C@@H](OC)C4)ccc3n2[C@H]2CC[C@@H](O)CC2)ccn1] | C | 6 | (M + H)$^+$ = 556, t$_{Ret}$ = 1.24 | LCMSBAS |
| I-160 | 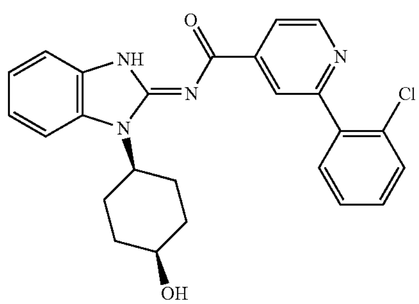 [SMILES: O=C(/N=c1\[nH]c2ccccc2n1[C@H]1CC[C@@H](O)CC1)c1ccnc(-c2ccccc2Cl)c1] | B | 6 | (M + H)$^+$ = 447, t$_{Ret}$ = 1.29 | LCMSBAS |
| I-161 | 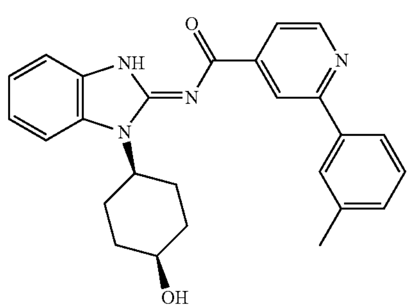 [SMILES: Cc1cccc(-c2cc(C(=O)/N=c3\[nH]c4ccccc4n3[C@H]3CC[C@@H](O)CC3)ccn2)c1] | B | 6 | (M + H)$^+$ = 427, t$_{Ret}$ = 1.35 | LCMSBAS |
| I-162 | 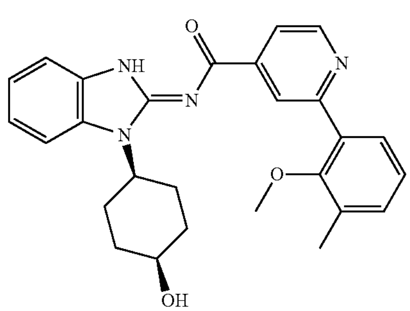 [SMILES: COc1c(C)cccc1-c1cc(C(=O)/N=c2\[nH]c3ccccc3n2[C@H]2CC[C@@H](O)CC2)ccn1] | B | 6 | (M + H)$^+$ = 457, t$_{Ret}$ = 1.31 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-163 | 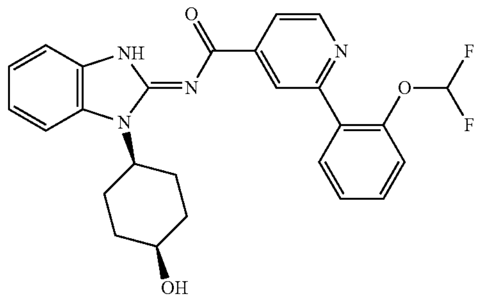 [SMILES: O=C(/N=c1\[nH]c2ccccc2n1[C@H]1CC[C@@H](O)CC1)c1ccnc(-c2ccccc2OC(F)F)c1] | A | 7 | (M + H)$^+$ = 479, t$_{Ret}$ = 1.29 | LCMSBAS |
| I-164 | 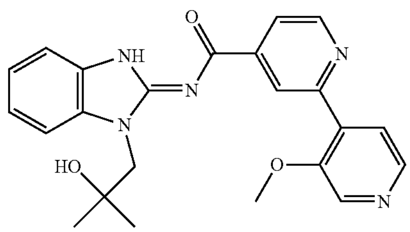 [SMILES: COc1cnccc1-c1cc(C(=O)/N=c2\[nH]c3ccccc3n2CC(C)(C)O)ccn1] | A | 7 | (M + H)$^+$ = 418, t$_{Ret}$ = 1.10 | LCMSBAS |
| I-165 | 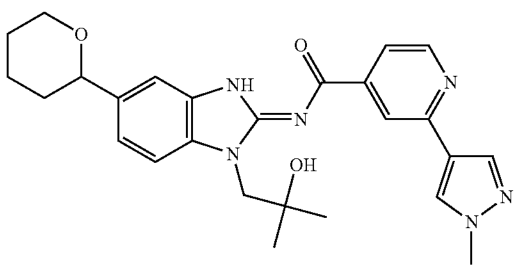 [SMILES: Cn1cc(-c2cc(C(=O)/N=c3\[nH]c4cc(C5CCCCO5)ccc4n3CC(C)(C)O)ccn2)cn1] | A | 7 | (M + H)$^+$ = 475, t$_{Ret}$ = 1.19 | LCMSBAS |
| I-166 | 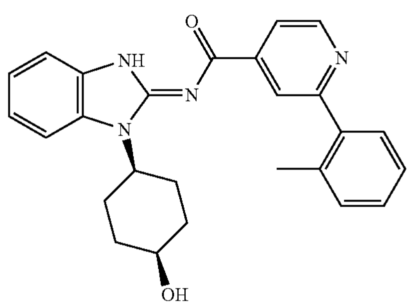 [SMILES: Cc1ccccc1-c1cc(C(=O)/N=c2\[nH]c3ccccc3n2[C@H]2CC[C@@H](O)CC2)ccn1] | A | 7 | (M + H)$^+$ = 427, t$_{Ret}$ = 1.29 | LCMSBAS |
| I-167 | 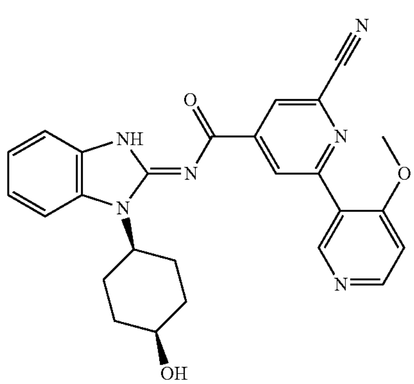 [SMILES: COc1ccncc1-c1cc(C(=O)/N=c2\[nH]c3ccccc3n2[C@H]2CC[C@@H](O)CC2)cc(C#N)n1] | A | 7 | (M + H)$^+$ = 469, t$_{Ret}$ = 0.9 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-168 | 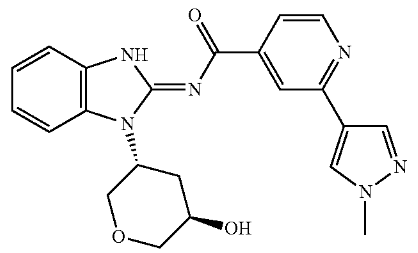 [SMILES: Cn1cc(-c2cc(C(=O)/N=c3\[nH]c4ccccc4n3[C@H]3COC[C@H](O)C3)ccn2)cn1] | A | 10 | (M + H)$^+$ = 419, t$_{Ret}$ = 1.00 | LCMSBAS |
| I-169 | 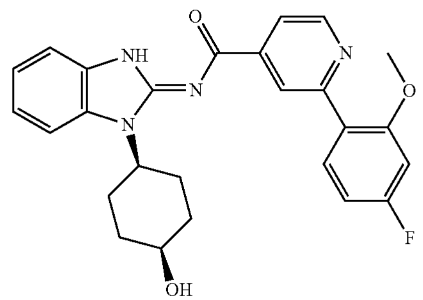 [SMILES: COc1cc(F)ccc1-c1cc(C(=O)/N=c2\[nH]c3ccccc3n2[C@H]2CC[C@@H](O)CC2)ccn1] | B | 11 | (M + H)$^+$ = 461, t$_{Ret}$ = 1.28 | LCMSBAS |
| I-170 | 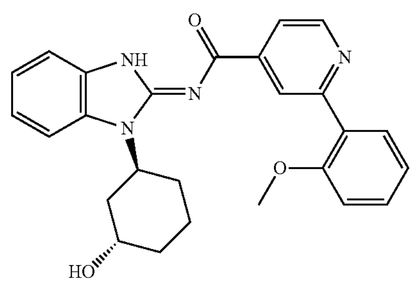 [SMILES: COc1ccccc1-c1cc(C(=O)/N=c2\[nH]c3ccccc3n2[C@H]2CCC[C@H](O)C2)ccn1] | A | 8 | (M + H)$^+$ = 443, t$_{Ret}$ = 1.27 | LCMSBAS |
| I-171 | 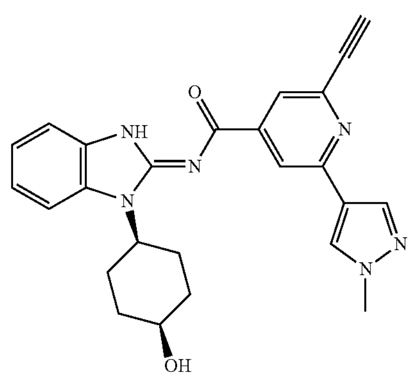 [SMILES: C#Cc1cc(C(=O)/N=c2\[nH]c3ccccc3n2[C@H]2CC[C@@H](O)CC2)cc(-c2cnn(C)c2)n1] | A | 8 | (M + H)$^+$ = 441, t$_{Ret}$ = 1.17 | LCMSBAS |
| I-172 | 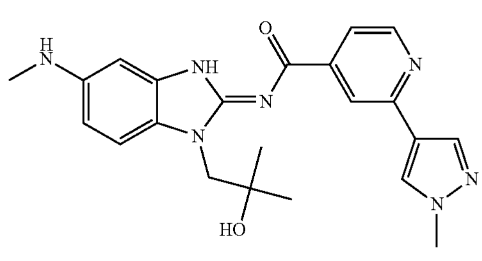 [SMILES: CNc1ccc2c(c1)[nH]/c(=N\C(=O)c1ccnc(-c3cnn(C)c3)c1)n2CC(C)(C)O] | C | 9 | (M + H)$^+$ = 420, t$_{Ret}$ = 1.01 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-173 | 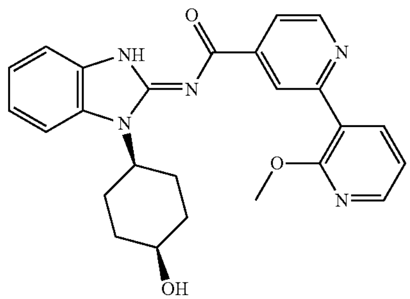 [SMILES: COc1ncccc1-c1cc(C(=O)/N=c2\[nH]c3ccccc3n2[C@H]2CC[C@@H](O)CC2)ccn1] | A | 9 | (M + H)$^+$ = 444, t$_{Ret}$ = 1.19 | LCMSBAS |
| I-174 | 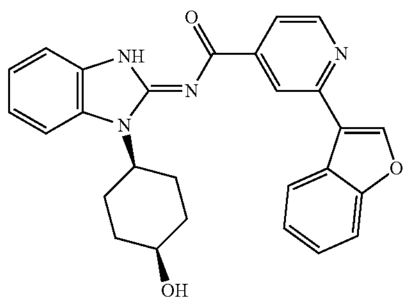 | A | 9 | (M + H)$^+$ = 453, t$_{Ret}$ = 1.39 | LCMSBAS |
| I-175 | 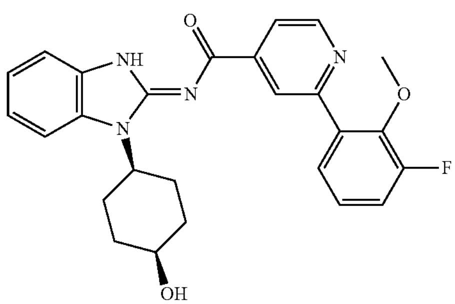 [SMILES: COc1c(F)cccc1-c1cc(C(=O)/N=c2\[nH]c3ccccc3n2[C@H]2CC[C@@H](O)CC2)ccn1] | B | 10 | (M + H)$^+$ = 461, t$_{Ret}$ = 1.29 | LCMSBAS |
| I-176 | 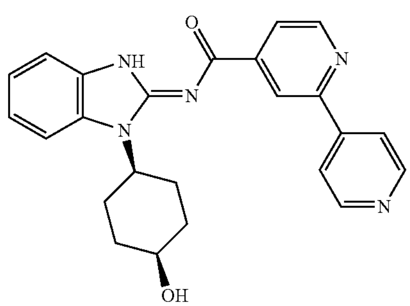 [SMILES: O=C(/N=c1\[nH]c2ccccc2n1[C@H]1CC[C@@H](O)CC1)c1ccnc(-c2ccncc2)c1] | A | 11 | (M + H)$^+$ = 414, t$_{Ret}$ = 1.21 | LCMSBAS |
| I-177 | 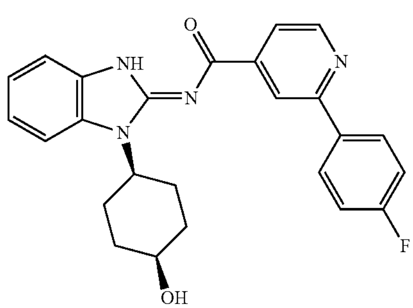 [SMILES: O=C(/N=c1\[nH]c2ccccc2n1[C@H]1CC[C@@H](O)CC1)c1ccnc(-c2ccc(F)cc2)c1] | B | 12 | (M + H)$^+$ = 431, t$_{Ret}$ = 1.33 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-178 | 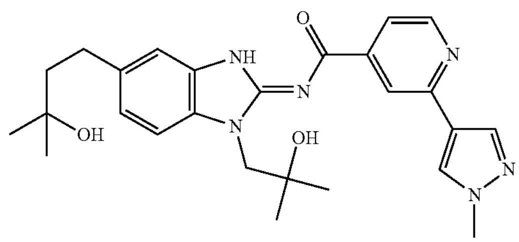 [SMILES: Cn1cc(-c2cc(C(=O)/N=c3\[nH]c4cc(CCC(C)(C)O)ccc4n3CC(C)(C)O)ccn2)cn1] | A | 12 | (M + H)$^+$ = 477, t$_{Ret}$ = 1.09 | LCMSBAS |
| I-179 | 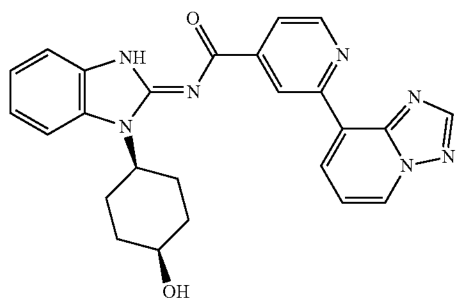 | A | 12 | (M + H)$^+$ = 454, t$_{Ret}$ = 1.11 | LCMSBAS |
| I-180 | 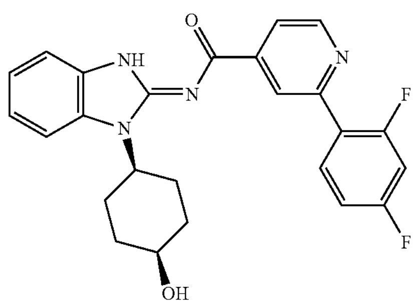 [SMILES: O=C(/N=c1\[nH]c2ccccc2n1[C@H]1CC[C@@H](O)CC1)c1ccnc(-c2ccc(F)cc2F)c1] | B | 12 | (M + H)$^+$ = 449, t$_{Ret}$ = 1.32 | LCMSBAS |
| I-181 | 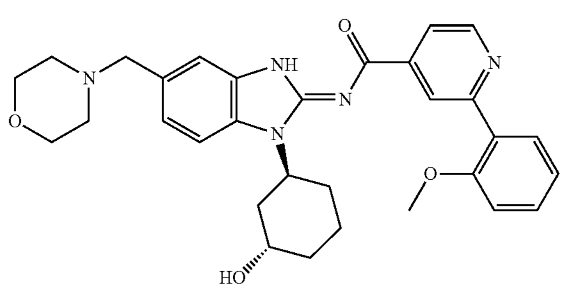 [SMILES: COc1ccccc1-c1cc(C(=O)/N=c2\[nH]c3cc(CN4CCOCC4)ccc3n2[C@H]2CCC[C@H](O)C2)ccn1] | C | 12 | (M + H)$^+$ = 542, t$_{Ret}$ = 1.23 | LCMSBAS |
| I-182 | 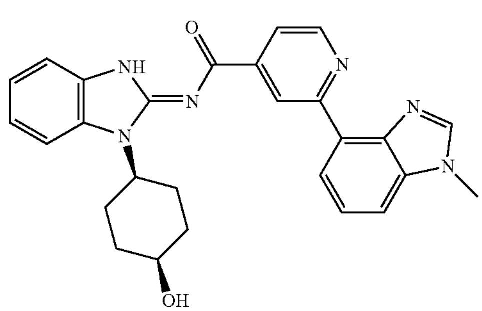 [SMILES: Cn1cnc2c(-c3cc(C(=O)/N=c4\[nH]c5ccccc5n4[C@H]4CC[C@@H](O)CC4)ccn3)cccc21] | A | 15 | (M + H)$^+$ = 467, t$_{Ret}$ = 1.14 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-183 | 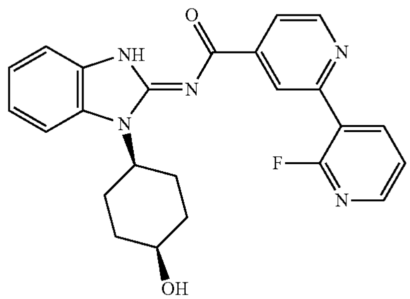 [SMILES: O=C(/N=c1\[nH]c2ccccc2n1[C@H]1CC[C@@H](O)CC1)c1ccnc(-c2cccnc2F)c1] | A | 16 | (M + H)$^+$ = 432, t$_{Ret}$ = 1.17 | LCMSBAS |
| I-184 | 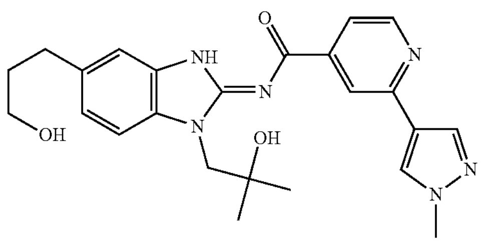 [SMILES: Cn1cc(-c2cc(C(=O)/N=c3\[nH]c4cc(CCCO)ccc4n3CC(C)(C)O)ccn2)cn1] | A | 19 | (M + H)$^+$ = 449, t$_{Ret}$ = 1.00 | LCMSBAS |
| I-185 | 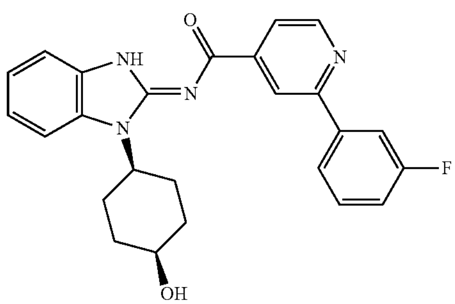 [SMILES: O=C(/N=c1\[nH]c2ccccc2n1[C@H]1CC[C@@H](O)CC1)c1ccnc(-c2cccc(F)c2)c1] | B | 23 | (M + H)$^+$ = 431, t$_{Ret}$ = 1.34 | LCMSBAS |
| I-186 | 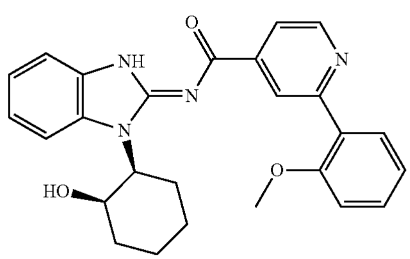 [SMILES: COc1ccccc1-c1cc(C(=O)/N=c2\[nH]c3ccccc3n2[C@H]2CCCC[C@H]2O)ccn1] | A | 23 | (M + H)$^+$ = 443, t$_{Ret}$ = 1.38 | LCMSBAS |
| I-187 | 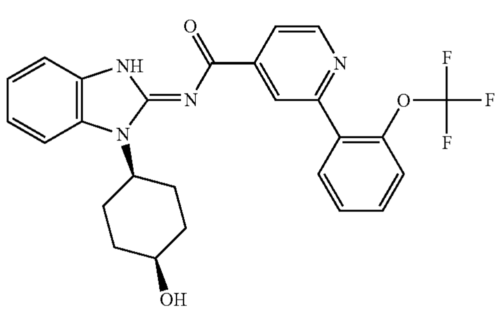 [SMILES: O=C(/N=c1\[nH]c2ccccc2n1[C@H]1CC[C@@H](O)CC1)c1ccnc(-c2ccccc2OC(F)(F)F)c1] | A | 24 | (M + H)$^+$ = 497, t$_{Ret}$ = 1.37 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-188 | 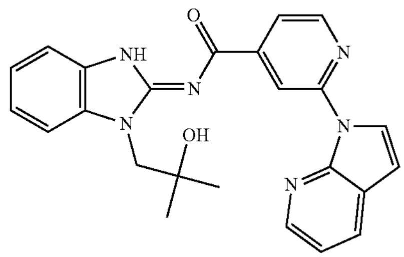 [SMILES: CC(C)(O)Cn1/c(=N/C(=O)c2ccnc(-n3ccc4cccnc43)c2)[nH]c2ccccc21] | A | 30 | (M + H)$^+$ = 427, t$_{Ret}$ = 1.37 | LCMSBAS |
| I-189 | 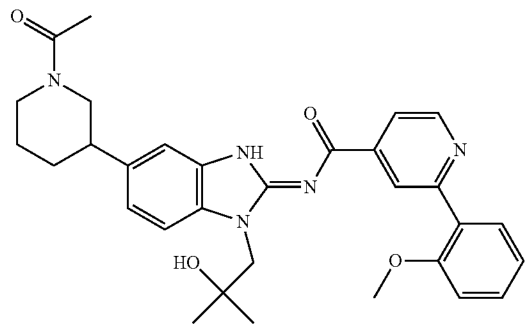 | A | 31 | (M + H)$^+$ = 452, t$_{Ret}$ = 1.32 | LCMSBAS |
| I-190 | 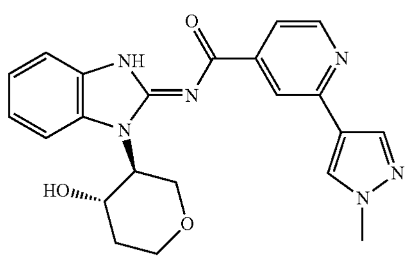 [SMILES: Cn1cc(-c2cc(C(=O)/N=c3\[nH]c4ccccc4n3[C@H]3COCC[C@@H]3O)ccn2)cn1] | A | 33 | (M + H)$^+$ = 419, t$_{Ret}$ = 0.97 | LCMSBAS |
| I-191 | 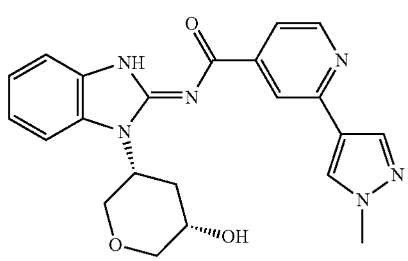 [SMILES: Cn1cc(-c2cc(C(=O)/N=c3\[nH]c4ccccc4n3[C@H]3COC[C@@H](O)C3)ccn2)cn1] | A | 44 | (M + H)$^+$ = 419, t$_{Ret}$ = 0.98 | LCMSBAS |
| I-192 | 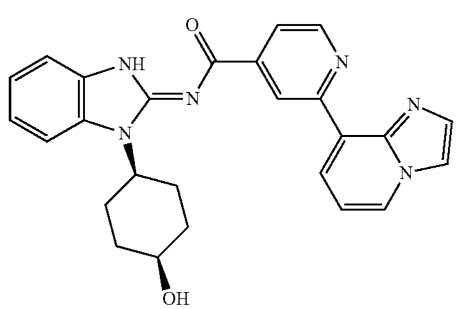 [SMILES: O=C(/N=c1\[nH]c2ccccc2n1[C@H]1CC[C@@H](O)CC1)c1ccnc(-c2cccn3ccnc23)c1] | A | 48 | (M + H)$^+$ = 543, t$_{Ret}$ = 1.12 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-193 | 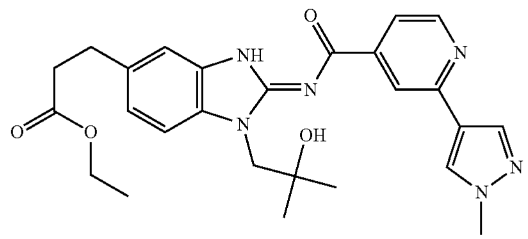 [SMILES: CCOC(=O)CCc1ccc2c(c1)[nH]/c(=N\C(=O)c1ccnc(-c3cnn(C)c3)c1)n2CC(C)(C)O] | A | 68 | (M + H)$^+$ = 491, t$_{Ret}$ = 1.17 | LCMSBAS |
| I-194 | 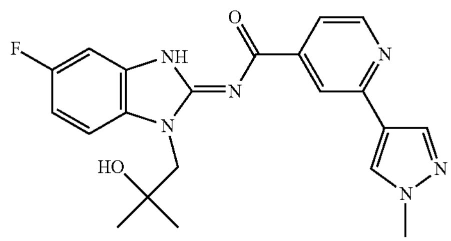 [SMILES: Cn1cc(-c2cc(C(=O)/N=c3\[nH]c4cc(F)ccc4n3CC(C)(C)O)ccn2)cn1] | A | 74 | (M + H)$^+$ = 409, t$_{Ret}$ = 1.07 | LCMSBAS |
| I-195 | 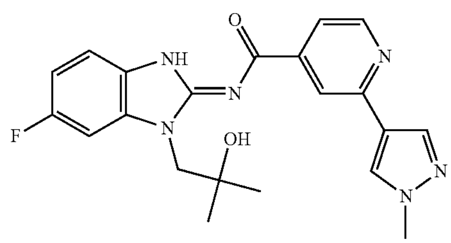 [SMILES: Cn1cc(-c2cc(C(=O)/N=c3\[nH]c4ccc(F)cc4n3CC(C)(C)O)ccn2)cn1] | A | 85 | (M + H)$^+$ = 409, t$_{Ret}$ = 1.09 | LCMSBAS |
| I-196 | 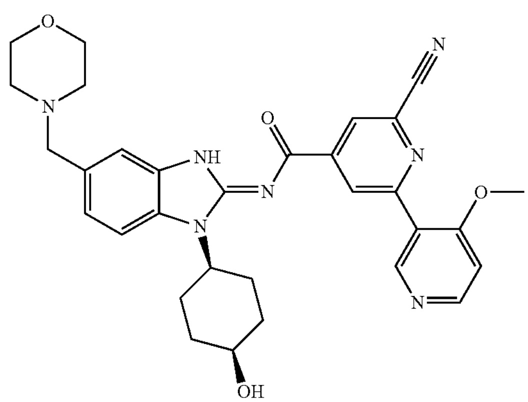 [SMILES: COc1ccncc1-c1cc(C(=O)/N=c2\[nH]c3cc(CN4CCOCC4)ccc3n2[C@H]2CC[C@@H](O)CC2)cc(C#N)n1] | A | 5 | (M + H)$^+$ = 568, t$_{Ret}$ = 1.15 | LCMSBAS |
| I-197 | 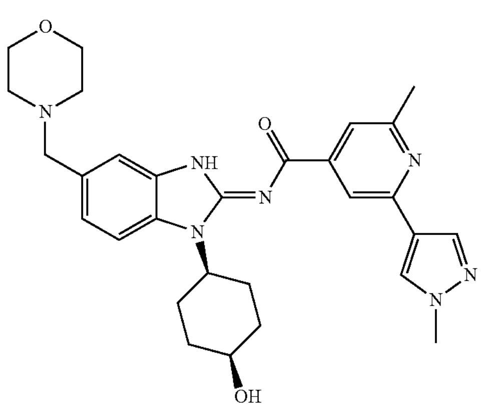 [SMILES: Cc1cc(C(=O)/N=c2\[nH]c3cc(CN4CCOCC4)ccc3n2[C@H]2CC[C@@H](O)CC2)cc(-c2cnn(C)c2)n1] | A | 7 | (M + H)$^+$ = 530, t$_{Ret}$ = 1.09 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-198 | 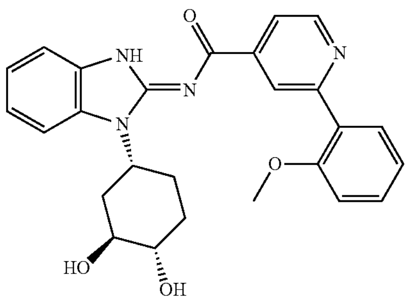 [SMILES: COc1ccccc1-c1cc(C(=O)/N=c2\[nH]c3ccccc3n2[C@@H]2CC[C@H](O)[C@@H](O)C2)ccn1] | A | 18 | (M + H)$^+$ = 459, t$_{Ret}$ = 1.11 | LCMSBAS |
| I-199 | 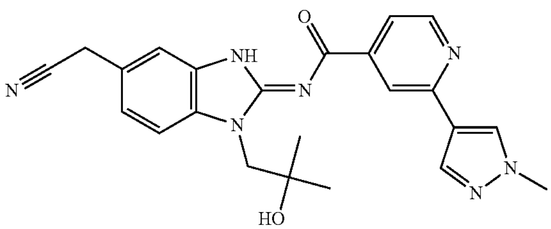 [SMILES: Cn1cc(-c2cc(C(=O)/N=c3\[nH]c4cc(CC#N)ccc4n3CC(C)(C)O)ccn2)cn1] | A | 15 | (M + H)$^+$ = 430, t$_{Ret}$ = 1.01 | LCMSBAS |
| I-200 | 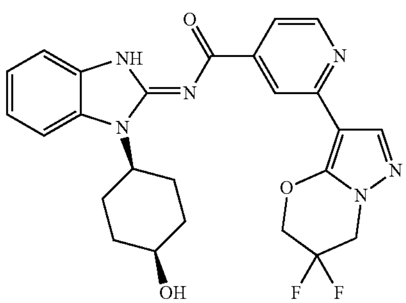 [SMILES: O=C(/N=c1\[nH]c2ccccc2n1[C@H]1CC[C@@H](O)CC1)c1ccnc(-c2cnn3c2OCC(F)(F)C3)c1] | B | 4 | (M + H)$^+$ = 405, t$_{Ret}$ = 1.14 | LCMSBAS |
| I-201 | 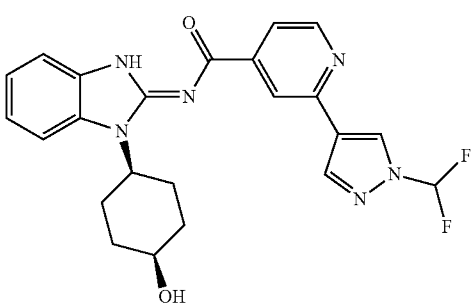 [SMILES: O=C(/N=c1\[nH]c2ccccc2n1[C@H]1CC[C@@H](O)CC1)c1ccnc(-c2cnn(C(F)F)c2)c1] | B | 2 | (M + H)$^+$ = 453, t$_{Ret}$ = 1.20 | LCMSBAS |
| I-202 | 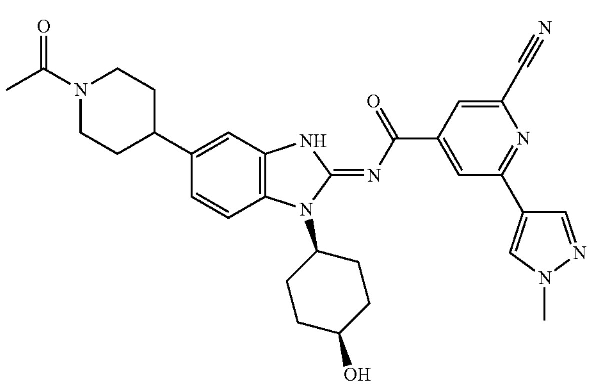 [SMILES: CC(=O)N1CCC(c2ccc3c(c2)[nH]/c(=N\C(=O)c2cc(C#N)nc(-c4cnn(C)c4)c2)n3[C@H]2CC[C@@H](O)CC2)CC1] | A | 5 | (M + H)$^+$ = 567, t$_{Ret}$ = 1.16 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-203 | 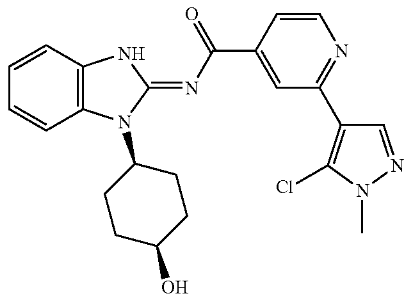 [SMILES: Cn1ncc(-c2cc(C(=O)/N=c3\[nH]c4ccccc4n3[C@H]3CC[C@@H](O)CC3)ccn2)c1Cl] | A | 2 | (M + H)$^+$ = 451, t$_{Ret}$ = 1.15 | LCMSBAS |
| I-204 | 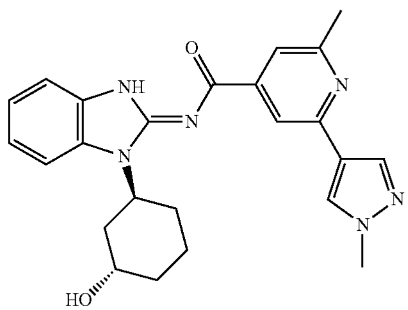 [SMILES: Cc1cc(C(=O)/N=c2\[nH]c3ccccc3n2[C@H]2CCC[C@H](O)C2)cc(-c2cnn(C)c2)n1] | A | 6 | (M + H)$^+$ = 431, t$_{Ret}$ = 1.15 | LCMSBAS |
| I-205 | 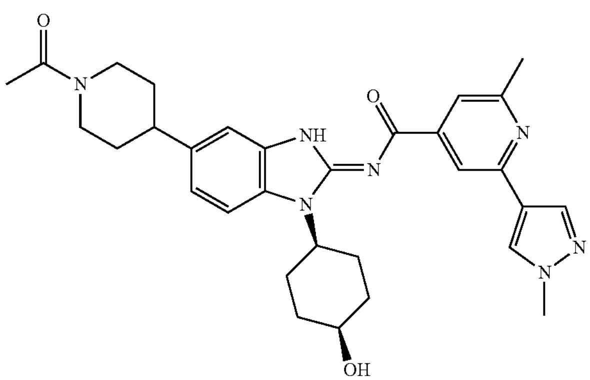 [SMILES: CC(=O)N1CCC(c2ccc3c(c2)[nH]/c(=N\C(=O)c2cc(C)nc(-c4cnn(C)c4)c2)n3[C@H]2CC[C@@H](O)CC2)CC1] | A | 8 | (M + H)$^+$ = 556, t$_{Ret}$ = 1.09 | LCMSBAS |
| I-206 | 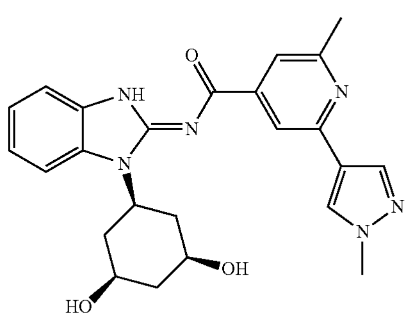 [SMILES: Cc1cc(C(=O)/N=c2\[nH]c3ccccc3n2[C@@H]2C[C@H](O)C[C@H](O)C2)cc(-c2cnn(C)c2)n1] | A | 37 | (M + H)$^+$ = 447, t$_{Ret}$ = 0.95 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-207 | 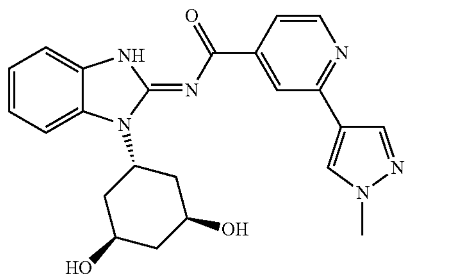 [SMILES: Cn1cc(-c2cc(C(=O)/N=c3\[nH]c4ccccc4n3[C@H]3C[C@H](O)C[C@H](O)C3)ccn2)cn1] | A | 26 | (M + H)$^+$ = 433, t$_{Ret}$ = 0.89 | LCMSBAS |
| I-208 | 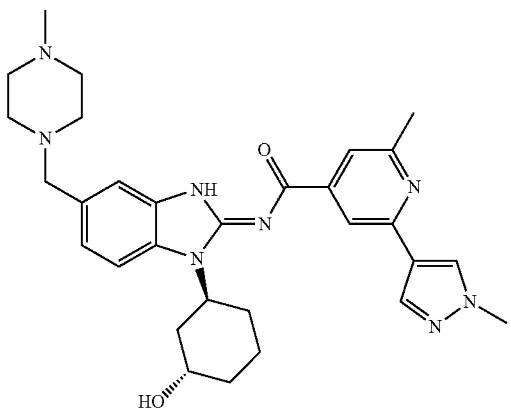 [SMILES: Cc1cc(C(=O)/N=c2\[nH]c3cc(CN4CCN(C)CC4)ccc3n2[C@H]2CCC[C@H](O)C2)cc(-c2cnn(C)c2)n1] | A | 44 | (M + H)$^+$ = 543, t$_{Ret}$ = 1.05 | LCMSBAS |
| I-209 | 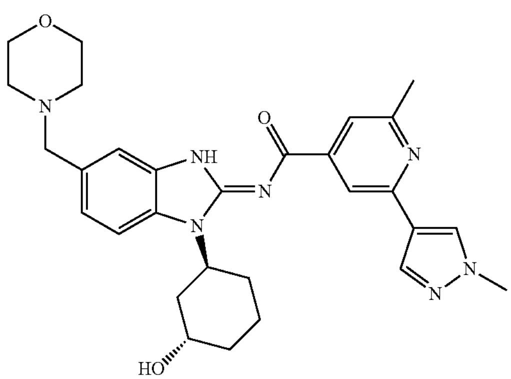 [SMILES: Cc1cc(C(=O)/N=c2\[nH]c3cc(CN4CCOCC4)ccc3n2[C@H]2CCC[C@H](O)C2)cc(-c2cnn(C)c2)n1] | A | 14 | (M + H)$^+$ = 530, t$_{Ret}$ = 1.06 | LCMSBAS |
| I-210 | 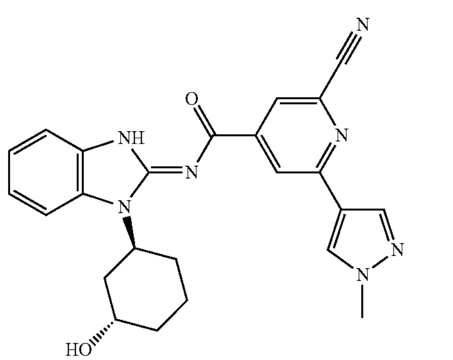 [SMILES: Cn1cc(-c2cc(C(=O)/N=c3\[nH]c4ccccc4n3[C@H]3CCC[C@H](O)C3)cc(C#N)n2)cn1] | A | 9 | (M + H)$^+$ = 442, t$_{Ret}$ = 1.12 | LCMSBAS |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-211 | 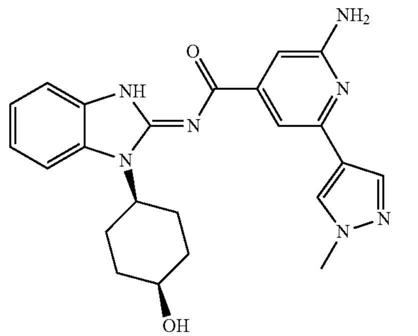 [SMILES: Cn1cc(-c2cc(C(=O)/N=c3\[nH]c4ccccc4n3[C@H]3CC[C@@H](O)CC3)cc(N)n2)cn1] | B | 1 | (M + H)$^+$ = 432, t$_{Ret}$ = 1.03 | LCMSBAS |
| I-212 | 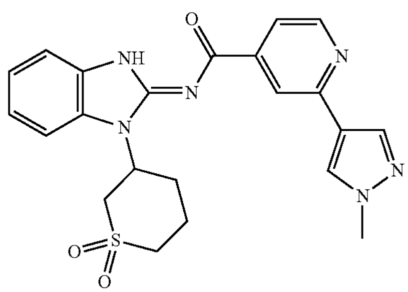 [SMILES: Cn1cc(-c2cc(C(=O)/N=c3\[nH]c4ccccc4n3C3CCCS(=O)(=O)C3)ccn2)cn1] | A | 22 | (M + H)$^+$ = 451, t$_{Ret}$ = 0.28 | LCMSBAS |
| I-213 | 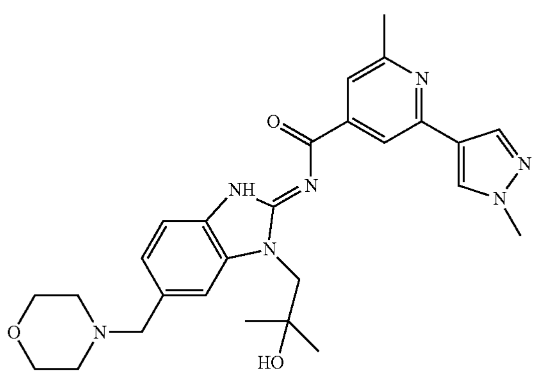 [SMILES: Cc1cc(C(=O)/N=c2\[nH]c3ccc(CN4CCOCC4)cc3n2CC(C)(C)O)cc(-c2cnn(C)c2)n1] | C | 45 | (M + H)$^+$ = 504, t$_{Ret}$ = 0.22 | LCMSBAS |
| I-214 | 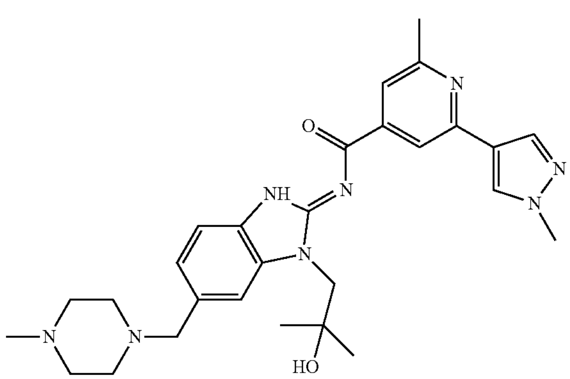 [SMILES: Cc1cc(C(=O)/N=c2\[nH]c3ccc(CN4CCN(C)CC4)cc3n2CC(C)(C)O)cc(-c2cnn(C)c2)n1] | C | 38 | (M + H)$^+$ = 517, t$_{Ret}$ = 0.26 | LCMSBAS |

TABLE 12-continued
| # | Structure | method | IC$_{50}$ [nM] | MS (M + H)$^+$ t$_{Ret}$ HPLC [min] | HPLC-MS method |
|---|---|---|---|---|---|
| I-215 | 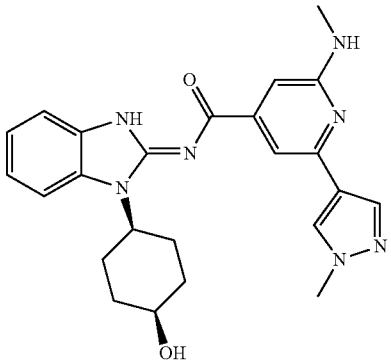 [SMILES: CNc1cc(C(=O)/N=c2\[nH]c3ccccc3n2[C@H]2CC[C@@H](O)CC2)cc(-c2cnn(C)c2)n1] | B | 14 | (M + H)$^+$ = 446, t$_{Ret}$ = 1.04 | LCMSBAS |
| I-216 | 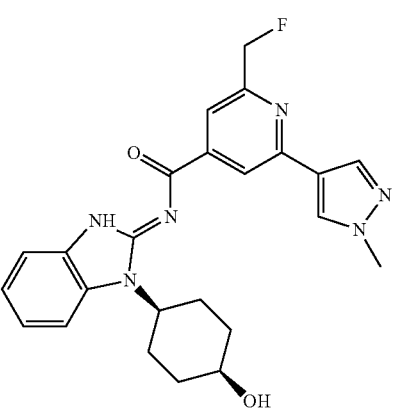 [SMILES: Cn1cc(-c2cc(C(=O)/N=c3\[nH]c4ccccc4n3[C@H]3CC[C@@H](O)CC3)cc(CF)n2)cn1] | A | 17 | (M + H)$^+$ = 449, t$_{Ret}$ = 1.09 | LCMSBAS |
| I-217 | 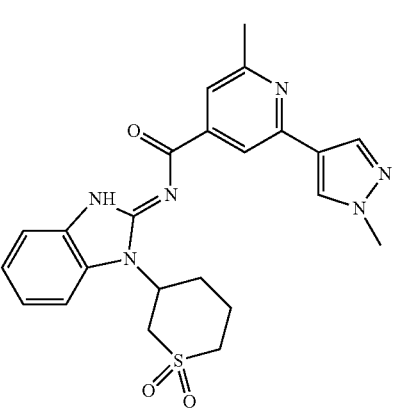 [SMILES: Cc1cc(C(=O)/N=c2\[nH]c3ccccc3n2C2CCCS(=O)(=O)C2)cc(-c2cnn(C)c2)n1] | A | 75 | (M + H)$^+$ = 465, t$_{Ret}$ = 1.06 | LCMSBAS |
| I-218 | 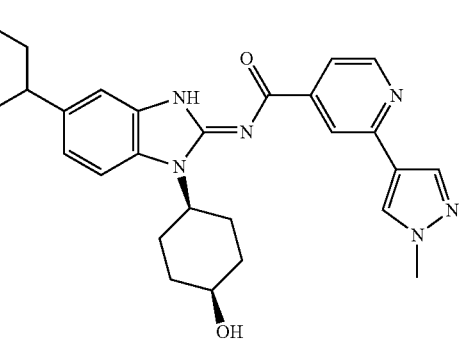 | C | 18 | (M + H)$^+$ = 500, t$_{Ret}$ = 1.08 | LCMS3, basisch_1 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-219 | 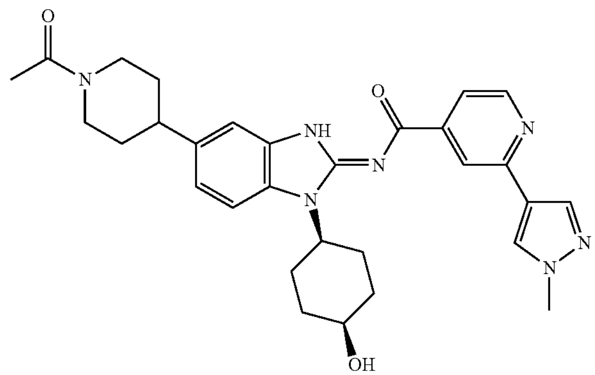 [SMILES: CC(=O)N1CCC(c2ccc3c(c2)[nH]/c(=N\C(=O)c2ccnc(-c4cnn(C)c4)c2)n3[C@H]2CC[C@@H](O)CC2)CC1] | C | 2 | (M + H)$^+$ = 542, t$_{Ret}$ = 1.04 | LCMS3, basisch_1 |
| I-220 | 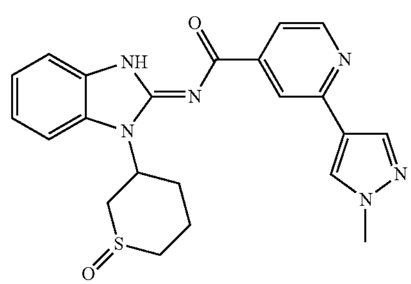 [SMILES: Cn1cc(-c2cc(C(=O)/N=c3\[nH]c4ccccc4n3C3CCCS(=O)C3)ccn2)cn1] | A | 59 | (M + H)$^+$ = 435, t$_{Ret}$ = 0.95 | LCMS3, basisch_1 |
| I-221 | 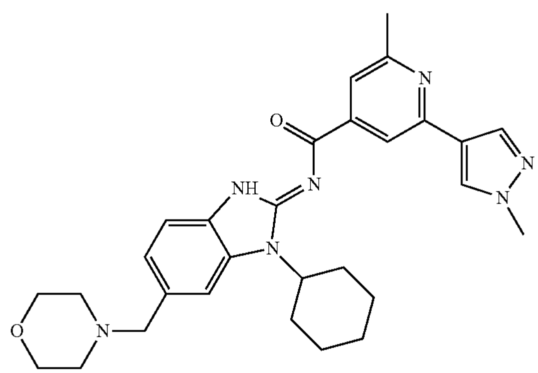 [SMILES: Cc1cc(C(=O)/N=c2\[nH]c3ccc(CN4CCOCC4)cc3n2C2CCCCC2)cc(-c2cnn(C)c2)n1] | C | 5 | (M + H)$^+$ = 514, t$_{Ret}$ = 1.35 | LCMS3, basisch_1 |
| I-222 | 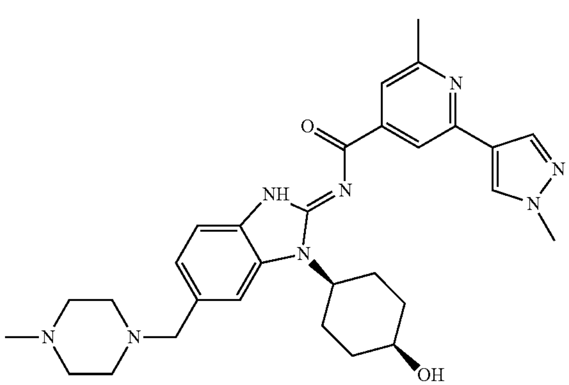 [SMILES: Cc1cc(C(=O)/N=c2\[nH]c3ccc(CN4CCN(C)CC4)cc3n2[C@H]2CC[C@@H](O)CC2)cc(-c2cnn(C)c2)n1] | C | 5 | (M + H)$^+$ = 543, t$_{Ret}$ = 1.05 | LCMS3, basisch_1 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-223 | 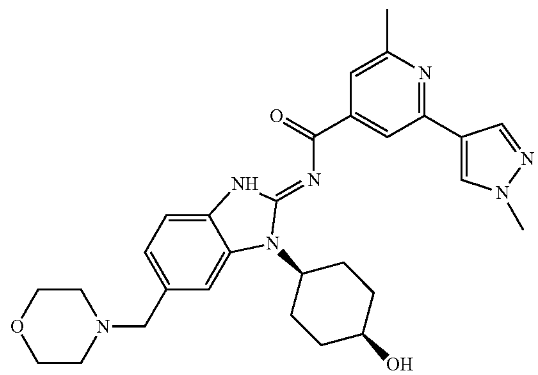 [SMILES: Cc1cc(C(=O)/N=c2\[nH]c3ccc(CN4CCOCC4)cc3n2[C@H]2CC[C@@H](O)CC2)cc(-c2cnn(C)c2)n1] | C | 4 | (M + H)$^+$ = 530, t$_{Ret}$ = 1.09 | LCMS3, basisch_1 |
| I-224 | 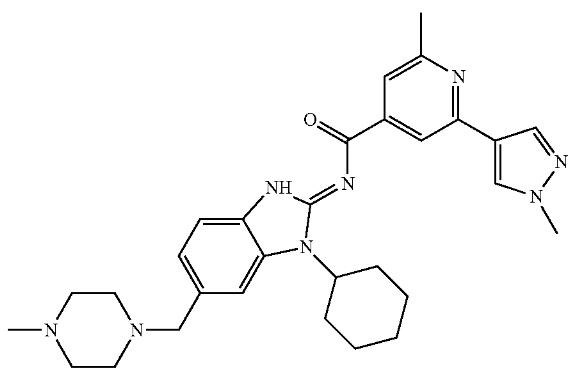 [SMILES: Cc1cc(C(=O)/N=c2\[nH]c3ccc(CN4CCN(C)CC4)cc3n2C2CCCCC2)cc(-c2cnn(C)c2)n1] | C | 3 | (M + H)$^+$ = 527, t$_{Ret}$ = 1.30 | LCMS3, basisch_1 |
| I-225 | 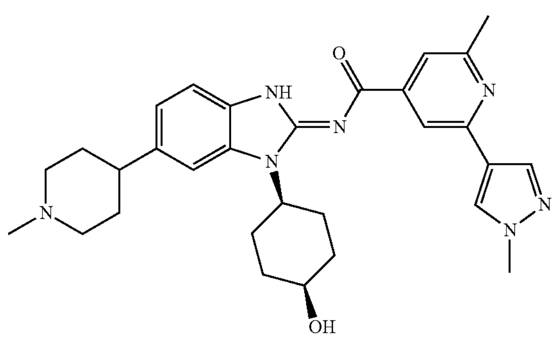 [SMILES: Cc1cc(C(=O)/N=c2\[nH]c3ccc(C4CCN(C)CC4)cc3n2[C@H]2CC[C@@H](O)CC2)cc(-c2cnn(C)c2)n1] | A | 2 | (M + H)$^+$ = 528, t$_{Ret}$ = 1.20 | LCMS3, basisch_1 |
| I-226 | 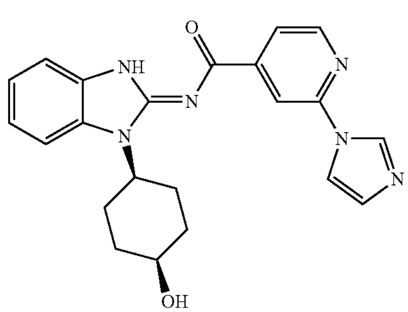 [SMILES: O=C(/N=c1\[nH]c2ccccc2n1[C@H]1CC[C@@H](O)CC1)c1ccnc(-n2ccnc2)c1] | A | 7 | (M + H)$^+$ = 403, t$_{Ret}$ = 1.10 | LCMS3, basisch_1 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-227 | 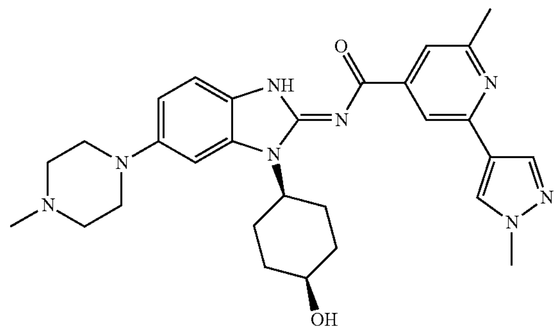 [SMILES: Cc1cc(C(=O)/N=c2\[nH]c3ccc(N4CCN(C)CC4)cc3n2[C@H]2CC[C@@H](O)CC2)cc(-c2cnn(C)c2)n1] | A | 2 | (M + H)$^+$ = 529, t$_{Ret}$ = 1.08 | LCMS3, basisch_1 |
| I-228 | 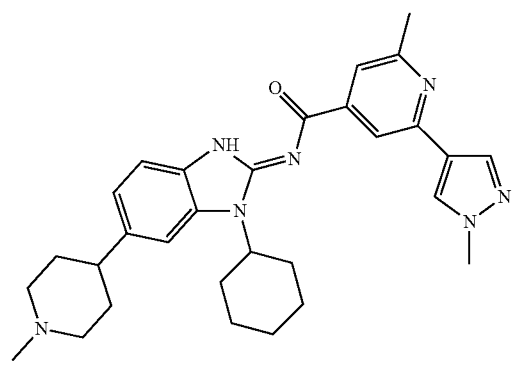 [SMILES: Cc1cc(C(=O)/N=c2\[nH]c3ccc(C4CCN(C)CC4)cc3n2C2CCCCC2)cc(-c2cnn(C)c2)n1] | C | 2 | (M + H)$^+$ = 512, t$_{Ret}$ = 1.53 | LCMS3, basisch_1 |
| I-229 | 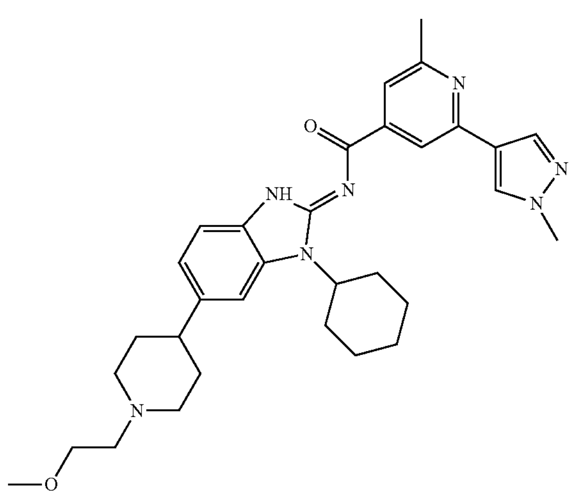 [SMILES: COCCN1CCC(c2ccc3[nH]/c(=N\C(=O)c4cc(C)nc(-c5cnn(C)c5)c4)n(C4CCCCC4)c3c2)CC1] | C | 23 | (M + H)$^+$ = 556, t$_{Ret}$ = 1.50 | LCMS3, basisch_1 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-230 | 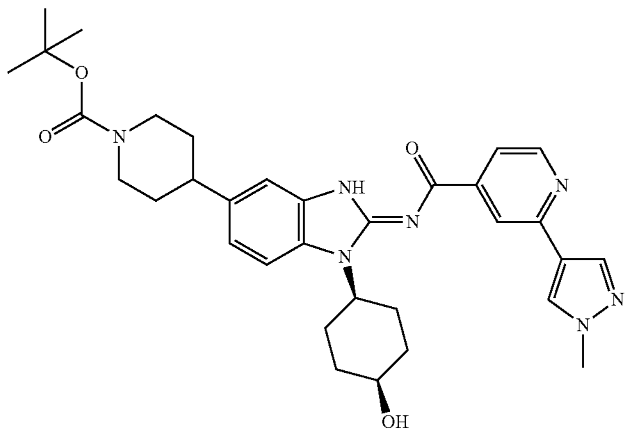 [SMILES: Cn1cc(-c2cc(C(=O)/N=c3\[nH]c4cc(C5CCN(C(=O)OC(C)(C)C)CC5)ccc4n3[C@H]3CC[C@@H](O)CC3)ccn2)cn1] | A | | (M + H)$^+$ = 600, t$_{Ret}$ = 1.0 | VAB |
| I-231 | 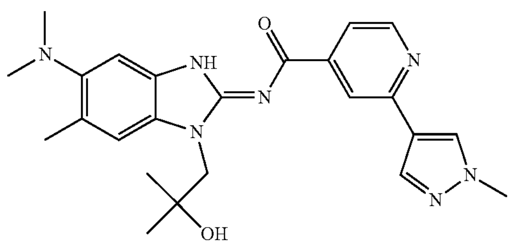 | A | 63 | (M + H)$^+$ = 448, t$_{Ret}$ = 0.7 | Z018_S04 |
| I-232 | 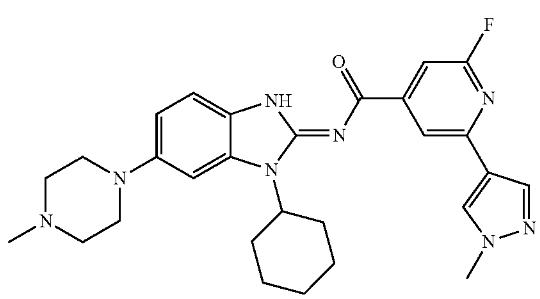 [SMILES: CN1CCN(c2ccc3[nH]/c(=N\C(=O)c4cc(F)nc(-c5cnn(C)c5)c4)n(C4CCCCC4)c3c2)CC1] | A | 1 | (M + H)$^+$ = 517, t$_{Ret}$ = 1.4 | LCMS3, basisch_1 |
| I-233 | 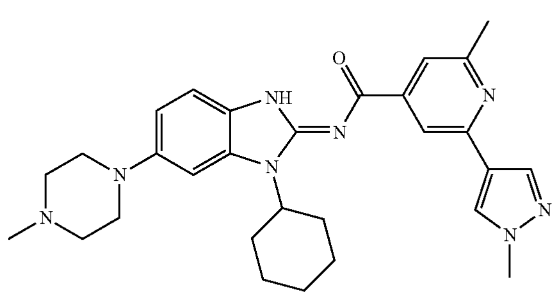 [SMILES: Cc1cc(C(=O)/N=c2\[nH]c3ccc(N4CCN(C)CC4)cc3n2C2CCCCC2)cc(-c2cnn(C)c2)n1] | A | 2 | (M + H)$^+$ = 513, t$_{Ret}$ = 1.3 | LCMS3, basisch_1 |

TABLE 12-continued

| # | Structure | method | IC$_{50}$ [nM] | MS (M + H)$^+$ t$_{Ret}$ HPLC [min] | HPLC-MS method |
|---|---|---|---|---|---|
| I-234 | 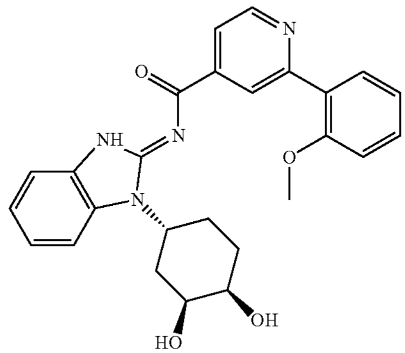 [SMILES: COc1ccccc1-c1cc(C(=O)/N=c2\[nH]c3ccccc3n2[C@@H]2CC[C@@H](O)[C@@H](O)C2)ccn1] | A | 4 | (M + H)$^+$ = 459, t$_{Ret}$ = 1.1 | LCMSBAS |
| I-235 | 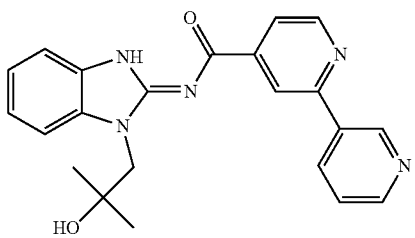 [SMILES: CC(C)(O)Cn1/c(=N/C(=O)c2ccnc(-c3cccnc3)c2)[nH]c2ccccc21] | A | 35 | (M + H)$^+$ = 388, t$_{Ret}$ = 1.0 | LCMSBAS |
| I-236 | 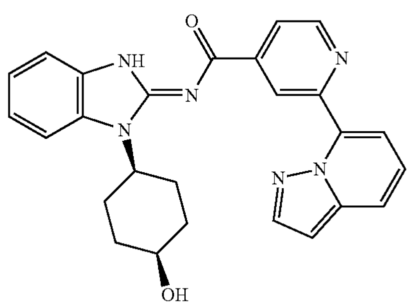 [SMILES: O=C(/N=c1\[nH]c2ccccc2n1[C@H]1CC[C@@H](O)CC1)c1ccnc(-c2cccc3ccnn23)c1] | A | 8 | (M + H)$^+$ = 453, t$_{Ret}$ = 1.2 | LCMSBAS |
| I-237 | 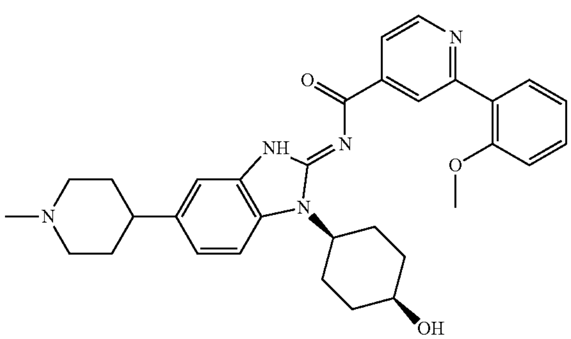 [SMILES: COc1ccccc1-c1cc(C(=O)/N=c2\[nH]c3cc(C4CCN(C)CC4)ccc3n2[C@H]2CC[C@@H](O)CC2)ccn1] | C | 2 | (M + H)$^+$ = 540, t$_{Ret}$ = 1.3 | LCMSBAS |
| I-238 | 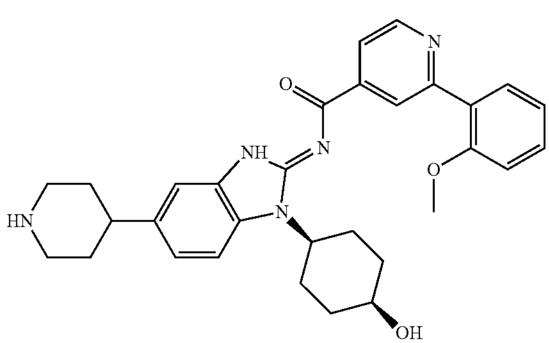 [SMILES: COc1ccccc1-c1cc(C(=O)/N=c2\[nH]c3cc(C4CCNCC4)ccc3n2[C@H]2CC[C@@H](O)CC2)ccn1] | C | 3 | (M + H)$^+$ = 526, t$_{Ret}$ = 1.2 | LCMSBAS |

The following Examples describe the biological activity of the compounds according to the invention, without restricting the invention to these Examples:
Biochemical EGFR Inhibition Assays Initially, the inhibitory effect of compounds according to the invention is measured in biochemical assays which measure the phosphorylation activity of EGFR enzyme forms on poly-GT substrate in the presence of different concentrations of ATP (5 μM and 100 μM final assay concentration).

The following enzyme forms of EGFR are representative examples that can be used in these assays at the given concentrations:
EGFR wt (Life technologies; PV4190); final assay concentration 1.5 nM
EGFR (d746-750 T790M C797S) (SignalChem; E10-12UG); final assay concentration 15 nM
EGFR (mutated) 695-1022, T790M, C797S, L858R (in house prep); final assay concentration 3 nM Test compounds dissolved in DMSO are dispensed onto assay plates (Proxiplate 384 PLUS, white, PerkinElmer; 6008289) using an Access Labcyte Workstation with the Labcyte Echo 55x. For the chosen highest assay concentration of 100 μM, 150 nL of compound solution is transferred from a 10 mM DMSO compound stock solution. A series of eleven fivefold dilutions per compound is transferred to the assay plate, compound dilutions are tested in duplicates. DMSO is added as backfill to a total volume of 150 nL. The assay runs on a fully automated robotic system.

5 μL of EGFR enzyme form in assay buffer (50 mM HEPES pH 7.3, 10 mM $MgCl_2$, 1 mM EGTA, 0.01% Tween 20, 2 mM DTT) are dispensed into columns 1-23, than 5 μL of ATP and ULight-poly-GT substrate (PerkinElmer; TRF0100-M) mix in assay buffer is added to all wells (final assay concentration of the ULight-poly-GT substrate 200 nM). Each of the different EGFR enzyme form assays is available at low ATP (final assay concentration 5 μM) and high ATP levels (final assay concentration 100 μM). After 90 minutes incubation at room temperature 5 μL EDTA (final assay concentration 50 mM) and LANCE Eu-anti-P-Tyr (PT66) antibody (PerkinElmer, AD0069) (final assay concentration 6 nM) mix are added to stop the reaction and start the binding of the antibody. After additional 60 minutes incubation at room temperature the signal is measured in a PerkinElmer Envision HTS Multilabel Reader using the TR-FRET LANCE Ultra specs of PerkinElmer (used wavelengths: excitation 320 nm, emission 1 665 nm, emission 2 615 nm). Each plate contains 16 wells of a negative control (diluted DMSO instead of test compound; w EGFR enzyme form; column 23) and 16 wells of a positive control (diluted DMSO instead of test compound; w/o EGFR enzyme form; column 24). Negative and positive control values are used for normalization and $IC_{50}$ values are calculated and analysed using a 4 parametric logistic model.

These biochemical EGFR enzyme form compound dose-response assays quantify the kinase activity via phosphorylation of a tagged poly-GT substrate. The results of the assay are provided as $IC_{50}$ values. The lower the reported $IC_{50}$ values for a given compound, the more potent the compound inhibits the kinase activity of the EGFR enzyme on poly-GT substrate.

Table 13 contains representative $IC_{50}$ data of compounds generated in the corresponding biochemical assays as described above:

TABLE 13

|  | Del_TM_CS (5 μM ATP) [nM] | Del_TM_CS (100 μM ATP) [nM] | LR_TM_CS (5 μM ATP) [nM] | LR_TM_CS (100 μM ATP) [nM] | wt (5 μM ATP) [nM] | wt (100 μM ATP) [nM] |
| --- | --- | --- | --- | --- | --- | --- |
| I-001 |  | 71.7 | 11.4 | 524.0 | 3290.1 | >100000 |
| I-002 |  | 4.6 |  | 67.4 |  | 2513.7 |
| I-003 |  | 9.9 |  | 61.7 |  | 4077.0 |
| I-004 |  | 4.7 |  | 38.5 |  | 1953.0 |
| I-005 |  | 14.2 |  | 104.6 |  | 236.3 |
| I-007 |  | 7.2 |  | 94.6 |  | >100000 |
| I-008 |  | 5.0 | 1.5 | 39.6 | 184.8 | >4000 |
| I-009 |  | 49.0 |  | 184.0 |  | 12352.3 |
| I-010 |  | 2.9 |  | 17.4 |  | 5108.5 |
| I-011 |  | 2.5 |  | 27.7 |  | 7063.0 |
| I-012 |  | 10.5 | 1.9 | 64.6 | 403.2 | >100000 |
| I-013 |  | 18.4 |  | 76.5 |  | 3767.3 |
| I-014 |  | 48.8 |  | 146.0 |  | >100000 |
| I-015 |  | 2.0 | 0.8 | 10.5 | 125.4 | 113.9 |
| I-017 |  | 14.2 | 3.9 | 110.8 | 1878.2 | 9961.3 |
| I-018 |  |  |  | 11.9 |  | 10005.0 |
| I-019 |  | 26.3 |  | 101.7 |  | 4374.7 |
| I-020 |  | 38.6 |  | 127.7 |  | 3166.5 |
| I-021 |  | 4.9 |  | 27.7 |  | 876.1 |
| I-022 |  | 61.8 |  | 168.9 |  | 5624.1 |
| I-023 |  | 7.7 |  | 78.2 |  | >100000 |
| I-024 |  | 2.1 |  | 19.0 |  | 2044.0 |
| I-025 |  | 27.9 |  | 112.7 |  | 7887.1 |
| I-026 |  | 4.4 |  | 34.5 |  | 1147.1 |
| I-028 |  | 2.4 |  | 4.2 |  | 591.2 |
| I-029 |  | 72.4 |  | 189.8 |  | 14832.0 |
| I-030 |  | 3.4 |  | 25.5 |  | 1964.9 |
| I-031 |  | 1.2 |  | 3.0 |  | 216.7 |
| I-032 |  | 0.6 |  | 3.0 |  | 365.5 |
| I-033 |  | 8.6 |  | 91.6 |  | 9506.8 |
| I-034 |  | 22.8 |  | 195.6 |  | 3953.7 |
| I-035 |  | 5.6 |  | 79.3 |  | 6668.0 |
| I-036 |  | 4.0 | 1.6 | 40.1 | 406.9 | 1248.2 |
| I-037 |  | 14.2 |  | 170.8 |  | >100000 |
| I-038 |  | 15.8 |  | 233.6 |  | 40835.5 |

TABLE 13-continued

| | Del_TM_CS (5 μM ATP) [nM] | Del_TM_CS (100 μM ATP) [nM] | LR_TM_CS (5 μM ATP) [nM] | LR_TM_CS (100 μM ATP) [nM] | wt (5 μM ATP) [nM] | wt (100 μM ATP) [nM] |
|---|---|---|---|---|---|---|
| I-039 | | 36.0 | | 507.5 | | >100000 |
| I-042 | | | | 24.3 | | 14604.3 |
| I-048 | | | 0.4 | 5.7 | 32.3 | 1312.0 |
| I-052 | | 6.6 | | 189.1 | | >100000 |
| I-053 | | 8.7 | | 94.1 | | 5735.4 |
| I-054 | | 4.1 | | 104.2 | | 79668.9 |
| I-055 | | 7.3 | | 86.9 | | 26289.1 |
| I-056 | | | 117.7 | | >100000 | |
| I-060 | | | 0.7 | 65.6 | | |
| I-064 | | | 13.1 | 267.1 | >4000 | >100000 |
| I-76 | | | | 216.7 | | >100000 |
| I-78 | | | | 95.2 | | 21071.8 |
| I-91 | | | 61.1 | | 14709.1 | |
| I-101 | | | | 11.3 | | 7533.3 |
| I-102 | | | 1.0 | 13.7 | 213.0 | 6064.6 |
| I-105 | | | 0.7 | 10.3 | | 1802.6 |
| I-107 | | | 1.8 | 45.7 | 336.5 | >100000 |
| I-108 | | | 0.6 | 10.3 | 19.3 | 1012.5 |
| I-109 | | | 0.5 | 8.8 | 12.5 | 549.4 |
| I-110 | | | | 3.7 | | 4419.1 |
| I-111 | | | | 10.3 | | 7038.1 |
| I-112 | | | 3.1 | | 777.0 | |
| I-113 | | | | 34.8 | | >100000 |
| I-114 | | | | 18.6 | | 6654.1 |
| I-115 | | | | 5.8 | | 2419.9 |
| I-116 | | | 0.7 | | 103.6 | |
| I-118 | | | 0.7 | | 34.5 | |
| I-119 | | | 0.9 | | 31.5 | |
| I-126 | | | 3.1 | | 304.9 | |
| I-128 | | | 4.0 | | 1128.5 | |
| I-130 | | | | 177.7 | | >100000 |
| I-135 | | | 0.8 | | 225.4 | |
| I-136 | 0.2 | | 0.8 | 31.6 | 163.6 | >100000 |
| I-137 | | | 0.8 | | 107.6 | |
| I-138 | | | 0.8 | | 256.5 | |
| I-141 | | | 2.0 | | 311.7 | |
| I-143 | 0.4 | | 1.9 | 103.9 | 2183.5 | >100000 |
| I-144 | | | 6.9 | | 110.1 | |
| I-145 | | | 1.7 | | 397.3 | |
| I-146 | | | 2.8 | | 1535.0 | |
| I-148 | | | 3.3 | | 77.8 | |
| I-149 | | | 8.5 | | 148.1 | |
| I-156 | | | 13.3 | | 3147.2 | |
| I-157 | | | 4.6 | | 70.4 | |
| I-158 | | | 1.5 | | 56.3 | |
| I-161 | | | 2.4 | | 204.8 | |
| I-162 | | | 14.2 | | 1178.9 | |
| I-163 | | | 10.4 | | 110.0 | |
| I-167 | | | 4.6 | | 994.9 | |
| I-168 | | | 5.0 | | 1272.6 | |
| I-169 | | | 2.8 | | 81.6 | |
| I-171 | | | 8.8 | | 2970.5 | |
| I-175 | | | 13.6 | | 557.4 | |
| I-176 | | | 4.0 | | 292.7 | |
| I-179 | | | 33.8 | | 3595.2 | |
| I-180 | | | 4.8 | | 302.0 | |
| I-181 | | | 1.7 | | 31.0 | |
| I-183 | | | 20.2 | | 958.3 | |
| I-184 | | | 7.8 | | 1515.2 | |
| I-185 | | | 35.6 | | 3242.4 | |
| I-189 | | | 1.4 | | 37.4 | |
| I-191 | | | 7.4 | | 1659.7 | |
| I-196 | | | 3.0 | | 1401.0 | |
| I-197 | | | 2.7 | | 5013.1 | |
| I-198 | | | 7.7 | | 77.1 | |
| I-199 | | | 6.8 | | 1522.3 | |
| I-200 | | | 2.3 | | 439.3 | |
| I-201 | | | 1.2 | | 230.6 | |
| I-202 | | | 0.9 | | 173.0 | |
| I-203 | | | 1.0 | | 178.8 | |
| I-204 | | | 26.2 | | 9287.1 | |
| I-205 | | | 3.6 | | 1483.1 | |
| I-206 | | | 17.7 | | 12886.5 | |
| I-207 | | | 3.0 | | 539.4 | |
| I-208 | | | 5.4 | | 7474.9 | |
| I-209 | | | 8.1 | | 5799.0 | |

TABLE 13-continued

| | Del_TM_CS (5 µM ATP) [nM] | Del_TM_CS (100 µM ATP) [nM] | LR_TM_CS (5 µM ATP) [nM] | LR_TM_CS (100 µM ATP) [nM] | wt (5 µM ATP) [nM] | wt (100 µM ATP) [nM] |
|---|---|---|---|---|---|---|
| I-210 | | | 4.3 | | 664.1 | |
| I-211 | | | 0.3 | | 249.2 | |
| I-212 | | | 2.5 | | 318.1 | |
| I-213 | | | 54.1 | | >100000 | |
| I-214 | | | 10.1 | | 9658.4 | |
| I-215 | | | 4.9 | | 8380.0 | |
| I-216 | | | 8.1 | | 2674.0 | |
| I-217 | | | 33.0 | | >100000 | |
| I-219 | 0.1 | | 0.4 | | 25.8 | |
| I-220 | 2.0 | | 32.7 | | 2856.8 | |
| I-221 | 0.4 | | 2.0 | | 2049.9 | |
| I-222 | 0.2 | | 0.6 | | 318.0 | |
| I-223 | 0.5 | | 1.8 | | 2024.0 | |
| I-224 | 0.2 | | 0.5 | | 267.4 | |
| I-225 | 0.2 | | 0.4 | | 162.5 | |
| I-235 | | 57.2 | 10.7 | 440.2 | 8852.6 | >100000 |

Ba/F3 Cell Model Generation and Proliferation Assays

Ba/F3 cells were ordered from DSMZ (ACC300, Lot17) and grown in RPMI-1640 (ATCC 30-2001)+10% FCS+10 ng/ml IL-3 at 37° C. in 5% $CO_2$ atmosphere. Plasmids containing EGFR mutants were obtained from GeneScript. To generate EGFR-dependent E3a/F3 models, E3a/F3 cells were transduced with retroviruses containing vectors that harbor EGFR isoforms. Platinum-E cells (Cell Biolabs) were used for retrovirus packaging. Retrovirus was added to Ba/F3 cells. To ensure infection, 4 µg/mL polybrene was added and cells were spinfected. Infection efficiency was confirmed by measuring GFP-positive cells using a cell analyzer. Cells with an infection efficiency of 10% to 20% were further cultivated and puromycin selection with 1 µg/mL was initiated. As a control, parental Ba/F3 cells were used to show selection status. Selection was considered successful when parental Ba/F3 cells cultures died. To evaluate the transforming potential of EGFR mutations, the growth medium was no longer supplemented with IL-3. Ba/F3 cells harboring the empty vector were used as a control. A switch from IL-3 to EGF was performed for Ba/F3 cells with the wildtype EGFR known for its dependency on EGF ligand. Approximately ten days before conducting the experiments, puromycin was left out. For proliferation assays (data in table 13), Ba/F3 cells were seeded into 96-well plates at $5 \times 10^3$ cells/100 µL in growth media. Compounds were added by using a HP D3000 Digital Dispenser. All treatments were performed in technical triplicates. Treated cells were incubated for 72 h at 37° C. with 5% $CO_2$. CellTiter-Glo® Luminescent Cell Viability Assay (Promega) was performed and chemoluminescence was measured by using the multilabel Plate Reader VICTOR X4. The raw data were imported into and analyzed with the Boehringer Ingelheim proprietary software MegaLab (curve fitting based on the program PRISM, GraphPad Inc.).

TABLE 14

Viability $IC_{50}$ values in nM of Ba/F3 cell lines driven by the indicated EGFR alleles and treated with the indicated compounds (average data of two independent biological experiments with three technical replicates are shown).

| | cell model | | |
|---|---|---|---|
| drug | $IC_{50}$ EGFR-indep. + IL-3 [nM] | $IC_{50}$ EGFR wt + EGFR [nM] | $IC_{50}$ EGFR del19 [nM] |
| erlotinib | >5000 | 38.9 | 2.0 |
| gefitinib | >5000 | 37.0 | 1.8 |
| afatinib | 1055.7 | 0.60 | 0.02 |
| dacomitinib | 977.9 | 0.64 | 0.01 |
| osimertinib | 960.3 | 26.7 | 0.5 |
| nazartinib | >5000 | 95.1 | 1.1 |
| nazartinib w/o warhead | 5026.1 | 1625.0 | 3435.7 |

TABLE 14-continued

Viability IC$_{50}$ values in nM of Ba/F3 cell lines driven by the indicated EGFR alleles and treated with the indicated compounds (average data of two independent biological experiments with three technical replicates are shown).

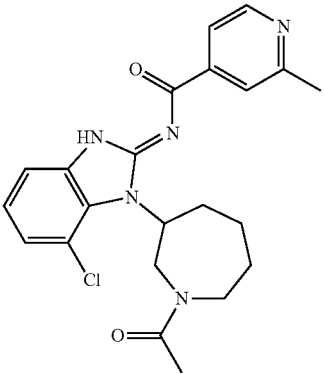 [SMILES: CC(=O)N1CCCCC(n2/c(=N/C(=O)c3ccnc(C)c3)[nH]c3cccc(Cl)c32)C1]

| | | | |
|---|---|---|---|
| I-109 | 8645.3 | 728.3 | 9.1 |
| I-048 | 7938.6 | 540.0 | 10.9 |
| I-015 | 6524.66 | 2223.4 | 45.8 |
| I-137 | 9059.0 | 2059.2 | 16.6 |

| | cell model | | |
|---|---|---|---|
| drug | IC$_{50}$ EGFR del19 T790M [nM] | IC$_{50}$ EGFR del19 C797S [nM] | IC$_{50}$ EGFR del19 T790M C797S [nM] |
| erlotinib | 1039.8 | 3.0 | 3562.5 |
| gefitinib | 852.7 | 2.6 | 2091.2 |
| afatinib | 31.2 | 1.9 | 807.3 |
| dacomitinib | 56.3 | 1.6 | 1170.3 |
| osimertinib | 1.6 | 628.4 | 729.6 |
| nazartinib | 4.1 | 744.8 | 455.2 |
| nazartinib w/o warhead | 2523.9 | 3518.7 | 2229.8 |
| I-109 | 52.9 | 7.0 | 23.5 |
| I-048 | 32.9 | 9.1 | 12.0 |
| I-015 | 169.4 | 21.1 | 47.0 |
| I-137 | 72.0 | 8.7 | 20.7 |

| | cell model | | |
|---|---|---|---|
| drug | IC$_{50}$ EGFR L858R [nM] | IC$_{50}$ EGFR L858R T790M [nM] | IC$_{50}$ EGFR L858R C797S [nM] |
| erlotinib | 4.6 | >5000 | 11.1 |
| gefitinib | 5.8 | 3399.6 | 11.5 |
| afatinib | 0.02 | 34.8 | 7.2 |
| dacomitinib | 0.03 | 61.4 | 6.9 |
| osimertinib | 1.1 | 1.9 | 768.7 |
| nazartinib | 5.1 | 7.3 | 1985.2 |
| nazartinib w/o warhead | 2706.3 | 2935.4 | 3615.9 |
| I-109 | 38.3 | 177.3 | 51.5 |
| I-048 | 39.2 | 79.4 | 52.1 |
| I-015 | 274.3 | 407.9 | 290.0 |
| I-137 | 91.6 | 177.6 | 100.3 |

| | cell model |
|---|---|
| drug | IC$_{50}$ EGFR L858R T790M C797S [nM] |
| erlotinib | >5000 |
| gefitinib | >5000 |
| afatinib | 1145.4 |
| dacomitinib | 1602.4 |
| osimertinib | 1082.3 |
| nazartinib | 758.8 |

TABLE 14-continued

Viability IC$_{50}$ values in nM of Ba/F3 cell lines driven by the indicated EGFR alleles and treated with the indicated compounds (average data of two independent biological experiments with three technical replicates are shown).

| | |
|---|---|
| nazartinib w/o warhead | 3545.5 |
| I-109 | 145.9 |
| I-048 | 48.2 |
| I-015 | 284.1 |
| I-137 | 137.1 | pEGFR Assay

This assay quantifies the phosphorylation of EGFR at Tyr1068 and was used to measure the inhibitory effect of compounds on the transgenic EGFR del19 T790M C797S protein in Ba/F3 cells. Murine Ba/F3 cells were grown in RPMI-1640 (ATCC 30-2001)+10% FCS+10 ng/mL IL-3 at 37° C. in 5% $CO_2$ atmosphere and transduced with a retroviral vector encoding EGFR del19 T790M C797S. Transduced cells were selected using puromycin. Following selection, IL-3 was withdrawn and IL-3 independent cells cultured. p-EGFR Tyr1068 was determined using the AlphaScreen Surefire pEGF Receptor (Tyr1068) Assay (PerkinElmer, TGRERS). For the assay, Ba/F3 EGFR del19 T790M C797S cells were seeded in DMEM medium with 10% FCS. 60 nL compound dilutions were added to each well of Greiner TC 384 plates using the Echo platform. Subsequently, 60.000 cells/well in 60 μL were added. Cells were incubated with compound for 4 h at 37° C. Following centrifugation and removal of the medium supernatant, 20 μL of 1.6-fold lysis buffer from TGR/Perkin Elmer kit with protease inhibitors was added. The mixture was incubated at room temperature with shaking (700 rpm) for 20 min. After centrifugation, 4 μL of the lysate were transferred to Proxiplates. 5 μL of Acceptor Mix (Activation Buffer diluted 1:25 in combined Reaction Buffer 1 and Reaction Buffer 2 (TGRERS Assay Kit, PerkinElmer) plus 1:50 of Protein A Acceptor Beads 6760137) were added to each well. Plates were shaken for 1 min (1400 rpm) and incubated for 2 h at room temperature in the dark. 3 μL of donor mix (AlphaScreen Streptavidin-coated Donor Beads (6760002, PerkinElmer) 1:50 diluted in Dilution Buffer (TGRERS Assay Kit, PerkinElmer) were added to each well. Plates were shaken for 1 min (1400 rpm) and incubated for 2 h at room temperature in the dark. Plates were subsequently analyzed using an Envision reader platform. Results were computed in the following way: The ratio of the value of the test compound and the value of the negative control (DMSO) was calculated. IC$_{50}$ values are computed from these values in the MEGASTAR IC$_{50}$ application using a 4 parametric logistic model.

This cellular phospho-EGFR (pEGFR) compound dose-response assay quantifies the phosphorylation of EGFR at Tyr1068 in Ba/F3 cells expressing the EGFR variant del19 T790M C797S. The results of the assay are provided as IC$_{50}$ values (see table 12). The lower the reported pEGFR IC$_{50}$ values for a given compound, the more potent the compound inhibits the EGFR del19 T790M C797S target protein in Ba/F3 cells.

The invention claimed is:
1. A compound of formula (I)

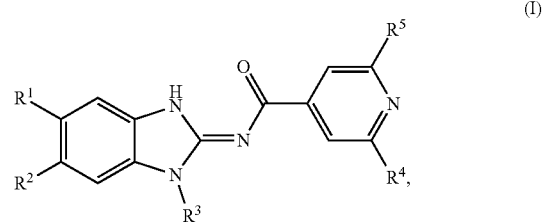

wherein
$R^1$ is —$(CH_2)_n$-A;
n is 0 or 1;
A is 3-11 membered heterocyclyl optionally substituted by one or more, identical or different substituents selected from the group consisting of $C_{1-4}$ alkyl, $C_{1-4}$ alkoxy, $C_{1-4}$alkoxy-C—C(O)O—$C_{1-4}$alkyl, —C(O)—$C_{1-4}$alkyl, $C_{3-6}$ cycloalkyl, —NH($C_{1-4}$alkyl), —N($C_{1-4}$alkyl)$_2$ and the bivalent substituent=O; or
$R^1$ is —$NR^A R^A$;
each $R^A$ is independently selected from the group consisting of hydrogen, $C_{1-4}$alkyl, $C_{1-4}$alkoxy-$C_{1-4}$alkyl, $C_{1-4}$ alkyl substituted with 4-6 membered heterocyclyl, ($C_{1-4}$alkyl)$_2$amino-$C_{1-4}$alkyl and ($C_{1-4}$alkyl)$_2$amino-$C_{1-4}$ alkoxy-$C_{1-4}$ alkyl; or
$R^1$ is $C_{1-6}$ alkyl optionally substituted with a substituent selected from the group consisting of ($C_{1-4}$alkyl)$_2$ amino, —C(O)NH-$C_{1-4}$ alkyl, —C(O)-heterocyclyl with a 5-6 membered heterocyclyl, —OH, —CN and —C(O)O—$C_{1-4}$ alkyl;
or
$R^1$ is selected from the group consisting of halogen and hydrogen;
$R^2$ is —$(CH_2)_m$—B;
m is 0 or 1;
B is 3-11 membered heterocyclyl optionally substituted by one or more, identical or different substituents selected from the group consisting of $C_{1-4}$ alkyl, $C_{1-4}$ alkoxy, $C_{1-4}$ alkoxy-$C_{1-4}$alkyl, —C(O)O—$C_{1-4}$alkyl, —C(O)—$C_{1-4}$alkyl, $C_{3-6}$cycloalkyl, —NH($C_{1-4}$alkyl), —N($C_{1-4}$ alkyl)$_2$ and the bivalent substituent=O; or
$R^2$ is —$NR^B R^B$;
each $R^B$ is independently selected from the group consisting of hydrogen, $C_{1-4}$alkyl, $C_{1-4}$ alkoxy-$C_{1-4}$alkyl, $C_{1-4}$ alkyl substituted with 4-6 membered heterocyclyl, ($C_{1-4}$ alkyl)$_2$amino-$C_{1-4}$alkyl and ($C_{1-4}$ alkyl)$_2$amino-$C_{1-4}$ alkoxy-$C_{1-4}$ alkyl; or
$R^2$ is $C_{1-6}$alkyl optionally substituted with a substituent selected from the group consisting of ($C_{1-4}$alkyl)$_2$ amino, —C(O)NH-$C_{1-4}$ alkyl, —C(O)-heterocyclyl with a 5-6 membered heterocyclyl, —OH, —CN and —C(O)O—$C_{1-4}$ alkyl; or R² is selected from the group consisting of halogen and hydrogen;

R³ is selected from the group consisting of C$_{3-6}$alkyl, C$_{3-6}$cycloalkyl and 4-7 membered heterocyclyl, wherein the C$_{3-6}$alkyl, C$_{3-6}$cycloalkyl and 4-7 membered heterocyclyl are all optionally substituted by one or more —OH;

R⁴ is selected from the group consisting of phenyl, 5-6 membered heteroaryl and 9-membered heteroaryl, wherein the phenyl, 5-6 membered heteroaryl and 9-membered heteroaryl are all optionally substituted by one or more, identical or different substituents selected from the group consisting of C$_{1-6}$ alkyl, C$_{1-6}$ haloalkyl, —O—C$_{1-6}$ alkyl, —O-C$_{1-6}$ haloalkyl, halogen, hydroxy, —NH-C$_{1-6}$alkyl, —N(C$_{1-6}$alkyl)$_2$, —C(O)NH-C$_{1-6}$ alkyl, —C(O)N(C$_{1-6}$alkyl)$_2$ and (C$_{1-6}$ alkyl)$_2$N—C$_{1-6}$ alkyl;

R⁵ is selected from the group consisting of hydrogen, C$_{1-4}$alkyl, C$_{2-4}$alkenyl, C$_{2-4}$ alkinyl, halogen, —CN, —NH$_2$, —NH(C$_{1-4}$alkyl) and —N(C$_{1-4}$ alkyl)$_2$;

or a salt thereof.

2. The compound or salt according to claim 1, wherein R¹ is —(CH$_2$)$_n$-A;

n is 0 or 1;

A is 4-6 membered heterocyclyl optionally substituted by one or more, identical or different substituents selected from the group consisting of C$_{1-4}$ alkyl, C$_{1-4}$ alkoxy, C$_{1-4}$alkoxy-C$_{1-4}$alkyl —C(O)O-C—C(O)-C$_{1-4}$alkyl, C$_{3-6}$cycloalkyl, —NH(C$_{1-4}$alkyl), —N(C$_{1-4}$alkyl)$_2$ and the bivalent substituent=O.

3. The compound or salt according to claim 1, wherein R¹ is selected from the group consisting of

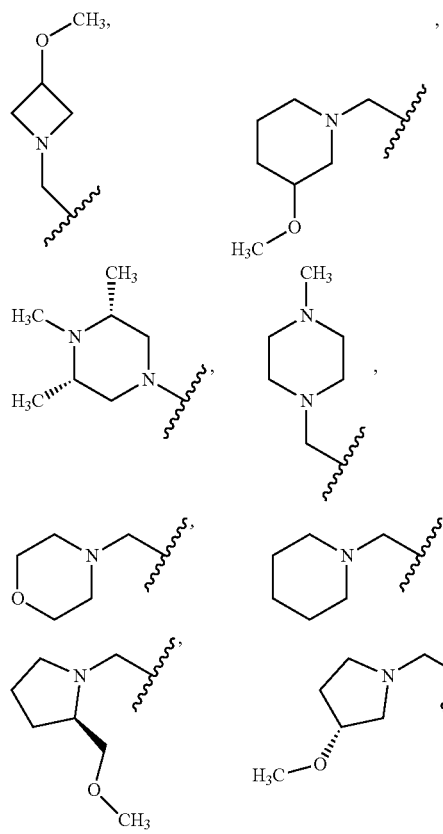

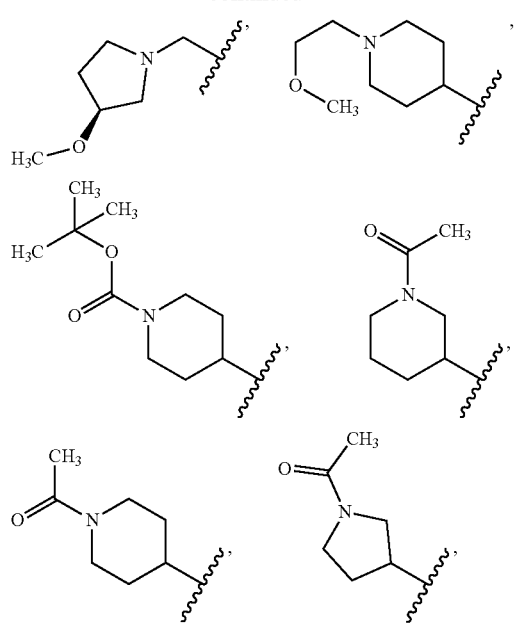

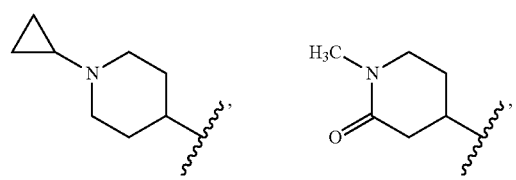

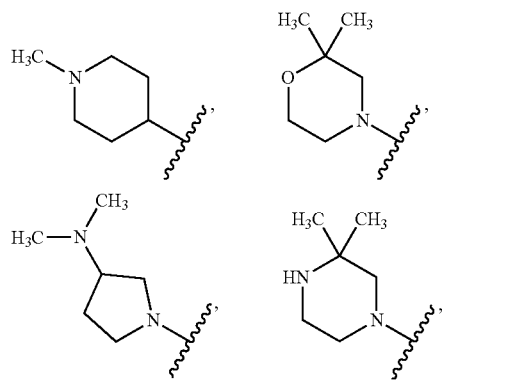

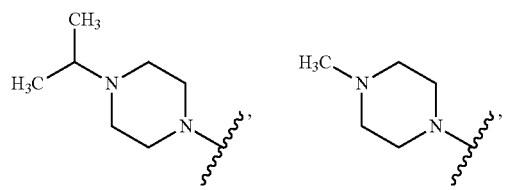

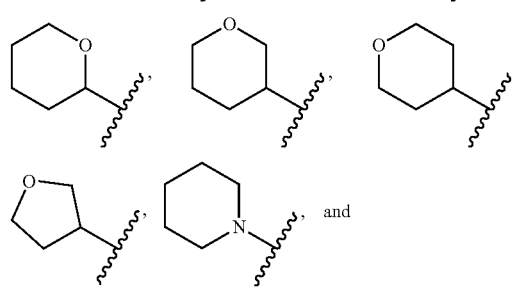

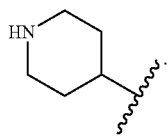

4. The compound or salt according to claim 1, wherein $R^1$ is $C_{1-4}$alkyl.

5. The compound or salt according to claim 1, wherein $R^1$ is hydrogen.

6. The compound or salt according to claim 1, wherein $R^2$ is —$(CH_2)_m$—B;

m is 0 or 1;

B is 4-6 membered heterocyclyl optionally substituted by one or more, identical or different substituents selected from the group consisting of $C_{1-4}$ alkyl, $C_{1-4}$ alkoxy, $C_{1-4}$alkoxy-$C_{1-4}$alkyl, —C(O)O-C—C(O)-$C_{1-4}$alkyl, $C_{3-6}$cycloalkyl, —NH($C_{1-4}$alkyl), —N($C_{1-4}$alkyl)$_2$ and the bivalent substituent=O.

7. The compound or salt according to claim 1, wherein $R^2$ is selected from the group consisting of

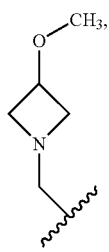
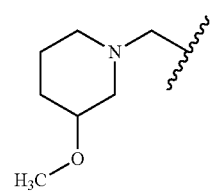
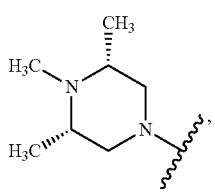
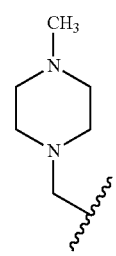
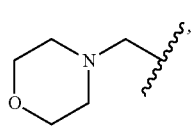
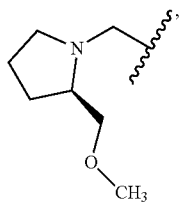
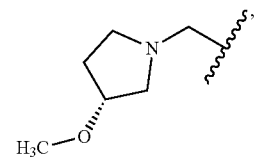
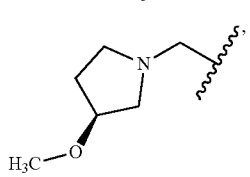
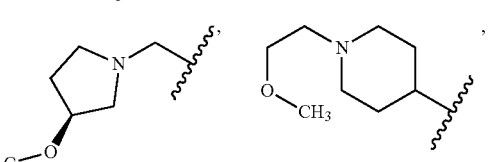

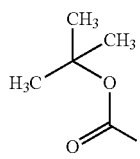
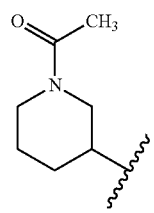
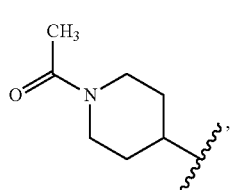
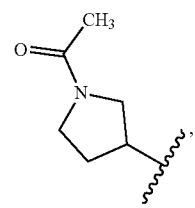
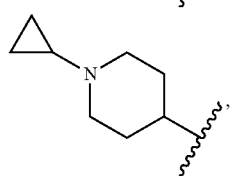
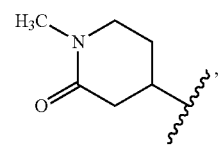
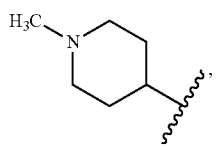
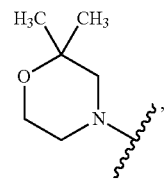
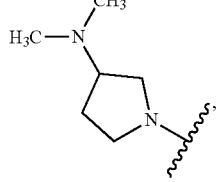
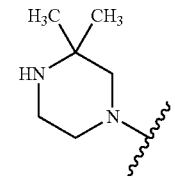
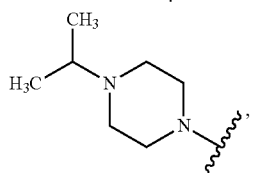
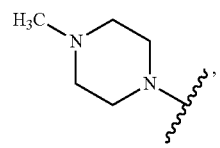
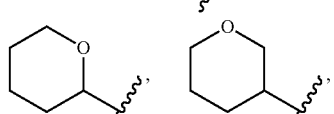
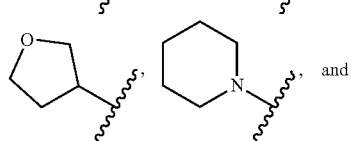
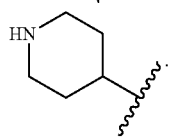

8. The compound or salt according to claim 1, wherein $R^2$ is hydrogen.

9. The compound or salt according to claim 1, wherein $R^3$ is $C_{3-6}$cycloalkyl.

10. The compound or salt according to claim 1, wherein $R^3$ is $C_{3-6}$cycloalkyl substituted by —OH.

11. The compound or salt according to claim 1, wherein $R^3$ is $C_{3-6}$alkyl substituted by —OH.

12. The compound or salt according to claim 1, wherein $R^4$ is selected from the group consisting of phenyl, pyrazolyl and pyridyl, wherein the phenyl, pyrazolyl and pyridyl are all optionally substituted by one or more, identical or different substituents selected from the group consisting of $C_{1-6}$alkyl, $C_{1-6}$haloalkyl, —O—$C_{1-6}$ alkyl, —O—$C_{1-6}$haloalkyl, halogen, hydroxy, —NH—$C_{1-6}$ alkyl, —N($C_{1-6}$alkyl)$_2$ –C(O)NH-$C_{1-6}$alkyl, —C(O)N($C_{1-6}$alkyl)$_2$ and ($C_{1-6}$alkyl)$_2$N-$C_{1-6}$alkyl.

13. The compound or salt according to claim 1, wherein $R^4$ is selected from the group consisting of phenyl, 1H-pyrazol-4-yl and pyridin-3-yl, wherein the phenyl, 1H-pyrazol-4-yl and pyridin-3-yl are all optionally substituted by one or more, identical or different substituents selected from the group consisting of $C_{1-6}$alkyl, $C_{1-6}$haloalkyl, —O—$C_{1-6}$alkyl, —O-$C_{1-6}$haloalkyl, halogen, hydroxy, —NH-$C_{1-6}$alkyl, —N($C_{1-6}$alkyl)$_2$,
—C(O)NH-$C_{1-6}$alkyl, —C(O)N($C_{1-6}$alkyl)$_2$ and ($C_{1-6}$alkyl)$_2$N-$C_{1-6}$alkyl.

14. The compound or salt according to claim 1, wherein $R^5$ is selected from the group consisting of hydrogen, $C_{1-4}$alkyl, $C_{1-4}$haloalkyl, $C_{2-4}$alkinyl, halogen, —CN, —NH$_2$ and —NH($C_{1-4}$ alkyl).

15. The compound or salt according to claim 1, wherein $R^5$ is hydrogen.

16. A method for the treatment of a disease and/or condition wherein the inhibition of mutant EGFR is of therapeutic benefit comprising administering a therapeutically effective amount of a compound of claim 1 or a pharmaceutically acceptable salt thereof to a human being.

17. A method for the treatment of cancer comprising administering a therapeutically effective amount of a compound of claim 1 or a pharmaceutically acceptable salt thereof to a human being.

18. A method according to 16, wherein the compound or a pharmaceutically acceptable salt thereof is administered before, after or together with at least one other pharmacologically active substance.

19. A method according to claim 16, wherein the compound or a pharmaceutically acceptable salt thereof is administered in combination with a therapeutically effective amount of at least one other pharmacologically active substance.

20. A pharmaceutical composition comprising a compound according to claim 1 or a pharmaceutically acceptable salt thereof and one or more pharmaceutically acceptable excipient(s).

21. A pharmaceutical preparation comprising a compound according to claim 1 or a pharmaceutically acceptable salt thereof and at least one other pharmacologically active substance.

22. A method according to claim 17, wherein the compound or a pharmaceutically acceptable salt thereof is administered before, after or together with at least one other pharmacologically active substance.

23. A method according to claim 17, wherein the compound or a pharmaceutically acceptable salt thereof is administered in combination with a therapeutically effective amount of at least one other pharmacologically active substance.

* * * * *